US008268859B2

(12) United States Patent
Harcken et al.

(10) Patent No.: US 8,268,859 B2
(45) Date of Patent: Sep. 18, 2012

(54) GLUCOCORTICOID MIMETICS, METHODS OF MAKING THEM, PHARMACEUTICAL COMPOSITIONS AND USES THEREOF

(75) Inventors: Christian Harcken, New Milford, CT (US); Rajashekhar Betageri, Bethel, CT (US); Todd Bosanac, New Milford, CT (US); Michael Jason Burke, Chesire, CT (US); Soojin Kim, Demarest, NJ (US); Daniel Kuzmich, Danbury, CT (US); Thomas Wai-ho Lee, Brookfield, CT (US); Zhibin Li, Berlin, CT (US); Pingrong Liu, Southbury, CT (US); John Lord, Poughkeepsie, NY (US); Hossein Razavi, Danbury, CT (US); Jonathan Timothy Reeves, New Milford, CT (US); David Thomson, Ridgefield, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 169 days.

(21) Appl. No.: 12/477,586

(22) Filed: Jun. 3, 2009

(65) Prior Publication Data

US 2009/0325988 A1    Dec. 31, 2009

Related U.S. Application Data

(60) Provisional application No. 61/059,388, filed on Jun. 6, 2008.

(51) Int. Cl.
| | |
|---|---|
| *C07D 471/02* | (2006.01) |
| *C07D 491/02* | (2006.01) |
| *C07D 498/02* | (2006.01) |
| *C07D 513/02* | (2006.01) |
| *A01N 43/42* | (2006.01) |
| *A61K 31/44* | (2006.01) |

(52) U.S. Cl. ........................................ 514/300; 546/113
(58) Field of Classification Search .................. 546/113; 514/300

See application file for complete search history.

(56) References Cited

U.S. PATENT DOCUMENTS

| | | | |
|---|---|---|---|
| 3,772,273 A | 11/1973 | Gilbert |
| 4,551,534 A | 11/1985 | Sulkowski et al. |
| 4,774,240 A | 9/1988 | Boshagen et al. |
| 4,880,839 A | 11/1989 | Tucker |
| 5,039,691 A | 8/1991 | Spagnuolo et al. |
| 5,206,377 A | 4/1993 | McAfee |
| 5,688,810 A | 11/1997 | Jones et al. |
| 5,948,820 A | 9/1999 | Fujita et al. |
| 6,169,106 B1 | 1/2001 | Heckel et al. |
| 6,187,918 B1 | 2/2001 | Nugent |
| 6,323,199 B1 | 11/2001 | Lehmann et al. |
| 6,329,534 B1 | 12/2001 | Kym et al. |
| 6,362,344 B1 | 3/2002 | Nugent |
| 6,380,223 B1 | 4/2002 | Dow et al. |
| 6,436,986 B1 | 8/2002 | Kym et al. |
| 6,506,766 B1 | 1/2003 | Coghlan et al. |
| 6,583,180 B2 | 6/2003 | Link et al. |
| 6,589,947 B1 | 7/2003 | Hamanaka et al. |
| 6,699,893 B2 | 3/2004 | Dow et al. |
| 6,777,404 B2 | 8/2004 | Hamanaka et al. |
| 6,858,627 B2 | 2/2005 | Bekkali et al. |
| 6,903,215 B2 | 6/2005 | Betageri et al. |
| 6,960,581 B2 | 11/2005 | Betageri et al. |
| 7,074,806 B2 | 7/2006 | Kirrane, Jr. et al. |
| 7,125,996 B2 | 10/2006 | Prokopowicz, III et al. |
| 7,166,593 B2 | 1/2007 | Dow et al. |
| 7,179,919 B2 | 2/2007 | Song et al. |
| 7,186,864 B2 | 3/2007 | Kirrane, Jr. et al. |
| 7,189,758 B2 | 3/2007 | Betageri et al. |
| 7,256,300 B2 | 8/2007 | Lee et al. |
| 7,268,152 B2 | 9/2007 | Bekkali et al. |
| 7,425,629 B2 | 9/2008 | Song et al. |
| 7,507,843 B2 | 3/2009 | Song et al. |
| 7,553,966 B2 | 6/2009 | Betageri et al. |
| 7,579,469 B2 | 8/2009 | Kuzmich et al. |

(Continued)

FOREIGN PATENT DOCUMENTS

BE    900594    3/1985

(Continued)

OTHER PUBLICATIONS

West, Anthony R., Solid State Chemistry and its Applications, Wiley, New York, 1988, pp. 358 & 365.* Banker (Modern Pharmaceutics)
Banker, G.S. et al, "Modern Pharmaceutics, 3ed.", Marcel Dekker, New York, 1996, pp. 451 and 596.*
Wolff, Manfred E. "Burger's Medicinal Chemistry, 5ed, Part I", John Wiley & Sons, 1995, pp. 975-977.*
Fleming et al.; CA 64:9697 f-g; 1966.

(Continued)

*Primary Examiner* — Niloofar Rahmani
(74) *Attorney, Agent, or Firm* — Michael P. Morris; Timothy X. Witkowski; Usha R. Patel

(57) ABSTRACT

Compounds of Formula (I)

(I)

[Chemical structure showing: $CH_3$, OH, $R^1$, $CH_3$, $CF_3$ on left side; bicyclic ring system with X, Y, $R^2$, N-H on right side]

wherein $R^1$, $R^2$, X, and Y are as defined herein, or a tautomer, optical isomer, prodrug, co-crystal, or salt thereof; pharmaceutical compositions containing such compounds, and methods of modulating the glucocorticoid receptor function and methods of treating disease-states or conditions mediated by the glucocorticoid receptor function or characterized by inflammatory, allergic, or proliferative processes in a patient using these compounds.

12 Claims, 29 Drawing Sheets

U.S. PATENT DOCUMENTS

| | | | |
|---|---|---|---|
| 7,622,594 | B2 | 11/2009 | Mugge et al. |
| 7,635,711 | B2 | 12/2009 | Kuzmich et al. |
| 7,713,989 | B2 | 5/2010 | Dow et al. |
| 7,741,361 | B2 | 6/2010 | Kuzmich et al. |
| 7,932,392 | B2 | 4/2011 | Betageri et al. |
| 2001/0014754 | A1 | 8/2001 | Suzuki et al. |
| 2002/0077356 | A1 | 6/2002 | Jaroch et al. |
| 2002/0156311 | A1 | 10/2002 | Link et al. |
| 2003/0105099 | A1 | 6/2003 | Graupe et al. |
| 2003/0108910 | A1 | 6/2003 | Toland et al. |
| 2003/0171359 | A1 | 9/2003 | Dahmann et al. |
| 2003/0232823 | A1 | 12/2003 | Betageri et al. |
| 2004/0010020 | A1 | 1/2004 | Kirrane et al. |
| 2004/0010148 | A1 | 1/2004 | Kirrane et al. |
| 2004/0023999 | A1 | 2/2004 | Bekkali et al. |
| 2004/0029932 | A1 | 2/2004 | Bekkali et al. |
| 2004/0058978 | A1 | 3/2004 | Walter et al. |
| 2004/0097574 | A1 | 5/2004 | Marshall |
| 2004/0116455 | A1 | 6/2004 | Bekkali et al. |
| 2004/0116694 | A1 | 6/2004 | Jaroch et al. |
| 2004/0162321 | A1 | 8/2004 | Kuzmich et al. |
| 2004/0209875 | A1 | 10/2004 | Schmees et al. |
| 2004/0224992 | A1 | 11/2004 | Cywin et al. |
| 2004/0242613 | A1 | 12/2004 | Cardozo et al. |
| 2004/0254249 | A1 | 12/2004 | Jaroch et al. |
| 2005/0043301 | A1 | 2/2005 | Liu et al. |
| 2005/0059714 | A1 | 3/2005 | Betageri et al. |
| 2005/0124640 | A1 | 6/2005 | Cardozo et al. |
| 2005/0131241 | A1 | 6/2005 | Song et al. |
| 2005/0176706 | A1 | 8/2005 | Bekkali et al. |
| 2005/0203128 | A1 | 9/2005 | Kirrane et al. |
| 2005/0209488 | A1 | 9/2005 | Song et al. |
| 2005/0234091 | A1 | 10/2005 | Regan et al. |
| 2005/0234250 | A1 | 10/2005 | Lee et al. |
| 2005/0282881 | A1 | 12/2005 | Bekkali et al. |
| 2006/0014787 | A1 | 1/2006 | Kirrane et al. |
| 2006/0030561 | A1 | 2/2006 | Betageri et al. |
| 2006/0030608 | A1 | 2/2006 | Nelson et al. |
| 2006/0122189 | A1 | 6/2006 | Feenstra et al. |
| 2006/0154925 | A1 | 7/2006 | Kuzmich et al. |
| 2006/0189646 | A1 | 8/2006 | Kuzmich et al. |
| 2006/0189647 | A1 | 8/2006 | Bekkali et al. |
| 2006/0205712 | A1 | 9/2006 | Calvani et al. |
| 2007/0060633 | A1 | 3/2007 | Mugge et al. |
| 2007/0100142 | A1 | 5/2007 | Song et al. |
| 2009/0176807 | A1 | 7/2009 | Regan et al. |
| 2009/0325988 | A1 | 12/2009 | Harcken et al. |

FOREIGN PATENT DOCUMENTS

| | | | |
|---|---|---|---|
| CA | 2305458 | A1 | 12/1998 |
| CA | 2323111 | A1 | 10/1999 |
| CA | 2342622 | A1 | 4/2000 |
| CA | 2411165 | A1 | 12/2002 |
| CA | 2463989 | A1 | 4/2003 |
| DE | 1017612 | B | 10/1957 |
| EP | 0154528 | | 9/1985 |
| EP | 0253500 | | 1/1988 |
| EP | 0253503 | | 1/1988 |
| EP | 0311447 | A1 | 4/1989 |
| GB | 2146987 | | 5/1985 |
| JP | 5194404 | A | 8/1993 |
| JP | 11080131 | A | 3/1999 |
| WO | 9315047 | A1 | 8/1993 |
| WO | 9619458 | | 6/1996 |
| WO | 9727852 | | 8/1997 |
| WO | 9854159 | | 12/1998 |
| WO | 9933786 | A1 | 7/1999 |
| WO | 9941256 | | 8/1999 |
| WO | 9952869 | A1 | 10/1999 |
| WO | 9963976 | A2 | 12/1999 |
| WO | 0018734 | A1 | 4/2000 |
| WO | 0032584 | A2 | 6/2000 |
| WO | 0066522 | | 11/2000 |
| WO | 0105784 | A1 | 1/2001 |
| WO | 0183471 | A1 | 11/2001 |
| WO | 189445 | A1 | 11/2001 |
| WO | 0202565 | | 1/2002 |
| WO | 0209702 | A2 | 2/2002 |
| WO | 0210143 | A1 | 2/2002 |
| WO | 02064550 | | 8/2002 |
| WO | 03031606 | A2 | 4/2003 |
| WO | 03032997 | A1 | 4/2003 |
| WO | 03059899 | A1 | 7/2003 |
| WO | 03082280 | * | 10/2003 |
| WO | 03082787 | A1 | 10/2003 |
| WO | 03082827 | A1 | 10/2003 |
| WO | 03104195 | A1 | 12/2003 |
| WO | 2004005278 | A1 | 1/2004 |
| WO | 2004018429 | A2 | 3/2004 |
| WO | 2004019935 | A1 | 3/2004 |
| WO | 2004063163 | A1 | 7/2004 |
| WO | 2004071389 | A2 | 8/2004 |
| WO | 2004075864 | A2 | 9/2004 |
| WO | 2004089415 | A2 | 10/2004 |
| WO | 2005019202 | A1 | 3/2005 |
| WO | 2005030213 | A1 | 4/2005 |
| WO | 2005090343 | A1 | 9/2005 |
| WO | 2006046916 | A1 | 5/2006 |
| WO | 2006071609 | A2 | 7/2006 |
| WO | 2006135826 | A1 | 12/2006 |
| WO | 2007040959 | A1 | 4/2007 |

OTHER PUBLICATIONS

Friedman et al.; Phosphoenolpyruvate Carboxykinase (GTP) Gene Transcription and Hyperglycemia Are Regulated by Glucocorticoids in Genetically Obese db/db Transgenic Mice; The Journal Biological Chemistry; 1997; vol. 272; No. 50; pp. 31475-31481.

Hagiwara et al.; Lewis Base Catalyzed Trifluoromethylation of Carbonyl Compounds with Trialkyl (trifluoromethyl) silanes; Main Group Chem.; 1997; vol. 2; pp. 13.

Hall et al.; Biogenetic-type Synthesis of the Calycanthaceous Alkaloids; Tetrahedron; 1967; vol. 23; pp. 4131-4141.

Hamann et al.; Discovery of a potent, Orally active, Nonsteroidal Androgen Receptor Agonist: 4-Ethyl-1,2,3,4-tetrahydro-6-(trifluoromethyl)-8-pyridono[5,6-g]quinoline(LG121071); Journal Medicinal Chemistry; 1999; No. 42; pp. 210-212.

Hamann, Lawrence, et al; Synthesis and Biological Activity of a Novel Series of Nonsteroidal, Peripherally Selective androgen Receptor Antagonists Derived from 1,2-Dihydropyridono[5,6-g]quinolines J. Med. Chem 1998, 41, 623-639.

Hawley's Condensed Chemical Dictionary 14th Edition (2001).

Heck et al.; A distinct modulating domain in glucocorticoid receptor monomers in the repression of activity of the transcription factor AP-1; The EMBO Journal; 1994; vol. 13; No. 17; pp. 4087-4095.

Ho et al.; Central Nervous System Depressive Activity of some Amides of Tryptamine; Journal Medicinal Chemistry; 1971; vol. 14; No. 6; pp. 553-554.

Ho et al.; Hydroxyindole-O-methyltransferase VI: Inhibitory Activities of Substituted Benzoyltryptamines and Benzenesulfonyltryptamines; Journal of Pharmaceutical Sciences; 1971; vol. 60; No. 4; pp. 636-637.

Hu et al.; Synthesis and protein kinase C inhibitory activities of indane analogs of balanol; Bioorganic & Medicinal Chemistry Letters; Apr. 23, 1996; Oxford, GB; vol. 6; No. 8; pp. 973-978.

International Search Report PCT/US07/85831 mailed Jul. 4, 2008.

International Search Report PCT1US2009/046058 mailed Oct. 1, 2009.

Iseki et al.; Asymmetric Trifluoromethylation of Aldehydes and Ketones with Trifluoromethyltrimethylsilane Catalysed by Chiral Quarternary Ammonium Fluorides; Tetrahedron Letters; 1994; vol. 35; No. 19; pp. 3137-3138.

Janoshazi et al.; Rapid Vitro Conformational Changes of the Catalytic Site of PKCalpha Assessed by FIM-1 Fluorescence; Biochemistry 1999; No. 38; pp. 13316-13327.

Jordan V.C., Nature Reviews: Drug Discovery, 2, 2003, p. 205.

K.Rishnamurti et al.; Preparation of Trifluoromethyl and Other Perfluoroalkyl Compounds with (Perfluoralkyl) trimethylsilanes; Journal of Organic Chemistry; 1991; No. 56; pp. 984-989.

Kutney et al.; Total synthesis of Dregamine and Epidregamine, A General Routge to 2 Acylindole Alkaloids; Journal of the American Chemical Society; Feb. 1, 1978; vol. 100; No. 3; pp. 938-943.

Lagidze et al.; CA 102:184944; 1985.

Lagidze et al.; Synthesis of Some new analogs of melatonin and beta carboline from 4 phenylpentanoic acid; 6001 Chemical Abstracts; Columbus, OH; 1981; vol. 94; No. 19; pp. 637.

Maligres et al.; Nosylaziridines: Activated Aziridine Electrophiles; Tetrahedron Letters; Jul. 28, 1997; Amsterdam; vol. 38; No. 30; pp. 5253-5256.

Marshall et al.; a-Methyltryptamine sulfonamide derivatives as novel glucocorticoid receptor ligands; Bioorganic and Medicinal Chemistry Letters 17; 2007; pp. 315-319.

Marshall et al.; Poster entitled: a-Methyltryptamine sulfonamide derivatives as novel glucocorticoid receptor ligands, presented at the 227th American Chemical Society National Meeting, Anaheim CA, Apr. 28-May 1, 2004.

McGill et al.; Telmisartan Plus Hydrochlorothiazide Versus Telmisartan or Hydrochlorothiazide Monotherapy in Patients with Mild to Moderate Hypertension: A Multicenter, Randomized, Double-Blind, Placebo-Controlled, Parallel-Group Trial; Clinical Therapeutics; 2001; vol. 23; No. 6; pp. 833-850.

Misztal et al.; New Synthesis of 5-Nitro-and 5-Benzyloxytryptamine and their N-acylderivatives; Polish Journal of Pharmacology and Pharmacy; 1984; No. 36; pp. 345-349.

Nenajdenko et al.; A new convenient approach to chiral-aryl(heteroaryl)alkylamines; Tetrahedron: Asymmetry; Oct. 15, 2001; vol. 12; No. 18; pp. 2517-2527.

Oakley et al.; The glucocorticoid receptor; expression, function and regulation of glucocorticoid responsiveness; Glucocorticoids; 2001; pp. 55-80.

Onistschenko et al.; CA 112:55520, 1990.

Osipov et al.; a-Fluoromethyl Tryptophans via Imino Ene Reaction; Synlett 2001; No. 8; pp. 1287-1289; Letter.

Otsuki et al.; Reaction of N-Haloamide. XXII. Reaction of N,N-dibromobenzenesulfonamide with safrole; Chemical Pharmaceutical Bulletin; 1975; vol. 23; No. 3; pp. 482-486.

Outinen et al.; Optimization of selectivity in high-performance liquid chromatography using desirability functions and mixture designs according to PRISMA; European Journal of Pharmaceutical Sciences; 1998); 6(3); pp. 197-205.

Palmisano et al.; Synthetic Studies on Indole Alkaloids. A Stereocontrolled Entry to the Cuanzine Structural Unit; Tetrahedron; Elsevier Science Publisher, Amsterdam, NL; 1989; vol. 45; No. 11; pp. 3583-3595.

Parente; The development of synthetic glucocorticoids; Glucocorticoids; 2001; pp. 35-54.

Pargellis et al.; Inhibition of P38 Map Kinase by Utilizing a Novel Allosteric Binding Site; Nature Structural Biology; 2002; vol. 9; No. 4; pp. 268-272.

Patani et al.; Bioisosterism: A Rational Approach in Drug Design; 1996; Chem. Rev.; No. 96; pp. 3147-3150.

Peeters et al.; Glucocorticoid Receptor Antagonists: New Tools to Investigate Disorders Characterized by Cortisol Hypersecretion; Stress; 2004; vol. 7; No. 4; pp. 233-241.

Pelicano et al.; Study of the Substrate-Binding Properties of Bovine Liver Adenosine Kinase and Inhibition by Fluorescent Nucleoside Analogues; European Journal of Biochemistry; 1997; vol. 248; pp. 930-937.

Plihal et al.; Corticosteroid Receptor Mediated Effect on Mood in Humans; Psychoneuroendocrinology; 1996; vol. 21; No. 6; pp. 515-523; Pergamon.

Pooley et al.; Discovery and Preliminary SAR Studies of a Novel Nonsteroidal Progesterone Receptor Antagonist Pharmacophore; Journal Medicinal Chemistry; 1998; No. 41; pp. 3461-3466.

Prakash et al.; Asymmetric Synthesis of Trifluoromethylated Allylic Amines Using alpha, beta-Unsaturated N-tert-Butanesulfinimines; Organic Letters; 2001; vol. 3; No. 18; pp. 2847-2850.

Prodrug [online], [retrieved on Mar. 26, 2007], Retrieved from the Internet, URL: http://en.wikipedia.org/wiki/Prodrug>.

Ramaiah et al.; Direct Trifluoromethylation of alpha-Keto Esters to beta,beta,beta-Trifluorolactic Acid Derivatives Using Trifluoromethyltrimethylsilane; Synlett; 1991; vol. 9; pp. 643-644.

Regan et al.; Advances Toward Dissociated Non-Steroidal Glucocorticoid Receptors Agonists; Annual Reports in Medicinal Chemistry; 2008; vol. 43; pp. 141-154.

Reichartd et al.; DNA Binding of the Glucocorticoid Receptor is not Essential for Survival; Cell; May 15, 1998; vol. 93; pp. 531-541.

Schisla et al; Quaternary-Substituted Hydrocarbons. A General Method of Synthesis of Hydrocarbons Interspersed with Four gem-Dimethyl Unites; Journal of Organic Chemistry; 1970; vol. 35; No. 10; pp. 3224-3230.

Shono et al.; Electroorganic Chemistry 81, Anodic Oxidation of Sulfonamides and Amidophosphates; Journal Organic Chemistry; 1984; No. 49; pp. 3711-3716.

Song et al.; Practical Steroselective Synthesis of an a-Trifluoromethyl-a-alkyl Epoxide via a Diasteroselective Trifluoromethylation Reaction; Journal of Organic Chemistry; 2007; No. 72; pp. 292-294.

Souillac et al.; Characterization of Delivery Systems, Differential Scanning Calorimetry; Encyclopedia of Controlled Drug Delivery; 1999; John Wiley & Sons; pp. 212-227.

Takami et al.; Synthesis of 4,4,4-trifluoro-3-indolylisocrotonamides as Steroid 5a-reductase inhibitors; Medicinal Chemistry Research; 1999; vol. 9; No. 4; pp. 239-248.

Tegley et al.; 5-Benzylidene 1,2-Dihydrochromeno[3,4-f]quinolines, A Novel Class of Nonsteroidal Human Progesterone Receptor Agonists; Journal Medicinal Chemistry; 1998; No. 41; pp. 4354-4359.

Abstract of DE 1017612 cited herein under foreign documents— 1959-121889 caplus 53:121889;53:21820H-i21821a-c; Tertiary Amines and Derivatives Thereof, Thomae GmbH DE 1017612.

Abstract—JP 59 053479A Mar. 28, 2984.

Abstract JP37004545, inventors Yoshida and Fukuda, assignee Nippon Shinyaku Co., Ltd, Jun. 14, 1962.

Abstract Mikhailitsyn, F.S, et al Search for New Antiparasitic Agents 10, Synthesis, Toxicity and Antimalarial Effect of Some Nitrogen Containing Heterocycles with 4-(4-alkylpiperazin-1yl)phenylamino-substituents-CAPLUS accession No. 1888, AN-1992:651317 (1992).

Abstract of JP 11080131A cited herein under Foreign documents— New ethynyl-pyrimidine derivatives have excellent tyrosine kinase inhibiting and cancer cell growth inhibiting activity Sep. 1, 1997 Mitsubishi Chemical Corporation.

Abstract of Japan; vol. 010; No. 004(C322); Jan. 9, 1986 & JP 60 163814A, (Wataru Mori); Aug. 26, 1985 Abstract.

Abstract, Mikhailitsyn, F.S. et al, New Synthesis of Derivatives of 6,6' diquinoline from 4,4'-diaminodiphenykl-3,3'dicarboxylic acid; -XP002266777 (1974).

Amat et al.; Preparations and Reactions of 4-, 5-, and 6-Methoxy Substituted 3-Lithioindoles and 3-Indolylzinc Derivatives; Synthesis 2001; No. 2; pp. 267-275.

Ambrosi et al.; Stereoselective Synthesis of Trifluoro-and Monofluro-Analogues of Frontaliln and Evaluation of Their Biological Activity; Journal of Organic Chemistry; 2001; No. 66; pp. 8336-8343.

Arnone et al.; Highly Diastereoselective Methylene Transfer from Diazomethane to the Carbonyl of b-Keto Sulfoxides. A General approach to Synthetically Versatile Fluorine-Containing Chiral Building Blocks; Tetrahedron 54; 1998; pp. 11841-11860.

Bailey et al.; CA 80:3337; 1974.

Bailey et al.; Further Examination of the reactions of Simple Indoles with Arenosulphonyl Azides, Journal Chemical Society; Perkin Trans.1; 1973; pp. 1602-1606.

Bailey et al.; New asymmetric route to bridged indole alkaloids: formal enantiospecific syntheses of (-)-suaveoline, (-)-raumacline and (-)-Nb-methylraumacline; Journal of the Chemical Society; 1997; Perkin Trans. pp. 1209-1214.

Bamberger et al.; Molecular mechanisms of dissociative glucocorticoid activity; European Journal Clinical Investment; 2000; No. 30; Suppl. 3; pp. 6-9.

Barnes; Anti-inflammatory actions of glucocorticoids; molecular mechanisms; Clinical Science; 1998; vol. 94; pp. 557-572.

Barnes; Anti-inflammatory actions of steroids; molecular mechanisms; TIPS Reviews; Dec. 1993; vol. 14; pp. 436-441.

Barnes; Relative safety and efficacy of inhaled corticosteroids; Journal Allergy Clinical Immunology; Apr. 1998; 101 (4 Pt 2), S460-464 Abstract.

Beilstein No. 7067440—J. Chem. Soc. Dalton, Trans., vol. 22, 1994, pp. 3202-3210.
Beilstein Registry No. 318403 and 341608; Beilstein Institut zur Foerderung ger Chemischen Wissenschaffen, Frankfurt Am Main, De, Entry date Jun. 27, 1998 update date May 13, 1992.
Beilstein Registry No. 7178110 and 7178430, Online, Bellstein Institut zur Foerderung ger Chemischen Wissenschaffen, Frankfurt Am Main, DE, (1989).
Berry et al.; A Convenient Method for the Preparation of Enantiomerically Pure 2-Substituted N-Tosylaziridines; Synlett; Jan. 1992; Letters; pp. 41-44.
Bledsoe et al.; Crystal Structure of the Glucocorticoid Receptor Ligand Binding Domain Reveals a Novel Mode of Receptor Dimerization and Coactivator Recognition; Cell; Jul. 12, 2002; vol. 110; pp. 93-105.
Bravo et al.; Synthesis of (-)-(1S,5R) and (+)-1R,5S)-trifluoroanalogues of frontalin; Tetrahedron Letters; 1999; No. 40; pp. 6317-6320.
Bundgaard; Design of prodrugs: Bioreversible derivatives for various functional groups and chemical entities; Design of Prodrugs; 1985; Chapter 1; Elsevier; pp. 1-3.
CA Registry No. 288843-68-5—entry date into Registry file on STN is Sep. 13, 2000.
CA Registry No. 311781-49-4—entry date into Registry file on STN is Dec. 28, 2000.
CA Registry No. 442531-80-8—entry date into Registry file on STN is Aug. 5, 2002.
CA Registry No. 442531-85-3—entry date into Registry file on STN is Aug. 5, 2002.
CA Registry No. 442630-99-1—entry date into Registry file on STN is Aug. 6, 2002.
CA Registry No. 442632-92-0—entry date into Registry file on STN is Aug. 6, 2002.
CA Registry No. 442632-93-1—entry date into Registry file on STN is Aug. 6, 2002.
CA Registry No. 442633-42-3—entry date into Registry file on STN is Aug. 6, 2002.
CA Registry No. 442657-75-2—entry date into Registry file on STN is Aug. 6, 2006.
CA Registry No. 442657-79-6—entry date into Registry file on STN is Aug. 6, 2006.
CA Registry No. 442657-92-3—entry date into Registry file on STN is Aug. 6, 2006.
CA Registry No. 442658-57-3—entry date into Registry file on STN is Aug. 6, 2006.
CA Registry No. 442658-66-4—entry date into Registry file on STN is Aug. 6, 2006.
CA Registry No. 442658-95-9—entry date into Registry file on STN is Aug. 6, 2006.
CA Registry No. 442666-01-5—entry date into Registry file on STN is Aug. 6, 2006.
CA Registry No. 442666-02-6—entry date into Registry file on STN is Aug. 6, 2006.
Casella, et al. "Cytochrome c Oxidase Models; Synthesis and Reactivity of Iron (III)-Copper (II) Complexes of Deuterohaemin-Polybenzimidazole Dinucleating Ligands " J. Chem. Soc. Dalton Trans, 1994, vol. 22, pp. 3202-3210.
Coghlan et al.; Synthesis and Characterization of Non-Steroidal Ligands for the Glucocorticoid Receptor: Selective Quinoline Derivatives with Prednisolone-Equivalent Functional Activity; J. Med Chem.; 2001; vol. 44; pp. 2879-2885.
Davis; CA 92:40803; 1980.
Doewald; Side Reactions in Organic Synthesis: A Guide o Successful Synthesis Design; 2005; Wiley & Co KGaA Weinheim.
Edwards et al.; 5-Aryl-1,2-dihydro-5H-chromeno[3,4-f]quinolines as Potent, Orally Active, Nonsteroidal Progesterone Receptor Agonists; The Effect of D-Ring Substituents; Journal Medicinal Chemistry; 1998; No. 41; pp. 303-310.
Edwards et al.; Preparation, Resolution and Biological Evaluation of 5-Aryl-1,2-dihydro-5H-chromeno[3,4-f]quinolines as Potent, Orally Active, Nonsteroidal Progestgerone Receptor Agonists; Journal Medicinal Chemistry; 1998; No. 41; pp. 2779-2785.
Elliott et al.; Studies in the Indole Series. Part IV. Sulphonamides derived from Indole; Journal of Chemical Society; 1944; pp. 632-633.
English Translation of WO/02/10143, Feb. 2002.
Epps et al.; An Experimental Method for the Determination of Ensyme-Competitive Inhibitor Dissociation Constants from Displacement Curves: Application to Human Renin Using Fluorescence Energy Transfer to a Synthetic Dansylated Inhibitor Peptide; Analytical Biochemistry; 1989; vol. 181; pp. 172-181.
Evans; The Steroid and Thyroid Hormone Receptor Superfamily; Science; May 1988; No. 240; pp. 889-895; Articles.
Tochilkin et al.; 8-Methoxy-5-Quinoline Sulphonyl Chloride—A New Fluorogenic Agent for Determining Amines and Amino Acids; Bioorganicheskaya Khimiya (Bioorganic Chemistry); 1990; vol. 16; No. 7; pp. 956-962.
Toogood; Glucocorticoids and Asthma; Glucocorticoids; 2001; pp. 161-174.
Tronche et al.; Genetic dissection of glucocorticoid receptor function in mice; Current Opinion in Genetics and Development; 1998; 8; pp. 532-538.
Troschuetz et al.; Sensitive and Specific Determination of Serotonin in the Presence of Tryptamine and 5-Methoxytryptamine by High-Pressure Liquid-Chromatography; Fresenious Zeitschrift fuer Analytische Chemi; 1978; No. 289; pp. 202-205.
Vainshtein et al.; A High-Throughput, Nonisotopic, Competitive Binding Assay for Kinases Using Nonselective Inhibitor Probes (ED-NSIP); Journal of Biomolecular Screening; 2002; vol. 7; No. 6; pp. 507-514.
Vankayalapati et al.; Targeting Aurora2 Kinase in Oncogenesis: A Structural Bioinformatics Approach to Target Validation and Rational Drug Design; Molecular Cancer Therapeutics; Mar. 2003; vol. 2; pp. 283-294.
Vas et al.; Antagonistic Binding of Substrates to 3-Phosphoglycerate Kinase Monitored by the Fluorescent Analogue 2'(3')-O-(2,4,6-Trinitrophenyl)Adenosine 5'-Triphosphate; Biochemical Journal; 1994; vol. 301; pp. 885-891.
Vippagunta et al.; Crystalline solids; Advanced Drug Delivery Reviews; 2001; No. 48; pp. 3-26.
Wu et al.; Regulatory perspectives of Type II prodrug development and time0-dependent toxicity management: Nonclinical PharmTox analysis and the role of comparative toxicology; Toxicology 236; 2007; pp. 1-6.
Zembower et al.; Enantiospecific Syntheses of Alpha-Fluoromethyl) Tryptophan Analogues: Interactions with Tryptophan Hydroxylase and Aromatic L-Amino Acid Decarboxylase; Journal of Medicinal Chemistry, American Chemical Society; Feb. 5, 1993; vol. 36; No. 3; pp. 305-313.
Zhi et al.; 5-Aryl-1,2,3,4-tetrahydrochromeno[3,4-f]quinolin-3-ones as a Novel Class Of Nonsteroidal Progesterone Receptor Agonists: Effect of A-Ring Modification; Journal Medicinal Chemistry; 1999; No. 42; pp. 1466-1472.
Zhi et al.; 5-Aryl-1,2-dihydro-5H-chromeno[3,4-f]quinolines: A Novel Class of Nonsteroidal Human Progesterone Receptor Agonists; Journal Medicinal Chemistry; 1998; No. 41; pp. 291-302.
WO02051983 (Part 1 of 2) International Publication Date: Jul. 4, 2002. Patentee: Celera, an Applera Corporation Business. Inventor: Frank Halley. Title: Novel Compounds and Compositions of Cathespin Inhibitors. Total pp. 724. Part 1 of 2. This foreign patent is too large for EFS submission via the Foreign patent section, therefore filing in two parts in the NPL section. pp. 1-350.
WO02051983 (Part 2 of 2) International Publication Date: Jul. 4, 2002. Patentee: Celera, an Applera Corporation Business. Inventor: Frank Halley. Title: Novel Compounds and Compositions of Cathespin Inhibitors. Total pp. 724. Part 2 of 2. This foreign patent is too large for EFS submission via the Foreign patent section, therefore filing in two parts in the NPL section. pp. 351-724.

* cited by examiner

FIG. 15

GLUCOCORTICOID MIMETICS, METHODS OF MAKING THEM, PHARMACEUTICAL COMPOSITIONS AND USES THEREOF

FIELD OF THE INVENTION

The present invention relates to glucocorticoid mimetics or ligands, methods of making such compounds, their use in pharmaceutical compositions, and their use in modulating the glucocorticoid receptor function, treating disease-states or conditions mediated by the glucocorticoid receptor function in a patient in need of such treatment, and other uses.

BACKGROUND OF THE INVENTION

Glucocorticoids, a class of corticosteroids, are endogenous hormones with profound effects on the immune system and multiple organ systems. They suppress a variety of immune and inflammatory functions by inhibition of inflammatory cytokines such as IL-1, IL-2, IL-6, and TNF, inhibition of arachidonic acid metabolites including prostaglandins and leukotrienes, depletion of T-lymphocytes, and reduction of the expression of adhesion molecules on endothelial cells (P. J. Barnes, Clin. Sci., 1998, 94, pp. 557-572; P. J. Barnes et al., Trends Pharmacol. Sci., 1993, 14, pp. 436-441). In addition to these effects, glucocorticoids stimulate glucose production in the liver and catabolism of proteins, play a role in electrolyte and water balance, reduce calcium absorption, and inhibit osteoblast function.

The anti-inflammatory and immune suppressive activities of endogenous glucocorticoids have stimulated the development of synthetic glucocorticoid derivatives including dexamethasone, prednisone, and prednisolone (L. Parente, *Glucocorticoids*, N. J. Goulding and R. J. Flowers (eds.), Boston: Birkhauser, 2001, pp. 35-54). These have found wide use in the treatment of inflammatory, immune, and allergic disorders including rheumatic diseases such as rheumatoid arthritis, juvenile arthritis, and ankylosing spondylitis, dermatological diseases including psoriasis and pemphigus, allergic disorders including allergic rhinitis, atopic dermatitis, and contact dermatitis, pulmonary conditions including asthma and chronic obstructive pulmonary disease (COPD), and other immune and inflammatory diseases including Crohn disease, ulcerative colitis, systemic lupus erythematosus, autoimmune chronic active hepatitis, osteoarthritis, tendonitis, and bursitis (J. Toogood, *Glucocorticoids*, N. J. Goulding and R. J. Flowers (eds.), Boston: Birkhauser, 2001, pp. 161-174). They have also been used to help prevent rejection in organ transplantation.

Unfortunately, in addition to the desired therapeutic effects of glucocorticoids, their use is associated with a number of adverse side effects, some of which can be severe and life-threatening. These include alterations in fluid and electrolyte balance, edema, weight gain, hypertension, muscle weakness, development or aggravation of diabetes mellitus, and osteoporosis. Therefore, a compound that exhibited a reduced side effect profile while maintaining the potent anti-inflammatory effects would be particularly desirable especially when treating a chronic disease.

The effects of glucocorticoids are mediated at the cellular level by the glucocorticoid receptor (R. H. Oakley and J. Cidlowski, *Glucocorticoids*, N. J. Goulding and R. J. Flowers (eds.), Boston: Birkhauser, 2001, pp. 55-80). The glucocorticoid receptor is a member of a class of structurally related intracellular receptors that when coupled with a ligand can function as a transcription factor that affects gene expression (R. M. Evans, Science, 1988, 240, pp. 889-895). Other members of the family of steroid receptors include the mineralocorticoid, progesterone, estrogen, and androgen receptors. In addition to the effects mentioned above for glucocorticoids, hormones that act on this receptor family have a profound influence on body homeostasis, mineral metabolism, the stress response, and development of sexual characteristics. *Glucocorticoids*, N. J. Goulding and R. J. Flowers (eds.), Boston: Birkhauser, 2001, is hereby incorporated by reference in its entirety to better describe the state of the art.

A molecular mechanism which accounts for the beneficial anti-inflammatory effects and the undesired side effects has been proposed (e.g., S. Heck et al., EMBO J, 1994, 17, pp. 4087-4095; H. M. Reichardt et al., Cell, 1998, 93, pp. 531-541; F. Tronche et al., Curr. Opin. in Genetics and Dev., 1998, 8, pp. 532-538). Many of the metabolic and cardiovascular side effects are thought to be the result of a process called transactivation. In transactivation, the translocation of the ligand-bound glucocorticoid receptor to the nucleus is followed by binding to glucocorticoid response elements (GREs) in the promoter region of side effect-associated genes, for example, phosphoenolpyruvate carboxy kinase (PEPCK), in the case of increased glucose production. The result is an increased transcription rate of these genes which is believed to result, ultimately, in the observed side effects. The anti-inflammatory effects are thought to be due to a process called transrepression. In general, transrepression is a process independent of DNA binding that results from inhibition of NF-kB and AP-1-mediated pathways, leading to down regulation of many inflammatory and immune mediators. Additionally, it is believed that a number of the observed side effects may be due to the cross-reactivity of the currently available glucocorticoids with other steroid receptors, particularly the mineralocorticoid and progesterone receptors.

Thus, it may be possible to discover ligands for the glucocorticoid receptor that are highly selective and, upon binding, can dissociate the transactivation and transrepression pathways, providing therapeutic agents with a reduced side effect profile. Assay systems to determine effects on transactivation and transrepression have been described (e.g., C. M. Bamberger and H. M. Schulte, Eur. J. Clin. Invest., 2000, 30 (suppl. 3), pp. 6-9). Selectivity for the glucocorticoid receptor may be determined by comparing the binding affinity for this receptor with that of other steroid family receptors including those mentioned above.

Glucocorticoids also stimulate the production of glucose in the liver by a process called gluconeogenesis and it is believed that this process is mediated by transactivation events. Increased glucose production can exacerbate type II diabetes, therefore a compound that selectivity inhibited glucocorticoid mediated glucose production may have therapeutic utility in this indication (J. E. Freidman et al., J. Biol. Chem., 1997, 272, pp. 31475-31481).

Novel ligands for the glucocorticoid receptor have been described in the scientific and patent literature. For example, PCT International Publication No. WO 99/33786 discloses triphenylpropanamide compounds with potential use in treating inflammatory diseases. PCT International Publication No. WO 00/66522 describes non-steroidal compounds as selective modulators of the glucocorticoid receptor potentially useful in treating metabolic and inflammatory diseases. PCT International Publication No. WO 99/41256 describes tetracyclic modulators of the glucocorticoid receptor potentially useful in treating immune, autoimmune, and inflammatory diseases. U.S. Pat. No. 5,688,810 describes various non-steroidal compounds as modulators of glucocorticoid and other steroid receptors. PCT International Publication No. WO 99/63976 describes a non-steroidal, liver-selective glucocorticoid antagonist potentially useful in the treatment of diabetes. PCT International Publication No. WO 00/32584 discloses non-steroidal compounds having anti-inflammatory activity with dissociation between anti-inflammatory and metabolic effects. PCT International Publication No. WO 98/54159 describes non-steroidal cyclically substituted acylanilides with mixed gestagen and androgen activity. U.S. Pat. No. 4,880,839 describes acylanilides having progestational activity and EP 253503 discloses acylanilides with antiandrogenic properties. PCT International Publication No. WO 97/27852 describes amides that are inhibitors of farnesylprotein transferase.

A compound that is found to interact with the glucocorticoid receptor in a binding assay could be an agonist or an antagonist. The agonist properties of the compound could be evaluated in the transactivation or transrepression assays described above. Given the efficacy demonstrated by available glucocorticoid drugs in inflammatory and immune diseases and their adverse side effects, there remains a need for novel glucocorticoid receptor agonists with selectivity over other members of the steroid receptor family and a dissociation of the transactivation and transrepression activities. Alternatively, the compound may be found to have antagonist activity. As mentioned above, glucocorticoids stimulate glucose production in the liver. Increased glucose production induced by glucocorticoid excess can exacerbate existing diabetes, or trigger latent diabetes. Thus a ligand for the glucocorticoid receptor that is found to be an antagonist may be useful, inter alia, for treating or preventing diabetes.

U.S. Pat. No. 6,903,215 and U.S. Patent Application Publication No. 2005/0176706 are each incorporated by reference in their entireties.

Previously U.S. Pat. No. 6,903,215 and U.S. Patent Application Publication No. 2005/0176706 have disclosed glucocorticoid mimetics that displayed glucocorticoid selectivity and potency. However, as can be appreciated by one skilled in the art, in order for a compound to become a drug, it must maintain the aforementioned favorable biological properties and have improved drug-like properties over such previously disclosed glucocorticoid mimetics, including reduced cytochrome P450 inhibition (indicative of drug-drug interaction potential); reduced hERG inhibition (indicative of QT prolongation of the heart); and/or improved pharmacokinetic properties and physical-chemical properties.

The compounds of the present invention solve this problem by maintaining their favorable biological profile and showing unexpected improvements in their drug-like properties

SUMMARY OF THE INVENTION

The instant invention is directed to compounds of Formula (I)

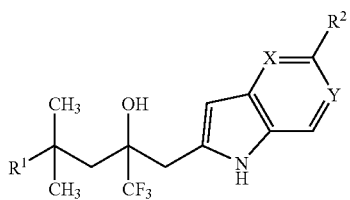

(I)

wherein:
$R^1$ is an aryl or heteroaryl group, each optionally independently substituted with one, two, or three substituent groups selected from $C_1$-$C_5$ alkyl, aminocarbonyl, $C_1$-$C_5$ alkylaminocarbonyl, $C_1$-$C_5$ dialkylaminocarbonyl, aminosulfonyl, $C_1$-$C_5$ alkylaminosulfonyl, $C_1$-$C_5$ dialkylaminosulfonyl, halogen, hydroxyl, cyano, and $C_1$-$C_5$ alkylthio wherein the sulfur atom is optionally oxidized to a sulfoxide or sulfone;
$R^2$ is $C_1$-$C_5$ alkylthio wherein the sulfur atom is optionally oxidized to a sulfoxide or sulfone, optionally independently substituted with one, two, or three substituent groups selected from halogen, hydroxy, oxo, cyano, alkoxyalkyl, and aminocarbonyl;
X is CH or N; and
Y is CH or N,
wherein X and Y are not both CH,
or a tautomer, optical isomer, prodrug, co-crystal, or salt thereof.

Another aspect of the invention includes compounds of Formula (I) wherein:
$R^1$ is an aryl or heteroaryl group, each optionally independently substituted with one, two, or three substituent groups selected from $C_1$-$C_5$ alkyl, aminocarbonyl, $C_1$-$C_5$ alkylaminocarbonyl, $C_1$-$C_5$ dialkylaminocarbonyl, aminosulfonyl, $C_1$-$C_5$ alkylaminosulfonyl, $C_1$-$C_5$ dialkylaminosulfonyl, halogen, hydroxyl, cyano, and $C_1$-$C_5$ alkylthio wherein the sulfur atom is optionally oxidized to a sulfoxide or sulfone;
$R^2$ is $C_1$-$C_5$ alkylthio wherein the sulfur atom is optionally oxidized to a sulfoxide or sulfone, each optionally independently substituted with one to three substituent groups selected from halogen, hydroxy, oxo, cyano, alkoxyalkyl, and aminocarbonyl;
X is CH; and
Y is N,
or a tautomer, prodrug, co-crystal, or salt thereof.

Yet another aspect of the invention includes compounds of Formula (I) wherein:
$R^1$ is an aryl group, optionally substituted with one, two, or three substituent groups independently selected from $C_1$, $C_2$, or $C_3$ alkyl, aminocarbonyl, halogen, and $C_1$, $C_2$, or $C_3$ alkylthio wherein the sulfur atom is optionally oxidized to a sulfoxide or sulfone;
$R^2$ is $C_1$, $C_2$, or $C_3$ alkylthio wherein the sulfur atom is optionally oxidized to a sulfoxide or sulfone, each optionally independently substituted with one to three substituent groups selected from halogen, hydroxy, oxo, cyano, alkoxyalkyl, and aminocarbonyl;
X is CH; and
Y is N,
or a tautomer, prodrug, co-crystal, or salt thereof.

Yet another aspect of the invention includes compounds of Formula (I) wherein:
$R^1$ is a phenyl group, optionally substituted with one or two substituent groups independently selected from aminocarbonyl, methyl, fluoro, chloro, bromo, and $C_1$ or $C_2$ alkylthio wherein the sulfur atom is optionally oxidized to a sulfoxide or sulfone;
$R^2$ is $C_1$, $C_2$, or $C_3$ alkylthio wherein the sulfur atom is optionally oxidized to a sulfoxide or sulfone;
X is CH; and
Y is N,
or a tautomer, prodrug, co-crystal, or salt thereof.

Still another aspect of the invention includes compounds of Formula (I) wherein:
$R^1$ is a phenyl group, optionally substituted with one or two substituent groups independently selected from aminocarbonyl, methyl, fluoro, chloro, bromo, and $C_1$ or $C_2$ alkylthio wherein the sulfur atom is optionally oxidized to a sulfoxide or sulfone;

$R^2$ is $C_1$ or $C_2$ alkylthio wherein the sulfur atom is optionally oxidized to a sulfoxide or sulfone;

X is CH; and

Y is N, or a tautomer, prodrug, co-crystal, or salt thereof.

An aspect of the invention includes a product resulting from the reaction of a compound of Formula (I) or a tautomer or optical isomer thereof as set forth above and herein, with a suitable acid. The suitable acid is preferably hydrochloric acid, hydrobromic acid, hydroiodic acid, sulfuric acid, sulfamic acid, nitric acid, phosphoric acid, and the like, and organic acids such as acetic acid, trichloroacetic acid, trifluoroacetic acid, adipic acid, alginic acid, ascorbic acid, aspartic acid, benzenesulfonic acid, benzoic acid, 2-acetoxybenzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, heptanoic acid, hexanoic acid, formic acid, fumaric acid, 2-hydroxyethanesulfonic acid (isethionic acid), lactic acid, maleic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, picric acid, pivalic acid, propionic acid, pyruvic acid, pyruvic acid, salicylic acid, stearic acid, succinic acid, sulfanilic acid, tartaric acid, p-toluenesulfonic acid, or undecanoic acid.

The following are representative preferred compounds of Formula (I) according to the invention:

TABLE 1

| CYP3A4 $IC_{50}$ [μM] | GR $IC_{50}$ [nM] | Structure | Name | observed m/z |
|---|---|---|---|---|
| 6.5 | 6 | 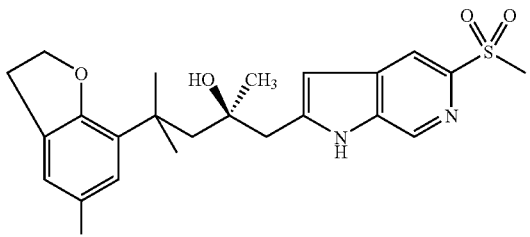 | (R)-4-(5-Chloro-2,3-dihydrobenzofuran-7-yl)-1,1,1-trifluoro-2-(5-methanesulfonyl-1H-pyrrolo[2,3-c]pyridin-2-ylmethyl)-4-methylpentan-2-ol | 517, 519 |
| >30 | 23 | 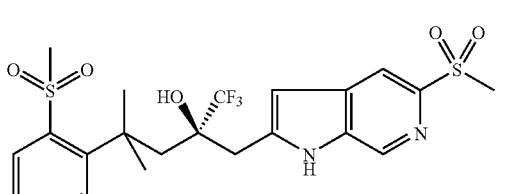 | (R)-1,1,1-Trifluoro-4-(2-methanesulfonylphenyl)-2-(5-methanesulfonyl-1H-pyrrolo[2,3-c]pyridin-2-ylmethyl)-4-methylpentan-2-ol | 519 |
| 1.8 | 7 | 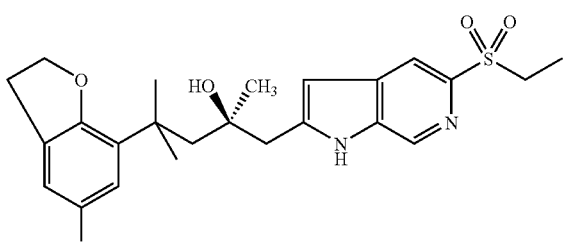 | (R)-4-(5-Chloro-2,3-dihydrobenzofuran-7-yl)-2-(5-ethanesulfonyl-1H-pyrrolo[2,3-c]pyridin-2-ylmethyl)-1,1,1-trifluoro-4-methylpentan-2-ol | 531, 533 |
| 20 | 9 | 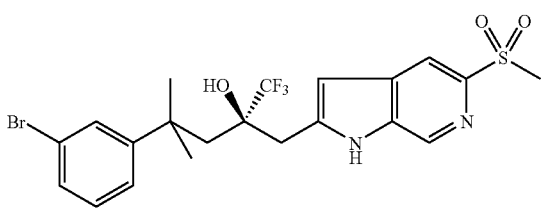 | (R)-4-(3-Bromophenyl)-1,1,1-trifluoro-2-(5-methanesulfonyl-1H-pyrrolo[2,3-c]pyridin-2-ylmethyl)-4-methylpentan-2-ol | 521, 519 |

TABLE 1-continued

Compounds

| CYP3A4 IC$_{50}$ [µM] | GR IC$_{50}$ [nM] | Structure | Name | observed m/z |
|---|---|---|---|---|
| 15 | 44 | 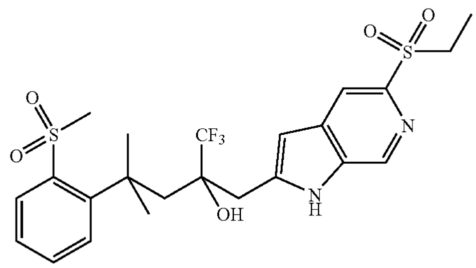 | 2-(5-Ethanesulfonyl-1H-pyrrolo[2,3-c]pyridin-2-ylmethyl)-1,1,1-trifluoro-4-(2-methanesulfonylphenyl)-4-methylpentan-2-ol | 533 |
| >30 | 91 | | (R)-2-[4,4,4-Trifluoro-3-hydroxy-3-(5-methanesulfonyl-1H-pyrrolo[2,3-c]pyridin-2-ylmethyl)-1,1-dimethylbutyl]benzamide | 484 |
| >30 | 62 | | 1,1,1-Trifluoro-4-(3-fluoro-2-methanesulfonylphenyl)-2-(5-methanesulfonyl-1H-pyrrolo[2,3-c]pyridin-2-ylmethyl)-4-methylpentan-2-ol | 537 |
| 14 | 28 | 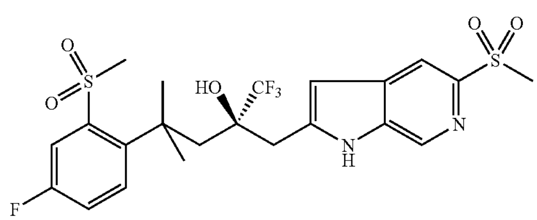 | (R)-1,1,1-Trifluoro-4-(4-fluoro-2-methanesulfonylphenyl)-2-(5-methanesulfonyl-1H-pyrrolo[2,3-c]pyridin-2-ylmethyl)-4-methylpentan-2-ol | 537, 538 |
| 24 | 19 | 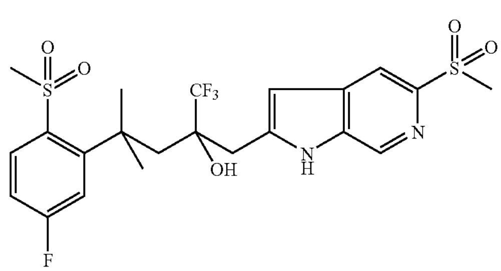 | 1,1,1-Trifluoro-4-(5-fluoro-2-methanesulfonylphenyl)-2-(5-methanesulfonyl-1H-pyrrolo[2,3-c]pyridin-2-ylmethyl)-4-methylpentan-2-ol | 537, 538, 489 |

TABLE 1-continued

| CYP3A4 IC$_{50}$ [μM] | GR IC$_{50}$ [nM] | Structure | Name | observed m/z |
|---|---|---|---|---|
| 1.4 | 10 | 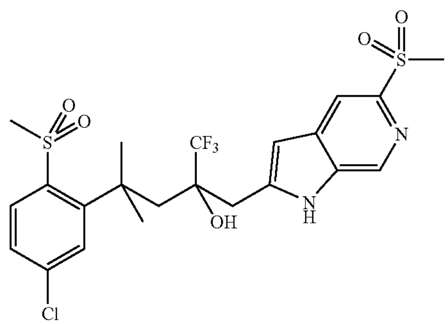 | 4-(5-Chloro-2-methanesulfonylphenyl)-1,1,1-trifluoro-2-(5-methanesulfonyl-1H-pyrrolo[2,3-c]pyridin-2-ylmethyl)-4-methylpentan-2-ol | 553 |
| 4.2 | 36 | 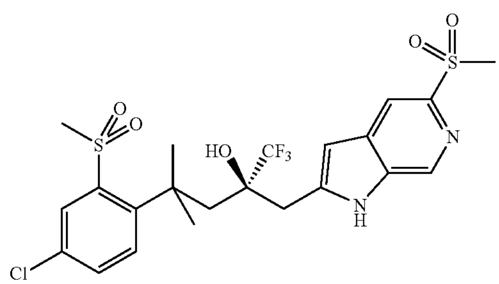 | (R)-4-(4-Chloro-2-methanesulfonylphenyl)-1,1,1-trifluoro-2-(5-methanesulfonyl-1H-pyrrolo[2,3-c]pyridin-2-ylmethyl)-4-methylpentan-2-ol | 553 |
| 23 | 7 | 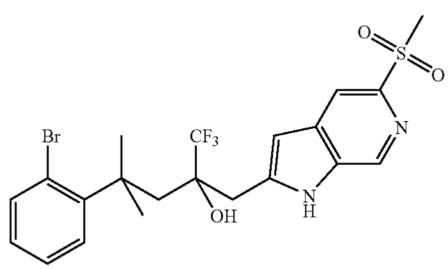 | 4-(2-Bromophenyl)-1,1,1-trifluoro-2-(5-methanesulfonyl-1H-pyrrolo[2,3-c]pyridin-2-ylmethyl)-4-methylpentan-2-ol | 519, 521 |
| >30 | 39 | | 4-(4-Chloro-2-methanesulfonylphenyl)-2-(5-ethanesulfonyl-1H-pyrrolo[2,3-c]pyridin-2-ylmethyl)-1,1,1-trifluoro-4-methylpentan-2-ol | 568, 570 |
| >30 | 29 | | 2-(5-Ethanesulfonyl-1H-pyrrolo[2,3-c]pyridin-2-ylmethyl)-1,1,1-trifluoro-4-(4-fluoro-2-methanesulfonylphenyl)-4-methylpentan-2-ol | 551, 552, 458 |

TABLE 1-continued

Compounds

| CYP3A4 IC$_{50}$ [μM] | GR IC$_{50}$ [nM] | Structure | Name | observed m/z |
|---|---|---|---|---|
| >30 | 95 | 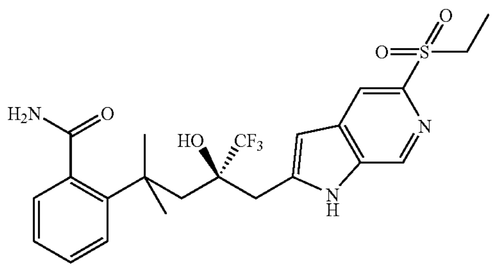 | (R)-2-[3-(5-Ethanesulfonyl-1H-pyrrolo[2,3-c]pyridin-2-ylmethyl)-4,4,4-trifluoro-3-hydroxy-1,1-dimethylbutyl]benzamide | 499 |
| 19 | 53 | 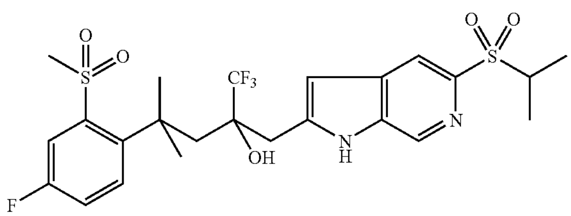 | 1,1,1-Trifluoro-4-(4-fluoro-2-methanesulfonylphenyl)-4-methyl-2-[5-(propane-2-sulfonyl)-1H-pyrrolo[2,3-c]pyridin-2-ylmethyl]pentan-2-ol | 565, 566 |
| 2.7 | 10 | 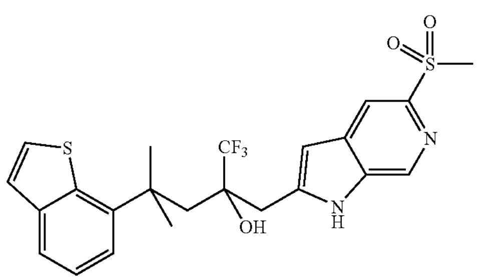 | 4-Benzo[b]thiophen-7-yl-1,1,1-trifluoro-2-(5-methanesulfonyl-1H-pyrrolo[2,3-c]pyridin-2-ylmethyl)-4-methylpentan-2-ol | 497 |
| 22 | 97 | 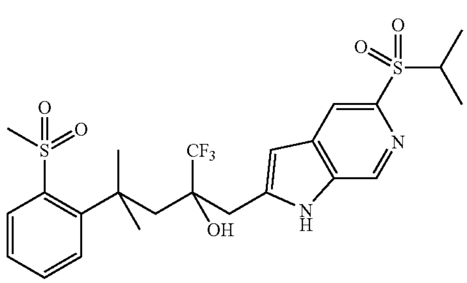 | 1,1,1-Trifluoro-4-(2-methanesulfonylphenyl)-4-methyl-2-[5-(propane-2-sulfonyl)-1H-pyrrolo[2,3-c]pyridin-2-ylmethyl]pentan-2-ol | 547 |
| 7.6 | 71 | 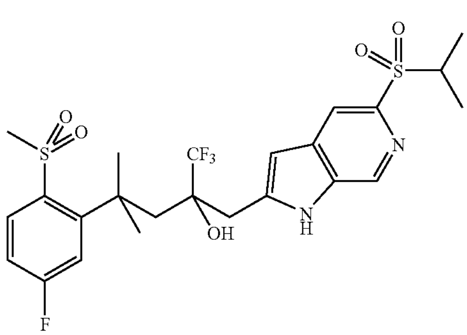 | 1,1,1-Trifluoro-4-(5-fluoro-2-methanesulfonylphenyl)-4-methyl-2-[5-(propane-2-sulfonyl)-1H-pyrrolo[2,3-c]pyridin-2-ylmethyl]pentan-2-ol | 565 |

TABLE 1-continued

| CYP3A4 IC$_{50}$ [μM] | GR IC$_{50}$ [nM] | Structure | Name | observed m/z |
|---|---|---|---|---|
| >30 | 210 | | 1,1,1-Trifluoro-4-(3-fluoro-2-methanesulfonylphenyl)-4-methyl-2-[5-(propane-2-sulfonyl)-1H-pyrrolo[2,3-c]pyridin-2-ylmethyl]pentan-2-ol | 565 |
| >30 | 55 | | 2-(5-Ethanesulfonyl-1H-pyrrolo[2,3-c]pyridin-2-ylmethyl)-1,1,1-trifluoro-4-(3-fluoro-2-methanesulfonylphenyl)-4-methylpentan-2-ol | 551 |
| 15 | 180 | 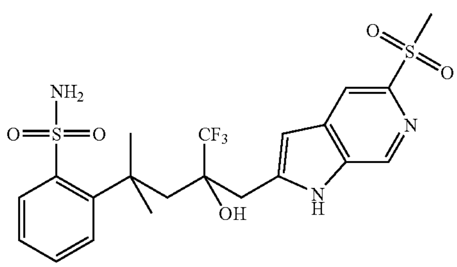 | 2-[4,4,4-Trifluoro-3-hydroxy-3-(5-methanesulfonyl-1H-pyrrolo[2,3-c]pyridin-2-ylmethyl)-1,1-dimethylbutyl]benzenesulfonamide | 520 |
| 7.4 | 89 | 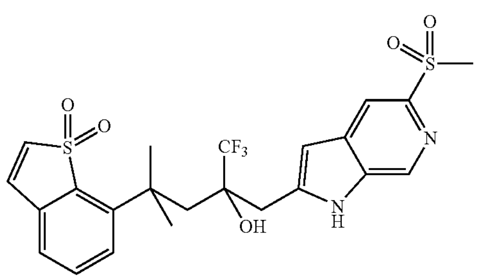 | 4-(1,1-Dioxo-1H-1λ$^6$-benzo[b]thiophen-7-yl)-1,1,1-trifluoro-2-(5-methanesulfonyl-1H-pyrrolo[2,3-c]pyridin-2-ylmethyl)-4-methylpentan-2-ol | 530 |
| 5.8 | 109 | 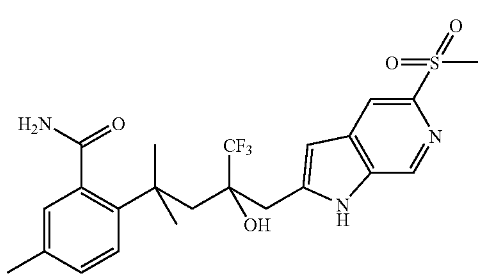 | 5-Methyl-2-[4,4,4-trifluoro-3-hydroxy-3-(5-methanesulfonyl-1H-pyrrolo[2,3-c]pyridin-2-ylmethyl)-1,1-dimethylbutyl]benzamide | 499 |

TABLE 1-continued

| CYP3A4 IC$_{50}$ [μM] | GR IC$_{50}$ [nM] | Structure | Name | observed m/z |
|---|---|---|---|---|
| 11 | 80 | 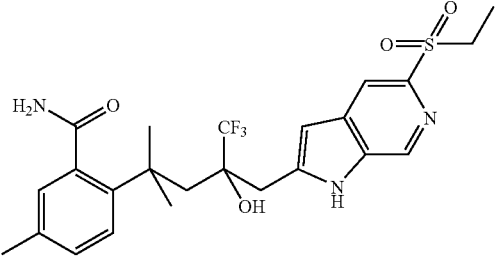 | 2-[3-(5-Ethanesulfonyl-1H-pyrrolo[2,3-c]pyridin-2-ylmethyl)-4,4,4-trifluoro-3-hydroxy-1,1-dimethylbutyl]-5-methylbenzamide | 513 |
| 4.1 | 58 | 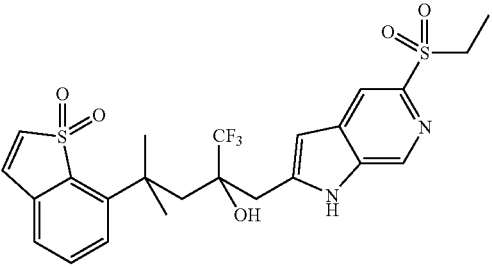 | 4-(1,1-Dioxo-1H-1 $\lambda^6$-benzo[b]thiophen-7-yl)-2-(5-ethanesulfonyl-1H-pyrrolo[2,3-c]pyridin-2-ylmethyl)-1,1,1-trifluoro-4-methylpentan-2-ol | 543 |
| 2.5 | 120 | 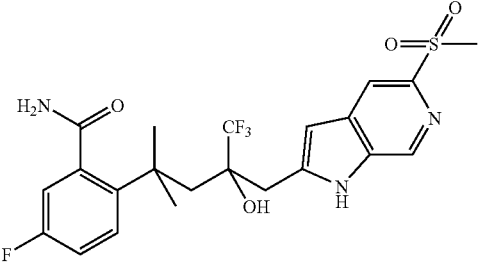 | 5-Fluoro-2-[4,4,4-trifluoro-3-hydroxy-3-(5-methanesulfonyl-1H-pyrrolo[2,3-c]pyridin-2-ylmethyl)-1,1-dimethylbutyl]benzamide | 502 |
| 26 | 55 | 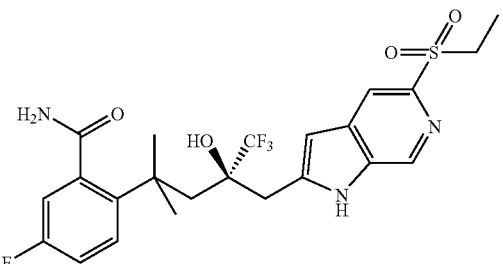 | (R)-2-[3-(5-Ethanesulfonyl-1H-pyrrolo[2,3-c]pyridin-2-ylmethyl)-4,4,4-trifluoro-3-hydroxy-1,1-dimethylbutyl]-5-fluorobenzamide | 516 |
| 6 | 17 | 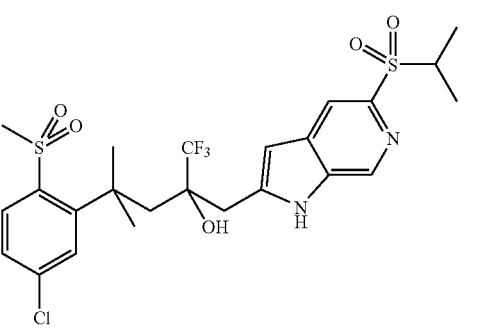 | 4-(5-Chloro-2-methanesulfonylphenyl)-1,1,1-trifluoro-4-methyl-2-[5-(propane-2-sulfonyl)-1H-pyrrolo[2,3-c]pyridin-2-ylmethyl]pentan-2-ol | 581 |

TABLE 1-continued

| CYP3A4 IC$_{50}$ [μM] | GR IC$_{50}$ [nM] | Structure | Name | observed m/z |
|---|---|---|---|---|
| 2.1 | 38 | 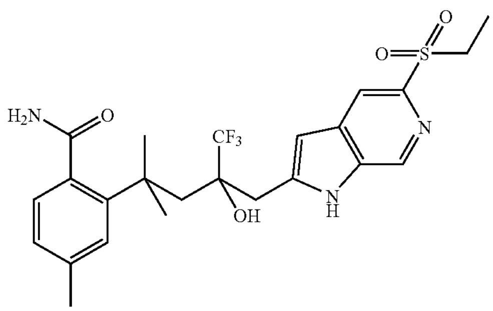 | 4-Methyl-2-[4,4,4-trifluoro-3-hydroxy-3-(5-ethanesulfonyl-1H-pyrrolo[2,3-c]pyridin-2-ylmethyl)-1,1-dimethylbutyl]benzamide | 513 |
| 14 | 140 | 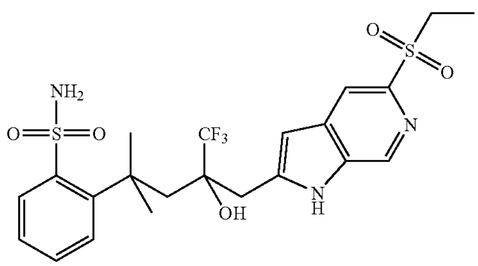 | 2-[3-(5-Ethanesulfonyl-1H-pyrrolo[2,3-c]pyridin-2-ylmethyl)-4,4,4-trifluoro-3-hydroxy-1,1-dimethylbutyl]benzenesulfonamide | 534 |
| 2.2 | 44 | 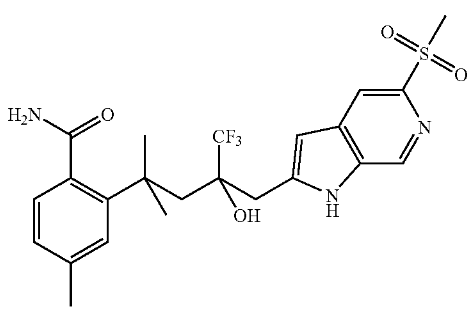 | 4-Methyl-2-[4,4,4-trifluoro-3-hydroxy-3-(5-methanesulfonyl-1H-pyrrolo[2,3-c]pyridin-2-ylmethyl)-1,1-dimethylbutyl]benzamide | 499 |
| 5.8 | 250 | 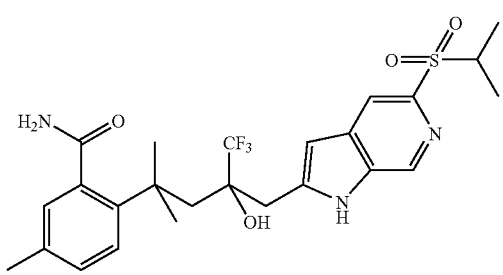 | 5-Methyl-2-{4,4,4-trifluoro-3-hydroxy-1,1-dimethyl-3-[5-(propane-2-sulfonyl)-1H-pyrrolo[2,3-c]pyridin-2-ylmethyl]butyl}benzamide | 527 |
| 3.6 | 370 | 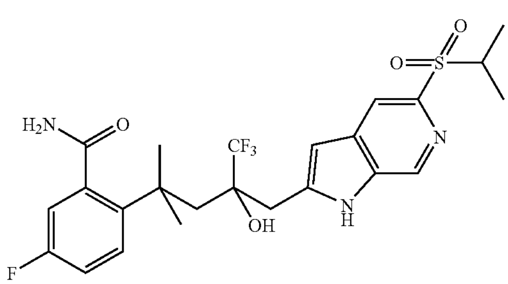 | 5-Fluoro-2-{4,4,4-trifluoro-3-hydroxy-1,1-dimethyl-3-[5-(propane-2-sulfonyl)-1H-pyrrolo[2,3-c]pyridin-2-ylmethyl]butyl}benzamide | 531 |

TABLE 1-continued

Compounds

| CYP3A4 IC$_{50}$ [μM] | GR IC$_{50}$ [nM] | Structure | Name | observed m/z |
|---|---|---|---|---|
| 1.6 | 13 | | 1,1,1-Trifluoro-4-(5-fluoro-2-methanesulfonylphenyl)-4-methyl-2-[5-(propane-1-sulfonyl)-1H-pyrrolo[2,3-c]pyridin-2-ylmethyl]pentan-2-ol | 566 |
| 1.6 | 24 | | 1,1,1-Trifluoro-4-(2-methanesulfonylphenyl)-4-methyl-2-[5-(propane-1-sulfonyl)-1H-pyrrolo[2,3-c]pyridin-2-ylmethyl]pentan-2-ol | 547 |
| 1.8 | 44 | 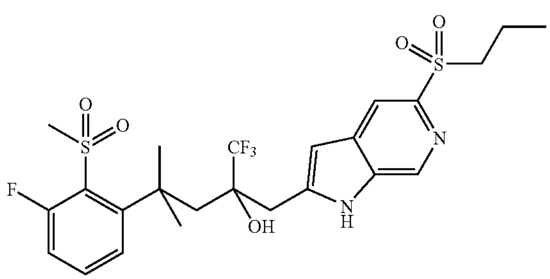 | 1,1,1-Trifluoro-4-(4-fluoro-2-methanesulfonylphenyl)-4-methyl-2-[5-(propane-1-sulfonyl)-1H-pyrrolo[2,3-c]pyridin-2-ylmethyl]pentan-2-ol | 565 |
| 0.9 | 14 | 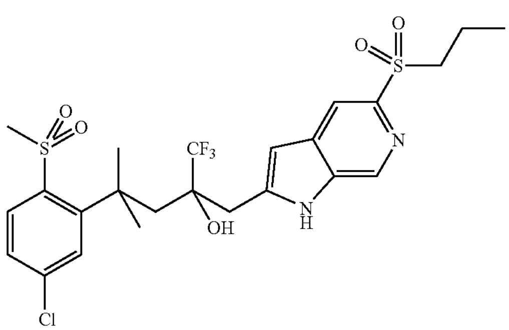 | 4-(5-Chloro-2-methanesulfonylphenyl)-1,1,1-trifluoro-4-methyl-2-[5-(propane-1-sulfonyl)-1H-pyrrolo[2,3-c]pyridin-2-ylmethyl]pentan-2-ol | 581 |
| 9.5 | 25 | 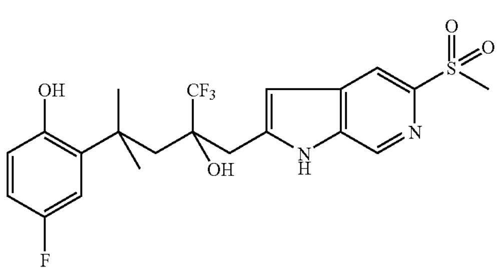 | 4-Fluoro-2-[4,4,4-trifluoro-3-hydroxy-3-(5-methanesulfonyl-1H-pyrrolo[2,3-c]pyridin-2-ylmethyl)-1,1-dimethylbutyl]phenol | 475, 476 |

TABLE 1-continued

| CYP3A4 IC$_{50}$ [μM] | GR IC$_{50}$ [nM] | Structure | Name | observed m/z |
|---|---|---|---|---|
| 11 | 44 | 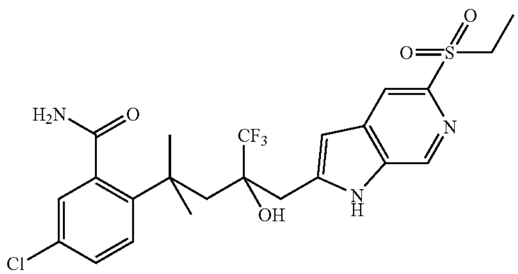 | 5-Chloro-2-[3-(5-ethanesulfonyl-1H-pyrrolo[2,3-c]pyridin-2-ylmethyl)-4,4,4-trifluoro-3-hydroxy-1,1-dimethylbutyl]benzamide | 532, 533 |
| 15 | 40 | 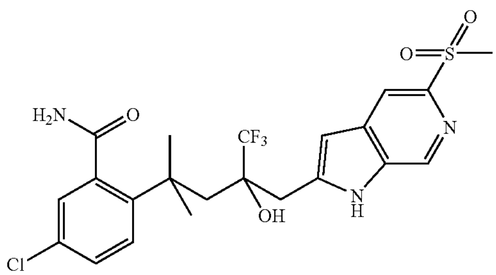 | 5-Chloro-2-[4,4,4-trifluoro-3-hydroxy-3-(5-methanesulfonyl-1H-pyrrolo[2,3-c]pyridin-2-ylmethyl)-1,1-dimethylbutyl]benzamide | 519, 520, 501 |
| 6.9 | 100 | 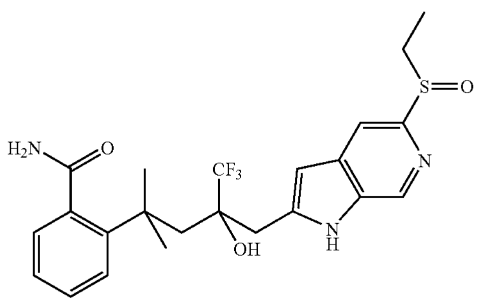 | 2-[3-(5-Ethanesulfonyl-1H-pyrrolo[2,3-c]pyridin-2-ylmethyl)-4,4,4-trifluoro-3-hydroxy-1,1-dimethylbutyl]benzamide | 454, 482 |
| 5.6 | 7 | 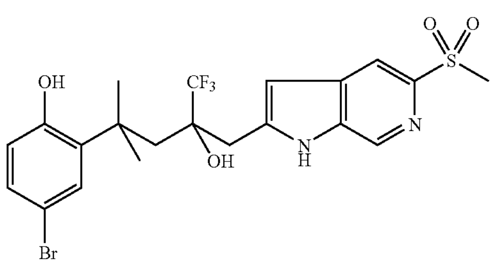 | 4-Bromo-2-[4,4,4-trifluoro-3-hydroxy-3-(5-methanesulfonyl-1H-pyrrolo[2,3-c]pyridin-2-ylmethyl)-1,1-dimethylbutyl]phenol | 537, 535, 538 |
| 21 | 6 | 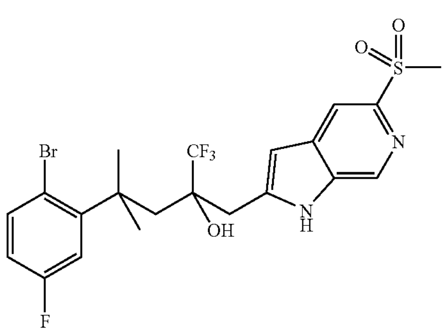 | 4-(2-Bromo-5-fluorophenyl)-1,1,1-trifluoro-2-(5-methanesulfonyl-1H-pyrrolo[2,3-c]pyridin-2-ylmethyl)-4-methylpentan-2-ol | 539 |

TABLE 1-continued

Compounds

| CYP3A 4 IC$_{50}$ [μM] | GR IC$_{50}$ [nM] | Structure | Name | observed m/z |
|---|---|---|---|---|
| 7 | 27 | 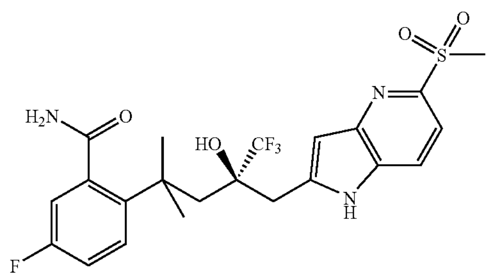 | 5-Fluoro-2-[(R)-4,4,4-trifluoro-3-hydroxy-3-(5-methanesulfonyl-1H-pyrrolo[3,2-b]pyridin-2-ylmethyl)-1,1-dimethyl-butyl]benzamide | 502 |
| 15 | 14 | 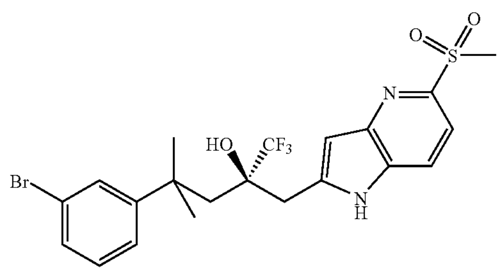 | (R)-4-(3-Bromophenyl)-1,1,1-trifluoro-2-(5-methanesulfonyl-1H-pyrrolo[3,2-b]pyridin-2-ylmethyl)-4-methylpentan-2-ol | 521 |
| 4.1 | 8 | 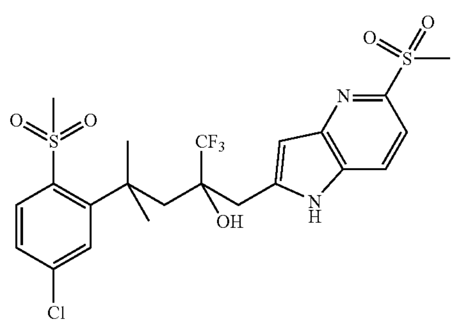 | 4-(5-Chloro-2-methanesulfonylphenyl)-1,1,1-trifluoro-2-(5-methanesulfonyl-1H-pyrrolo[3,2-b]pyridin-2-ylmethyl)-4-methylpentan-2-ol | 553 |
| 8.5 | 58 | 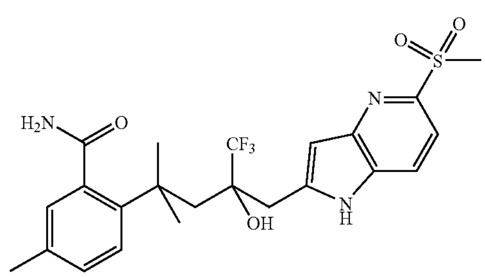 | 5-Methyl-2-[4,4,4-trifluoro-3-hydroxy-3-(5-methanesulfonyl-1H-pyrrolo[3,2-b]pyridin-2-ylmethyl)-1,1-dimethylbutyl]benzamide | 498 |
| 12 | 65 | 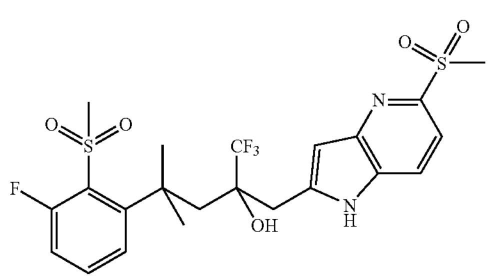 | 1,1,1-Trifluoro-4-(3-fluoro-2-methanesulfonylphenyl)-2-(5-meethanesulfonyl-1H-pyrrolo[3,2-b]pyridin-2-ylmethyl)-4-methylpentan-2-ol | 537 |

TABLE 1-continued

Compounds

| CYP3A4 IC$_{50}$ [µM] | GR IC$_{50}$ [nM] | Structure | Name | observed m/z |
|---|---|---|---|---|
| ND | 32 | 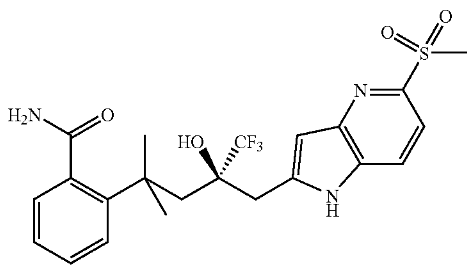 | 2-[(R)-4,4,4-Trifluoro-2-hydroxy-3-(5-meethanesulfonyl-1H-pyrrolo[3,2-b]pyridin-2-ylmethyl)-1,1-dimethylbutyl]benzamide | 484 |
| 11 | 210 | | 5-Fluoro-2-[(R)-4,4,4-trifluoro-3-hydroxy-3-(2-methanesulfonyl-5H-pyrrolo[3,2-d]pyrimidin-6-ylmethyl)-1,1-dimethylbutyl]benzamide | 503 | or a tautomer, prodrug, co-crystal, or salt thereof.
ND = not determined

More preferred compounds of Formula (I) include the following:
- (R)-4-(5-Chloro-2,3-dihydrobenzofuran-7-yl)-1,1,1-trifluoro-2-(5-methanesulfonyl-1H-pyrrolo[2,3-c]pyridin-2-ylmethyl)-4-methylpentan-2-ol;
- (R)-1,1,1-Trifluoro-4-(2-methanesulfonylphenyl)-2-(5-methanesulfonyl-1H-pyrrolo[2,3-c]pyridin-2-ylmethyl)-4-methylpentan-2-ol;
- (R)-4-(5-Chloro-2,3-dihydrobenzofuran-7-yl)-2-(5-ethanesulfonyl-1H-pyrrolo[2,3-c]pyridin-2-ylmethyl)-1,1,1-trifluoro-4-methylpentan-2-ol;
- (R)-4-(3-Bromophenyl)-1,1,1-trifluoro-2-(5-methanesulfonyl-1H-pyrrolo[2,3-c]pyridin-2-ylmethyl)-4-methylpentan-2-ol;
- 2-(5-Ethanesulfonyl-1H-pyrrolo[2,3-c]pyridin-2-ylmethyl)-1,1,1-trifluoro-4-(2-methanesulfonylphenyl)-4-methylpentan-2-ol;
- (R)-2-[4,4,4-Trifluoro-3-hydroxy-3-(5-methanesulfonyl-1H-pyrrolo[2,3-c]pyridin-2-ylmethyl)-1,1-dimethylbutyl]benzamide;
- 1,1,1-Trifluoro-4-(3-fluoro-2-methanesulfonylphenyl)-2-(5-methanesulfonyl-1H-pyrrolo[2,3-c]pyridin-2-ylmethyl)-4-methylpentan-2-ol;
- (R)-1,1,1-Trifluoro-4-(4-fluoro-2-methanesulfonylphenyl)-2-(5-methanesulfonyl-1H-pyrrolo[2,3-c]pyridin-2-ylmethyl)-4-methylpentan-2-ol;
- 1,1,1-Trifluoro-4-(5-fluoro-2-methanesulfonylphenyl)-2-(5-methanesulfonyl-1H-pyrrolo[2,3-c]pyridin-2-ylmethyl)-4-methylpentan-2-ol;
- 4-(5-Chloro-2-methanesulfonylphenyl)-1,1,1-trifluoro-2-(5-methanesulfonyl-1H-pyrrolo[2,3-c]pyridin-2-ylmethyl)-4-methylpentan-2-ol;
- (R)-4-(4-Chloro-2-methanesulfonylphenyl)-1,1,1-trifluoro-2-(5-methanesulfonyl-1H-pyrrolo[2,3-c]pyridin-2-ylmethyl)-4-methylpentan-2-ol;
- 4-(2-Bromophenyl)-1,1,1-trifluoro-2-(5-methanesulfonyl-1H-pyrrolo[2,3-c]pyridin-2-ylmethyl)-4-methylpentan-2-ol;
- 4-(4-Chloro-2-methanesulfonylphenyl)-2-(5-ethanesulfonyl-1H-pyrrolo[2,3-c]pyridin-2-ylmethyl)-1,1,1-trifluoro-4-methylpentan-2-ol;
- 2-(5-Ethanesulfonyl-1H-pyrrolo[2,3-c]pyridin-2-ylmethyl)-1,1,1-trifluoro-4-(4-fluoro-2-methanesulfonylphenyl)-4-methylpentan-2-ol;
- (R)-2-[3-(5-Ethanesulfonyl-1H-pyrrolo[2,3-c]pyridin-2-ylmethyl)-4,4,4-trifluoro-3-hydroxy-1,1-dimethylbutyl]benzamide;
- 1,1,1-Trifluoro-4-(4-fluoro-2-methanesulfonylphenyl)-4-methyl-2-[5-(propane-2-sulfonyl)-1H-pyrrolo[2,3-c]pyridin-2-ylmethyl]pentan-2-ol;
- 4-Benzo[b]thiophen-7-yl-1,1,1-trifluoro-2-(5-methanesulfonyl-1H-pyrrolo[2,3-c]pyridin-2-ylmethyl)-4-methylpentan-2-ol;
- 1,1,1-Trifluoro-4-(2-methanesulfonylphenyl)-4-methyl-2-[5-(propane-2-sulfonyl)-1H-pyrrolo[2,3-c]pyridin-2-ylmethyl]pentan-2-ol;
- 1,1,1-Trifluoro-4-(5-fluoro-2-methanesulfonylphenyl)-4-methyl-2-[5-(propane-2-sulfonyl)-1H-pyrrolo[2,3-c]pyridin-2-ylmethyl]pentan-2-ol;
- 1,1,1-Trifluoro-4-(3-fluoro-2-methanesulfonylphenyl)-4-methyl-2-[5-(propane-2-sulfonyl)-1H-pyrrolo[2,3-c]pyridin-2-ylmethyl]pentan-2-ol;
- 2-(5-Ethanesulfonyl-1H-pyrrolo[2,3-c]pyridin-2-ylmethyl)-1,1,1-trifluoro-4-(3-fluoro-2-methanesulfonylphenyl)-4-methylpentan-2-ol;
- 2-[4,4,4-Trifluoro-3-hydroxy-3-(5-methanesulfonyl-1H-pyrrolo[2,3-c]pyridin-2-ylmethyl)-1,1-dimethylbutyl]benzenesulfonamide;
- 4-(1,1-Dioxo-1H-1$\lambda^6$-benzo[b]thiophen-7-yl)-1,1,1-trifluoro-2-(5-methanesulfonyl-1H-pyrrolo[2,3-c]pyridin-2-ylmethyl)-4-methylpentan-2-ol;

5-Methyl-2-[4,4,4-trifluoro-3-hydroxy-3-(5-methanesulfonyl-1H-pyrrolo[2,3-c]pyridin-2-ylmethyl)-1,1-dimethylbutyl]benzamide;
2-[3-(5-Ethanesulfonyl-1H-pyrrolo[2,3-c]pyridin-2-ylmethyl)-4,4,4-trifluoro-3-hydroxy-1,1-dimethylbutyl]-5-methylbenzamide;
4-(1,1-Dioxo-1H-1λ$^6$-benzo[b]thiophen-7-yl)-2-(5-ethanesulfonyl-1H-pyrrolo[2,3-c]pyridin-2-ylmethyl)-1,1,1-trifluoro-4-methylpentan-2-ol;
5-Fluoro-2-[4,4,4-trifluoro-3-hydroxy-3-(5-methanesulfonyl-1H-pyrrolo[2,3-c]pyridin-2-ylmethyl)-1,1-dimethylbutyl]benzamide;
(R)-2-[3-(5-Ethanesulfonyl-1H-pyrrolo[2,3-c]pyridin-2-ylmethyl)-4,4,4-trifluoro-3-hydroxy-1,1-dimethylbutyl]-5-fluorobenzamide;
4-(5-Chloro-2-methanesulfonylphenyl)-1,1,1-trifluoro-4-methyl-2-[5-(propane-2-sulfonyl)-1H-pyrrolo[2,3-c]pyridin-2-ylmethyl]pentan-2-ol;
4-Methyl-2-[4,4,4-trifluoro-3-hydroxy-3-(5-ethanesulfonyl-1H-pyrrolo[2,3-c]pyridin-2-ylmethyl)-1,1-dimethylbutyl]benzamide;
2-[3-(5-Ethanesulfonyl-1H-pyrrolo[2,3-c]pyridin-2-ylmethyl)-4,4,4-trifluoro-3-hydroxy-1,1-dimethylbutyl]benzenesulfonamide;
4-Methyl-2-[4,4,4-trifluoro-3-hydroxy-3-(5-methanesulfonyl-1H-pyrrolo[2,3-c]pyridin-2-ylmethyl)-1,1-dimethylbutyl]benzamide;
5-Methyl-2-{4,4,4-trifluoro-3-hydroxy-1,1-dimethyl-3-[5-(propane-2-sulfonyl)-1H-pyrrolo[2,3-c]pyridin-2-ylmethyl]butyl}benzamide;
5-Fluoro-2-{4,4,4-trifluoro-3-hydroxy-1,1-dimethyl-3-[5-(propane-2-sulfonyl)-1H-pyrrolo[2,3-c]pyridin-2-ylmethyl]butyl}benzamide;
1,1,1-Trifluoro-4-(5-fluoro-2-methanesulfonylphenyl)-4-methyl-2-[5-(propane-1-sulfonyl)-1H-pyrrolo[2,3-c]pyridin-2-ylmethyl]pentan-2-ol;
1,1,1-Trifluoro-4-(2-methanesulfonylphenyl)-4-methyl-2-[5-(propane-1-sulfonyl)-1H-pyrrolo[2,3-c]pyridin-2-ylmethyl]pentan-2-ol;
1,1,1-Trifluoro-4-(3-fluoro-2-methanesulfonylphenyl)-4-methyl-2-[5-(propane-1-sulfonyl)-1H-pyrrolo[2,3-c]pyridin-2-ylmethyl]pentan-2-ol;
4-(5-Chloro-2-methanesulfonylphenyl)-1,1,1-trifluoro-4-methyl-2-[5-(propane-1-sulfonyl)-1H-pyrrolo[2,3-c]pyridin-2-ylmethyl]pentan-2-ol;
4-Fluoro-2-[4,4,4-trifluoro-3-hydroxy-3-(5-methanesulfonyl-1H-pyrrolo[2,3-c]pyridin-2-ylmethyl)-1,1-dimethylbutyl]phenol;
5-Chloro-2-[3-(5-ethanesulfonyl-1H-pyrrolo[2,3-c]pyridin-2-ylmethyl)-4,4,4-trifluoro-3-hydroxy-1,1-dimethylbutyl]benzamide;
5-Chloro-2-[4,4,4-trifluoro-3-hydroxy-3-(5-methanesulfonyl-1H-pyrrolo[2,3-c]pyridin-2-ylmethyl)-1,1-dimethylbutyl]benzamide;
2-[3-(5-Ethanesulfinyl-1H-pyrrolo[2,3-c]pyridin-2-ylmethyl)-4,4,4-trifluoro-3-hydroxy-1,1-dimethylbutyl]benzamide;
4-Bromo-2-[4,4,4-trifluoro-3-hydroxy-3-(5-methanesulfonyl-1H-pyrrolo[2,3-c]pyridin-2-ylmethyl)-1,1-dimethylbutyl]phenol; and
4-(2-Bromo-5-fluorophenyl)-1,1,1-trifluoro-2-(5-methanesulfonyl-1H-pyrrolo[2,3-c]pyridin-2-ylmethyl)-4-methylpentan-2-ol,
or a tautomer, prodrug, co-crystal, or salt thereof.

Most preferred compounds of Formula (I) include the following:

(R)-1,1,1-Trifluoro-4-(2-methanesulfonylphenyl)-2-(5-methanesulfonyl-1H-pyrrolo[2,3-c]pyridin-2-ylmethyl)-4-methylpentan-2-ol;
2-(5-Ethanesulfonyl-1H-pyrrolo[2,3-c]pyridin-2-ylmethyl)-1,1,1-trifluoro-4-(2-methanesulfonylphenyl)-4-methylpentan-2-ol;
(R)-2-[4,4,4-Trifluoro-3-hydroxy-3-(5-methanesulfonyl-1H-pyrrolo[2,3-c]pyridin-2-ylmethyl)-1,1-dimethylbutyl]benzamide;
1,1,1-Trifluoro-4-(3-fluoro-2-methanesulfonylphenyl)-2-(5-methanesulfonyl-1H-pyrrolo[2,3-c]pyridin-2-ylmethyl)-4-methylpentan-2-ol;
(R)-1,1,1-Trifluoro-4-(4-fluoro-2-methanesulfonylphenyl)-2-(5-methanesulfonyl-1H-pyrrolo[2,3-c]pyridin-2-ylmethyl)-4-methylpentan-2-ol;
1,1,1-Trifluoro-4-(5-fluoro-2-methanesulfonylphenyl)-2-(5-methanesulfonyl-1H-pyrrolo[2,3-c]pyridin-2-ylmethyl)-4-methylpentan-2-ol;
4-(5-Chloro-2-methanesulfonylphenyl)-1,1,1-trifluoro-2-(5-methanesulfonyl-1H-pyrrolo[2,3-c]pyridin-2-ylmethyl)-4-methylpentan-2-ol;
(R)-4-(4-Chloro-2-methanesulfonylphenyl)-1,1,1-trifluoro-2-(5-methanesulfonyl-1H-pyrrolo[2,3-c]pyridin-2-ylmethyl)-4-methylpentan-2-ol;
4-(4-Chloro-2-methanesulfonylphenyl)-2-(5-ethanesulfonyl-1H-pyrrolo[2,3-c]pyridin-2-ylmethyl)-1,1,1-trifluoro-4-methylpentan-2-ol;
2-(5-Ethanesulfonyl-1H-pyrrolo[2,3-c]pyridin-2-ylmethyl)-1,1,1-trifluoro-4-(4-fluoro-2-methanesulfonylphenyl)-4-methylpentan-2-ol;
(R)-2-[3-(5-Ethanesulfonyl-1H-pyrrolo[2,3-c]pyridin-2-ylmethyl)-4,4,4-trifluoro-3-hydroxy-1,1-dimethylbutyl]benzamide;
2-(5-Ethanesulfonyl-1H-pyrrolo[2,3-c]pyridin-2-ylmethyl)-1,1,1-trifluoro-4-(3-fluoro-2-methanesulfonylphenyl)-4-methylpentan-2-ol;
2-[4,4,4-Trifluoro-3-hydroxy-3-(5-methanesulfonyl-1H-pyrrolo[2,3-c]pyridin-2-ylmethyl)-1,1-dimethylbutyl]benzenesulfonamide;
5-Methyl-2-[4,4,4-trifluoro-3-hydroxy-3-(5-methanesulfonyl-1H-pyrrolo[2,3-c]pyridin-2-ylmethyl)-1,1-dimethylbutyl]benzamide;
2-[3-(5-Ethanesulfonyl-1H-pyrrolo[2,3-c]pyridin-2-ylmethyl)-4,4,4-trifluoro-3-hydroxy-1,1-dimethylbutyl]-5-methylbenzamide;
5-Fluoro-2-[4,4,4-trifluoro-3-hydroxy-3-(5-methanesulfonyl-1H-pyrrolo[2,3-c]pyridin-2-ylmethyl)-1,1-dimethylbutyl]benzamide;
(R)-2-[3-(5-Ethanesulfonyl-1H-pyrrolo[2,3-c]pyridin-2-ylmethyl)-4,4,4-trifluoro-3-hydroxy-1,1-dimethylbutyl]-5-fluorobenzamide;
4-Methyl-2-[4,4,4-trifluoro-3-hydroxy-3-(5-ethanesulfonyl-1H-pyrrolo[2,3-c]pyridin-2-ylmethyl)-1,1-dimethylbutyl]benzamide;
2-[3-(5-Ethanesulfonyl-1H-pyrrolo[2,3-c]pyridin-2-ylmethyl)-4,4,4-trifluoro-3-hydroxy-1,1-dimethylbutyl]benzenesulfonamide;
4-Methyl-2-[4,4,4-trifluoro-3-hydroxy-3-(5-methanesulfonyl-1H-pyrrolo[2,3-c]pyridin-2-ylmethyl)-1,1-dimethylbutyl]benzamide;
5-Chloro-2-[3-(5-ethanesulfonyl-1H-pyrrolo[2,3-c]pyridin-2-ylmethyl)-4,4,4-trifluoro-3-hydroxy-1,1-dimethylbutyl]benzamide; and
5-Chloro-2-[4,4,4-trifluoro-3-hydroxy-3-(5-methanesulfonyl-1H-pyrrolo[2,3-c]pyridin-2-ylmethyl)-1,1-dimethylbutyl]benzamide, or a tautomer, prodrug, co-crystal, or salt thereof.

In another aspect of the invention, the compounds according to the invention are formulated into pharmaceutical compositions comprising an effective amount, preferably a pharmaceutically effective amount, of a compound according to the invention or a tautomer, prodrug, co-crystal, or salt thereof, and a pharmaceutically acceptable excipient or carrier.

The invention also provides a method of modulating the glucocorticoid receptor function in a patient, the method comprising administering to the patient an effective amount of a compound according to the invention or a tautomer, prodrug, co-crystal, or salt thereof.

The invention further provides a method of treating a disease-state or condition mediated by the glucocorticoid receptor function in a patient in need of such treatment, the method comprising administering to the patient an effective amount of a pharmaceutically acceptable compound according to the invention or a tautomer, prodrug, co-crystal, or salt thereof.

In addition, the invention also provides a method of treating a disease-state or condition selected from: type II diabetes, obesity, cardiovascular diseases, hypertension, arteriosclerosis, neurological diseases, adrenal and pituitary tumors, and glaucoma, in a patient in need of such treatment, the method comprising administering to the patient an effective amount of a pharmaceutically acceptable compound according to the invention or a tautomer, prodrug, co-crystal, or salt thereof.

The invention provides a method of treating a disease characterized by inflammatory, allergic, or proliferative processes, in a patient in need of such treatment, the method comprising administering to the patient an effective amount of a pharmaceutically acceptable compound according to the invention or a tautomer, prodrug, co-crystal, or salt thereof. In a preferred embodiment of the invention, the disease characterized by inflammatory, allergic, or proliferative processes is selected from: (i) lung diseases; (ii) rheumatic diseases or autoimmune diseases or joint diseases; (iii) allergic diseases; (iv) vasculitis diseases; (v) dermatological diseases; (vi) renal diseases; (vii) hepatic diseases; (viii) gastrointestinal diseases; (ix) proctological diseases; (x) eye diseases; (xi) diseases of the ear, nose, and throat (ENT) area; (xii) neurological diseases; (xiii) blood diseases; (xiv) tumor diseases; (xv) endocrine diseases; (xvi) organ and tissue transplantations and graft-versus-host diseases; (xvii) severe states of shock; (xviii) substitution therapy; and (xix) pain of inflammatory genesis. In another preferred embodiment of the invention, the disease characterized by inflammatory, allergic, or proliferative processes is selected from: type I diabetes, osteoarthritis, Guillain-Barre syndrome, restenosis following percutaneous transluminal coronary angioplasty, Alzheimer disease, acute and chronic pain, atherosclerosis, reperfusion injury, bone resorption diseases, congestive heart failure, myocardial infarction, thermal injury, multiple organ injury secondary to trauma, acute purulent meningitis, necrotizing enterocolitis, and syndromes associated with hemodialysis, leukopheresis, and granulocyte transfusion.

The invention further provides methods of treating the disease-states or conditions mentioned above, in a patient in need of such treatment, the methods comprising sequentially or simultaneously administering to the patient: (a) an effective amount of a pharmaceutically acceptable compound according to the invention or a tautomer, prodrug, co-crystal, or salt thereof; and (b) a pharmaceutically acceptable glucocorticoid.

The invention further provides a method of assaying the glucocorticoid receptor function in a sample, comprising: (a) contacting the sample with a selected amount of a compound according to the invention or a tautomer, prodrug, co-crystal, or salt thereof; and (b) detecting the amount of the compound according to the invention or a tautomer, prodrug, co-crystal, or salt thereof bound to glucocorticoid receptors in the sample. In a preferred embodiment of the invention, the compound according to the invention or a tautomer, prodrug, co-crystal, or salt thereof is labeled with a detectable marker selected from: a radiolabel, fluorescent tag, a chemiluminescent tag, a chromophore, and a spin label.

The invention also provides a method of imaging the glucocorticoid receptor distribution in a sample or patient, the method comprising: (a) contacting the sample or administering to a patient a compound according to the invention or a tautomer, prodrug, co-crystal, or salt thereof having a detectable marker; (b) detecting the spatial distribution and amount of the compound according to the invention or a tautomer, prodrug, co-crystal, or salt thereof having a detectable marker bound to glucocorticoid receptors in the sample or patient using an imaging means to obtain an image; and (c) displaying an image of the spatial distribution and amount of the compound according to the invention or a tautomer, prodrug, co-crystal, or salt thereof having a detectable marker bound to glucocorticoid receptors in the sample. In a preferred embodiment of the invention, the imaging means is selected from: radioscintigraphy, nuclear magnetic resonance imaging (MRI), computed tomography (CT scan), or positron emission tomography (PET).

The invention also provides a kit for the in vitro diagnostic determination of the glucocorticoid receptor function in a sample, comprising: (a) a diagnostically effective amount of a compound according to the invention or a tautomer, prodrug, co-crystal, or salt thereof; and (b) instructions for use of the diagnostic kit.

Another aspect of the invention provides a method of making the intermediate (6-ethanesulfonyl-4-iodopyridin-3-yl) carbamic acid tert-butyl ester, the method comprising:
  (a) reacting 5-nitro-2-chloropyridine with sodium ethanethiolate to obtain 2-ethylsulfanyl-5-nitropyridine;
  (b) hydrogenating the 2-ethylsulfanyl-5-nitropyridine to obtain 6-ethylsulfanylpyridin-3-ylamine;
  (c) reacting the 6-ethylsulfanylpyridin-3-ylamine with di-tert-butyl dicarbonate to obtain (6-ethylsulfanylpyridin-3-yl)carbamic acid tert-butyl ester;
  (d) adding n-butyllithium dropwise to a solution of the (6-ethylsulfanylpyridin-3-yl)carbamic acid tert-butyl ester and N,N,N',N'-tetramethylethylenediamine in a suitable solvent;
  (e) adding iodine in a suitable solvent dropwise to the solution of step (d) followed by workup to obtain (6-ethylsulfanyl-4-iodopyridin-3-yl)carbamic acid tert-butyl ester; and
  (f) combining the (6-ethylsulfanyl-4-iodopyridin-3-yl)carbamic acid tert-butyl ester, NaIO$_4$, and ruthenium (III) chloride in a suitable solvent, followed by stirring and workup to obtain (6-ethanesulfonyl-4-iodopyridin-3-yl) carbamic acid tert-butyl ester.

Another aspect of the invention is the intermediate (6-Ethylsulfanylpyridin-3-yl)carbamic acid tert-butyl ester.

Another aspect of the invention is the intermediate (6-Ethylsulfanyl-4-iodopyridin-3-yl)carbamic acid tert-butyl ester.

Another aspect of the invention provides a method of making the intermediate (6-Methanesulfonyl-4-iodopyridin-3-yl) carbamic acid tert-butyl ester, the method comprising:
  (a) reacting 5-nitro-2-chloropyridine with sodium methanethiolate to obtain 2-methylsulfanyl-5-nitropyridine;

(b) hydrogenating the 2-methylsulfanyl-5-nitropyridine to obtain 6-methylsulfanylpyridin-3-ylamine;

(c) reacting the 6-methylsulfanylpyridin-3-ylamine with di-tert-butyl dicarbonate to obtain (6-methylsulfanylpyridin-3-yl)carbamic acid tert-butyl ester;

(d) adding n-butyllithium dropwise to a solution of the (6-methylsulfanylpyridin-3-yl)carbamic acid tert-butyl ester and N,N,N',N'-tetramethylethylenediamine in a suitable solvent;

(e) adding iodine in a suitable solvent dropwise to the solution of step (d) followed by workup to obtain (6-methylsulfanyl-4-iodopyridin-3-yl)carbamic acid tert-butyl ester; and (f) combining the (6-methylsulfanyl-4-iodopyridin-3-yl) carbamic acid tert-butyl ester, NaIO$_4$, and ruthenium (III) chloride in a suitable solvent, followed by stirring and workup to obtain (6-methanesulfonyl-4-iodopyridin-3-yl)carbamic acid tert-butyl ester.

Another aspect of the invention is the intermediate (6-Methylsulfanylpyridin-3-yl)carbamic acid tert-butyl ester.

Another aspect of the invention is the intermediate (6-Methylsulfanyl-4-iodopyridin-3-yl)carbamic acid tert-butyl ester.

BRIEF DESCRIPTION OF THE FIGURES

FIG. 15: $^1$H NMR of (R)-2-[3-(5-Ethanesulfonyl-1H-pyrrolo[2,3-c]pyridin-2-ylmethyl)-4,4,4-trifluoro-3-hydroxy-1,1-dimethylbutyl]benzamide Isonicotinamide Co-Crystal;

DETAILED DESCRIPTION OF THE INVENTION

Definition of Terms and Conventions Used

Figure 1:
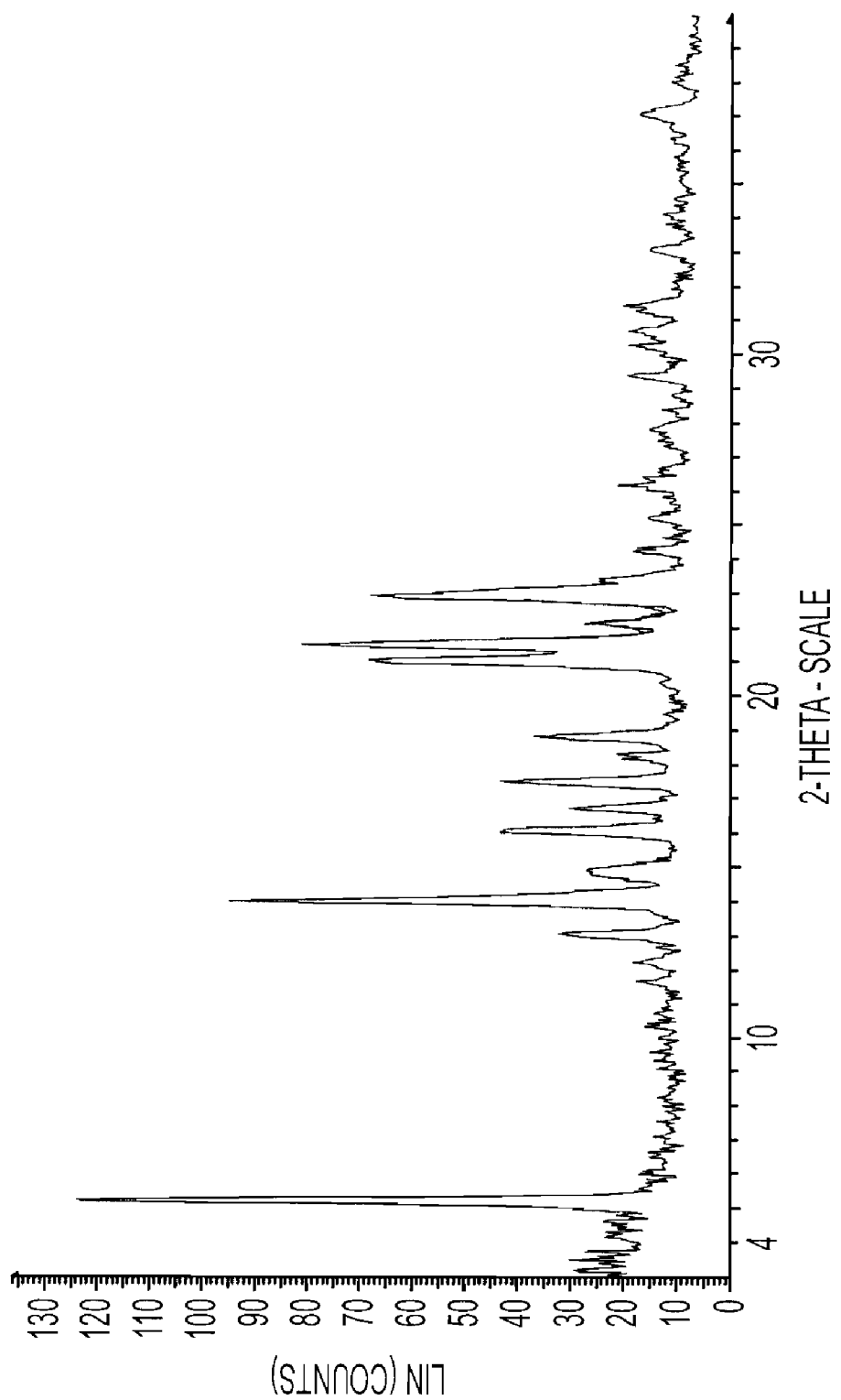
FIG. 1: XRPD of (R)-2-[3-(5-Ethanesulfonyl-1H-pyrrolo[2,3-c]pyridin-2-ylmethyl)-4,4,4-trifluoro-3-hydroxy-1,1-dimethylbutyl]-5-fluorobenzamide Phosphoric Acid Co-Crystal.

Terms not specifically defined herein should be given the meanings that would be given to them by one of skill in the art in light of the disclosure and the context. As used in the specification and appended claims, however, unless specified to the contrary, the following terms have the meaning indicated and the following conventions are adhered to.

A. Chemical Nomenclature, Terms, and Conventions

In the groups, radicals, or moieties defined below, the number of carbon atoms is often specified preceding the group, for example, $C_1$-$C_{10}$ alkyl means an alkyl group or radical having 1 to 10 carbon atoms. The term "lower" applied to any carbon-containing group means a group containing from 1 to 8 carbon atoms, as appropriate to the group (i.e., a cyclic group must have at least 3 atoms to constitute a ring). In general, for groups comprising two or more subgroups, the last named group is the radical attachment point, for example, "alkylaryl" means a monovalent radical of the formula Alk-Ar—, while "arylalkyl" means a monovalent radical of the formula Ar-Alk- (where Alk is an alkyl group and Ar is an aryl group). Furthermore, the use of a term designating a monovalent radical where a divalent radical is appropriate shall be construed to designate the respective divalent radical and vice versa. Unless otherwise specified, conventional definitions of terms control and conventional stable atom valences are presumed and achieved in all formulas and groups.

The terms "alkyl" or "alkyl group" mean a branched or straight-chain saturated aliphatic hydrocarbon monovalent radical. This term is exemplified by groups such as methyl, ethyl, n-propyl, 1-methylethyl (isopropyl), n-butyl, n-pentyl, 1,1-dimethylethyl (tert-butyl), and the like. It may be abbreviated "Alk".

The terms "alkylene" or "alkylene group" mean a branched or straight-chain saturated aliphatic hydrocarbon divalent radical having the specified number of carbon atoms. This term is exemplified by groups such as methylene, ethylene, propylene, n-butylene, and the like, and may alternatively and equivalently be denoted herein as -(alkyl)-.

The terms "alkoxy" or "alkoxy group" mean a monovalent radical of the formula AlkO-, where Alk is an alkyl group. This term is exemplified by groups such as methoxy, ethoxy, propoxy, isopropoxy, butoxy, sec-butoxy, tert-butoxy, pentoxy, and the like.

The terms "aminocarbonyl", "alkylaminocarbonyl" and "dialkylaminocarbonyl" mean a monovalent radical of the formula $R_2NC(O)$—, where each R is independently hydrogen or lower alkyl.

The terms "amino" or "amino group" mean an —$NH_2$ group.

The terms "alkylamino" or "alkylamino group" mean a monovalent radical of the formula (Alk)NH—, where Alk is alkyl. Exemplary alkylamino groups include methylamino, ethylamino, propylamino, butylamino, tert-butylamino, and the like.

The terms "dialkylamino" or "dialkylamino group" mean a monovalent radical of the formula (Alk)(Alk)N—, where each Alk is independently alkyl. Exemplary dialkylamino groups include dimethylamino, methylethylamino, diethylamino, dipropylamino, ethylpropylamino, and the like.

The terms "substituted amino" or "substituted amino group" mean a monovalent radical of the formula —$NR_2$, where each R is independently a substituent selected from hydrogen or the specified substituents (but where both Rs cannot be hydrogen). Exemplary substituents include alkyl, alkanoyl, aryl, arylalkyl, cycloalkyl, heterocyclyl, heteroaryl, heteroarylalkyl, and the like.

The terms "halogen" or "halogen group" mean a fluoro, chloro, bromo, or iodo group.

The term "halo" means one or more hydrogen atoms of the group are replaced by halogen groups.

The terms "haloalkyl" or "haloalkyl group" mean a branched or straight-chain saturated aliphatic hydrocarbon monovalent radical, wherein one or more hydrogen atoms thereof are each independently replaced with halogen atoms. This term is exemplified by groups such as chloromethyl, 1,2-dibromoethyl, 1,1,1-trifluoropropyl, 2-iodobutyl, 1-chloro-2-bromo-3-fluoropentyl, and the like.

The terms "sulfanyl", "sulfanyl group", "thioether", or "thioether group" mean a divalent radical of the formula —S—.

The terms "alkylthio" or "alkylthio group" mean a monovalent radical of the formula AlkS-, where Alk is alkyl. Exemplary groups include methylthio, ethylthio, n-propylthio, isopropylthio, n-butylthio, and the like.

The terms "sulfonyl" or "sulfonyl group" mean a divalent radical of the formula —$SO_2$—.

The terms "alkylsulfonyl" or "alkylsulfonyl group" mean a monovalent radical of the formula R—$SO_2$—, where R is alkyl.

The terms "sulfonylamino" or "sulfonylamino group" mean a divalent radical of the formula —$SO_2NR$—, where R is a hydrogen or a substituent group.

The terms "aminosulfonyl" or "aminosulfonyl group" mean a monovalent radical of the formula $NR_2SO_2$—, where R is each independently a hydrogen or a substituent group.

The term "oxo" means a double-bonded divalent oxygen radical of the formula (=O), for example, one example of an alkyl group substituted by an "oxo" would be a group of the formula Alk-C(O)-Alk, wherein each Alk is an alkyl.

The terms "carbocycle" or "carbocyclic group" mean a stable aliphatic 3- to 15-membered monocyclic or polycyclic monovalent or divalent radical consisting solely of carbon and hydrogen atoms which may comprise one or more fused or bridged ring(s), preferably a 5- to 7-membered monocyclic or 7- to 10-membered bicyclic ring. Unless otherwise specified, the carbocycle may be attached at any carbon atom which results in a stable structure and, if substituted, may be substituted at any suitable carbon atom which results in a stable structure. The term comprises cycloalkyl (including spiro cycloalkyl), cycloalkylene, cycloalkenyl, cycloalkenylene, cycloalkynyl, and cycloalkenylene, and the like.

The terms "cycloalkyl" or "cycloalkyl group" mean a stable aliphatic saturated 3- to 15-membered monocyclic or polycyclic monovalent radical consisting solely of carbon and hydrogen atoms which may comprise one or more fused or bridged ring(s), preferably a 5- to 7-membered monocyclic or 7- to 10-membered bicyclic ring. Unless otherwise specified, the cycloalkyl ring may be attached at any carbon atom which results in a stable structure and, if substituted, may be substituted at any suitable carbon atom which results in a stable structure. Exemplary cycloalkyl groups include cyclopropyl, cyclobutyl, cyclopentyl, cyclohexyl, cycloheptyl, cyclooctyl, cyclononyl, cyclodecyl, norbornanyl, adamantyl, tetrahydronaphthyl (tetralin), 1-decalinyl, bicyclo[2.2.2]octanyl, 1-methylcyclopropyl, 2-methylcyclopentyl, 2-methylcyclooctyl, and the like.

The terms "cycloalkylene" or "cycloalkylene group" mean a stable saturated aliphatic 3- to 15-membered monocyclic or polycyclic divalent radical consisting solely of carbon and hydrogen atoms which may comprise one or more fused or bridged ring(s), preferably a 5- to 7-membered monocyclic or 7- to 10-membered bicyclic ring. Unless otherwise specified, the cycloalkyl ring may be attached at any carbon atom which results in a stable structure and, if substituted, may be substituted at any suitable carbon atom which results in a stable structure. Exemplary cycloalkylene groups include cyclopentylene, and the like.

The terms "aryl" or "aryl group" mean an aromatic carbocyclic monovalent or divalent radical of from 6 to 14 carbon atoms having a single ring (e.g., phenyl or phenylene) or multiple condensed rings (e.g., naphthyl or anthranyl). Unless otherwise specified, the aryl ring may be attached at any suitable carbon atom which results in a stable structure and, if substituted, may be substituted at any suitable carbon atom which results in a stable structure. Exemplary aryl groups include phenyl, naphthyl, anthryl, phenanthryl, indanyl, indenyl, biphenyl, and the like. It may be abbreviated "Ar".

The terms "heteroaryl" or "heteroaryl group" mean a stable aromatic 5- to 14-membered, monocyclic or polycyclic monovalent or divalent radical which may comprise one or more fused or bridged ring(s), preferably a 5- to 7-membered monocyclic or 7- to 10-membered bicyclic radical, having from one to four heteroatoms in the ring(s) independently selected from nitrogen, oxygen, and sulfur, wherein any sulfur heteroatoms may optionally be oxidized and any nitrogen heteroatom may optionally be oxidized or be quaternized. Unless otherwise specified, the heteroaryl ring may be attached at any suitable heteroatom or carbon atom which results in a stable structure and, if substituted, may be substituted at any suitable heteroatom or carbon atom which results in a stable structure. Exemplary and preferred heteroaryls include furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, triazinyl, indolizinyl, azaindolizinyl, indolyl, azaindolyl also known as pyrrolopyridinyl, diazaindolyl, dihydroindolyl, dihydroazaindoyl, isoindolyl, azaisoindolyl, benzofuranyl, furanopyridinyl, furanopyrimidinyl, furanopyrazinyl, furanopyridazinyl, dihydrobenzofuranyl, dihydrofuranopyridinyl, dihydrofuranopyrimidinyl, benzodioxolanyl, benzothienyl, thienopyridinyl, thienopyrimidinyl, thienopyrazinyl, thienopyridazinyl, dihydrobenzothienyl, dihydrothienopyridinyl, dihydrothienopyrimidinyl, indazolyl, azaindazolyl, diazaindazolyl, benzimidazolyl, imidazopyridinyl, benzthiazolyl, thiazolopyridinyl, thiazolopyrimidinyl, benzoxazolyl, oxazolopyridinyl, oxazolopyrimidinyl, benzisoxazolyl, purinyl, chromanyl, azachromanyl, quinolizinyl, quinolinyl, dihydroquinolinyl, tetrahydroquinolinyl, isoquinolinyl, dihydroisoquinolinyl, tetrahydroisoquinolinyl, cinnolinyl, azacinnolinyl, phthalazinyl, azaphthalazinyl, quinazolinyl, azaquinazolinyl, quinoxalinyl, azaquinoxalinyl, naphthyridinyl, dihydronaphthyridinyl, tetrahydronaphthyridinyl, pteridinyl, carbazolyl, acridinyl, phenazinyl, phenothiazinyl, and phenoxazinyl, and the like.

The terms "heterocycle", "heterocycle group", "heterocyclyl", or "heterocyclyl group" mean a stable non-aromatic 5- to 14-membered monocyclic or polycyclic, monovalent or divalent, ring which may comprise one or more fused or bridged ring(s), preferably a 5- to 7-membered monocyclic or 7- to 10-membered bicyclic ring, having from one to three heteroatoms in the ring(s) independently selected from nitrogen, oxygen, and sulfur, wherein any sulfur heteroatoms may optionally be oxidized and any nitrogen heteroatom may optionally be oxidized or be quaternized. Unless otherwise specified, the heterocyclyl ring may be attached at any suitable heteroatom or carbon atom which results in a stable structure and, if substituted, may be substituted at any suitable heteroatom or carbon atom which results in a stable structure. Exemplary and preferred heterocycles include pyrrolinyl, pyrrolidinyl, pyrazolinyl, pyrazolidinyl, piperidinyl, morpholinyl, thiomorpholinyl, piperazinyl, tetrahydropyranyl, tetrahydrothiopyranyl, tetrahydrofuranyl, hexahydropyrimidinyl, hexahydropyridazinyl, and the like.

The term "compounds of Formula (I)" and equivalent expressions are mean to embrace compounds of Formula (I), either individually, in some combination, or all of them, as the context permits.

The term "compounds of the invention" and equivalent expressions are meant to embrace compounds of Formula (I) as herein described, including the tautomers, the prodrugs, the co-crystals, or the salts, particularly the pharmaceutically acceptable salts, and the solvates and hydrates thereof, where the context so permits. In general and preferably, the compounds of the invention and the formulas designating the compounds of the invention are understood to only include the stable compounds thereof and exclude unstable compounds, even if an unstable compound might be considered to be literally embraced by the compound formula. Similarly, reference to intermediates, whether or not they themselves are claimed, is meant to embrace their salts and solvates, where the context so permits. For the sake of clarity, particular instances when the context so permits are sometimes indicated in the text, but these instances are purely illustrative and it is not intended to exclude other instances when the context so permits. Compounds of the invention as disclosed and claimed herein also are intended to include both compounds with normal (naturally-occurring) isotopic distributions of atoms as well as the corresponding isotopically-enriched compounds. Thus, unless otherwise stated, structures depicted herein are also meant to include compounds that differ only by being enriched with certain isotopes of a given atom. For example, compounds having the present structures except for the replacement of hydrogen ($^1$H) by deuterium ($^2$H) or tritium ($^3$H), or the replacement of a carbon by a $^{13}$C- or $^{14}$C-enriched carbon are within the scope of this invention. Examples of isotopes that can be incorporated into the compounds of the invention in accordance with well-established procedures include isotopes of hydrogen, carbon, nitrogen, oxygen, phosphorous, fluorine, and chlorine, for example, $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Certain isotopically-labeled compounds described herein, for example, those into which radioactive isotopes such as $^3$H and $^{14}$C are incorporated, are useful in drug and/or substrate tissue distribution assays. Further, substitution with isotopes such as deuterium can afford certain therapeutic advantages resulting from greater metabolic stability, for example, increased in vivo half-life, lower toxicity, or reduced dosage requirements (see *Nature,* 458, 269 (2009)).

The terms "optional" or "optionally" mean that the subsequently described event or circumstances may or may not occur, and that the description includes instances where the event or circumstance occurs and instances in which it does not. For example, "optionally substituted aryl" means that the aryl radical may or may not be substituted and that the description includes both substituted aryl radicals and aryl radicals having no substitution.

The terms "stable compound" or "stable structure" mean a compound that is sufficiently robust to survive isolation to a useful degree of purity from a reaction mixture, and formulation into an efficacious therapeutic or diagnostic agent. For example, a compound which would have a "dangling valency" or is a carbanion is not a compound contemplated by the invention.

The term "substituted" means that any one or more hydrogens on an atom of a group or moiety, whether specifically designated or not, is replaced with a selection from the indicated group of substituents, provided that the atom's normal valency is not exceeded and that the substitution results in a stable compound. If a bond to a substituent is shown to cross the bond connecting two atoms in a ring, then such substituent may be bonded to any atom on the ring. When a substituent is listed without indicating the atom via which such substituent is bonded to the rest of the compound, then such substituent may be bonded via any atom in such substituent. For example, when the substituent is piperazinyl, piperidinyl, or tetrazolyl, unless specified otherwise, such piperazinyl, piperidinyl, or tetrazolyl group may be bonded to the rest of the compound of the invention via any atom in such piperazinyl, piperidinyl, or tetrazolyl group. Generally, when any substituent or group occurs more than one time in any constituent or compound, its definition on each occurrence is independent of its definition at every other occurrence. Thus, for example, if a group is shown to be substituted with 0 to 2 R, then such group is optionally substituted with up to two R groups and R at each occurrence is selected independently from the defined list of possible R. Additionally, if a group is shown to be substituted with $C_1$-$C_5$ R group (e.g., $C_1$-$C_5$ alkylthio), then such group is optionally substituted with $C_1$, $C_2$, $C_3$, $C_4$, or $C_5$ R groups (e.g., $C_1$, $C_2$, $C_3$, $C_4$, or $C_5$ alkylthio). Such combinations of substituents and/or variables, however, are permissible only if such combinations result in stable compounds.

In a specific embodiment, the term "about" or "approximately" means within 20%, preferably within 10%, and more preferably within 5% of a given value or range.

The yield of each of the reactions described herein is expressed as a percentage of the theoretical yield.

B. Co-Crystals, Salt, Prodrug, Derivative, and Solvate Terms and Conventions

The terms "prodrug" or "prodrug derivative" mean a covalently-bonded derivative or carrier of the parent compound or active drug substance which undergoes at least some biotransformation prior to exhibiting its pharmacological effect(s). In general, such prodrugs have metabolically cleavable groups and are rapidly transformed in vivo to yield the parent compound, for example, by hydrolysis in blood, and generally include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in *A Textbook of Drug Design and Development*, Krogsgaard-Larsen and H. Bundgaard (eds.), Gordon & Breach, 1991, particularly Chapter 5: "Design and Applications of Prodrugs"; *Design of Prodrugs*, H. Bundgaard (ed.), Elsevier, 1985; *Prodrugs: Topical and Ocular Drug Delivery*, K. B. Sloan (ed.), Marcel Dekker, 1998; *Methods in Enzymology*, K. Widder et al. (eds.), Vol. 42, Academic Press, 1985, particularly pp. 309-396; *Burger's Medicinal Chemistry and Drug Discovery*, 5th Ed., M. Wolff (ed.), John Wiley & Sons, 1995, particularly Vol. 1 and pp. 172-178 and pp. 949-982; *Pro-Drugs as Novel Delivery Systems*, T. Higuchi and V. Stella (eds.), Am. Chem. Soc., 1975; *Bioreversible Carriers in Drug Design*, E. B. Roche (ed.), Elsevier, 1987, each of which is incorporated herein by reference in their entireties.

The term "pharmaceutically acceptable prodrug" as used herein means a prodrug of a compound of the invention which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

The term "salt" means an ionic form of the parent compound or the product of the reaction between the parent compound with a suitable acid or base to make the acid salt or base salt of the parent compound. Salts of the compounds of the present invention can be synthesized from the parent compounds which contain a basic or acidic moiety by conventional chemical methods. Generally, the salts are prepared by reacting the free base or acid parent compound with stoichiometric amounts or with an excess of the desired salt-forming inorganic or organic acid or base in a suitable solvent or various combinations of solvents.

The term "pharmaceutically acceptable salt" means a salt of a compound of the invention which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. As the compounds of the present invention are useful in both free base and salt form, in practice, the use of the salt form amounts to use of the base form. Lists of suitable salts are found in, e.g., S. M. Birge et al., J. Pharm. Sci., 1977, 66, pp. 1-19, which is hereby incorporated by reference in its entirety.

The term "pharmaceutically-acceptable acid addition salt" means those salts which retain the biological effectiveness and properties of the free bases and which are not biologically or otherwise undesirable, formed with inorganic acids such as hydrochloric acid, hydrobromic acid, hydroiodic acid, sulfuric acid, sulfamic acid, nitric acid, phosphoric acid, and the like, and organic acids such as acetic acid, trichloroacetic acid, trifluoroacetic acid, adipic acid, alginic acid, ascorbic acid, aspartic acid, benzenesulfonic acid, benzoic acid, 2-acetoxybenzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, heptanoic acid, hexanoic acid, formic acid, fumaric acid, 2-hydroxyethanesulfonic acid (isethionic acid), lactic acid, maleic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, picric acid, pivalic acid, propionic acid, pyruvic acid, pyruvic acid, salicylic acid, stearic acid, succinic acid, sulfanilic acid, tartaric acid, p-toluenesulfonic acid, undecanoic acid, and the like.

The term "pharmaceutically-acceptable base addition salt" means those salts which retain the biological effectiveness and properties of the free acids and which are not biologically or otherwise undesirable, formed with inorganic bases such as ammonia or hydroxide, carbonate, or bicarbonate of ammonium or a metal cation such as sodium, potassium, lithium, calcium, magnesium, iron, zinc, copper, manganese, aluminum, and the like. Particularly preferred are the ammonium, potassium, sodium, calcium, and magnesium salts. Salts derived from pharmaceutically-acceptable organic nontoxic bases include salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins, and the like. Particularly preferred organic nontoxic bases are isopropylamine, diethylamine, ethanolamine, trimethylamine, dicyclohexylamine, choline, and caffeine.

The term "solvate" means a physical association of a compound with one or more solvent molecules or a complex of variable stoichiometry formed by a solute (for example, a compound of Formula (I)) and a solvent, for example, water, ethanol, or acetic acid. In certain instances, the solvate will be capable of isolation, for example, when one or more solvent molecules are incorporated in the crystal lattice of the crystalline solid. In general, the solvents selected do not interfere with the biological activity of the solute. Solvates encompasses both solution-phase and isolatable solvates. Representative solvates include hydrates, ethanolates, methanolates, and the like.

The term "co-crystal" means a crystalline material comprised of one or more compounds of the invention and one or more unique co-crystal formers which may include acidic, basic, or neutral molecules that are solids or liquids at room temperature. Accordingly, co-crystals encompass molecular compounds, molecular complexes, solvates, inclusion compounds, channel compounds, clathrates, and possibly other types of multi-component crystals.

The term "pharmaceutical co-crystal" means co-crystals that comprise one or more unique pharmaceutically acceptable co-crystal formers.

The compounds of the present invention as discussed below include the free base or acid thereof, their salts, co-crystals, and prodrugs and may include oxidized sulfur atoms or quaternized nitrogen atoms in their structure, although not explicitly stated or shown, particularly the pharmaceutically acceptable forms thereof. Such forms, particularly the pharmaceutically acceptable forms, are intended to be embraced by the appended claims.

C. Isomer Terms and Conventions

The term "isomers" means compounds having the same number and kind of atoms, and hence the same molecular weight, but differing with respect to the arrangement or configuration of the atoms in space. The term includes stereoisomers and geometric isomers.

The terms "stereoisomer" or "optical isomer" mean a stable isomer that has at least one chiral atom or restricted rotation giving rise to perpendicular dissymmetric planes (e.g., certain biphenyls, allenes, and spiro compounds) and can rotate plane-polarized light. Because asymmetric centers and other chemical structure exist in the compounds of the invention which may give rise to stereoisomerism, the invention contemplates stereoisomers and mixtures thereof. The compounds of the invention and their salts include asymmetric carbon atoms and may therefore exist as single stereoisomers, racemates, and as mixtures of enantiomers and diastereomers. Typically, such compounds will be prepared as a racemic mixture. If desired, however, such compounds can be prepared or isolated as pure stereoisomers, i.e., as individual enantiomers or diastereomers, or as stereoisomer-enriched mixtures. As discussed in more detail below, individual stereoisomers of compounds are prepared by synthesis from optically active starting materials containing the desired chiral centers or by preparation of mixtures of enantiomeric products followed by separation or resolution, such as conversion to a mixture of diastereomers followed by separation or recrystallization, chromatographic techniques, use of chiral resolving agents, or direct separation of the enantiomers on chiral chromatographic columns. Starting compounds of particular stereochemistry are either commercially available or are made by the methods described below and resolved by techniques well-known in the art.

The term "enantiomers" means a pair of stereoisomers that are non-superimposable mirror images of each other.

The terms "diastereoisomers" or "diastereomers" mean optical isomers which are not mirror images of each other.

The terms "racemic mixture" or "racemate" mean a mixture containing equal parts of individual enantiomers.

The term "non-racemic mixture" means a mixture containing unequal parts of individual enantiomers.

The term "geometrical isomer" means a stable isomer which results from restricted freedom of rotation about double bonds (e.g., cis-2-butene and trans-2-butene) or in a cyclic structure (e.g., cis-1,3-dichlorocyclobutane and trans-1,3-dichlorocyclobutane). Because carbon-carbon double (olefinic) bonds, C=N double bonds, cyclic structures, and the like may be present in the compounds of the invention, the invention contemplates each of the various stable geometric isomers and mixtures thereof resulting from the arrangement of substituents around these double bonds and in these cyclic structures. The substituents and the isomers are designated using the cis/trans convention or using the E or Z system, wherein the term "E" means higher order substituents on opposite sides of the double bond, and the term "Z" means higher order substituents on the same side of the double bond. A thorough discussion of E and Z isomerism is provided in J. March, *Advanced Organic Chemistry: Reactions, Mechanisms, and Structure*, 4th ed., John Wiley & Sons, 1992, which is hereby incorporated by reference in its entirety. Several of the following examples represent single E isomers, single Z isomers, and mixtures of E/Z isomers. Determination of the E and Z isomers can be done by analytical methods such as x-ray crystallography, $^1$H NMR, and $^{13}$C NMR.

Some of the compounds of the invention can exist in more than one tautomeric form. As mentioned above, the compounds of the invention include all such tautomers.

It is well-known in the art that the biological and pharmacological activity of a compound is sensitive to the stereochemistry of the compound. Thus, for example, enantiomers often exhibit strikingly different biological activity including differences in pharmacokinetic properties, including metabolism, protein binding, and the like, and pharmacological properties, including the type of activity displayed, the degree of activity, toxicity, and the like. Thus, one skilled in the art will appreciate that one enantiomer may be more active or may exhibit beneficial effects when enriched relative to the other enantiomer or when separated from the other enantiomer. Additionally, one skilled in the art would know how to separate, enrich, or selectively prepare the enantiomers of the compounds of the invention from this disclosure and the knowledge of the prior art.

Thus, although the racemic form of drug may be used, it is often less effective than administering an equal amount of enantiomerically pure drug; indeed, in some cases, one enantiomer may be pharmacologically inactive and would merely serve as a simple diluent. For example, although ibuprofen had been previously administered as a racemate, it has been shown that only the S-isomer of ibuprofen is effective as an anti-inflammatory agent (in the case of ibuprofen, however, although the R-isomer is inactive, it is converted in vivo to the S-isomer, thus, the rapidity of action of the racemic form of the drug is less than that of the pure S-isomer). Furthermore, the pharmacological activities of enantiomers may have distinct biological activity. For example, S-penicillamine is a therapeutic agent for chronic arthritis, while R-penicillamine is toxic. Indeed, some purified enantiomers have advantages over the racemates, as it has been reported that purified individual isomers have faster transdermal penetration rates compared to the racemic mixture. See U.S. Pat. Nos. 5,114,946 and 4,818,541.

Thus, if one enantiomer is pharmacologically more active, less toxic, or has a preferred disposition in the body than the other enantiomer, it would be therapeutically more beneficial to administer that enantiomer preferentially. In this way, the patient undergoing treatment would be exposed to a lower total dose of the drug and to a lower dose of an enantiomer that is possibly toxic or an inhibitor of the other enantiomer.

Preparation of pure enantiomers or mixtures of desired enantiomeric excess (ee) or enantiomeric purity are accomplished by one or more of the many methods of (a) separation or resolution of enantiomers, or (b) enantioselective synthesis known to those of skill in the art, or a combination thereof. These resolution methods generally rely on chiral recognition and include, for example, chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in *Chiral Separation Techniques: A Practical Approach* (2nd Ed.), G. Subramanian (ed.), Wiley-VCH, 2000; T. E. Beesley and R. P. W. Scott, *Chiral Chromatography*, John Wiley & Sons, 1999; and Satinder Ahuja, *Chiral Separations by Chromatography*, Am. Chem. Soc., 2000. Furthermore, there are equally well-known methods for the quantitation of enantiomeric excess or purity, for example, GC, HPLC, CE, or NMR, and assignment of absolute configuration and conformation, for example, CD ORD, X-ray crystallography, or NMR.

In general, all tautomeric forms and isomeric forms and mixtures, whether individual geometric isomers or stereoisomers or racemic or non-racemic mixtures, of a chemical structure or compound is intended, unless the specific stereochemistry or isomeric form is specifically indicated in the compound name or structure.

D. Pharmaceutical Administration and Diagnostic and Treatment Terms and Conventions The term "patient" includes both human and non-human mammals.

The term "effective amount" means an amount of a compound according to the invention which, in the context of which it is administered or used, is sufficient to achieve the desired effect or result. Depending on the context, the term effective amount may include or be synonymous with a pharmaceutically effective amount or a diagnostically effective amount.

The terms "pharmaceutically effective amount" or "therapeutically effective amount" means an amount of a compound according to the invention which, when administered to a patient in need thereof, is sufficient to effect treatment for disease-states, conditions, or disorders for which the compounds have utility. Such an amount would be sufficient to elicit the biological or medical response of a tissue, system, or patient that is sought by a researcher or clinician. The amount of a compound according to the invention which constitutes a therapeutically effective amount will vary depending on such factors as the compound and its biological activity, the composition used for administration, the time of administration, the route of administration, the rate of excretion of the compound, the duration of treatment, the type of disease-state or disorder being treated and its severity, drugs used in combination with or coincidentally with the compounds of the invention, and the age, body weight, general health, sex, and diet of the patient. Such a therapeutically effective amount can be determined routinely by one of ordinary skill in the art having regard to their own knowledge, the prior art, and this disclosure.

The term "diagnostically effective amount" means an amount of a compound according to the invention which, when used in a diagnostic method, apparatus, or assay, is sufficient to achieve the desired diagnostic effect or the desired biological activity necessary for the diagnostic method, apparatus, or assay. Such an amount would be sufficient to elicit the biological or medical response in a diagnostic method, apparatus, or assay, which may include a biological or medical response in a patient or in a in vitro or in vivo tissue or system, that is sought by a researcher or clinician. The amount of a compound according to the invention which constitutes a diagnostically effective amount will vary depending on such factors as the compound and its biological activity, the diagnostic method, apparatus, or assay used, the composition used for administration, the time of administration, the route of administration, the rate of excretion of the compound, the duration of administration, drugs and other compounds used in combination with or coincidentally with the compounds of the invention, and, if a patient is the subject of the diagnostic administration, the age, body weight, general health, sex, and diet of the patient. Such a diagnostically effective amount can be determined routinely by one of ordinary skill in the art having regard to their own knowledge, the prior art, and this disclosure.

The term "modulate" means the ability of a compound to alter the function of the glucocorticoid receptor by, for example, binding to and stimulating or inhibiting the glucocorticoid receptor functional responses.

The term "modulator" in the context of describing compounds according to the invention means a compound that modulates the glucocorticoid receptor function. As such, modulators include, but are not limited to, agonists, partial agonists, antagonists, and partial antagonists.

The term "agonist" in the context of describing compounds according to the invention means a compound that, when bound to the glucocorticoid receptor, enhances or increases the glucocorticoid receptor function. As such, agonists include partial agonists and full agonists.

The term "full agonist" in the context of describing compounds according to the invention means a compound that evokes the maximal stimulatory response from the glucocorticoid receptor, even when there are spare (unoccupied) glucocorticoid receptors present.

The term "partial agonist" in the context of describing compounds according to the invention means a compound that is unable to evoke the maximal stimulatory response from the glucocorticoid receptor, even at concentrations sufficient to saturate the glucocorticoid receptors present.

The term "antagonist" in the context of describing compounds according to the invention means a compound that directly or indirectly inhibits or suppresses the glucocorticoid receptor function. As such, antagonists include partial antagonists and full antagonists.

The term "full antagonist" in the context of describing compounds according to the invention means a compound that evokes the maximal inhibitory response from the glucocorticoid receptor, even when there are spare (unoccupied) glucocorticoid receptors present.

The term "partial antagonist" in the context of describing compounds according to the invention means a compound that is unable to evoke the maximal inhibitory response from the glucocorticoid receptor, even at concentrations sufficient to saturate the glucocorticoid receptors present.

The terms "treating" or "treatment" mean the treatment of a disease-state in a patient, and include:
(i) preventing the disease-state from occurring in a patient, in particular, when such patient is genetically or otherwise predisposed to the disease-state but has not yet been diagnosed as having it;
(ii) inhibiting or ameliorating the disease-state in a patient, i.e., arresting or slowing its development; or
(iii) relieving the disease-state in a patient, i.e., causing regression or cure of the disease-state.

General Synthetic Methods for Making Compounds of Formula (I)

The invention also provides processes for making compounds of Formula (I). In all schemes, unless specified otherwise, $R^1$, $R^2$, X, and Y in the formulas below shall have the meaning of $R^1$, $R^2$, X, and Y in the Formula (I) of the invention described hereinabove. Intermediates used in the preparation of compounds of the invention are either commercially available or readily prepared by methods known to those skilled in the art.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Experimental Examples section. Typically, reaction progress may be monitored by thin layer chromatography (TLC), if desired, and intermediates and products may be purified by chromatography on silica gel and/or by recrystallization.

Compounds of Formula (I) may be prepared by the method outlined in Scheme I.

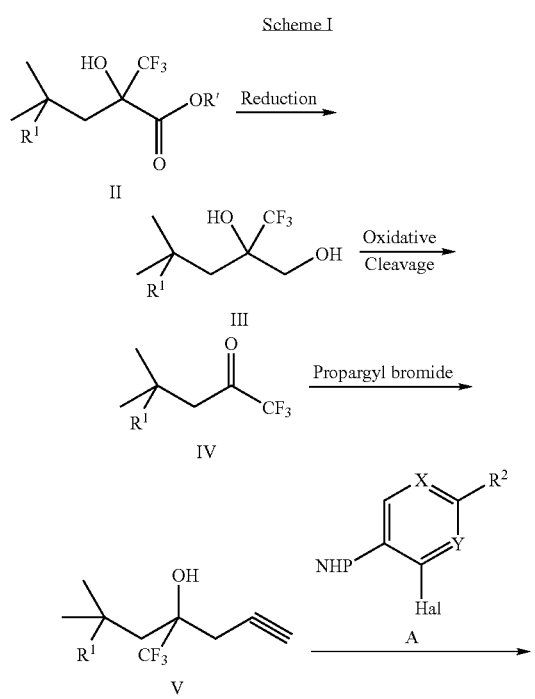

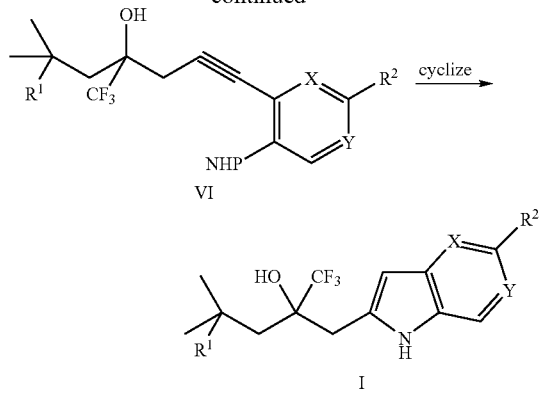

As illustrated in Scheme I, an ester intermediate of Formula (II) where R' is Me or Et, is reduced with a suitable reducing agent, such as lithium aluminum hydride, in a suitable solvent, such as THF or diethyl ether, to produce the 1,2-diol of Formula (III). Oxidative cleavage of 1,2-diols is well-known in the art and may be achieved with periodic acid or lead tetraacetate, for example, in a suitable solvent, such as methanol, to provide the ketone (IV). Reaction of ketone (IV) with a suitable alkyne, such as propargyl bromide, in a suitable solvent, in the presence of suitable metals, such as aluminum, and suitable salts, such as mercuric chloride, provides an alkyne of Formula (V). Reaction of the alkyne of Formula (V) with a an appropriately substituted heteroaryl halide (A), where P is a protecting group on the amine and A is Br or I, in a suitable solvent, in the presence of a suitable base, provides a compound of Formula (VI). Cyclization of the compound of Formula (VI), in a suitable solvent, in the presence of a suitable base, provides a compound of Formula (I).

Compounds of Formula (I) may also be prepared by the method outlined in Scheme II.

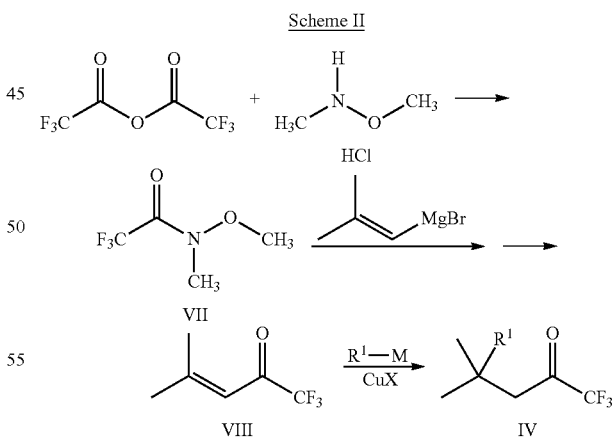

In this approach, trifluoroacetic anhydride and N,O-dimethylhydroxylamine hydrochloride are coupled under basic conditions to afford trifluoroacetamide (VII). The Weinreb amide (VII) is reacted with a dimethyl vinyl magnesium bromide to afford the trifluoromethylenone intermediate (VII). The trifluoromethylenone intermediate (VII) is treated with an organocopper reagent, derived from a Grignard or organolithium reagent by treating with a copper salt, to afford the 1,4-addition product (IV). This trifluoro ketone intermediate (IV) is converted to a compound of Formula (I) by the steps shown in Scheme I.

Compounds of Formula (I) may be also be prepared by the method outlined in Scheme III.

Scheme III

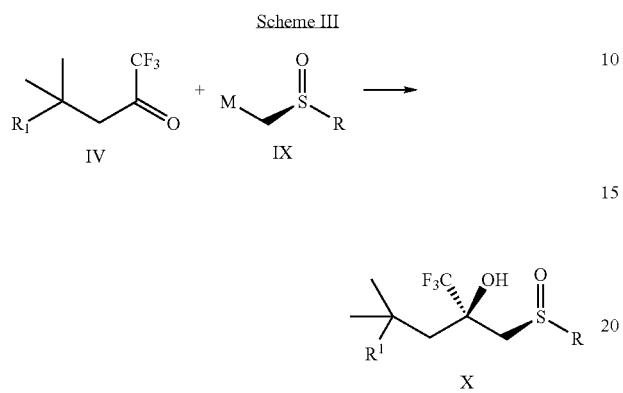

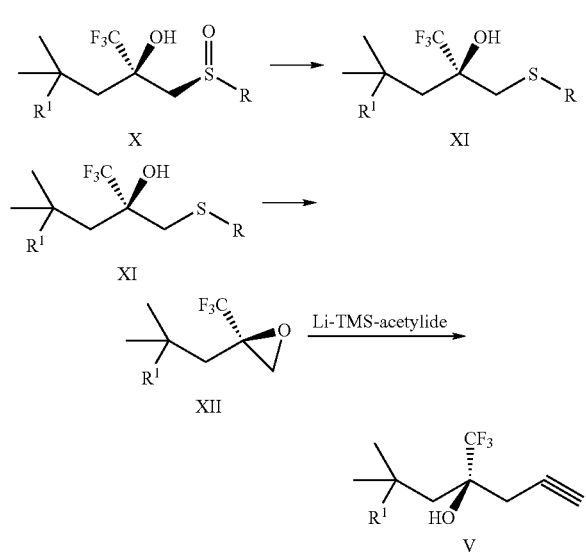

As illustrated in Scheme III reacting the intermediate of Formula (IV) with a chiral sulfoxide anion source (IX) in the presence of a suitable base, such as LDA, in a suitable solvent, such as THF, provides a compound of Formula (X). Reduction of the sulfoxide of Formula (X) with suitable reducing agents affords the compound of Formula (XI). Reaction of the compound of Formula (XI) with reagents such as trimethyloxonium tetrafluoroborate in a suitable solvent, such as dichloromethane, in the presence of a suitable base, such as potassium carbonate, provides epoxide of Formula (XII). The analogous reaction can be performed to make the isomeric epoxide. Reaction of epoxide (XII) with a suitable nucleophile, such as lithium trimethylsilylacetylide, in a suitable solvent, provides an alkyne of Formula (V) which is then converted to a compound of Formula (I) by the method outlined in Scheme I.

The appropriately substituted heteroaryl halide (A) intermediate may be prepared by the method shown in Scheme IV.

Scheme IV

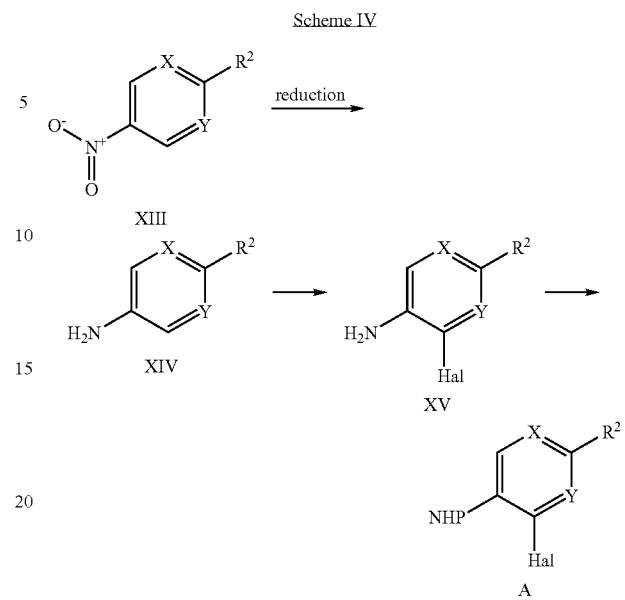

As outlined in Scheme IV, the starting nitro compound (XIII) is reduced under standard reaction conditions and catalyst, to provide the corresponding amine of Formula (XIV). Halogenation of the intermediate of Formula (XIV) using a suitable reagent, in a suitable solvent, provides a halogenated compound of Formula (XV). Protecting the amino group of compound of Formula (XV) with a suitable protecting group, under standard conditions, provides the desired substituted intermediate of Formula (A).

Making seed crystals useful for making, for example, co-crystal compounds within the scope of the invention can be made by any method known by one of skill in the art for making crystalline organic compounds. Evaporative methods involve selecting solvents or solvent mixtures for optimizing crystal growth conditions to dissolve the compound, allowing for slow evaporation of the solvent, and possibly increasing the number of nucleation sites by scratching the exposed surfaces of the glass vessel. Liquid and vapor diffusion methods generally require finding two solvent systems in which the compound is soluble in one system but insoluble in the other (the two solvent systems are immiscible or nearly immiscible for liquid diffusion and miscible for vapor diffusion). Crystals grow at the interface between the solutions in liquid diffusion methods. Vapor diffusion requires dissolving the compound in a solvent system in a container, sealing this container inside a larger container that contains another solvent system, and allowing vapor from the solvent of the larger container to diffuse into the solution in the inner container, causing the compound to crystallize. Gel diffusion methods involve greatly decreasing the rate at which the reactants combine by making the reactants diffuse through a gel barrier. Thermal gradient methods include slow cooling of sealed, saturated solutions, refluxing of saturated solutions, and sublimation.

In order that this invention be more fully understood, the following examples are set forth. These examples are for the purpose of illustrating embodiments of this invention, and are not to be construed as limiting the scope of the invention in any way since, as recognized by one skilled in the art, particular reagents or conditions could be modified as needed for individual compounds. Starting materials used are either commercially available or easily prepared from commercially available materials by those skilled in the art.

Methods of making the compounds of the invention are found, for example, in U.S. Application Ser. Nos. 61/183,601; 61/183,606; 61/183,607; and 61/183,610, each entitled Stereoselective Synthesis of Certain Trifluoromethyl-Substituted Alcohols and filed Jun. 3, 2009; U.S. Application Ser. No. 60/183,615, entitled Process for Optimizing the Particle Size of an Active Pharmaceutical Ingredient by Crystallization, filed Jun. 3, 2009; and U.S. Application Ser. No. 61/059,388, filed Jun. 6, 2008, each of which is incorporated by reference in their entireties.

EXPERIMENTAL EXAMPLES

Example 1

Preparation of (6-Methanesulfonyl-4-iodopyridin-3-yl)carbamic acid tert-butyl ester

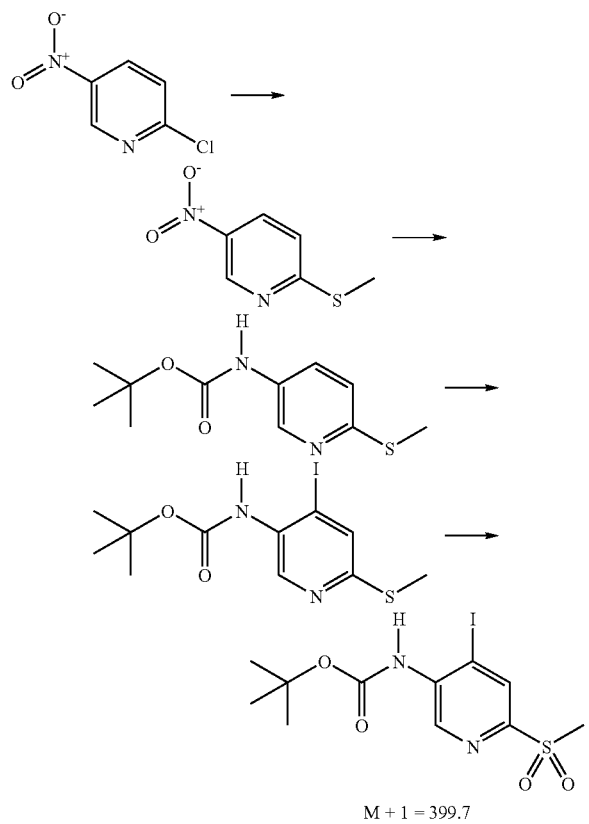

M + 1 = 399.7

The sodium salt of methylthiol (as 15% solution in water, 70 g, 150 mmol), 2-chloro-5-nitropyridine (20 g, 126 mmol), and tetrahydrofuran (THF; 300 mL) were combined in a 500 mL Erlenmeyer flask equipped with a stir bar. The resulting mixture was stirred at normal room temperature for 24 hours. The reaction mixture was diluted by pouring into 750 mL of diethyl ether and 200 mL of 1N NaOH. The layers were separated and the organic was washed with 200 mL of 1N NaOH. The organic was concentrated, using two 50 mL portions of methanol as a chaser. The yellow paste was redissolved in 100 mL of methanol and the product was precipitated with 500 mL of 1N ammonium chloride solution. The yellow 2-methylsulfanyl-5-nitropyridine (20.9 g, 97%) was collected by filtration and washed with two 200 mL portions of water, dried in a stream of air, and used without further manipulation.

2-Methylsulfanyl-5-nitropyridine (20.9 g, 123 mmol), di-tert-butyl dicarbonate (39.9 g, 183 mmol), and Pd (10% on carbon, 7.5 g, 7.0 mmol) were mixed in a hydrogenation bottle in 250 mL of methanol and shaken at 50 psi for 24 hours. The mixture was filtered on CELITE® filter aid using methanol to wash. Another 10 g of di-tert-butyl dicarbonate was added to the filtrate and it was stirred for 16 hours. The solution was concentrated using three 50 mL portions of methylene chloride as a chaser. The yellow paste was dissolved in 70 mL of methylene chloride, and with stirring, 350 mL of hexanes was added. Within a few minutes a fine microcrystalline material precipitated. After stirring for 40 minutes, the solid was collected by filtration and the solid was washed two 30 mL portions of hexanes. The solid was dried in a stream of air (18.6 g). The filtrate was concentrated to a yellow paste, redissolved in about 20 mL of methylene chloride, and 250 mL of hexanes were added to form a second crop of product. This solid was collected by filtration and washed with two 30 mL portions of hexanes to give 3.4 grams of the desired product. The two crops were combined and dried in vacuo at 80° C. for 1 hour to give (6-methylsulfanylpyridin-3-yl)carbamic acid tert-butyl ester (22 g, 75%).

(6-Methylsulfanylpyridin-3-yl)carbamic acid tert-butyl ester (22.0 g, 91.5 mmol) was suspended in 350 mL of anhydrous diethyl ether in a 1 L flask equipped with a stir bar. The system was sealed with a septum and flushed with a flow of argon for 10 minutes and sealed under argon. TMEDA (34.5 mL, 229 mmol) was added by syringe and the resulting mixture was cooled to −78° C. n-Butyllithium (91.5 mL, 229 mmol) was added and the resulting mixture was stirred for 15 minutes at −78° C. The mixture was stirred at 0° C. for 3 hours and cooled to −78° C. again. A second round bottom flask was charged with iodine (34.8 g, 137.0 mmol), sealed with a septum, and 60 mL of anhydrous THF was added. The iodine was dissolved by sonicating for 2 minutes. This solution was transferred onto the mixture prepared above by double-ended needle and positive argon pressure. The reaction mixture was stirred at −78° C. for 30 minutes, at which time the dry ice/acetone bath was removed and the mixture was stirred at room temperature over the next 2 hours. The reaction mixture was diluted with 350 mL of saturated aqueous ammonium chloride solution. 20 g of sodium thiosulfate was added with another 200 mL of water. The layers were thoroughly mixed by stirring for 10 minutes and then separated. The aqueous layer was washed with 500 mL of diethyl ether and the organic layers were combined and dried over sodium sulfate, decanted, and concentrated in vacuo. The orange residue was purified on silica to give 6-methylsulfanyl-4-iodopyridin-3-yl)carbamic acid tert-butyl ester (8.0 g, 24%) as a thick oil.

To a solution of (6-methylsulfanylpyridin-3-yl)carbamic acid tert-butyl ester (8.0 g, 21.8 mmol) in 150 mL of MeCN and 50 mL of water was added NaIO$_4$ (11.8, 55.0 mmol) followed by the addition of ruthenium (III) chloride (RuCl$_3$; 0.275 g, 1.3 mmol) and the reaction mixture was stirred at normal room temperature for 75 minutes. The reaction mixture was diluted with 350 mL of diethyl ether and 200 mL of water, thoroughly mixed, and layers separated. The aqueous layer was washed with two 200 mL portions of diethyl ether. The organic layers were combined and dried over sodium sulfate, decanted, and concentrated in vacuo to obtain a blackish paste. The blackish paste was redissolved in 100 mL of diethyl ether and filtered through a cake of CELITE® filter aid. The filtrate was concentrated in vacuo and redissolved in 50 mL of methylene chloride. This solution was slowly drained through a 40 g SiO₂ cartridge using a total of 250 mL of methylene chloride in 20 mL aliquots. The nearly colorless filtrate was concentrated in vacuo down to about 20 mL and the product was precipitated with hexanes (120 mL). The white solid was collected by filtration and dried. The filtrate was concentrated in vacuo and redissolved in 10 mL of methylene chloride and a second crop of product was isolated by precipitating with 75 mL of hexanes. The two crops were combined to give (6-methanesulfonyl-4-iodopyridin-3-yl)carbamic acid tert-butyl ester as a white solid (6.1 g, 70%), MS (ES⁺) m/z 399.7 [M+H]⁺.

Example 2

Preparation of (6-Ethanesulfonyl-4-iodopyridin-3-yl)carbamic acid tert-butyl ester

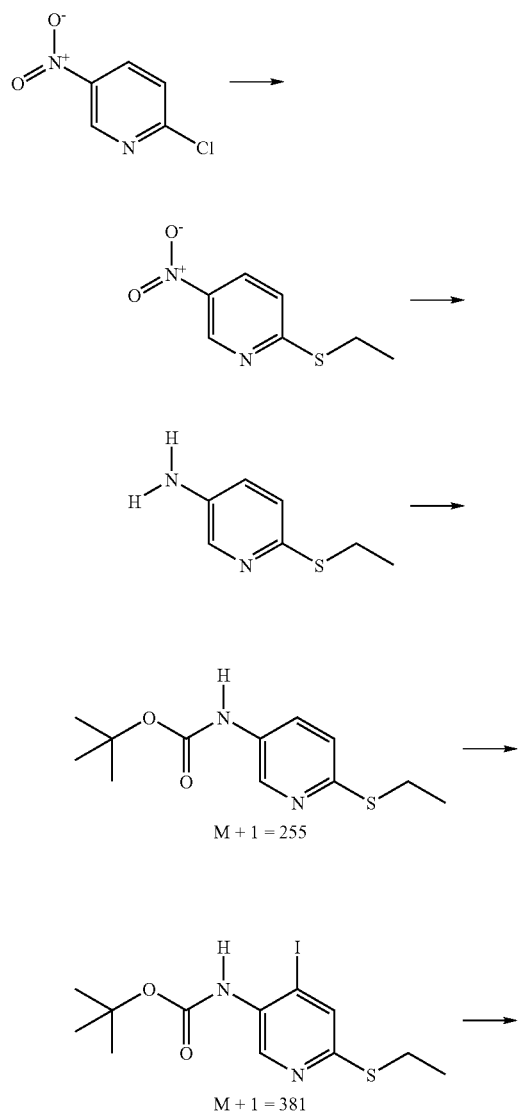

-continued

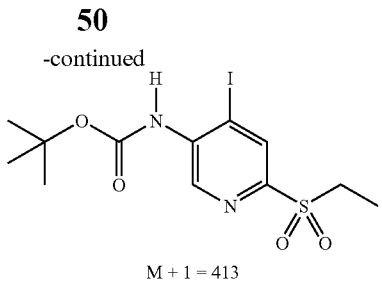

M + 1 = 413

To a stirred mixture of sodium ethanethiolate (15.9 g; 0.189 mol) in 250 mL of THF and 100 mL of water at 0° C.-5° C. was added 5-nitro-2-chloropyridine (25.0 g; 0.158 mol). After 2 hours, the mixture was poured into 1200 mL of ice water, stirred for 15 minutes, and filtered. The solid was washed with water and dried in vacuo to provide 2-ethylsulfanyl-5-nitropyridine which was used without additional purification (28.1 g; 96%).

A mixture of 2-ethylsulfanyl-5-nitropyridine (57.4 g) and 10% Pd on carbon (10.0 g; wet) in 1000 mL of ethanol was hydrogenated at 50 psi for 20 hours and filtered over CELITE® filter aid. The solution of 6-ethylsulfanylpyridin-3-ylamine was used without additional purification.

A solution of 6-ethylsulfanylpyridin-3-ylamine (48.1 g; 0.312 mol) in 1000 mL of ethanol (from the above reaction) and di-tert-butyl dicarbonate (85.9 g; 0.393 mol) was stirred at normal room temperature for 18 hours. The volatiles were removed in vacuo and the solid (6-ethylsulfanylpyridin-3-yl)carbamic acid tert-butyl ester was used without further purification (79.4 g; 100%), MS (ES⁺) m/z 255 [M+H]⁺.

To (6-ethylsulfanylpyridin-3-yl)carbamic acid tert-butyl ester (27.6 g; 0.108 mol) and N,N,N',N'-tetramethylethylenediamine (27 mL; 0.180 mol) in 300 mL diethyl ether at −78° C. was added dropwise n-butyllithium (100 mL of a 2.5 M solution in hexanes; 0.25 mol). The mixture was stirred mechanically for 15 minutes, warmed to 0° C.-5° C., stirred for 3 hours, cooled to −78° C. and iodine (60.6 g; 0.239 mol) in 300 mL of diethyl ether was added dropwise. The mixture was slowly warmed to room temperature, stirred overnight, and quenched with aqueous ammonium chloride and diethyl ether. The organic layer was washed with aqueous sodium metabisulfite, water, and brine, and dried over magnesium sulfate (MgSO₄). Removal of the volatiles in vacuo provided a residue which was purified by CombiFlash chromatography using ethyl acetate and hexanes as the eluent. The product-rich fractions were concentrated in vacuo to provide (6-ethylsulfanyl-4-iodopyridin-3-yl)carbamic acid tert-butyl ester (27.7 g; 67%), MS (ES⁺) m/z 381 [M+H]⁺.

A mixture of (6-ethylsulfanyl-4-iodopyridin-3-yl)carbamic acid tert-butyl ester (27.6 g; 72.5 mmol), NaIO₄ (34.1 g; 159 mmol), and ruthenium (III) chloride (0.753 g; 3.62 mmol) in 450 mL of acetonitrile and 210 mL of water was stirred at room temperature for 18 hours and diluted with diethyl ether and aqueous sodium chloride. The organic layer was washed with water and brine, dried over magnesium sulfate, treated with decolorizing charcoal, and filtered over CELITE® filter aid. Removal of the volatiles in vacuo provided (6-ethanesulfonyl-4-iodopyridin-3-yl)carbamic acid tert-butyl ester as a solid (25.4 g; 84%), MS (ES⁺) m/z 413 [M+H]⁺.

The following compounds were prepared analogously: 6-propanesulfonyl-4-iodopyridin-3-yl)carbamic acid tert-butyl ester and 6-(propane-2-sulfonyl)-4-iodopyridin-3-yl)

carbamic acid tert-butyl ester; 6-methanesulfonyl-4-iodopyridin-3-yl)carbamic acid tert-butyl ester can also be prepared using this procedure.

Example 3

Preparation of (6-Ethanesulfinyl-4-iodopyridin-3-yl)carbamic acid tert-butyl ester

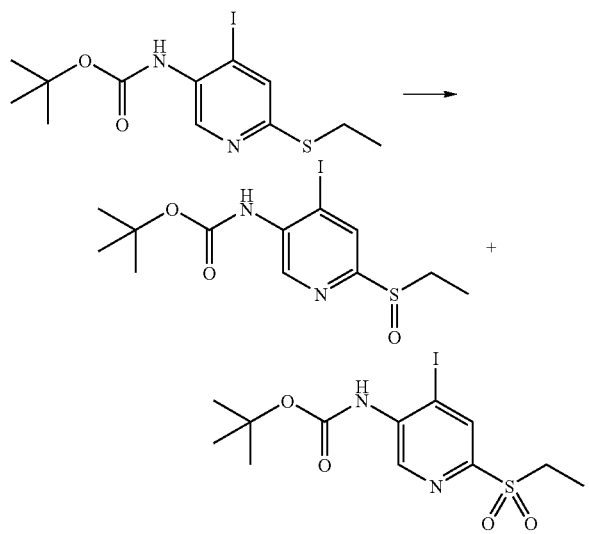

A mixture of (6-ethylsulfanyl-4-iodopyridin-3-yl)carbamic acid tert-butyl ester (8.7 g; 22.9 mmol) and $NaIO_4$ (12.2 g; 57.2 mmol) was stirred at room temperature in 175 mL of acetonitrile and 53 mL of water for 15 minutes. Ruthenium (III) chloride (0.322 g; 1.6 mmol) was added at room temperature and the mixture stirred for an additional 15 minutes. The mixture was diluted with water and extracted with dichloromethane ($CH_2Cl_2$). The combined extracts were dried over magnesium sulfate, filtered, and concentrated in vacuo. The residue was purified by Flash Chromatography to give (6-ethylsulfanyl-4-iodopyridin-3-yl)carbamic acid tert-butyl ester (4.5 g, 52%), (6-ethylsulfinyl-4-iodopyridin-3-yl) carbamic acid tert-butyl ester (1.7 g, 18%), and (6-ethylsulfonyl-4-iodopyridin-3-yl)carbamic acid tert-butyl ester (1.8 g, 20%).

Example 4

Preparation of (4-Bromo-2-methanesulfonylpyrimidin-5-yl)carbamic acid tert-butyl ester

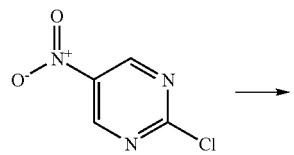

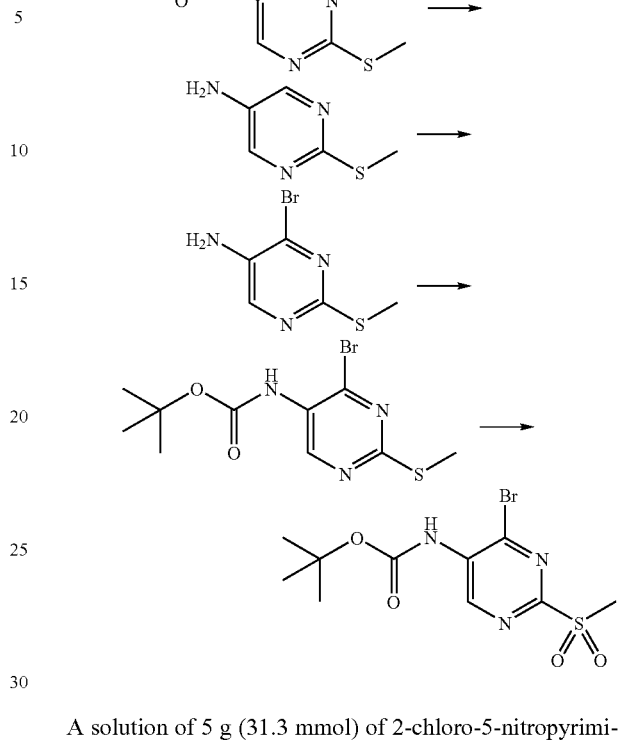

A solution of 5 g (31.3 mmol) of 2-chloro-5-nitropyrimidine in 50 mL of THF was cooled to 0° C. under nitrogen. 2.26 g (32.3 mmol) of sodium thiomethoxide was added. The reaction was stirred at room temperature for 24 hours. The reaction was monitored by LCMS indicating formation of desired product. The mixture was diluted with 250 mL of diethyl ether and a solid precipitated. The solid was removed by filtration and rinsed with dichloromethane. The filtrate was concentrated in vacuo to afford 5.3 g (99%) of 2-methylsulfanyl-5-nitropyrimidine.

A solution of 5 g (29.2 mmol) of 2-methylsulfanyl-5-nitropyrimidine in 200 mL of absolute ethanol and 120 mL of glacial acetic acid was added 16.31 g (292 mmol) of iron powder and the mixture was heated in an oil bath maintained at 80° C. for 2 hours. The reaction was diluted with 250 mL of ethyl acetate and filtered through CELITE® filter aid. The filtrate was washed with two portions of 100 mL of water, and the pH of the organic layer was adjusted by adding saturated aqueous sodium carbonate solution until the pH was 8. The organic layer washed with brine, dried over sodium sulfate, and concentrated in vacuo to afford 2.1 g (51%) of 2-methylsulfanylpyrimidin-5-ylamine.

A stirred solution of 2.0 g (14.2 mmol) of 2-methylsulfanylpyrimidin-5-ylamine in 50 mL of dichloromethane and 10 mL of methanol was cooled in an ice bath. 6.08 g (15.6 mmol) of benzyltrimethylammonium tribromide was added in portions over a period of 10 minutes. The mixture was stirred at 0° C. for 15 minutes and then at room temperature for 3 minutes. The mixture was quenched with saturated aqueous sodium bicarbonate solution until the pH was 8. The organic layer separated and was removed. The aqueous layer was extracted with two 200 mL portions of ethyl acetate. The organic layers were combined, washed with water and brine, dried over sodium sulfate, and concentrated in vacuo. The crude mixture was absorbed onto silica gel and chromatographed on silica gel using ethyl acetate-hexanes to afford 150 mg (5%) 4-bromo-2-methylsulfanylpyrimidin-5-ylamine.

A solution of 150 mg (0.68 mmol) of 4-bromo-2-methylsulfanylpyrimidin-5-ylamine in 1.5 mL of THF was added 1.5 mL (1.5 mmol) of 1N sodium bis(trimethylsilyl)amide solution in THF at 0° C. dropwise. After stirring the black solution for 15 minutes, a solution of 149 mg (0.68 mmol) of di-tert-butyldicarbonate in 0.5 mL of THF was added. The reaction was stirred at 0° C. for 90 minutes. 13 mL of 0.2 N aqueous HCl solution and 13 mL of ethyl acetate were added and the layers were separated. The aqueous layer was extracted with two 250 mL portions of ethyl acetate. The combined organic layers were dried over magnesium sulfate and concentrated in vacuo to afford 218 mg (100%) of (4-bromo-2-methylsulfanylpyrimidin-5-yl)carbamic acid tert-butyl ester.

A mixture of 218 mg (0.68 mmol) of (4-bromo-2-methylsulfanylpyrimidin-5-yl)carbamic acid tert-butyl ester, 364 mg (1.7 mmol) of sodium periodate, and 7 mg (0.03 mmol) of ruthenium (III) chloride in 4 mL of acetonitrile and 1.7 mL of water was stirred at room temperature overnight. The reaction was diluted with 50 mL of diethyl ether and filtered over CELITE® filter aid. 20 mL of water was added to the filtrate, and layer was separated. The organic layer was washed brine, dried over magnesium sulfate, and filtered and concentrated in vacuo to yield 125 mg (52%) of (4-bromo-2-methanesulfonylpyrimidin-5-yl)carbamic acid tert-butyl ester.

Example 5

Preparation of N-(2-Bromo-6-methanesulfonylpyridin-3-yl)-2,2,2-trifluoroacetamide

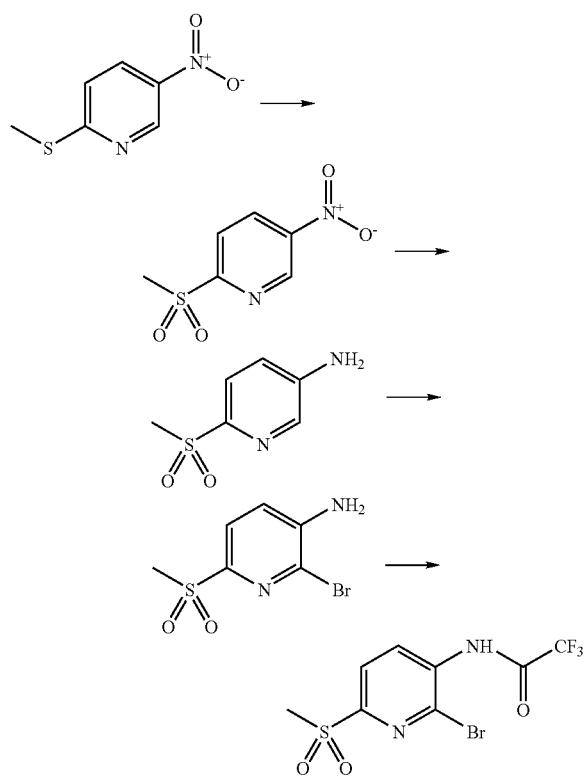

A solution of 620 mg (3.64 mmol) of 2-methylsulfanyl-5-nitropyridine in 33 mL of MeCN and 9 mL of water was added 2.34 g (10.9 mmol) of sodium periodate followed by the addition of 15 mg (0.07 mmol) of ruthenium (III) chloride and the reaction was stirred at room temperature for 16 hours. The solids were filtered and the filtrate was diluted with 50 mL of water, extracted with 150 mL of ethyl acetate, dried over magnesium sulfate, filtered, and concentrated in vacuo. The grey solid was purified by filtration through a silica column with DCM to afford 693 mg (94%) of 2-methanesulfonyl-5-nitropyridine.

A suspension of 241 mg (0.34 mmol) of 20% of Pearlman's catalyst on carbon and 693 mg (3.43 mmol) of the 2-methanesulfonyl-5-nitropyridine in 15 mL of MeOH and 3 mL of ethyl acetate was stirred under an atmosphere of hydrogen for 3 hours. The solution was filtered and concentrated. The crude mixture was further purified by filtration through a silica column with ethyl acetate to afford 510 mg (86%) of 6-methanesulfonylpyridin-3-ylamine.

A solution of 510 mg (2.96 mmol) of 6-methanesulfonylpyridin-3-ylamine in 1.25 mL of AcOH was added a solution of 0.15 mL (2.96 mmol) of bromine in 0.5 mL of AcOH at room temperature dropwise. The resulting slurry was stirred for 1 hour. The reaction was carefully basified to pH=10 with 6 M NaOH. The solution was then extracted with two 150 mL portions of dichloromethane, dried with magnesium sulfate, filtered, and concentrated in vacuo. The crude mixture showed a 3:1 mixture of product:dibromo product by NMR. These two products were separated by silica chromatography (hexanes/EtOAc) to afford 294 mg (40%) of 2-bromo-6-methanesulfonylpyridin-3-ylamine.

A solution of 5.0 g (19.9 mmol) of 2-bromo-6-methanesulfonylpyridin-3-ylamine in 100 mL of dichloromethane at room temperature was added 3.37 mL (23.9 mmol) of trifluoroacetic anhydride. The reaction was stirred for 30 minutes. The solvent was evaporated to give a pink solid. Water was added and the compound was collected via suction filtration to afford 6.7 g (97%) of N-(2-Bromo-6-methanesulfonylpyridin-3-yl)-2,2,2-trifluoroacetamide.

Example 6

Preparation of 1,1,1-trifluoro-4-(5-fluoro-2-methylphenyl)-4-methylpentan-2-one

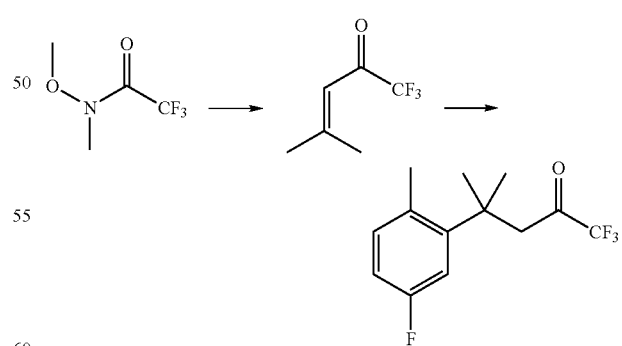

A 3 L 2-neck round bottom flask was equipped with a stir bar, one neck was sealed with a rubber septum, and the second neck was fitted with a 500 mL graduated dropping funnel. The system was flushed with argon for 30 minutes via a needle inlet through the lower neck up through the open dropping funnel. The system was sealed under slow argon flow. 2-methyl-1-propenylmagnesium bromide (0.5 M in THF, 1220 mL, 610 mmol, 1.1 equiv.) was added via cannula to the addition funnel in two 500 mL aliquots followed by a 220 mL aliquot followed by a 50 mL anhydrous THF wash of the addition funnel. The system was then immersed in an ice bath at 0° C. for 1 hour. 2,2,2-Trifluoro-N-methoxy-N-methylacetamide (86.4 g, 550 mmol, 1.0 equiv.) in 100 mL of THF was added dropwise, with stirring, over 90 minutes. After the addition was complete, the reaction was stirred for another 30 minutes. The addition funnel was charged with 500 mL of cold concentrated HCl. HCl was added dropwise over a 30 minute period while keeping the internal temperature below 15° C. Once the addition is complete, the entire mixture is poured into stirring 6N HCl (1000 mL). The resulting solution was diluted with 750 mL of diethyl ether and the layers were separated. The aqueous layer was washed with two 500 mL portions of diethyl ether. The organic layers were combined and washed with 750 mL of 1N HCl. The pH of the aqueous layer was monitored to be <1. The organic layers were dried over magnesium sulfate, filtered, and concentrated in vacuo on the rotovap while maintaining the bath temperature at 20° C. The distillate was removed from the collection flask and the removal of solvent was continued until no more condensed. The product was an orange liquid in the distillation flask (about 47 g) which is poured onto sodium sulfate (7.5 g). The distillate was dried over sodium sulfate and concentrated in vacuo on the rotovap as before to yield another 15 g of a light yellow liquid which is added to the first batch. Repeating again the distillate drying and concentrating in vacuo provided another 2.6 g of liquid. The combined 1,1,1-trifluoro-4-methylpent-3-en-2-one (total of 65 g, contains 20% wt. THF, 63%) was stored at room temperature over sodium sulfate.

To a slurry of 1,1,1-trifluoro-4-methylpent-3-en-2-one (49.5 g, 0.325 mol) and copper (I) iodide (61.9 g, 0.325 mol) in 700 mL of anhydrous diethyl ether at 0° C. was added a solution of 2-methyl-5-fluorophenyl magnesium bromide (0.5 M in THF, 706 mL, 0.353 mol) dropwise over 1.5 hours. The mixture was warmed to room temperature and stirred for a total of 18 hours. The reaction was quenched by addition of 500 mL of cold saturated ammonium chloride (NH₄Cl) solution and the layers were separated. The aqueous layer was extracted with two 300 mL portions of diethyl ether. The combined organic fractions were washed with 300 mL of saturated ammonium chloride solution, three 300 mL portions of water and one 200 mL portion of brine, dried over magnesium sulfate, filtered, and concentrated in vacuo. Purification by column chromatography with silica gel (eluted with hexanes) afforded 1,1,1-trifluoro-4-(5-fluoro-2-methylphenyl)-4-methylpentan-2-one (68.1 g, 80%).

The following compounds were prepared analogously:
1,1,1-trifluoro-4-methyl-4-(2-methylsulfanylphenyl)pentan-2-one;
1,1,1-trifluoro-4-methyl-4-(3-fluoro-2-methylsulfanylphenyl)pentan-2-one;
1,1,1-trifluoro-4-methyl-4-(4-fluoro-2-methylsulfanylphenyl)pentan-2-one;
1,1,1-trifluoro-4-methyl-4-(5-fluoro-2-methylsulfanylphenyl)pentan-2-one;
1,1,1-trifluoro-4-methyl-4-(4-chloro-2-methylsulfanylphenyl)pentan-2-one;
1,1,1-trifluoro-4-methyl-4-(5-chloro-2-methylsulfanylphenyl)pentan-2-one;
4-(3-bromophenyl)-1,1,1-trifluoro-4-methylpentan-2-one;
4-(2-bromophenyl)-1,1,1-trifluoro-4-methylpentan-2-one;
1,1,1-trifluoro-4-(5-fluoro-2-methoxyphenyl)-4-methylpentan-2-one;
4-(5-bromo-2-methoxyphenyl)-1,1,1-trifluoro-4-methylpentan-2-one;
4-(5-bromo-2-fluorophenyl)-1,1,1-trifluoro-4-methylpentan-2-one;
1,1,1-trifluoro-4-methyl-4-(4-fluoro-2-methylphenyl)pentan-2-one;
1,1,1-trifluoro-4-methyl-4-(2-methylphenyl)pentan-2-one;
4-Benzo[b]thiophen-7-yl-1,1,1-trifluoro-4-methylpentan-2-one;
4-(2-1,3-Dioxinan-2-ylphenyl)-1,1,1-trifluoro-4-methylpentan-2-one;
4-(2-1,3-Dioxinan-2-yl-3-fluorophenyl)-1,1,1-trifluoro-4-methylpentan-2-one;
4-(2-1,3-Dioxinan-2-yl-4-fluorophenyl)-1,1,1-trifluoro-4-methylpentan-2-one;
4-(2-1,3-Dioxinan-2-yl-5-fluorophenyl)-1,1,1-trifluoro-4-methylpentan-2-one;
4-(2-1,3-Dioxinan-2-yl-4-methylphenyl)-1,1,1-trifluoro-4-methylpentan-2-one;
4-(2-1,3-Dioxinan-2-yl-5-methylphenyl)-1,1,1-trifluoro-5-methylpentan-2-one;
4-(4-Chloro-2-1,3-Dioxinan-2-ylphenyl)-1,1,1-trifluoro-4-methylpentan-2-one; and
1,1,1-trifluoro-4-methyl-4-(2-bromo-5-fluorophenyl)pentan-2-one.

Example 7

Preparation of 4-(5-Chloro-2,3-dihydrobenzofuran-7-yl)-1,1,1-trifluoro-4-methylpentan-2-one

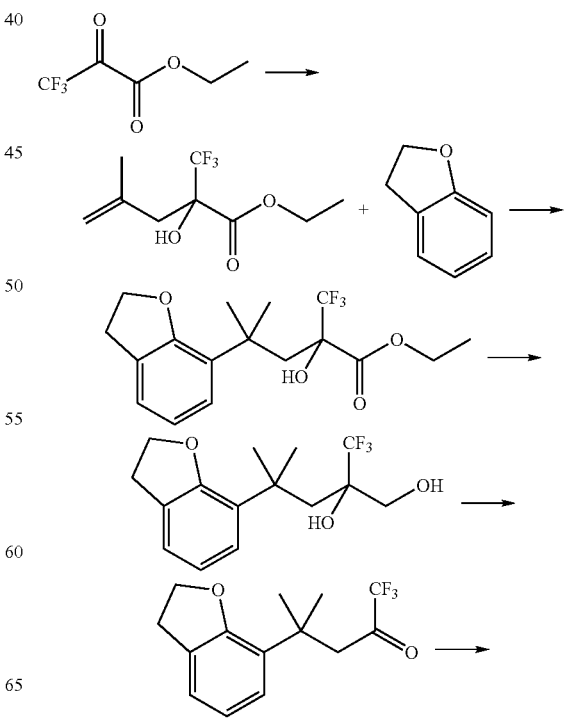

-continued

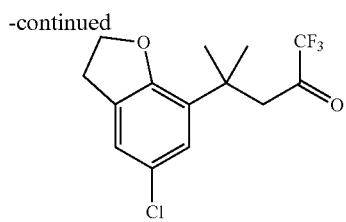

A solution of ethyl trifluoropyruvate (125 g, 0.734 mol) in 2.0 L of THF was treated with methylallyl magnesium chloride (0.5 M in THF, 1.90 L, 0.954 mol) over 4 hours while the internal temperature was maintained below −60° C. The reaction mixture was allowed to reach room temperature overnight, concentrated in vacuo to remove THF, quenched with 1 L of saturated ammonium chloride solution, and extracted with three 1 L portions of diethyl ether. The combined organic phases were washed with 100 mL of brine, dried over magnesium sulfate, filtered, and concentrated in vacuo. Vacuum distillation at 60 mmHg afforded 100.1 g of 2-hydroxy-4-methyl-2-trifluoromethylpent-4-enoic acid ethyl ester as a clear oil (b.p. 97° C.-103° C., 60%).

A solution of 2-hydroxy-4-methyl-2-trifluoromethylpent-4-enoic acid ethyl ester (100 g, 442 mmol) and 2,3-dihydrobenzofuran (57.7 g, 480 mmol) in 500 mL of dichloroethane was treated with $AlCl_3$ (87.8 g, 660 mmol) while maintaining the internal temperature below 10° C. The reaction was allowed to warm to room temperature overnight and quenched with 1 L of cold 1 N HCl. The mixture was then extracted with three 1 L portions of ethyl acetate. The combined organic layers were washed with 1 L of saturated aqueous sodium bicarbonate solution, 1 L of brine, dried over magnesium sulfate, filtered, and concentrated in vacuo. The residue was purified on $SiO_2$ (10% diethyl ether in hexanes). The resulting solid was recrystallized from hot hexanes to afford 39.5 g of 4-(2,3-dihydrobenzofuran-7-yl)-2-hydroxy-4-methyl-2-trifluoromethylpentanoic acid ethyl ester as a white solid (26%).

A suspension of $LiAlH_4$ (4.52 g, 119 mmol) in 230 mL of THF was treated with a solution of 4-(2,3-dihydrobenzofuran-7-yl)-2-hydroxy-4-methyl-2-trifluoromethylpentanoic acid ethyl ester (27.5 g, 79.4 mmol) in 40 mL of THF at 0° C. over 30 minutes. After stirring overnight, the reaction was cooled to 0° C., quenched with 3 mL of water, and treated with 3 mL of 4 M NaOH solution. After 10 minutes, the mixture was treated with additional 18 mL portion of water and the resulting mixture was warmed to room temperature for 4 hours. The mixture was filtered and the filter cake was washed with five 100 mL portions of diethyl ether. The filtrate was concentrated in vacuo to give 24.0 g of 4-(2,3-dihydrobenzofuran-7-yl)-4-methyl-2-trifluoromethylpentane-1,2-diol as an oil (99%).

A solution of 4-(2,3-dihydrobenzofuran-7-yl)-4-methyl-2-trifluoromethylpentane-1,2-diol (24.0 g, 78.9 mmol) and $NaIO_4$ (84.3 g, 394 mmol) in 360 mL of methanol was stirred at room temperature overnight. The resulting mixture was filtered through pad of CELITE® filter aid and the filter cake was washed with three 100 mL portions of methanol. The filtrate was concentrated in vacuo, taken up in hexanes, filtered again, and concentrated in vacuo to give 21.4 g of 4-(2,3-dihydrobenzofuran-7-yl)-1,1,1-trifluoro-4-methylpentan-2-one as colorless oil (100%), which was used without purification.

A solution of 4-(2,3-dihydrobenzofuran-7-yl)-1,1,1-trifluoro-4-methylpentan-2-one (20.8 g, 76.2 mmol) in 200 mL of acetic acid was treated with a solution of chlorine gas in acetic acid (~1.19 M). The reaction was monitored by $^1$H-NMR. The mixture was quenched with 500 mL of water and solid sodium bicarbonate (~500 g) was added carefully during 1 hour. The mixture was poured onto 500 mL of ethyl acetate. The phases were separated and the aqueous layer was extracted with three 500 mL portions of ethyl acetate. The combined organic layers were washed with two 100 mL portions of brine, dried over magnesium sulfate, filtered, and concentrated in vacuo to afford 23.4 g of 4-(5-chloro-2,3-dihydrobenzofuran-7-yl)-1,1,1-trifluoro-4-methylpentan-2-one (100%), which was used without purification.

Example 8

Preparation of 6-(5-Fluoro-2-methylphenyl)-6-methyl-4-trifluoromethylhept-1-yn-4-ol

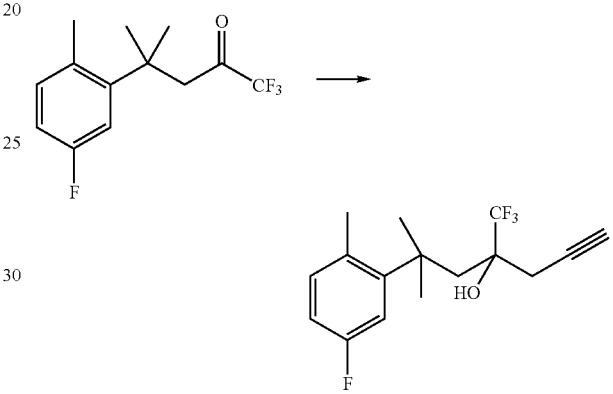

Aluminum foil (324 mg, 12 mmol) and mercuric chloride (5.0 g, 0.02 mmol) were added to THF (6 mL) and vigorously stirred for 1 hour. Propargyl bromide (1.34 mL, 80% in toluene, 12 mmol) in 6 mL of THF was added slowly and the mixture heated up. After completion of the addition, the mixture was stirred for 2 hours at 40° C. and for 3 hours at room temperature. Half of the generated suspension was added via syringe to a solution of 1,1,1-trifluoro-4-(5-fluoro-2-methylphenyl)-4-methylpentan-2-one (500 mg, 1.91 mmol) in 20 mL of diethyl ether at −78° C. The reaction mixture was warmed up slowly to room temperature overnight. Water (20 mL) and ethyl acetate (20 mL) were added slowly. The organic phase was separated and the aqueous layer was extracted with two 10 mL portions of ethyl acetate. The combined organic phases were dried over magnesium sulfate. The solvent was removed to give 6-(5-fluoro-2-methylphenyl)-6-methyl-4-trifluoromethylhept-1-yn-4-ol (580 mg, 100%) as a colorless oil.

The following compounds were prepared analogously:
N-[1-dimethylaminomethylidene]-2-(3-hydroxy-1,1-dimethyl-3-trifluoromethylhex-5-ynyl)benzenesulfonamide;
6-(4-fluoro-2-methylphenyl)-6-methyl-4-trifluoromethylhept-1-yn-4-ol;
6-(2-methylphenyl)-6-methyl-4-trifluoromethylhept-1-yn-4-ol;
6-(2-bromo-5-fluorophenyl)-6-methyl-4-trifluoromethylhept-1-yn-4-ol;
6-(2-methoxy-5-fluorophenyl)-6-methyl-4-trifluoromethylhept-1-yn-4-ol;
6-(2-methoxy-5-bromophenyl)-6-methyl-4-trifluoromethylhept-1-yn-4-ol;

6-(2-methanesulfonylphenyl)-6-methyl-4-trifluoromethyl-hept-1-yn-4-ol;
6-(3-fluoro-2-methanesulfonylphenyl)-6-methyl-4-trifluoromethylhept-1-yn-4-ol;
6-(4-fluoro-2-methanesulfonylphenyl)-6-methyl-4-trifluoromethylhept-1-yn-4-ol;
6-(5-fluoro-2-methanesulfonylphenyl)-6-methyl-4-trifluoromethylhept-1-yn-4-ol;
6-(4-chloro-2-methanesulfonylphenyl)-6-methyl-4-trifluoromethylhept-1-yn-4-ol;
6-(5-chloro-2-methanesulfonylphenyl)-6-methyl-4-trifluoromethylhept-1-yn-4-ol;
6-(2-bromophenyl)-6-methyl-4-trifluoromethylhept-1-yn-4-ol;
6-(3-bromophenyl)-6-methyl-4-trifluoromethylhept-1-yn-4-ol;
6-(5-Chloro-2,3-dihydrobenzofuran-7-yl)-6-methyl-4-trifluoromethylhept-1-yn-4-ol; and
6-Benzo[b]thiophen-7-yl-6-methyl-4-trifluoromethylhept-1-yn-4-ol.

Example 9

Preparation of (S)-6-(5-Fluoro-2-methylphenyl)-6-methyl-4-trifluoromethylhept-1-yn-4-ol

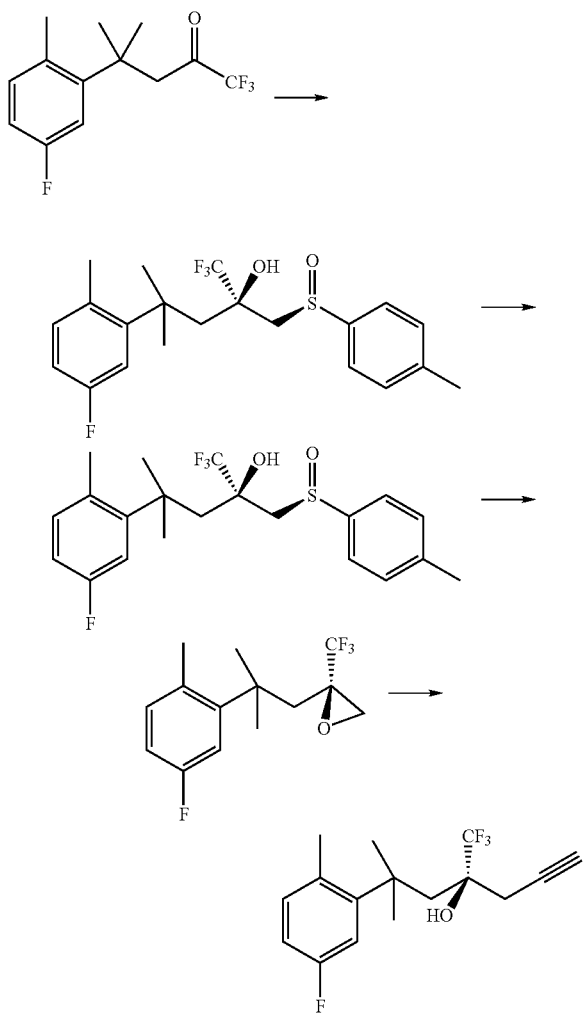

To a suspension of (R)-(+)-methyl p-tolylsulfoxide (23.6 g, 153 mmol) in 200 mL of anhydrous THF at −78° C. was added lithium diisopropylamide mono(tetrahydrofuran) (LDA), 1.5 M solution in cyclohexane, 102 mL, 153 mmol) over 20 minutes. The resulting clear yellow solution was stirred for an additional 15 minutes. 1,1,1-Trifluoro-4-(5-fluoro-2-methylphenyl)-4-methylpentan-2-one (36.4 g, 139 mmol) was then added via cannula with the aid of 125 mL of THF over 30 minutes. After 1.5 hours at −78° C., the reaction mixture was quenched with 600 mL of water and extracted with two 500 mL portions of ethyl acetate. The combined organic phases were washed with saturated aqueous sodium bicarbonate solution and brine, dried over magnesium sulfate, filtered, and concentrated in vacuo. Purification by column chromatography with silica gel (eluted with 10%-30% EtOAc/hexanes) afforded sequentially (S)-1,1,1-trifluoro-4-(5-fluoro-2-methylphenyl)-4-methyl-2-((R)-toluene-4-sulfinylmethyl)pentan-2-ol (31.9 g, 55%, 99% de) and (R)-1,1,1-trifluoro-4-(5-fluoro-2-methylphenyl)-4-methyl-2-((R)-toluene-4-sulfinylmethyl)pentan-2-ol.

To a suspension of (S)-1,1,1-trifluoro-4-(5-fluoro-2-methylphenyl)-4-methyl-2-((R)-toluene-4-sulfinylmethyl)pentan-2-ol (31.9 g, 76.6 mmol) and sodium iodide (34.4 g, 230 mmol) in 450 mL of anhydrous acetone at −40° C. was added a solution of trifluoroacetic acid anhydride (54.1 mL, 383 mmol) in 200 mL of anhydrous acetone via an addition funnel dropwise over 30 minutes. A greenish brown mixture formed instantaneously. After 15 minutes, the reaction mixture was quenched by slow addition of saturated aqueous sodium sulfite solution and neutralized with saturated aqueous sodium carbonate solution. The mixture became colorless and was concentrated in vacuo to remove most of the acetone solvent. The resulting material was diluted with 400 mL of water and extracted with three 400 mL portions of diethyl ether. The combined organic phases were washed with brine, dried over magnesium sulfate, filtered, and concentrated in vacuo to afford (S)-1,1,1-trifluoro-4-(5-fluoro-2-methylphenyl)-4-methyl-2-p-tolylsulfanylmethylpentan-2-ol as a yellow oil (31.0 g, 100%).

To a solution of (S)-1,1,1-trifluoro-4-(5-fluoro-2-methylphenyl)-4-methyl-2-p-tolylsulfanylmethylpentan-2-ol (31.0 g, 77.0 mmol) in 200 mL of anhydrous dichloromethane was added trimethyloxonium tetrafluoroborate (17.2 g, 116 mmol). The resulting suspension was stirred at room temperature for 4.5 hours. A solution of potassium carbonate ($K_2CO_3$, 32.1 g, 232 mmol) in 200 mL of water was then added. After 19 hours, the reaction mixture was poured into 400 mL of saturated aqueous sodium bicarbonate solution and extracted with three 400 mL portions of dichloromethane. The combined organic phases were washed with brine, dried over magnesium sulfate, filtered, and concentrated in vacuo. The crude mixture can be used in the next step without reducing the yield or can be purified by column chromatography with silica gel (eluted with 0%-2% EtOAc/hexanes) to afford (R)-2-[2-(5-fluoro-2-methylphenyl)-2-methylpropyl]-2-trifluoromethyloxirane as a clear oil (23.2 g, contains 20% methyl tolyl thioether, 87%) which was used without further purification.

To a solution of (R)-2-[2-(5-fluoro-2-methylphenyl)-2-methylpropyl]-2-trifluoromethyloxirane (18.5 g, 67.0 mmol) in 200 mL of anhydrous DMSO was added lithium trimethylsilylacetylide (0.5 M in THF, 201 mL, 101 mmol). The resulting brown solution was stirred at room temperature for 5 hours. The reaction mixture was poured into 500 mL of water and extracted with three 500 mL portions of 10% ethyl acetate/hexanes. The combined organic phases were washed with two 500 mL portions of water and one 500 mL portion of brine, dried over magnesium sulfate, filtered, and concentrated in vacuo. The crude material was redissolved in 200 mL of THF and cooled to 0° C. A solution of tetrabutylammonium fluoride (1.0 M in THF, 67.0 mL, 67.0 mmol) was added over 5 minutes. The reaction mixture was stirred for 1 hour, poured into 150 mL of saturated aqueous ammonium chloride solution, and extracted with three 300 mL portions of diethyl ether. The combined organic phases were washed with 300 mL of brine, dried over magnesium sulfate, filtered, and concentrated in vacuo. Purification by column chromatography with silica gel (eluted with 0%-3% EtOAc/hexanes) afforded (S)-6-(5-fluoro-2-methylphenyl)-6-methyl-4-trifluoromethylhept-1-yn-4-ol as a yellow oil (13.2 g, 65%).

The following compounds were prepared analogously:
(S)-6-(4-Fluoro-2-methylphenyl)-6-methyl-4-trifluoromethylhept-1-yn-4-ol;
(S)-6-(2-methylphenyl)-6-methyl-4-trifluoromethylhept-1-yn-4-ol;
(S)-6-(3-bromophenyl)-6-methyl-4-trifluoromethylhept-1-yn-4-ol;
(S)-6-(5-Chloro-2,3-dihydrobenzofuran-7-yl)-6-methyl-4-trifluoromethylhept-1-yn-4-ol; and
(S)-6-(5-fluoro-2-methoxyphenyl)-6-methyl-4-trifluoromethylhept-1-yn-4-ol.

Example 10

Preparation of 1,1,1-Trifluoro-4-(2-methanesulfonylphenyl)-4-methylpentan-2-one

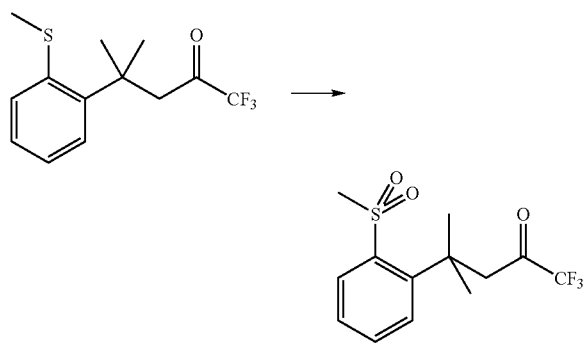

1,1,1-Trifluoro-4-methyl-4-(2-methylsulfanylphenyl)pentan-2-one (21.0 g, 60.8 mmol) was dissolved in 240 mL of acetonitrile. 80 mL of water was added followed by sodium metaperiodate (44.9 g, 210 mmol) and ruthenium (III) chloride (0.622 g, 3.0 mmol). The resulting reaction was stirred for 18 hours. The reaction mixture was diluted with 500 mL of diethyl ether (Et$_2$O) and the layers were mixed and separated. The aqueous was washed with 500 mL of diethyl ether and the organics were combined, dried over sodium sulfate (Na$_2$SO$_4$), decanted, and concentrated in vacuo to a thick orange oil. The crude material was separated by flash column chromatography with 0-35% EtOAc/hexanes as the eluent. 1,1,1-Trifluoro-4-(2-methanesulfonylphenyl)-4-methylpentan-2-one (16.9 g, 90%) was obtained as a colorless oil.

The following compounds were prepared analogously:
1,1,1-Trifluoro-4-(3-fluoro-2-methanesulfonylphenyl)-4-methylpentan-2-one;
1,1,1-Trifluoro-4-(4-fluoro-2-methanesulfonylphenyl)-4-methylpentan-2-one;
1,1,1-Trifluoro-4-(5-fluoro-2-methanesulfonylphenyl)-4-methylpentan-2-one;
1,1,1-Trifluoro-4-(5-chloro-2-methanesulfonylphenyl)-4-methylpentan-2-one; and
1,1,1-Trifluoro-4-(4-chloro-2-methanesulfonylphenyl)-4-methylpentan-2-one.

Example 11

Preparation of 1-Bromo-4-chloro-2-methylsulfanylbenzene

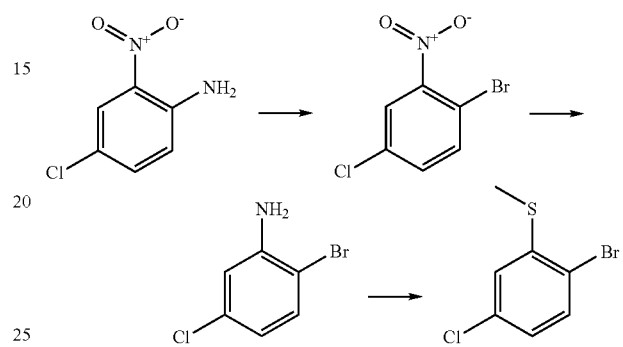

A 2 L round bottom flask was charged with 188 g (0.84 mol) of copper (II) bromide, 900 mL of anhydrous acetonitrile, and 121 g (0.70 mol) of 2-nitro-4-chloroaniline. After stirring for 15 minutes, 100 mL (0.84 mol) of tert-butylnitrite was carefully added in 5 portions. The reaction flask was immersed in a water bath maintained at 60° C. for an additional hour. The reaction mixture was cooled and the acetonitrile removed under vacuum using two 200 mL portions of dichloromethane as a chaser. 30% dichloromethane in hexanes (500 mL) was added to the residue and stirred for 20 minutes at room temperature. The resulting slurry was filtered through a vacuum frit with CELITE® filter aid and washed with 100 mL more solvent to provide a dark yellow filtrate. The filtrate was concentrated in vacuo to provide 1-bromo-4-chloro-2-nitrobenzene as a bright yellow solid (155 g, 94%).

1-Bromo-4-chloro-2-nitrobenzene (140 g, 0.59 mol) was dissolved in 2.5 L of MeOH with gentle heating (50° C.) in a hot water bath. A solution of ammonium formate (303 g, 4.81 mol) in 500 mL of water was added. Zinc powder (155 g, 2.36 mol) was added in small portions, resulting in heat evolution and refluxing of the solvent. Subsequent additions were made cautiously as to avoid build up of excess unreacted zinc. The reaction was cooled to room temperature and filtered through a large plug of CELITE® filter aid. The filtrate was then concentrated until a biphasic mixture of red oil and water was evident. The product was extracted with five 200 mL portions of diethyl ether. The organics were combined and dried over sodium sulfate, decanted, and concentrated in vacuo to a reddish-brown oil. The oil was redissolved in 150 mL of dichloromethane/hexanes and filtered through a plug of silica gel. The filtrate was concentrated to an orange oil. Addition of hexanes (200 mL) and cooling in a dry ice bath resulted in precipitation of 2-bromo-5-chloroaniline as a pale yellow solid (92.1 g, 75%) that was collected via vacuum filtration.

2-Bromo-5-chloroaniline (85.2 g, 0.41 mol) was dissolved in 1 L of acetonitrile followed by the addition of dimethydisulfide (30.0 mL, 0.33 mol). The flask was immersed in a water bath warmed to 60° C., equipped with a reflux condenser, and tert-butyl nitrite (54.0, 0.45 mol) was added in portions over 15 minutes. Once the addition was complete, the reaction was refluxed for 2 hours. After cooling to room temperature, the acetonitrile was evaporated, followed by re-dissolving in dichloromethane and subsequent concentration to remove remaining acetonitrile. The residue was re-dissolved in a minimal amount of dichloromethane and diluted with hexanes until precipitation was initiated. The mixture was filtered through a plug of silica and washed with hexanes. The filtrate was then concentrated in vacuo and crystallized upon cooling. 1-Bromo-4-chloro-2-methylsulfanylbenzene (52.0 g, 53%) was isolated via suction filtration.

Example 12

Preparation of (S)-6-(4-Chloro-2-methanesulfonylphenyl)-6-methyl-4-trifluoromethylhept-1-yn-4-ol

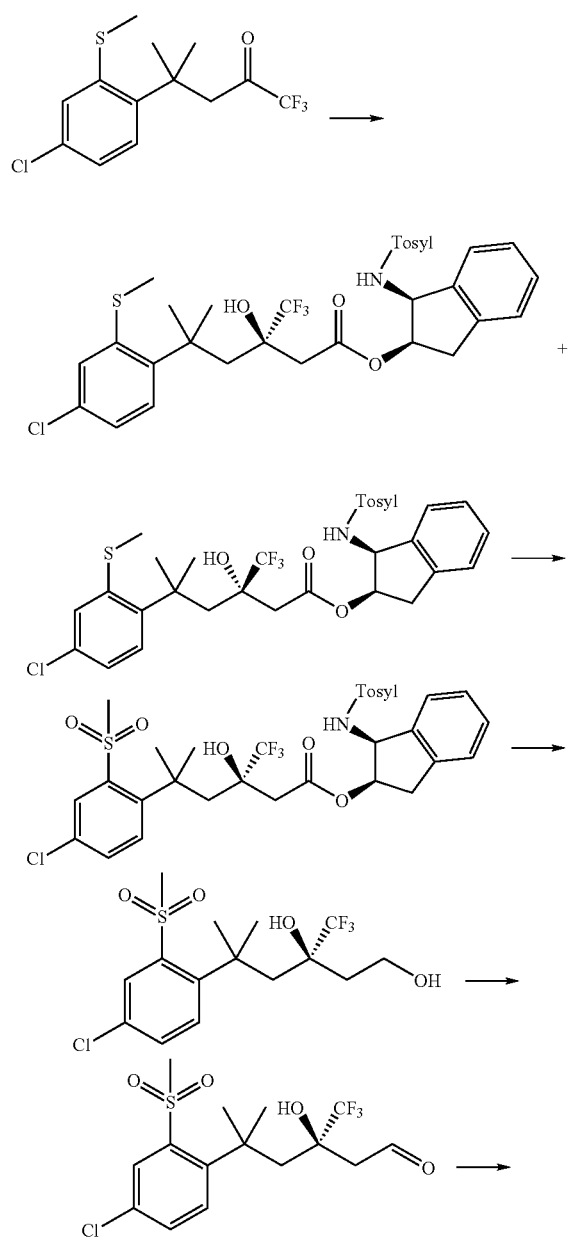

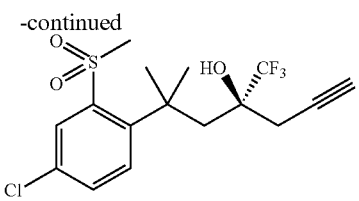

To a solution of (1S,2R)-1-(toluene-4-sulfonylamino)indan-2-yl ester (61.1 g, 0.18 mol) in 500 mL of THF at −70° C. was added a 1 M solution of LiHMDS (407.1 mL, 0.41 mol, 1.0 M) in THF at a rate of 5 mL/min while keeping the temperature below −65° C. The mixture was warmed to −35° C. and stirred for 40 minutes. The mixture was again cooled to −78° C. and a solution of 4-(4-chloro-2-methylsulfanylphenyl)-1,1,1-trifluoro-4-methylpentan-2-one (50.0 g, 0.16 mol) in 500 mL of THF was added dropwise at a rate of 8 mL/min while keeping the temperature below −66° C. The mixture stirred for 1 hour at −35° C. and was then quenched through the addition of 200 mL of saturated aqueous ammonium chloride solution followed by extraction with three 250 mL portions of diethyl ether. The combined organic layers were washed with brine (300 mL), dried over magnesium sulfate, filtered, and concentrated in vacuo.

The crude material was adhered to silica and loaded unto silica in a suction frit (3 L) with the pure product being eluted according to the following method. 4 L of 5% EtOAc/hexanes was first used to remove the ketone starting material. The solvent system was changed to 20% EtOAc/hexanes and the desired 5-(4-chloro-2-methylsulfanylphenyl)-3-hydroxy-5-methyl-3-trifluoromethylhexanoic acid (1S,2R)-1-(toluene-4-sulfonylamino)indan-2-yl ester (103.0 g, 0.16 mol, 98% yield of diastereomeric mixture) was eluted in 6 L.

To a solution of 5-(4-chloro-2-methylsulfanylphenyl)-3-hydroxy-5-methyl-3-trifluoromethylhexanoic acid (1S,2R)-1-(toluene-4-sulfonylamino)indan-2-yl ester (103 g, 0.16 mol) in acetonitrile (800 mL) was added water (400 mL) resulting in the mixture becoming cloudy. To this slurry was added sodium periodate (83.8 g, 0.39 mol), followed by the addition of 20 mg (0.096 mmol) of ruthenium (III) chloride. The solution was stirred for 18 hours and the reaction mixture was filtered through CELITE® filter aid. The solution was transferred to a separatory funnel and extracted with dichloromethane. The combined organic layers were dried over magnesium sulfate, filtered through a frit containing 50:50 layers of CELITE® filter aid and silica, and the solvent was evaporated. A stirring bar was added to the thick viscous oil and diethyl ether (approximately 1 L) was added with rapid stirring resulting in the precipitation of a white solid (approximately 75 g). NMR and HPLC analysis revealed the presence of the desired diastereomer (R)-5-(4-chloro-2-methylsulfonylphenyl)-3-hydroxy-5-methyl-3-trifluoromethylhexanoic acid (1S,2R)-1-(toluene-4-sulfonylamino)indan-2-yl ester in approximately 93% de. To this material was added a minimal amount of dichloromethane, followed by the addition of diethyl ether resulting in precipitation of a white solid. This second collection resulted in highly enriched material with >98.5% de (68.0 g, 63%).

LiAlH$_4$ (10.2 g, 0.29 mol) was added slowly in 2 g portions to (R)-5-(4-chloro-2-methylsulfanylphenyl)-3-hydroxy-5-methyl-3-trifluoromethylhexanoic acid (1S,2R)-1-(toluene-4-sulfonylamino)indan-2-yl ester (60.0 g, 0.09 mol) as a solution in THF at 0° C. over 30 minutes under a flow of nitrogen. The ice bath was removed and the mixture was stirred at room temperature for 30 minutes. The reaction was next cooled to 0° C. and quenched by the slow addition of water until foaming ceased. An additional 100 mL of water was added followed by acidification through the addition of 1N HCl. The aqueous phase was then washed with two 250 mL portions of 1:1 Et$_2$O/hexanes. The organic was then washed with brine followed by ten 200 mL portions of 1N NaOH. The organic layer was next washed with brine and saturated aqueous ammonium chloride followed by drying over magnesium sulfate. The magnesium sulfate was filtered and the filtrate concentrated in vacuo to provide a crude solid. The solid was taken up in diethyl ether (not completely dissolved) and an equal portion of hexanes was added resulting in the precipitation of (R)-5-(4-chloro-2-methanesulfonylphenyl)-5-methyl-3-trifluoromethylhexane-1,3-diol (27.6 g, 81%) as a white solid.

(R)-5-(4-Chloro-2-methanesulfonylphenyl)-5-methyl-3-trifluoromethylhexane-1,3-diol (27.6 g, 0.07 mol) was dissolved in methylene chloride (400 mL) with mild heating (50° C.). Dess-Martin periodinane (33.1 g, 0.08 mol) was added and the mixture was stirred at room temperature. After 1 hour the reaction was concentrated in vacuo, diluted with 300 mL of diethyl ether and filtered through a plug of CELITE® filter aid. The organic layer was washed with six 100 mL portions of saturated aqueous sodium bicarbonate solution followed by brine and drying over magnesium sulfate. The solution was filtered through CELITE® filter aid and the solvent was evaporated to give a viscous oil. The oil was dissolved in 30% Et$_2$O/hexanes and passed through a plug of silica. Evaporation of the eluent provided (R)-5-(4-chloro-2-methanesulfonylphenyl)-3-hydroxy-5-methyl-3-trifluoromethylhexanal as a viscous oil (23.8 g, 87%).

To a stirred solution of (1-diazo-2-oxopropyl)phosphonic acid dimethyl ester (12.5 g, 0.065 mol) and (R)-5-(4-chloro-2-methanesulfonylphenyl)-3-hydroxy-5-methyl-3-trifluoromethylhexanal (20.5 g, 0.054 mol) in 150 mL of dry MeOH was added potassium carbonate (13.8 g, 0.100 mol) at room temperature. The reaction was stirred overnight. The reaction was diluted with 200 mL of water and extracted with diethyl ether. The organic layers was washed with brine, dried over sodium sulfate, filtered, and the solvent was evaporated in vacuo. The crude material was eluted through a plug of silica using 20-25% diethyl ether/hexanes to provide (S)-6-(4-chloro-2-methanesulfonylphenyl)-6-methyl-4-trifluoromethylhept-1-yn-4-ol (18.5 g, 89%).

Example 13

Preparation of 2-(3-hydroxy-1,1-dimethyl-3-trifluoromethylhex-5-ynyl)benzamide

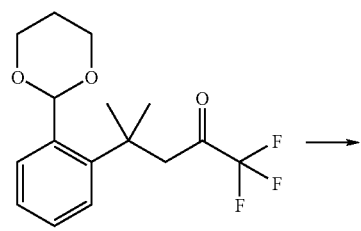

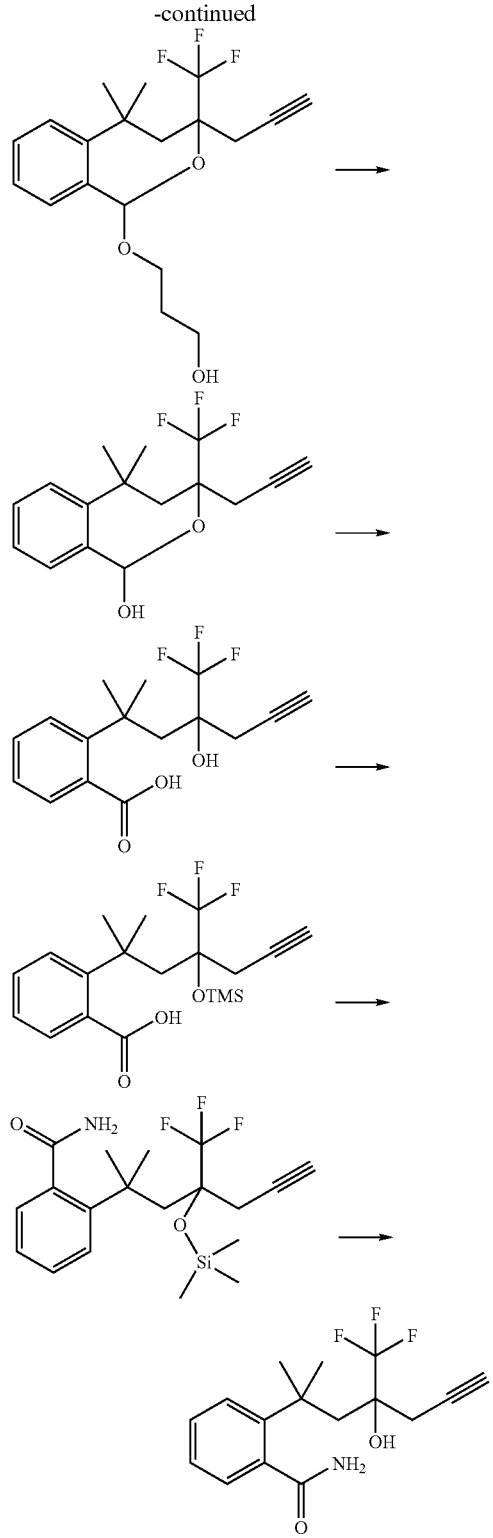

A flask was charged with aluminum (4.1 g of aluminum foil cut into 50 mg pieces, 152 mmol) and mercuric chloride (0.27 g, 1 mmol). The flask was sealed with a septum, flushed with argon, and anhydrous THF (300 mL) was added. Propargyl bromide (80% in toluene, 16.9 mL, 152 mmol) was added via syringe slowly and the resulting mixture was stirred for 30 minutes at 23° C. then warmed to 55° C.-60° C. and stirred an additional 2 hours. A second flask was charged with a 1:2 inseparable mixture of the 4-(2-[1,3]dioxan-2-ylphenyl)-1,1,1-trifluoro-4-methylpentan-2-one and 2-phenyl [1,3]dioxane (15.5 g). Anhydrous THF (150 mL) was added and the solution was cooled to −78° C. The solution of the propargyl aluminum solution was transferred to the ketone solution via cannula. The resulting solution was allowed to warm to 23° C. over a period of 75 minutes then stirred overnight. The reaction was quenched by carefully pouring into an aqueous saturated solution of ammonium chloride (500 mL). The mixture was diluted with diethyl ether (500 mL) and the layers were separated. The aqueous layer was washed with diethyl ether (250 mL) and the organics were combined, dried over sodium sulfate, filtered, and concentrated in vacuo to yield 3-(5,5-dimethyl-3-prop-2-ynyl-3-trifluoromethyl-1,3,4,5-tetrahydrobenzo[c]oxepin-1-yloxy)propan-1-ol as an orange oil (15.0 g) that was used without purification.

A solution of 3-(5,5-dimethyl-3-prop-2-ynyl-3-trifluoromethyl-1,3,4,5-tetrahydrobenzo[c]oxepin-1-yloxy)propan-1-ol (15.0 g) in THF (150 mL) was treated with 1M aqueous HCl (75 mL) and heated at 40° C. for 16 hours. The volatiles were then removed in vacuo and the aqueous layer extracted with ethyl acetate (300 mL), washed with two 100 mL portions of saturated aqueous sodium bicarbonate solution, dried over magnesium sulfate, filtered, and concentrated in vacuo. The crude was purified by flash chromatography (300 g SiO$_2$, hexanes to 4:1 hexanes:EtOAc) to give 5,5-dimethyl-3-prop-2-ynyl-3-trifluoromethyl-1,3,4,5-tetrahydrobenzo[c]oxepin-1-ol (5.75 g, 46%) as a 1:1 mixture of lactol and aldehyde by NMR. The mixture was used without further purification in the next transformation.

To a solution of 5,5-dimethyl-3-prop-2-ynyl-3-trifluoromethyl-1,3,4,5-tetrahydrobenzo[c]oxepin-1-ol (2.50 g, 8.38 mmol) in tert-BuOH (75 mL) was added a 2.0 M solution of 2-methyl-2-butene in THF (58 mL, 117 mmol). To this solution was added a solution of sodium chlorite (4.74 g, 42.0 mmol) and sodium hydrogen phosphate (11.57 g, 84.0 mmol) in water (37.5 mL). The reaction mixture was stirred for 6 hours then the volatiles were removed in vacuo. The aqueous mixture was then acidified to pH=1 with aqueous 1M HCl, extracted with 300 mL of ethyl acetate, dried with magnesium sulfate, filtered, and concentrated in vacuo. The crude was purified by flash chromatography (120 g SiO$_2$, hexanes to 1:1 hexanes:EtOAc) to give 2-(3-hydroxy-1,1-dimethyl-3-trifluoromethylhex-5-ynyl)benzoic acid (2.30 g, 87%). MS (ES$^+$) m/z 315 [M+H]$^+$.

To a solution of 2-(3-hydroxy-1,1-dimethyl-3-trifluoromethylhex-5-ynyl)benzoic acid (345 mg, 1.10 mmol) and imidazole (374 mg, 5.49 mmol) in 1 mL of DMF was added chlorotrimethylsilane (0.42 mL, 3.29 mmol). The reaction mixture was stirred for 2 hours then diluted with 75 mL of diethyl ether, washed with two 50 mL portions of 1M aqueous HCl, dried over magnesium sulfate, filtered, and concentrated in vacuo to afford 2-(1,1-dimethyl-3-trifluoromethyl-3-trimethylsilanyloxy-hex-5-ynyl)benzoic acid (424 mg, 100%). MS (ES$^+$) m/z 387 [M+H]$^+$.

To a solution of 2-(1,1-dimethyl-3-trifluoromethyl-3-trimethylsilanyloxyhex-5-ynyl)benzoic acid (246 mg, 0.64 mmol) in 5 mL of dichloromethane was added pyridine (77 μL, 0.96 mmol) followed by thionyl chloride (56 μL, 0.76 mmol). The reaction was stirred for 15 minutes then the volatiles were removed in vacuo. The crude acid chloride was treated with 7 M ammonia in 5.0 mL of MeOH. The mixture was stirred for 15 minutes then diluted with 75 mL of EtOAc, washed with two 25 mL portions of saturated aqueous sodium bicarbonate solution, dried over magnesium sulfate, filtered, and concentrated in vacuo. Purification of the crude by flash chromatography (12 g SiO$_2$, hexanes to 1:1 hexanes:EtOAc) gave 2-(1,1-dimethyl-3-trifluoromethyl-3-trimethylsilanyloxyhex-5-ynyl)benzamide as a pale yellow solid (108 mg, 44%). MS (ES$^+$) m/z 386 [M+H]$^+$.

2-(1,1-dimethyl-3-trifluoromethyl-3-trimethylsilanyloxyhex-5-ynyl)benzamide (108 mg, 0.28 mmol) was treated with a 1M solution of TBAF in 3 mL of THF. The reaction mixture was stirred for 1 hour then diluted with 50 mL of ethyl acetate, washed with 25 mL of 1 M aqueous HCl, two 25 mL portions of saturated aqueous sodium bicarbonate solution, dried over magnesium sulfate, filtered, and concentrated in vacuo. The crude was purified by flash chromatography (12 g SiO$_2$, hexanes to 1:1 hexanes:EtOAc) to give 2-(3-hydroxy-1,1-dimethyl-3-trifluoromethylhex-5-ynyl)benzamide as a white solid (82 mg, 93%). MS (ES$^+$) m/z 314 [M+H]$^+$.

The following compounds were prepared analogously:

3-Fluoro-2-(3-hydroxy-1,1-dimethyl-3-trifluoromethylhex-5-ynyl)benzamide;

4-Fluoro-2-(3-hydroxy-1,1-dimethyl-3-trifluoromethylhex-5-ynyl)benzamide;

5-Fluoro-2-(3-hydroxy-1,1-dimethyl-3-trifluoromethylhex-5-ynyl)benzamide;

2-(3-Hydroxy-1,1-dimethyl-3-trifluoromethylhex-5-ynyl)-4-methylbenzamide;

2-(3-Hydroxy-1,1-dimethyl-3-trifluoromethylhex-5-ynyl)-5-methylbenzamide; and

4-Chloro-2-(3-hydroxy-1,1-dimethyl-3-trifluoromethylhex-5-ynyl)benzamide.

Example 14

Preparation of 5-Fluoro-2-((S)-3-hydroxy-1,1-dimethyl-3-trifluoromethylhex-5-ynyl)benzamide

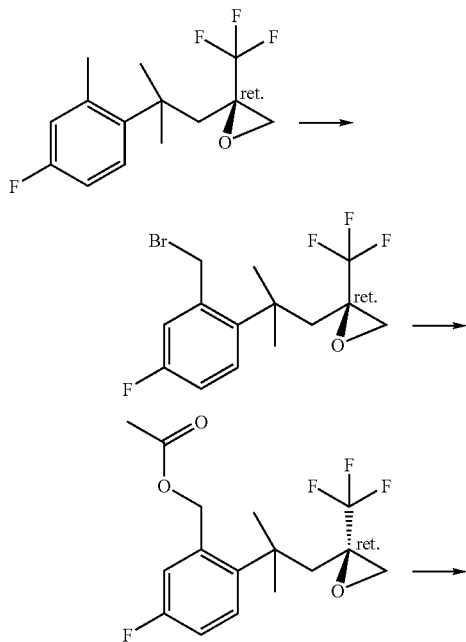

-continued

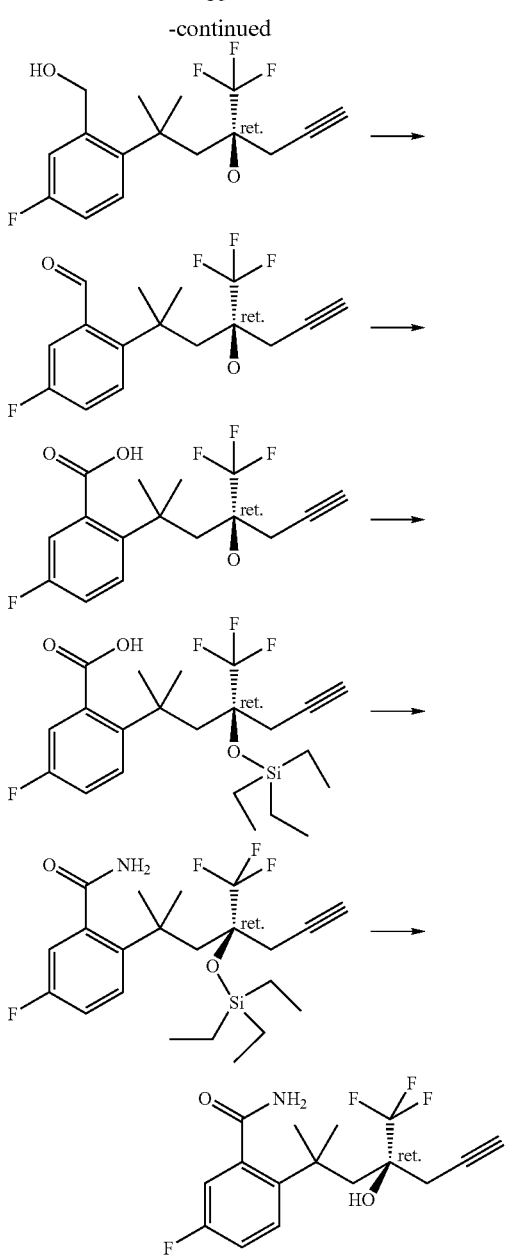

To a solution of 17.7 g (R)-2-[2-(4-fluoro-2-methylphenyl)-2-methylpropyl]-2-trifluoromethyloxirane (0.064 mol) in 250 mL of $CCl_4$ was added 14.8 g (0.083 mol) of NBS followed by 1.5 g (0.006 mol) benzoyl peroxide and heated to 80° C. for 2 hours. The mixture was cooled to room temperature, diluted with 1800 mL of hexanes, filtered through a pad of CELITE® filter aid, and concentrated in vacuo. The crude mixture was chromatographed on silica gel using 0-5% ethyl acetate/hexanes to afford 24 g (69%) (R)-2-[2-(2-bromomethyl-4-fluorophenyl)-2-methylpropyl]-2-trifluoromethyloxirane.

To 48 g (0.087 mol) of (R)-2-[2-(2-bromomethyl-4-fluorophenyl)-2-methylpropyl]-2-trifluoromethyloxirane in 1.3 L of DMF was added 36 g of sodium acetate (0.439 mol). The mixture was heated at 45° C. for 3 hours. The mixture was then cooled to room temperature and poured into 1.3 L of saturated aqueous sodium bicarbonate solution and extracted with 1800 mL of diethyl ether. The aqueous phase was filtered to remove a solid residue. The solid was washed with 1.3 L of diethyl ether. The organic phases were combined and washed with 2 L of brine and separated. The aqueous phase was extracted with 1800 mL of diethyl ether. The combined organic phases were dried over magnesium sulfate, filtered, and concentrated in vacuo. The crude mixture was chromatographed on silica gel using 0-5% ethyl acetate/hexanes to afford 74.2 g (83%) of acetic acid 2-[1,1-dimethyl-2-((R)-2-trifluoromethyloxiranyl)ethyl]-5-fluorobenzyl ester.

To 19.1 g (0.057 mol) of acetic acid 2-[1,1-dimethyl-2-((R)-2-trifluoromethyloxiranyl)ethyl]-5-fluorobenzyl ester in 450 mL of DMSO at 15° C. was added 481 mL (0.240 mol) lithium trimethylsilylacetylide (0.5 M in THF). The mixture was warmed to room temperature and stirred for 3 hours. The mixture was then cooled to 0° C. and 300 mL of 3N NaOH was added and the mixture was stirred for 1 hour. The mixture was neutralized by the addition of 400 mL of 3N HCl. The organic phase was removed and the aqueous layers were extracted four times with diethyl ether. The organic phases were washed with 300 mL of water and 300 mL of brine, dried over magnesium sulfate, filtered, and concentrated in vacuo. The crude mixture was chromatographed on silica gel using 10-12% ethyl acetate/hexanes to afford 15 g (83%) of (S)-6-(4-fluoro-2-hydroxymethylphenyl)-6-methyl-4-trifluoromethylhept-1-yn-4-ol.

To a solution of 15 g (0.040 mol) of (S)-6-(4-fluoro-2-hydroxymethylphenyl)-6-methyl-4-trifluoromethylhept-1-yn-4-ol in 150 mL DCM at 0° C. was added 21.3 mL of DMSO and 21.2 mL of triethylamine. The reaction was cooled to 0° C. then 19.1 g (0.12 mol) of $Pyr-SO_3$ was added. The reaction mixture was stirred at 0° C. for 1 hour. The reaction was then quenched with 500 mL of water, acidified with 1 N HCl to pH=2, and the organic layer was separated. The aqueous phases were then extracted with DCM. The combined organic phases were washed with brine, dried over magnesium sulfate, filtered, and concentrated in vacuo to afford 5-fluoro-2-((S)-3-hydroxy-1,1-dimethyl-3-trifluoromethylhex-5-ynyl)benzaldehyde as a thick yellow oil.

To a solution of 15 g (0.031 mol) of 5-fluoro-2-((S)-3-hydroxy-1,1-dimethyl-3-trifluoromethylhex-5-ynyl)benzaldehyde in 240 mL of tert-BuOH was added a solution of the 62 mL (0.124 mol) of 2-methyl-2-butene in THF (2 M). To this solution was added a solution of the 17.5 g of sodium chlorite (0.150 mol) and 42.8 g of sodium hydrogen phosphate (0.138 mol) in water. The reaction mixture was stirred overnight. The volatiles were removed in vacuo. The aqueous mixture was then acidified to pH=1 with 1 M HCl, extracted with 1200 mL of ethyl acetate, dried over magnesium sulfate, filtered, and concentrated in vacuo. The crude mixture was chromatographed on silica gel using 10-100% ethyl acetate/hexanes to afford 10.6 g (103%) of 5-fluoro-2-((S)-3-hydroxy-1,1-dimethyl-3-trifluoromethylhex-5-ynyl)benzoic acid.

To a solution of 10.6 g (0.032 mol) of 5-fluoro-2-((S)-3-hydroxy-1,1-dimethyl-3-trifluoromethylhex-5-ynyl)benzoic acid and 17.8 g (0.026 mol) of imidazole in 70 mL of DMF was added 75.6 mL (0.45 mol) of TESCl. The reaction mixture was stirred at 100° C. for 3 days. Volatiles were removed in vacuo, the reaction mixture was cooled to 10° C. with an ice bath, and 1 L of 1 N HCl was added. The ice bath was removed and the mixture was stirred at room temperature for 2 hours. Ethyl acetate was added and the mixture was washed with 1 N HCl, brine, dried over sodium sulfate, filtered, and concentrated in vacuo. 200 mL of 1 N HCl is added and stirred for 1 hour. Ethyl acetate was added and the mixture was washed with 1 N HCl, brine, dried over sodium sulfate, filtered, and concentrated in vacuo to afford 2-((S)-1,1-dimethyl-3-triethylsilanyloxy-3-trifluoromethylhex-5-ynyl)-5-fluorobenzoic acid.

To a solution of 14.2 g of 2-((S)-1,1-dimethyl-3-triethylsilanyloxy-3-trifluoromethylhex-5-ynyl)-5-fluorobenzoic acid (0.030 mol) in 400 mL of DCM was added 4.6 mL of pyridine (0.057 mol) followed by 3.3 mL of thionyl chloride (0.045 mol). The reaction was stirred for 25 minutes then carried on to next step. The crude acid chloride was cannulated into a flask containing ammonia (7 M in MeOH, 185 mL, 1.30 mol). The mixture was stirred for 40 minutes then quenched with saturated aqueous sodium bicarbonate solution. The mixture was then diluted with 20 mL of ethyl acetate, washed with two 100 mL portions of saturated aqueous sodium bicarbonate solution, dried over magnesium sulfate, filtered, and concentrated in vacuo. The crude mixture was chromatographed on silica gel using 0-50% ethyl acetate/hexanes to afford 7.1 g (50%) of 2-((S)-1,1-dimethyl-3-triethylsilanyloxy-3-trifluoromethylhex-5-ynyl)-5-fluorobenzamide.

To a solution of 7.1 g of 2-((S)-1,1-dimethyl-3-triethylsilanyloxy-3-trifluoromethylhex-5-ynyl)-5-fluorobenzamide (15.7 mmol) in 80 mL of MeOH was added 400 mL of HCl (4 N in dioxane, 1.6 mol). The reaction was stirred for 2 hours at room temperature. The volatiles were concentrated in vacuo and 500 mL of water was added. The reaction mixture was then extracted with ethyl acetate, dried over sodium sulfate, and concentrated in vacuo to afford 5.2 g (100%) of 5-fluoro-2-((S)-3-hydroxy-1,1-dimethyl-3-trifluoromethylhex-5-ynyl)benzamide.

The following compound was prepared analogously: 2-((S)-3-Hydroxy-1,1-dimethyl-3-trifluoromethylhex-5-ynyl)benzamide.

Example 15

2-((S)-3-Hydroxy-1,1-dimethyl-3-trifluoromethylhex-5-ynyl)benzamide

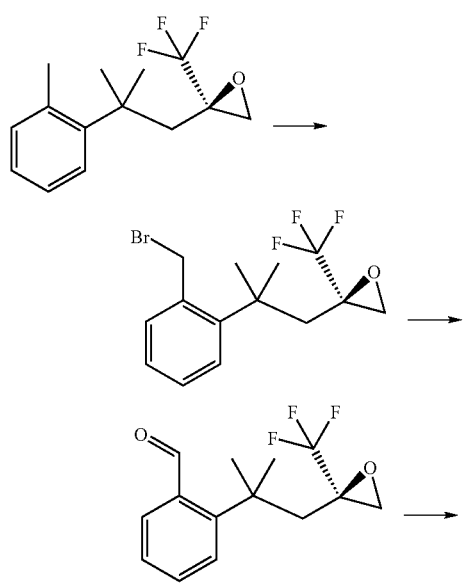

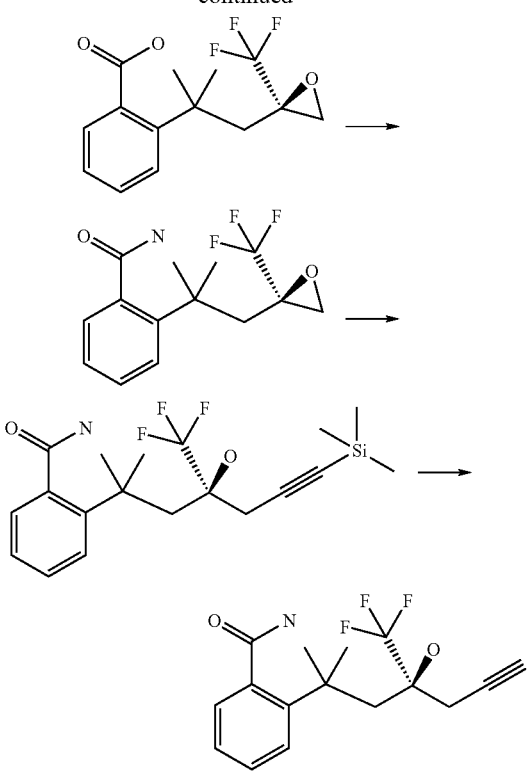

To a stirred solution of (R)-2-[2-(2-methylphenyl)-2-methylpropyl]-2-trifluoromethyloxirane (37 g, 0.143 mmol) in 500 mL of anhydrous $CCl_4$ at room temperature was added N-bromosuccinimide (26 g, 0.146 mmol). The reaction mixture was heated to 70° C. and the reaction flask was irradiated with a UV light (500 W) for 1 hour. The reaction mixture, after cooling to normal room temperature, was washed with saturated aqueous sodium bicarbonate solution followed by water, dried over anhydrous sodium sulfate, and the solvent evaporated in vacuo to give (R)-2-[2-(2-bromomethylphenyl)-2-methylpropyl]-2-trifluoromethyloxirane as a light yellow oil (46.6 g, 81%; ~85% pure) which was used for the next reaction without purification.

To a stirred solution of (R)-2-[2-(2-bromomethylphenyl)-2-methylpropyl]-2-trifluoromethyloxirane (46.6 g, 0.138 mol) in 300 mL of DMSO was added sodium bicarbonate (24 g, 0.285 mol) and the reaction mixture was heated to 70° C. After 24 hours, the reaction mixture was cooled to normal room temperature, diluted with 1200 mL of saturated aqueous ammonium chloride solution and extracted with four 250 mL portions of diethyl ether. The combined diethyl ether extracts were washed with brine, dried over anhydrous sodium sulfate, and the solvent evaporated in vacuo. The crude material was purified by column chromatography over silica gel (400 g) eluting with 0-15% ethyl acetate in hexanes and fractions corresponding to the major peak were pooled and solvent removed in vacuo to give 2-[1,1-dimethyl-2-((R)-2-trifluoromethyloxiranyl)ethyl]benzaldehyde as a light yellow oil (20 g, 62%).

To a stirred, ice-cooled, acetonitrile (250 mL) solution of 2-[1,1-dimethyl-2-((R)-2-trifluoromethyloxiranyl)ethyl]benzaldehyde (20 g, 73.5 mmol) was added a solution of sodium chlorite (7.4 g, 73.5 mmol in 100 mL water) followed immediately by a solution of sulfamic acid (7.13 g, 73.5 mmol in 100 mL water). After 30 minutes, the ice-cooled reaction mixture was treated with 500 mL of brine and extracted with three 300 mL portions of ethyl acetate. The combined extracts were washed with brine, dried over anhydrous sodium sulfate, and the solvent evaporated in vacuo to give 2-[1,1-dimethyl-2-((R)-2-trifluoromethyloxiranyl)ethyl]benzoic acid as a colorless thick oil (18 g, 85%).

A stirred, ice-cooled, DMF (60 mL) solution of the 2-[1,1-dimethyl-2-((R)-2-trifluoromethyloxiranyl)ethyl]benzoic acid (8.5 g, ~80%, 23.6 mmol) triethylamine (6.6 mL, 47.2 mmol) was added and after 2-3 minutes TBTU (8.3 g, 26 mmol) was added. After stirring for 30 minutes, ammonium hydroxide solution (7 mL, 98 mmol) was added and stirred for 40 minutes. The reaction mixture was diluted with 500 mL of saturated aqueous sodium bicarbonate solution and extracted with three 200 mL portions of dichloromethane. The combined organic extracts were washed with saturated aqueous sodium bicarbonate solution and brine, dried over anhydrous sodium sulfate, and the solvent evaporated in vacuo to give 2-[1,1-dimethyl-2-((R)-2-trifluoromethyloxiranyl)ethyl]benzamide as a colorless thick oil which solidified on standing (6.0 g, 90%).

To a stirred, ice-cooled, solution of (trimethylsilyl)acetylene (72.6 mL, 514 mmol) in 500 mL of ethylene glycol dimethyl ether was added n-butyllithium (185 mL of 2.5 M solution in hexanes, 462 mmol). The reaction mixture, which turned from a colorless to a yellowish solution, was stirred for 50 minutes to give a solution of 462 mmol of lithium (trimethylsilyl)acetylide. A stirred solution of 2-[1,1-dimethyl-2-((R)-2-trifluoromethyloxiranyl)ethyl]benzamide (26.5 g, 92.3 mmol) in ethylene glycol dimethyl ether (250 mL) was cooled to −30° C. Dibutylmagnesium (50.8 mL of 1 M solution in heptane, 50.8 mmol) was added and the mixture stirred for 45 minutes. The above solution of lithium (trimethylsilyl)acetylide was added and the stirring continued at −20° C. After 5 minutes, cooling bath was removed and the reaction mixture was stirred for 3 hours and 15 minutes. The reaction was quenched with 600 mL of saturated ammonium chloride solution and extracted with four 250 mL portions of ethyl acetate. The combined organic extracts were washed with two 250 mL portions of brine, dried over anhydrous sodium sulfate, and the solvent removed in vacuo to give 2-((R)-3-hydroxy-1,1-dimethyl-3-trifluoromethyl-6-trimethylsilanyl-hex-5-ynyl)benzamide as brownish oil (27 g).

To a stirred, ice-cooled, THF solution (100 mL) of 2-((R)-3-hydroxy-1,1-dimethyl-3-trifluoromethyl-6-trimethylsilanylhex-5-ynyl)benzamide (17.8 g, 46.2 mmol) n-tetrabutylammonium fluoride was added (51 mL of 1 M solution in THF, 51 mmol) dropwise via addition funnel. After 30 minutes, the reaction was quenched with 200 mL of 1 M HCl and further diluted with brine. The mixture was extracted with ethyl acetate. The combined extract was washed with water and brine, dried over anhydrous sodium sulfate, and the solvent removed in vacuo. The residue was redissolved in dichloromethane and the solvent evaporated. The residue was then dissolved in 30 mL of diethyl ether and triturated with hexanes. The precipitated solid was filtered. The filtrate was collected and the solvent evaporated, and the residue treated with diethyl ether/hexanes as before to obtain more solid precipitate. The solids were combined and dried in vacuo to give 2-((S)-3-hydroxy-1,1-dimethyl-3-trifluoromethylhex-5-ynyl)benzamide (10 g, 33% over two steps). This material was used without further purification.

Example 16

Preparation of N-[1-Dimethylaminomethylidene]-2-(4,4,4-trifluoro-1,1-dimethyl-3-oxobutyl)benzenesulfonamide

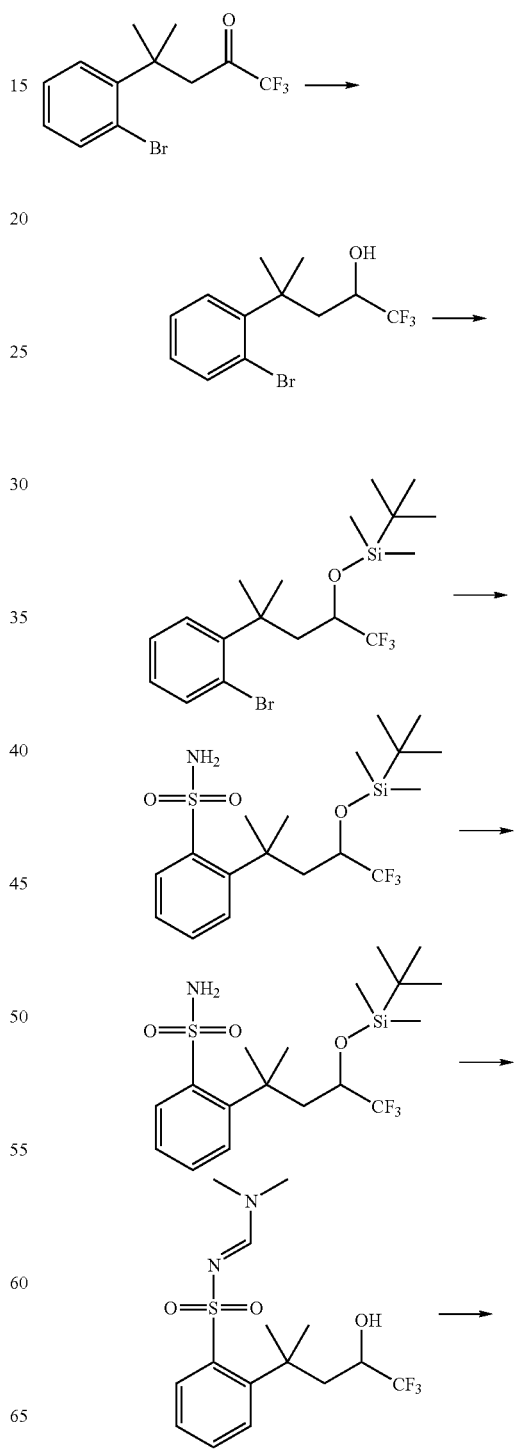

-continued

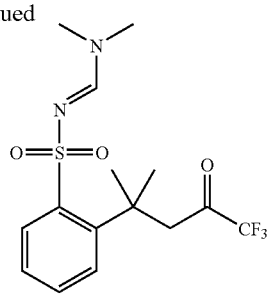

To a round bottom flask was added 4-(2-bromophenyl)-1,1,1-trifluoro-4-methylpentan-2-one (3.0 g, 9.7 mmol) in 70 mL of MeOH and 70 mL of THF at 0° C., followed by the slow addition of NaBH$_4$ (1.1 g, 29.1 mmol). The reaction mixture was stirred at room temperature for 24 hours and then concentrated in vacuo. The residue was diluted with 1000 mL of ethyl acetate, washed with 200 mL of saturated aqueous sodium bicarbonate solution, 200 mL of brine, dried over sodium sulfate, filtered, and concentrated in vacuo. The crude mixture was purified by flash chromatography. The column was eluted with 0-20% EtOAc/hexanes to afford 1.76 g (58%) of 4-(2-bromophenyl)-1,1,1-trifluoro-4-methylpentan-2-ol.

To a round bottom flask was added 4-(2-bromophenyl)-1,1,1-trifluoro-4-methylpentan-2-ol (1.76 g, 5.66 mmol) in 30 mL of dry THF at 0° C. under nitrogen, followed by the dropwise addition of a solution of 2 M lithium diisopropylamine in THF (5.7 mL, 11.4 mmol). The reaction mixture was stirred at 0° C. for 30 minutes, followed by the addition of tert-butyldimethylsilyl chloride (4.26 g, 28.3 mmol). The reaction mixture was stirred at room temperature for 24 hours. The reaction mixture was then concentrated, diluted with 500 mL of ethyl acetate, and washed with 100 mL of saturated sodium bicarbonate solution. The organic phase was separated, washed with 100 mL of water, 100 mL of brine, dried over sodium sulfate, filtered, and concentrated in vacuo. The crude mixture was purified by flash chromatography. The column was eluted with hexane to afford 875 mg (36%) of [3-(2-bromophenyl)-3-methyl-1-trifluoromethylbutoxy]-tert-butyldimethylsilane.

To a round bottom flask was added [3-(2-bromophenyl)-3-methyl-1-trifluoromethylbutoxy]-tert-butyldimethylsilane (853 mg, 2.00 mmol) in 20 mL of dry THF under nitrogen. The reaction mixture was cooled to −78° C., followed by the addition of a solution of 1.6 M n-butyllithium in hexane (1.4 mL, 2.24 mmol) dropwise. The reaction mixture was stirred at −78° C. for 45 minutes, followed by bubbling of sulfur dioxide gas into the reaction solution for 10 minutes. The reaction mixture was warmed up to −40° C. to −20° C. and stirred for 45 minutes.

To the reaction mixture was added sulfuryl chloride (0.24 mL, 3 mmol). The reaction mixture turned clear from cloudy after this addition and was stirred at room temperature for 30 minutes. The solvent was removed and the resulting residue was dissolved in 15 mL of dry THF, followed by the addition of 15 mL of 7 M ammonia in methanol. The reaction mixture was stirred at room temperature for 18 hours. The reaction mixture was then concentrated in vacuo. The crude mixture was diluted with 500 mL of ethyl acetate, washed with 100 mL of saturated aqueous sodium bicarbonate solution, 100 mL of water, and 100 mL of brine, dried under sodium sulfate, filtered, and concentrated in vacuo to afford 750 mg (88%) of 2-[3-(tert-butyldimethylsilanyloxy)-4,4,4-trifluoro-1,1-dimethylbutyl]benzenesulfonamide. MS (ES$^+$) m/z 426 [M+H]$^+$.

To a round bottom flask was added 2-[3-(tert-butyldimethylsilanyloxy)-4,4,4-trifluoro-1,1-dimethylbutyl]benzenesulfonamide (750 mg, 1.76 mmol) in 25 mL of dry dichloromethane, followed by the addition of N,N-dimethylformamide dimethyl acetal (420 mg, 3.53 mmol). The reaction mixture was stirred at room temperature for 30 minutes. The reaction mixture was concentrated under high vacuum to afford 820 mg (100%) of 2-[3-(tert-butyldimethylsilanyloxy)-4,4,4-trifluoro-1,1-dimethylbutyl]-N-[1-dimethylaminomethylidene]benzenesulfonamide. MS (ES$^+$) m/z 481 [M+H]$^+$.

To a round bottom flask was added 2-[3-(tert-butyldimethylsilanyloxy)-4,4,4-trifluoro-1,1-dimethylbutyl]-N-[1-dimethylaminomethylidene]benzenesulfonamide (820 mg, 1.76 mmol) in 15 mL of dry THF, followed by the addition of a solution of 1M TBAF in THF (1.76 mL, 1.76 mmol). The reaction mixture was stirred at room temperature for 10 minutes, quenched with 100 mL of saturated aqueous sodium bicarbonate solution, and extracted with 250 mL of ethyl acetate. The organic layer was separated, washed with 100 mL of water and 100 mL of brine, dried over sodium sulfate, filtered, and concentrated in vacuo. The crude mixture was purified by flash chromatography. The column was eluted with 0-40% EtOAc/hexanes to afford 381 mg (59%) of N-[1-dimethylaminomethylidene]-2-(4,4,4-trifluoro-3-hydroxy-1,1-dimethylbutyl)benzenesulfonamide. MS (ES$^+$) m/z 367 [M+H]$^+$.

To a round bottom flask was added N-[1-dimethylaminomethylidene]-2-(4,4,4-trifluoro-3-hydroxy-1,1-dimethylbutyl)benzenesulfonamide (367 mg, 1.00 mmol) in 25 mL of dry dichloromethane, followed by the addition of Dess-Martin periodinane (600 mg, 1.42 mmol). The reaction mixture was stirred at room temperature for 2 hours. The reaction mixture was quenched with 50 mL of saturated aqueous sodium bicarbonate solution and extracted with 250 mL of ethyl acetate. The organic layer was separated, washed with 50 mL of brine, dried over sodium sulfate, filtered, and concentrated in vacuo. Dichloromethane was added to the residue and the solid which did not dissolve in dichloromethane was filtered. The mother liquor was then concentrated in vacuo and the crude mixture was purified by flash chromatography. The column was eluted with 0-40% EtOAc/hexanes to afford 345 mg (95%) of N-[1-dimethylaminomethylidene]-2-(4,4,4-trifluoro-1,1-dimethyl-3-oxobutyl)benzenesulfonamide. MS (ES$^+$) m/z 365 [M+H]$^+$.

Example 17

Preparation of 6-(1,1-dioxo-1H-1$\lambda^6$-benzo[b]thiophen-7-yl)-6-methyl-4-trifluoromethylhept-1-yn-4-ol

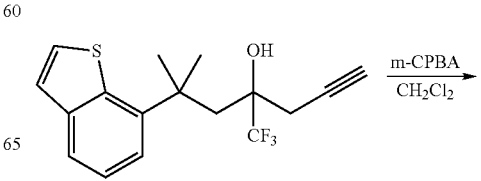

-continued

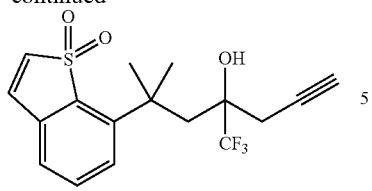

To a solution of 150 mg (0.47 mmol) of 6-benzo[b]thiophen-7-yl-6-methyl-4-trifluoromethylhept-1-yn-4-ol in 15 mL of dichloromethane was added 280 mg (~1.2 mmol) of m-chloroperoxybenzoic acid. After stirring at room temperature for 2.5 hours, the reaction mixture was poured into 30 mL of 1N aqueous NaOH solution and extracted with two 30 mL portions of dichloromethane. The combined organic layers were dried over sodium sulfate, filtered, and concentrated in vacuo. The crude 6-(1,1-dioxo-1H-1$\lambda^6$-benzo[b]thiophen-7-yl)-6-methyl-4-trifluoromethylhept-1-yn-4-ol was used without further purification.

Example 18

Preparation of (R)-4-(4-Chloro-2-methanesulfonylphenyl)-1,1,1-trifluoro-2-(5-methanesulfonyl-1H-pyrrolo[2,3-c]pyridin-2-ylmethyl)-4-methylpentan-2-ol

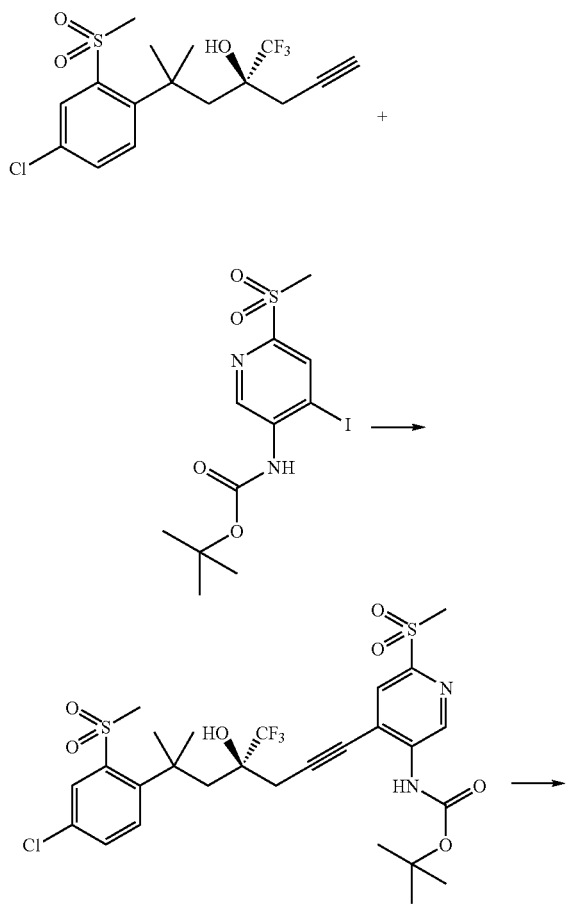

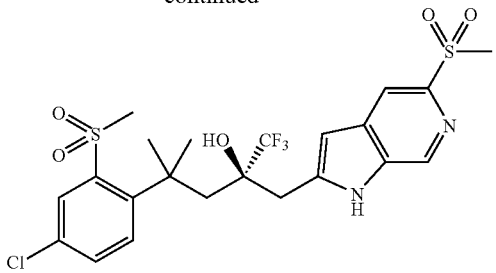

To a solution of (S)-6-(4-chloro-2-methanesulfonylphenyl)-6-methyl-4-trifluoromethylhept-1-yn-4-ol (15.6 g, 40.8 mmol), triethylamine (23.0 mL, 165 mmol), and (4-iodo-6-methanesulfonylpyridin-3-yl)carbamic acid tert-butyl ester (18.0 g, 45.2 mmol) in 150 mL of DMF was added CuI (1.6 g, 8.4 mmol) and Pd(PPh$_3$)$_2$Cl$_2$ (3.0 g, 4.3 mmol) as one mixed solid batch. The mixture was stirred at room temperature for 18 hours resulting in the color changing to deep red. Saturated aqueous ammonium chloride solution and ethyl acetate were added. The aqueous layer was extracted with ethyl acetate and the combined organic layers were washed with water, brine, dried over sodium sulfate, filtered through CELITE® filter aid, and evaporated. The crude material was separated by flash column chromatography using a 0-75% EtOAc/hexanes gradient. Evaporation of the solvent yielded an off-white foam as the pure {4-[(S)-6-(4-chloro-2-methanesulfonylphenyl)-4-hydroxy-6-methyl-4-trifluoromethylhept-1-ynyl]-6-methanesulfonylpyridin-3-yl}carbamic acid tert-butyl ester (18.1 g, 68%).

To a solution of the {4-[(S)-6-(4-chloro-2-methanesulfonylphenyl)-4-hydroxy-6-methyl-4-trifluoromethylhept-1-ynyl]-6-methanesulfonylpyridin-3-yl}carbamic acid tert-butyl ester (18.3 g, 28.0 mmol) in 200 mL of methanol was added DBU (12.5 mL, 84.0 mmol). The reaction was heated to 70° C. for 1.5 hours. The reaction was added to a solution of saturated aqueous ammonium chloride solution resulting in the precipitation of a white solid that was collected by vacuum filtration. The solid was washed with water and, after drying under vacuum for 30 minutes, was suspended in 50 mL of cold diethyl ether then vacuum filtered again and washed with 50 mL of cold diethyl ether. The colorless solid was dried on the filter paper under suction to provide (R)-4-(4-chloro-2-methanesulfonylphenyl)-1,1,1-trifluoro-2-(5-methanesulfonyl-1H-pyrrolo[2,3-c]pyridin-2-ylmethyl)-4-methylpentan-2-ol (15.4 g, 99%).

The following compounds have been prepared analogously:

(R)-4-(5-Chloro-2,3-dihydrobenzofuran-7-yl)-1,1,1-trifluoro-2-(5-methanesulfonyl-1H-pyrrolo[2,3-c]pyridin-2-ylmethyl)-4-methylpentan-2-ol;

1,1,1-Trifluoro-4-(2-methanesulfonylphenyl)-2-(5-methanesulfonyl-1H-pyrrolo[2,3-c]pyridin-2-ylmethyl)-4-methylpentan-2-ol;

(R)-4-(5-Chloro-2,3-dihydrobenzofuran-7-yl)-2-(5-ethanesulfonyl-1H-pyrrolo[2,3-c]pyridin-2-ylmethyl)-1,1,1-trifluoro-4-methylpentan-2-ol;

(R)-4-(3-Bromophenyl)-1,1,1-trifluoro-2-(5-methanesulfonyl-1H-pyrrolo[2,3-c]pyridin-2-ylmethyl)-4-methylpentan-2-ol;

2-(5-Ethanesulfonyl-1H-pyrrolo[2,3-c]pyridin-2-ylmethyl)-1,1,1-trifluoro-4-(2-methanesulfonylphenyl)-4-methylpentan-2-ol;

2-[4,4,4-Trifluoro-3-hydroxy-3-(5-methanesulfonyl-1H-pyrrolo[2,3-c]pyridin-2-ylmethyl)-1,1-dimethylbutyl]benzamide;

1,1,1-Trifluoro-4-(3-fluoro-2-methanesulfonylphenyl)-2-(5-methanesulfonyl-1H-pyrrolo[2,3-c]pyridin-2-ylmethyl)-4-methylpentan-2-ol;

1,1,1-Trifluoro-4-(4-fluoro-2-methanesulfonylphenyl)-2-(5-methanesulfonyl-1H-pyrrolo[2,3-c]pyridin-2-ylmethyl)-4-methylpentan-2-ol;

1,1,1-Trifluoro-4-(5-fluoro-2-methanesulfonylphenyl)-2-(5-methanesulfonyl-1H-pyrrolo[2,3-c]pyridin-2-ylmethyl)-4-methylpentan-2-ol;

4-(5-Chloro-2-methanesulfonylphenyl)-1,1,1-trifluoro-2-(5-methanesulfonyl-1H-pyrrolo[2,3-c]pyridin-2-ylmethyl)-4-methylpentan-2-ol;

4-(4-Chloro-2-methanesulfonylphenyl)-1,1,1-trifluoro-2-(5-methanesulfonyl-1H-pyrrolo[2,3-c]pyridin-2-ylmethyl)-4-methylpentan-2-ol;

4-(2-Bromophenyl)-1,1,1-trifluoro-2-(5-methanesulfonyl-1H-pyrrolo[2,3-c]pyridin-2-ylmethyl)-4-methylpentan-2-ol;

4-(4-Chloro-2-methanesulfonylphenyl)-2-(5-ethanesulfonyl-1H-pyrrolo[2,3-c]pyridin-2-ylmethyl)-1,1,1-trifluoro-4-methylpentan-2-ol;

2-(5-Ethanesulfonyl-1H-pyrrolo[2,3-c]pyridin-2-ylmethyl)-1,1,1-trifluoro-4-(4-fluoro-2-methanesulfonylphenyl)-4-methylpentan-2-ol;

2-[3-(5-Ethanesulfonyl-1H-pyrrolo[2,3-c]pyridin-2-ylmethyl)-4,4,4-trifluoro-3-hydroxy-1,1-dimethylbutyl]benzamide;

1,1,1-Trifluoro-4-(4-fluoro-2-methanesulfonylphenyl)-4-methyl-2-[5-(propane-2-sulfonyl)-1H-pyrrolo[2,3-c]pyridin-2-ylmethyl]pentan-2-ol;

4-Benzo[b]thiophen-7-yl-1,1,1-trifluoro-2-(5-methanesulfonyl-1H-pyrrolo[2,3-c]pyridin-2-ylmethyl)-4-methylpentan-2-ol;

1,1,1-Trifluoro-4-(2-methanesulfonylphenyl)-4-methyl-2-[5-(propane-2-sulfonyl)-1H-pyrrolo[2,3-c]pyridin-2-ylmethyl]pentan-2-ol;

1,1,1-Trifluoro-4-(5-fluoro-2-methanesulfonylphenyl)-4-methyl-2-[5-(propane-2-sulfonyl)-1H-pyrrolo[2,3-c]pyridin-2-ylmethyl]pentan-2-ol;

1,1,1-Trifluoro-4-(3-fluoro-2-methanesulfonylphenyl)-4-methyl-2-[5-(propane-2-sulfonyl)-1H-pyrrolo[2,3-c]pyridin-2-ylmethyl]pentan-2-ol;

2-(5-Ethanesulfonyl-1H-pyrrolo[2,3-c]pyridin-2-ylmethyl)-1,1,1-trifluoro-4-(3-fluoro-2-methanesulfonylphenyl)-4-methylpentan-2-ol;

4-(1,1-Dioxo-1H-1$\lambda^6$-benzo[b]thiophen-7-yl)-1,1,1-trifluoro-2-(5-methanesulfonyl-1H-pyrrolo[2,3-c]pyridin-2-ylmethyl)-4-methylpentan-2-ol;

5-Methyl-2-[4,4,4-trifluoro-3-hydroxy-3-(5-methanesulfonyl-1H-pyrrolo[2,3-c]pyridin-2-ylmethyl)-1,1-dimethylbutyl]benzamide;

2-[3-(5-Ethanesulfonyl-1H-pyrrolo[2,3-c]pyridin-2-ylmethyl)-4,4,4-trifluoro-3-hydroxy-1,1-dimethylbutyl]-5-methylbenzamide;

4-(1,1-Dioxo-1H-1$\lambda^6$-benzo[b]thiophen-7-yl)-2-(5-ethanesulfonyl-1H-pyrrolo[2,3-c]pyridin-2-ylmethyl)-1,1,1-trifluoro-4-methylpentan-2-ol;

5-Fluoro-2-[4,4,4-trifluoro-3-hydroxy-3-(5-methanesulfonyl-1H-pyrrolo[2,3-c]pyridin-2-ylmethyl)-1,1-dimethylbutyl]benzamide;

(R)-2-[3-(5-Ethanesulfonyl-1H-pyrrolo[2,3-c]pyridin-2-ylmethyl)-4,4,4-trifluoro-3-hydroxy-1,1-dimethylbutyl]-5-fluorobenzamide;

4-(5-Chloro-2-methanesulfonylphenyl)-1,1,1-trifluoro-4-methyl-2-[5-(propane-2-sulfonyl)-1H-pyrrolo[2,3-c]pyridin-2-ylmethyl]pentan-2-ol;

4-Methyl-2-[4,4,4-trifluoro-3-hydroxy-3-(5-ethanesulfonyl-1H-pyrrolo[2,3-c]pyridin-2-ylmethyl)-1,1-dimethylbutyl]benzamide;

4-Methyl-2-[4,4,4-trifluoro-3-hydroxy-3-(5-methanesulfonyl-1H-pyrrolo[2,3-c]pyridin-2-ylmethyl)-1,1-dimethylbutyl]benzamide;

5-Methyl-2-{4,4,4-trifluoro-3-hydroxy-1,1-dimethyl-3-[5-(propane-2-sulfonyl)-1H-pyrrolo[2,3-c]pyridin-2-ylmethyl]butyl}benzamide;

5-Fluoro-2-{4,4,4-trifluoro-3-hydroxy-1,1-dimethyl-3-[5-(propane-2-sulfonyl)-1H-pyrrolo[2,3-c]pyridin-2-ylmethyl]butyl}benzamide;

1,1,1-Trifluoro-4-(5-fluoro-2-methanesulfonylphenyl)-4-methyl-2-[5-(propane-1-sulfonyl)-1H-pyrrolo[2,3-c]pyridin-2-ylmethyl]pentan-2-ol;

1,1,1-Trifluoro-4-(2-methanesulfonylphenyl)-4-methyl-2-[5-(propane-1-sulfonyl)-1H-pyrrolo[2,3-c]pyridin-2-ylmethyl]pentan-2-ol;

1,1,1-Trifluoro-4-(3-fluoro-2-methanesulfonylphenyl)-4-methyl-2-[5-(propane-1-sulfonyl)-1H-pyrrolo[2,3-c]pyridin-2-ylmethyl]pentan-2-ol;

4-(5-Chloro-2-methanesulfonylphenyl)-1,1,1-trifluoro-4-methyl-2-[5-(propane-1-sulfonyl)-1H-pyrrolo[2,3-c]pyridin-2-ylmethyl]pentan-2-ol;

5-Chloro-2-[3-(5-ethanesulfonyl-1H-pyrrolo[2,3-c]pyridin-2-ylmethyl)-4,4,4-trifluoro-3-hydroxy-1,1-dimethylbutyl]benzamide;

5-Chloro-2-[4,4,4-trifluoro-3-hydroxy-3-(5-methanesulfonyl-1H-pyrrolo[2,3-c]pyridin-2-ylmethyl)-1,1-dimethylbutyl]benzamide;

2-[3-(5-Ethanesulfinyl-1H-pyrrolo[2,3-c]pyridin-2-ylmethyl)-4,4,4-trifluoro-3-hydroxy-1,1-dimethylbutyl]benzamide;

4-(2-Bromo-5-fluorophenyl)-1,1,1-trifluoro-2-(5-methanesulfonyl-1H-pyrrolo[2,3-c]pyridin-2-ylmethyl)-4-methylpentan-2-ol;

4-(2-Bromo-5-fluorophenyl)-1,1,1-trifluoro-2-(5-methanesulfonyl-1H-pyrrolo[2,3-c]pyridin-2-ylmethyl)-4-methylpentan-2-ol;

(R)-4-(3-Bromophenyl)-1,1,1-trifluoro-2-(5-methanesulfonyl-1H-pyrrolo[3,2-b]pyridin-2-ylmethyl)-4-methylpentan-2-ol;

4-(5-Chloro-2-methanesulfonylphenyl)-1,1,1-trifluoro-2-(5-methanesulfonyl-1H-pyrrolo[3,2-b]pyridin-2-ylmethyl)-4-methylpentan-2-ol;

5-Methyl-2-[4,4,4-trifluoro-3-hydroxy-3-(5-methanesulfonyl-1H-pyrrolo[3,2-b]pyridin-2-ylmethyl)-1,1-dimethylbutyl]benzamide;

1,1,1-Trifluoro-4-(3-fluoro-2-methanesulfonylphenyl)-2-(5-methanesulfonyl-1H-pyrrolo[3,2-b]pyridin-2-ylmethyl)-4-methylpentan-2-ol;

2-[(R)-4,4,4-Trifluoro-3-hydroxy-3-(5-methanesulfonyl-1H-pyrrolo[3,2-b]pyridin-2-ylmethyl)-1,1-dimethylbutyl]benzamide; and 5-Fluoro-2-[(R)-4,4,4-trifluoro-3-hydroxy-3-(2-methanesulfonyl-5H-pyrrolo[3,2-d]pyrimidin-6-ylmethyl)-1,1-dimethylbutyl]benzamide.

Example 19

Preparation of 2-[3-(5-Ethanesulfonyl-1H-pyrrolo[2,3-c]pyridin-2-ylmethyl)-4,4,4-trifluoro-3-hydroxy-1,1-dimethylbutyl]benzenesulfonamide

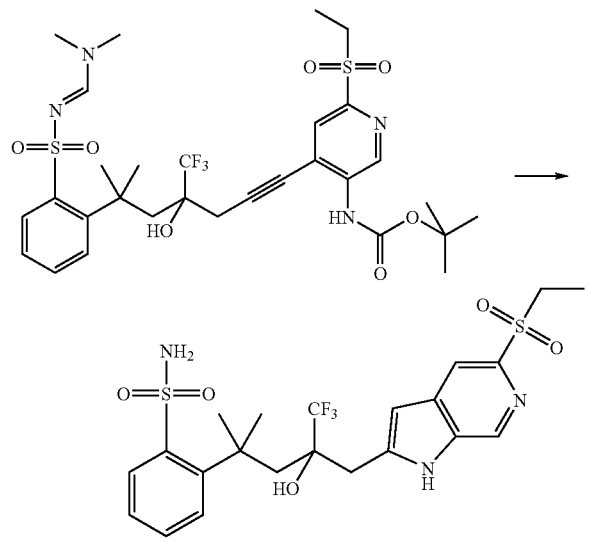

To a vial was added {4-[6-(2-{[1-dimethylaminomethylidene]sulfamoyl}phenyl)-4-hydroxy-6-methyl-4-trifluoromethylhept-1-ynyl]-6-ethanesulfonylpyridin-3-yl}carbamic acid tert-butyl ester (48 mg, 0.07 mmol) in 3 mL of methanol, followed by the addition of DBU (106 mg, 0.7 mmol). The reaction mixture was stirred at 70° C. for 90 minutes. To the reaction was added 0.5 mL of water, and the reaction mixture was stirred at 70° C. for 1.5 hours. The reaction mixture was concentrated in vacuo. The crude mixture was purified by flash chromatography. The column was eluted with 0-5% MeOH/CH$_2$Cl$_2$ to afford 18 mg (48%) of 2-[3-(5-ethanesulfonyl-1H-pyrrolo[2,3-c]pyridin-2-ylmethyl)-4,4,4-trifluoro-3-hydroxy-1,1-dimethylbutyl]benzenesulfonamide. MS (ES$^+$) m/z 534 [M+H]$^+$.

The following compound was prepared analogously: 2-[4,4,4-Trifluoro-3-hydroxy-3-(5-methanesulfonyl-1H-pyrrolo[2,3-c]pyridin-2-ylmethyl)-1,1-dimethylbutyl]benzenesulfonamide.

Example 20

Preparation of (R)-4-(3-Bromophenyl)-1,1,1-trifluoro-2-(5-methanesulfonyl-1H-pyrrolo[3,2-b]pyridin-2-ylmethyl)-4-methylpentan-2-ol

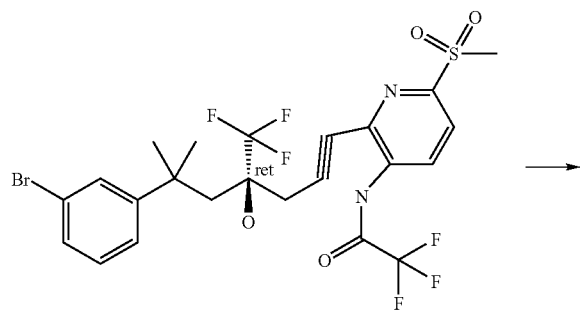

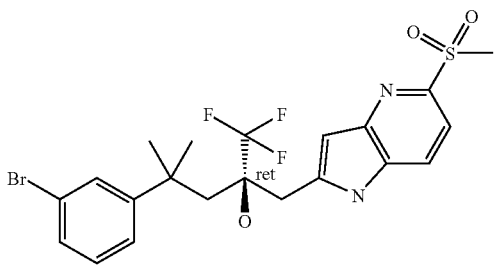

N-{2-[(S)-6-(3-Bromophenyl)-4-hydroxy-6-methyl-4-trifluoromethylhept-1-ynyl]-6-methanesulfonylpyridin-3-yl}-2,2,2-trifluoroacetamide (351 mg, 0.57 mmol) was dissolved in 3.4 mL of DMSO and tetramethylguanidine (0.43 mL, 3.42 mmol) was added. The mixture was stirred at 70° C. for 7 hours. Then it was diluted with ethyl acetate, washed with saturated aqueous ammonium chloride solution, and brine, dried over sodium sulfate, and concentrated in vacuo. The mixture was purified by flash chromatography (gradient 0→8% MeOH in DCM). The product was further purified by crystallization (DCM) to give (R)-4-(3-bromophenyl)-1,1,1-trifluoro-2-(5-methanesulfonyl-1H-pyrrolo[3,2-b]pyridin-2-ylmethyl)-4-methylpentan-2-ol as a white solid (181 mg, 61%).

The following compounds were prepared analogously:

4-(5-Chloro-2-methanesulfonylphenyl)-1,1,1-trifluoro-2-(5-methanesulfonyl-1H-pyrrolo[3,2-b]pyridin-2-ylmethyl)-4-methylpentan-2-ol;

5-Methyl-2-[4,4,4-trifluoro-3-hydroxy-3-(5-methanesulfonyl-1H-pyrrolo[3,2-b]pyridin-2-ylmethyl)-1,1-dimethylbutyl]benzamide;

1,1,1-Trifluoro-4-(3-fluoro-2-methanesulfonylphenyl)-2-(5-methanesulfonyl-1H-pyrrolo[3,2-b]pyridin-2-ylmethyl)-4-methylpentan-2-ol;

2-[(R)-4,4,4-Trifluoro-3-hydroxy-3-(5-methanesulfonyl-1H-pyrrolo[3,2-b]pyridin-2-ylmethyl)-1,1-dimethylbutyl]benzamide; and 4-Fluoro-2-[4,4,4-trifluoro-3-hydroxy-3-(5-methanesulfonyl-1H-pyrrolo[3,2-b]pyridin-2-ylmethyl)-1,1-dimethylbutyl]benzamide.

Example 21

Preparation of 4-Fluoro-2-[4,4,4-trifluoro-3-hydroxy-3-(5-methanesulfonyl-1H-pyrrolo[2,3-c]pyridin-2-ylmethyl)-1,1-dimethylbutyl]phenol

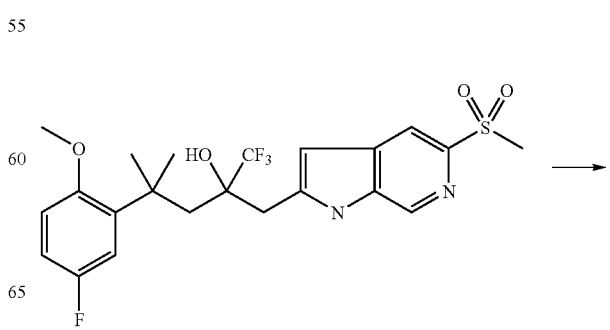

-continued

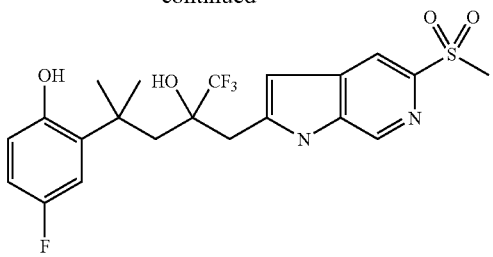

1,1,1-Trifluoro-4-(5-fluoro-2-methoxyphenyl)-2-(5-methanesulfonyl-1H-pyrrolo[2,3-c]pyridin-2-ylmethyl)-4-methylpentan-2-ol (179 mg, 0.37 mmol) was dissolved in 10 mL of dichloromethane. 3.7 mL of a 1 M solution of boron tribromide (3.7 mmol) in dichloromethane were added. The resulting solution was stirred at normal room temperature overnight. After dropwise addition of MeOH (1 mL) at 0° C., the solvent was evaporated. The residue was dissolved in ethyl acetate and washed with saturated sodium bicarbonate (NaHCO$_3$) solution. The organic phase was separated and the aqueous layer was extracted with four 10 mL portions of ethyl acetate. The combined organic phases were dried over magnesium sulfate. The solvent was removed. Flash chromatography of the residue yielded 4-fluoro-2-[4,4,4-trifluoro-3-hydroxy-3-(5-methanesulfonyl-1H-pyrrolo[2,3-c]pyridin-2-ylmethyl)-1,1-dimethylbutyl]phenol as a white solid.

The following compound was prepared analogously:
4-Bromo-2-[4,4,4-trifluoro-3-hydroxy-3-(5-methanesulfonyl-1H-pyrrolo[2,3-c]pyridin-2-ylmethyl)-1,1-dimethylbutyl]phenol.

Example 22

Synthesis of (R)-2-[3-(5-Ethanesulfonyl-1H-pyrrolo[2,3-c]pyridin-2-ylmethyl)-4,4,4-trifluoro-3-hydroxy-1,1-dimethylbutyl]-5-fluorobenzamide Phosphoric Acid Co-Crystal Seed Crystals (R)-2-[3-(5-Ethanesulfonyl-1H-pyrrolo[2,3-c]pyridin-2-ylmethyl)-4,4,4-trifluoro-3-hydroxy-1,1-dimethylbutyl]-5-fluorobenzamide phosphoric acid co-crystal seed crystals used in the synthesis was initially generated from methyl isobutyl ketone (MIBK). A mixture of 10 mg (0.0194 mmol) of (R)-2-[3-(5-Ethanesulfonyl-1H-pyrrolo[2,3-c]pyridin-2-ylmethyl)-4,4,4-trifluoro-3-hydroxy-1,1-dimethylbutyl]-5-fluorobenzamide in 400 µL of methanol and 0.0194 mmol of phosphoric acid in 158.5 µL of THF was added into a vial in a SYMYX high-throughput master plate. After methanol and THF were removed from the master plate, 800 µL of MIBK was added. The MIBK mixture was stirred at 65° C. for 2 hours, cooled down to room temperature in 2 hours and continued stirring at room temperature overnight. (R)-2-[3-(5-Ethanesulfonyl-1H-pyrrolo[2,3-c]pyridin-2-ylmethyl)-4,4,4-trifluoro-3-hydroxy-1,1-dimethylbutyl]-5-fluorobenzamide phosphoric acid crystals were produced from MIBK mixtures and used in the following synthesis procedures as seed crystals in Examples 23 and 24.

Example 23

Figure 2:
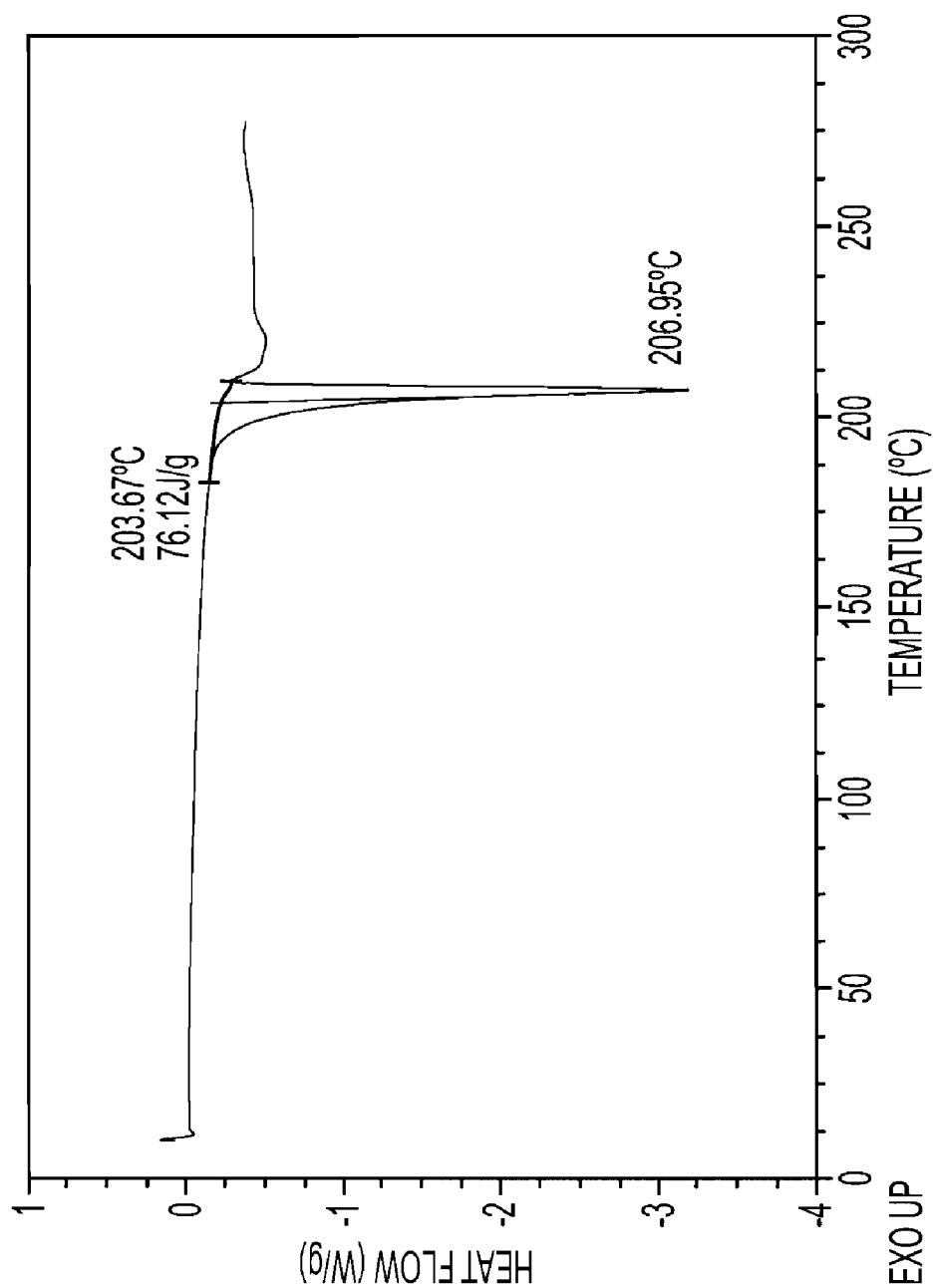
FIG. 2: DSC of (R)-2-[3-(5-Ethanesulfonyl-1H-pyrrolo[2,3-c]pyridin-2-ylmethyl)-4,4,4-trifluoro-3-hydroxy-1,1-dimethylbutyl]-5-fluorobenzamide Phosphoric Acid Co-Crystal.
Figure 3:
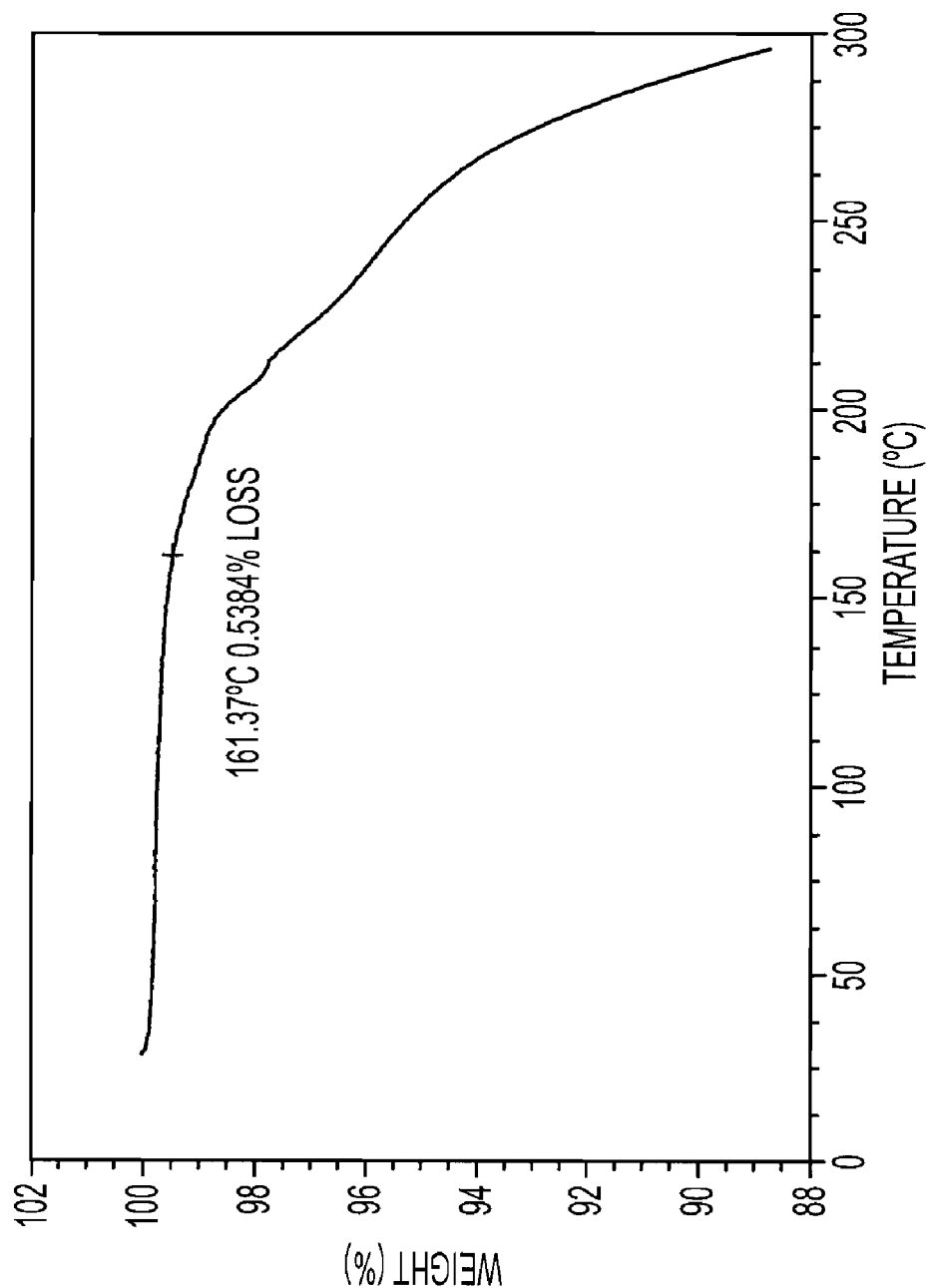
FIG. 3: TGA of (R)-2-[3-(5-Ethanesulfonyl-1H-pyrrolo[2,3-c]pyridin-2-ylmethyl)-4,4,4-trifluoro-3-hydroxy-1,1-dimethylbutyl]-5-fluorobenzamide Phosphoric Acid Co-Crystal.
Figure 4:
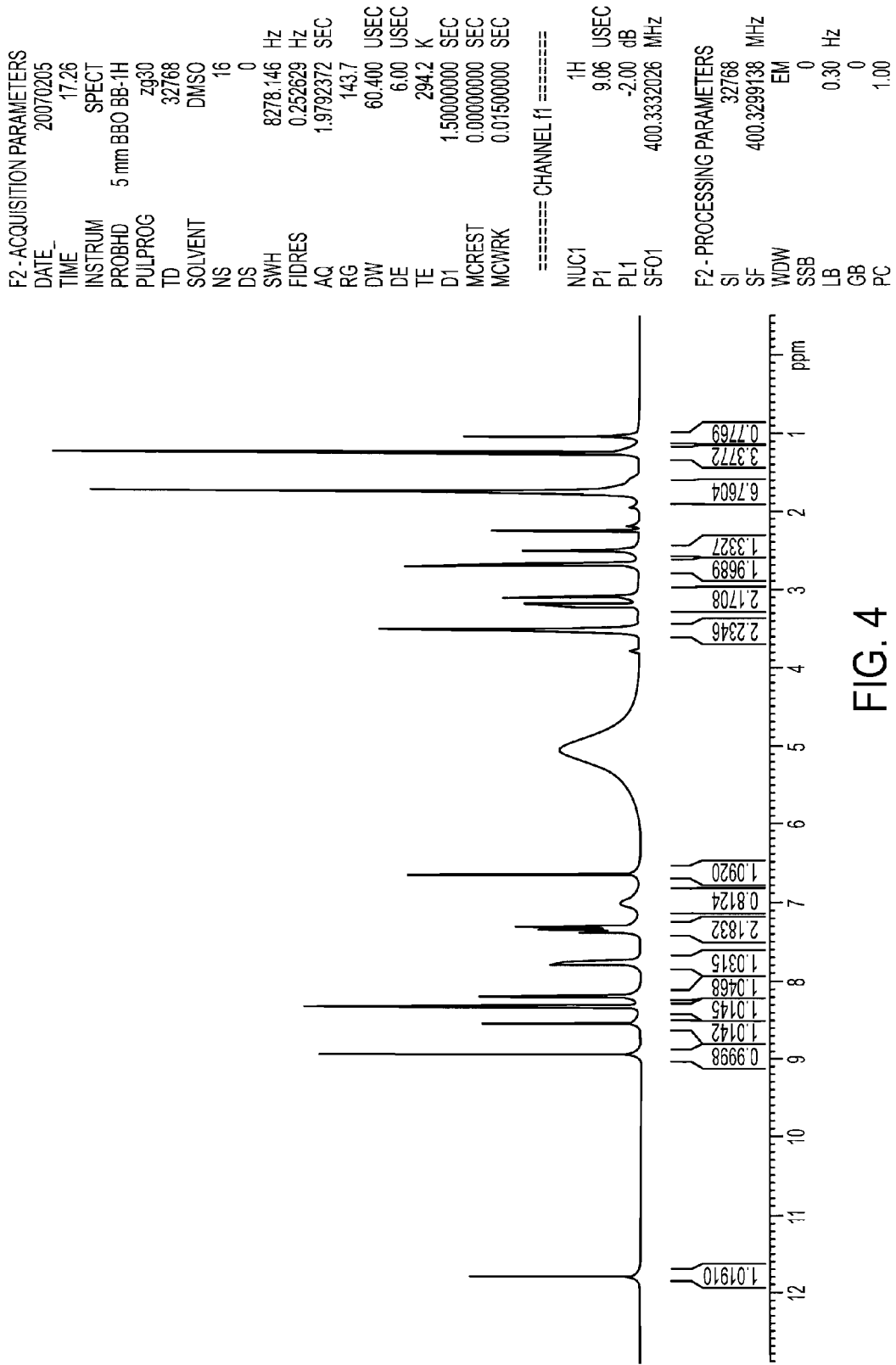
FIG. 4: $^1$H NMR of (R)-2-[3-(5-Ethanesulfonyl-1H-pyrrolo[2,3-c]pyridin-2-ylmethyl)-4,4,4-trifluoro-3-hydroxy-1,1-dimethylbutyl]-5-fluorobenzamide Phosphoric Acid Co-Crystal.
Figure 5:
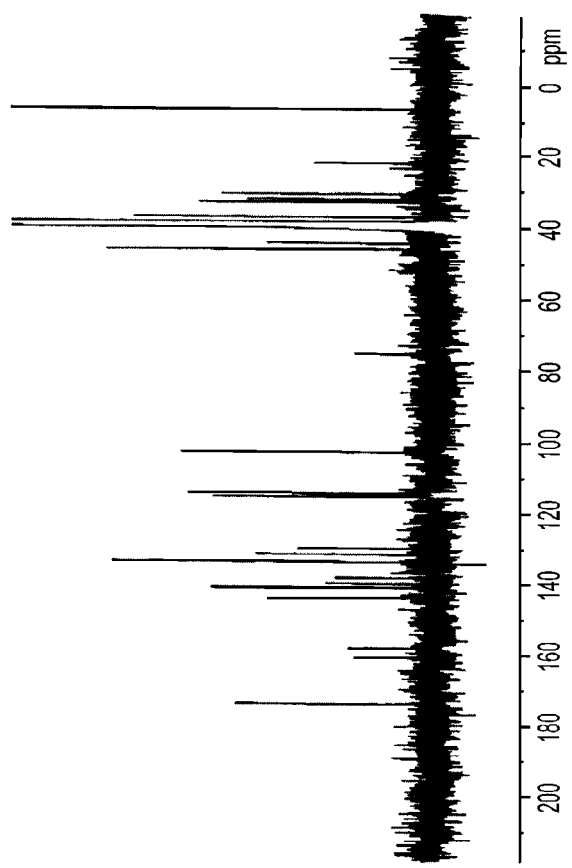
FIG. 5: $^{13}$C NMR of (R)-2-[3-(5-Ethanesulfonyl-1H-pyrrolo[2,3-c]pyridin-2-ylmethyl)-4,4,4-trifluoro-3-hydroxy-1,1-dimethylbutyl]-5-fluorobenzamide Phosphoric Acid Co-Crystal.
Figure 6:
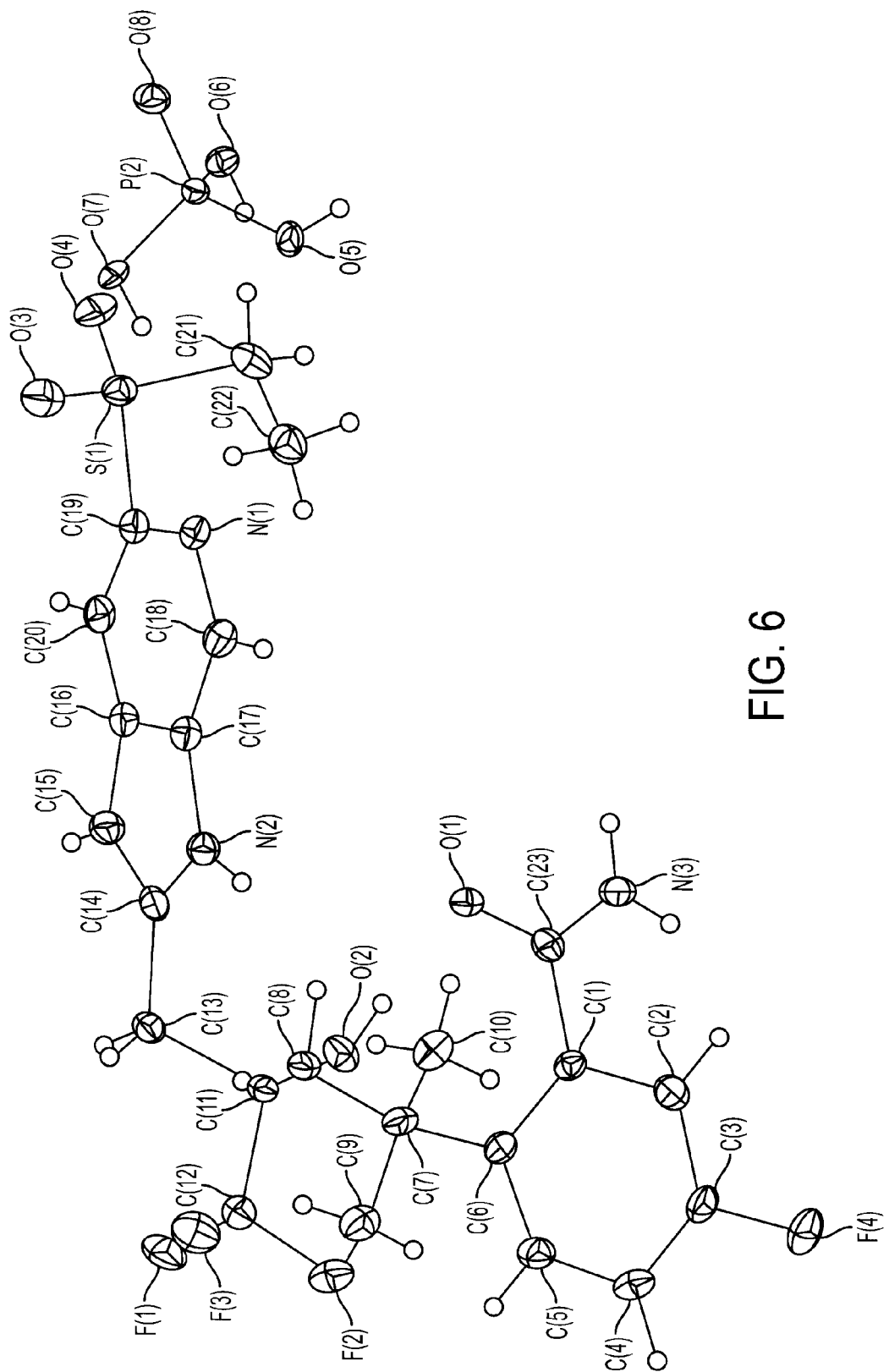
FIG. 6: ORTEP plot of (R)-2-[3-(5-Ethanesulfonyl-1H-pyrrolo[2,3-c]pyridin-2-ylmethyl)-4,4,4-trifluoro-3-hydroxy-1,1-dimethylbutyl]-5-fluorobenzamide Phosphoric Acid Co-Crystal.

Synthesis of (R)-2-[3-(5-Ethanesulfonyl-1H-pyrrolo[2,3-c]pyridin-2-ylmethyl)-4,4,4-trifluoro-3-hydroxy-1,1-dimethylbutyl]-5-fluorobenzamide phosphoric acid Co-Crystal using 2-Butanone/Heptane Approximately 15 g of acetic acid solvate form of the free base of (R)-2-[3-(5-Ethanesulfonyl-1H-pyrrolo[2,3-c]pyridin-2-ylmethyl)-4,4,4-trifluoro-3-hydroxy-1,1-dimethylbutyl]-5-fluorobenzamide (82.4 wt. % of free base, KF=0.42%) is dissolved in 90 mL of 2-butanone at 60° C. The resulting solution is polish filtered and combined with the filter rinse of 30 mL of 2-butanone to give a clear solution at 50° C. To the solution at 50° C. is added approximately 3.05 g of 85 wt. % aqueous phosphoric acid (H$_3$PO$_4$, 1.05 equiv.). Approximately 20 mL to 30 mL of heptane is added to the solution slowly while the solution remains clear. Then approximately 15 mg of the (R)-2-[3-(5-Ethanesulfonyl-1H-pyrrolo[2,3-c]pyridin-2-ylmethyl)-4,4,4-trifluoro-3-hydroxy-1,1-dimethylbutyl]-5-fluorobenzamide phosphoric acid co-crystal crystal seeds, for example, made by the process in Example 22, is added to the solution, upon which crystallization is initiated and a crystal slurry is developed within 10 to 20 minutes. To the slurry at 50° C., another 30 mL to 40 mL of heptane is slowly added over 1 hour. The slurry is then cooled linearly to 20° C. over 2 hours and aged at 20° C. for at least 2 hours. The batch is filtered and the wet cake washed with 1:2 (v/v) 2-butanone/heptane mixture. The solid is dried at 70° C.-80° C. for 15 hours to 48 hours. The dry product (R)-2-[3-(5-Ethanesulfonyl-1H-pyrrolo[2,3-c]pyridin-2-ylmethyl)-4,4,4-trifluoro-3-hydroxy-1,1-dimethylbutyl]-5-fluorobenzamide phosphoric acid co-crystal is obtained as a white solid in 92% to 96% yield and >99.5 area % purity by HPLC. FIGS. 1 to 6 show physical measurements and spectral data that characterize the product obtained.

Example 24

Synthesis of (R)-2-[3-(5-Ethanesulfonyl-1H-pyrrolo[2,3-c]pyridin-2-ylmethyl)-4,4,4-trifluoro-3-hydroxy-1,1-dimethylbutyl]benzamide Phosphoric Acid Co-Crystal Seed Crystals (R)-2-[3-(5-Ethanesulfonyl-1H-pyrrolo[2,3-c]pyridin-2-ylmethyl)-4,4,4-trifluoro-3-hydroxy-1,1-dimethylbutyl]benzamide phosphoric acid co-crystal seed crystals were initially generated from MIBK. A mixture of 10 mg (0.0201 mmol) of (R)-2-[3-(5-ethanesulfonyl-1H-pyrrolo[2,3-c]pyridin-2-ylmethyl)-4,4,4-trifluoro-3-hydroxy-1,1-dimethylbutyl]benzamide in 400 µL of methanol and 0.0201 mmol of phosphoric acid in 164.2 µL of THF was added into a vial in SYMYX high-throughput master plate. After the methanol and THF were removed from the master plate, 800 µL of MIBK was added. The MIBK mixture was stirred at 65° C. for 2 hours and cooled down to room temperature over 2 hours. The mixture was stirred at room temperature overnight. This afforded (R)-2-[3-(5-ethanesulfonyl-1H-pyrrolo[2,3-c]pyridin-2-ylmethyl)-4,4,4-trifluoro-3-hydroxy-1,1-dimethylbutyl]benzamide phosphoric acid co-crystal seed crystals.

Example 25

Figure 7:
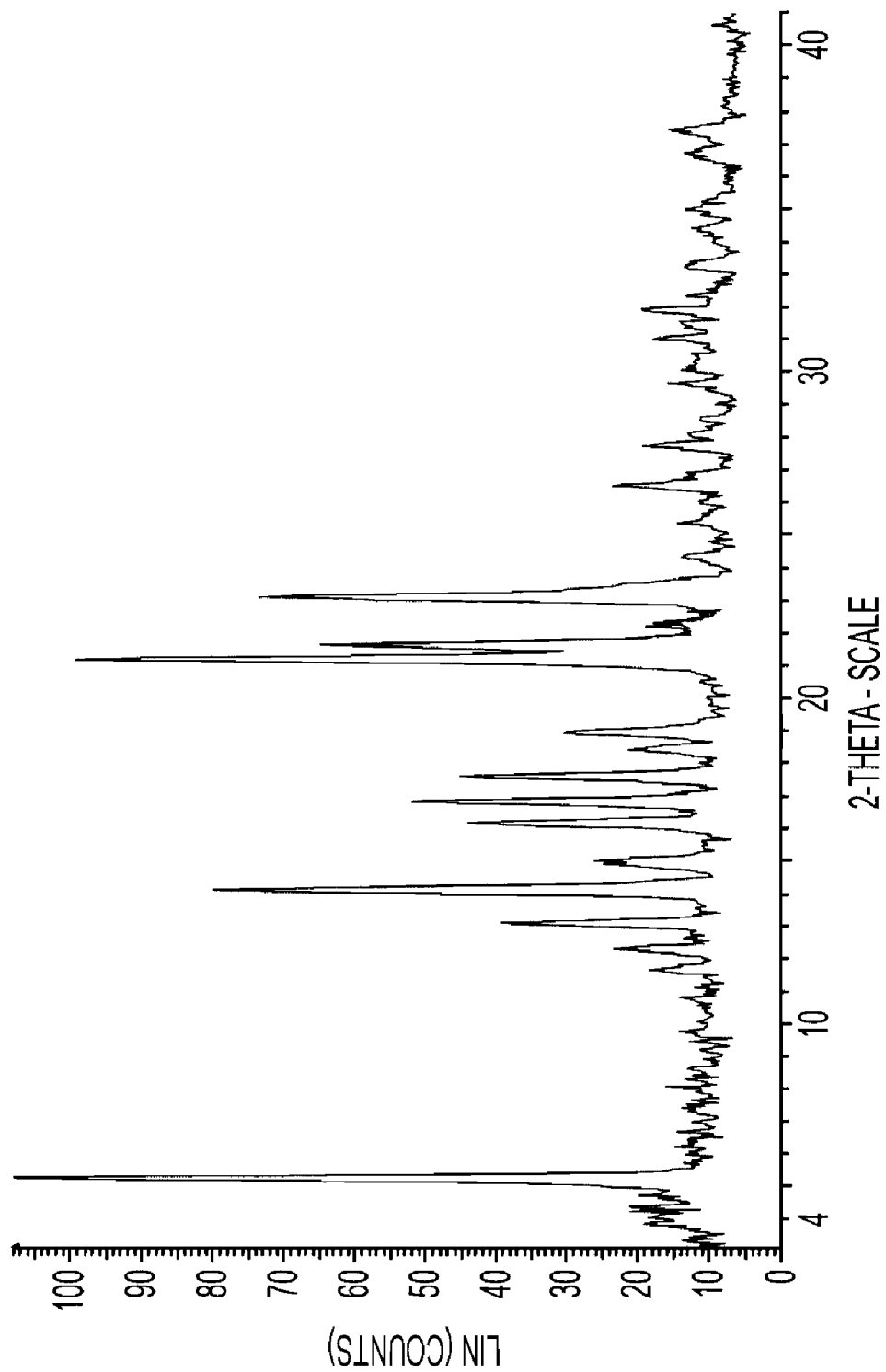
FIG. 7: XRPD of (R)-2-[3-(5-Ethanesulfonyl-1H-pyrrolo[2,3-c]pyridin-2-ylmethyl)-4,4,4-trifluoro-3-hydroxy-1,1-dimethylbutyl]benzamide Phosphoric Acid Co-Crystal.
Figure 8:
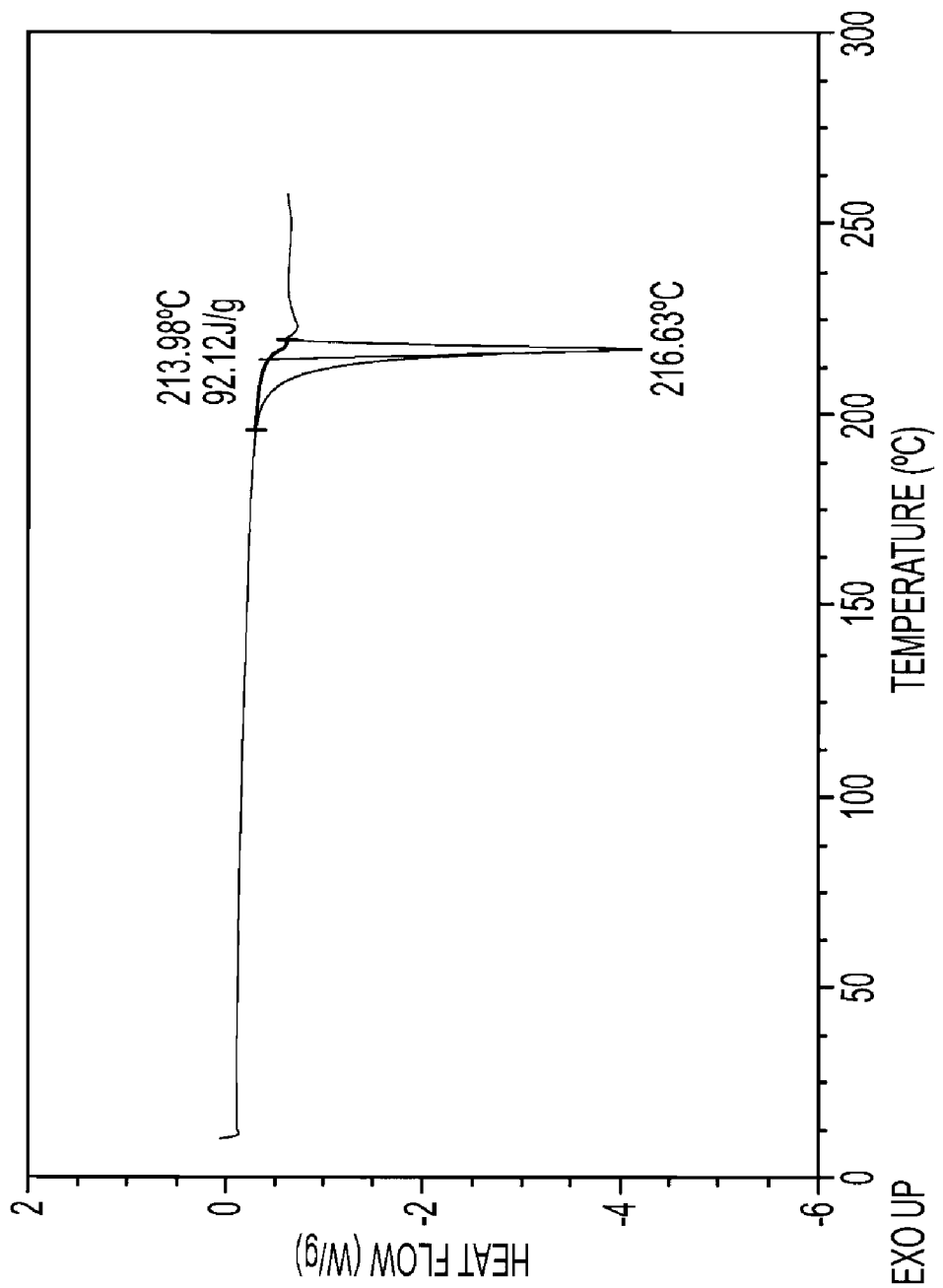
FIG. 8: DSC of (R)-2-[3-(5-Ethanesulfonyl-1H-pyrrolo[2,3-c]pyridin-2-ylmethyl)-4,4,4-trifluoro-3-hydroxy-1,1-dimethylbutyl]benzamide Phosphoric Acid Co-Crystal.
Figure 9:
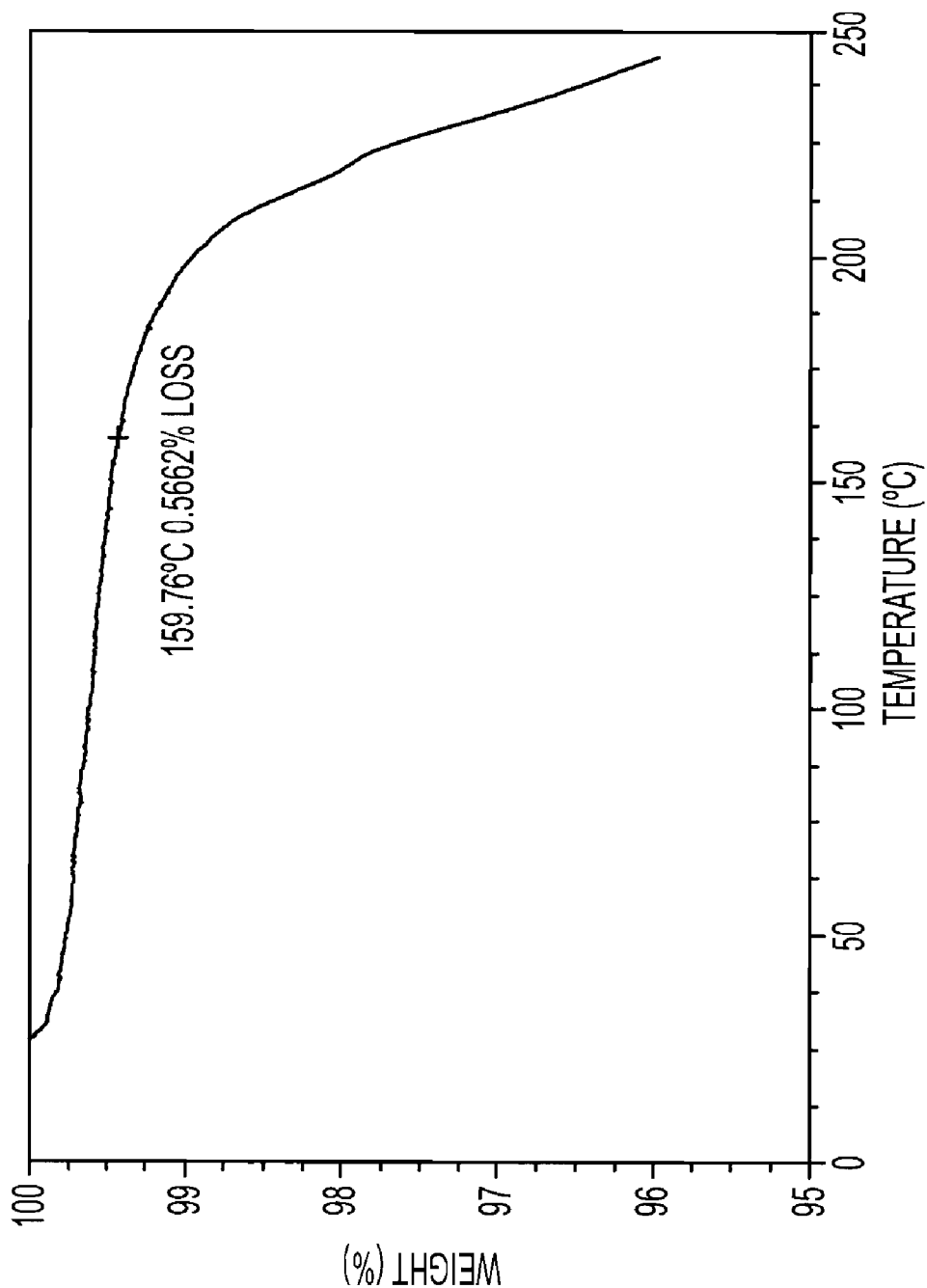
FIG. 9: TGA of (R)-2-[3-(5-Ethanesulfonyl-1H-pyrrolo[2,3-c]pyridin-2-ylmethyl)-4,4,4-trifluoro-3-hydroxy-1,1-dimethylbutyl]benzamide Phosphoric Acid Co-Crystal.
Figure 10:
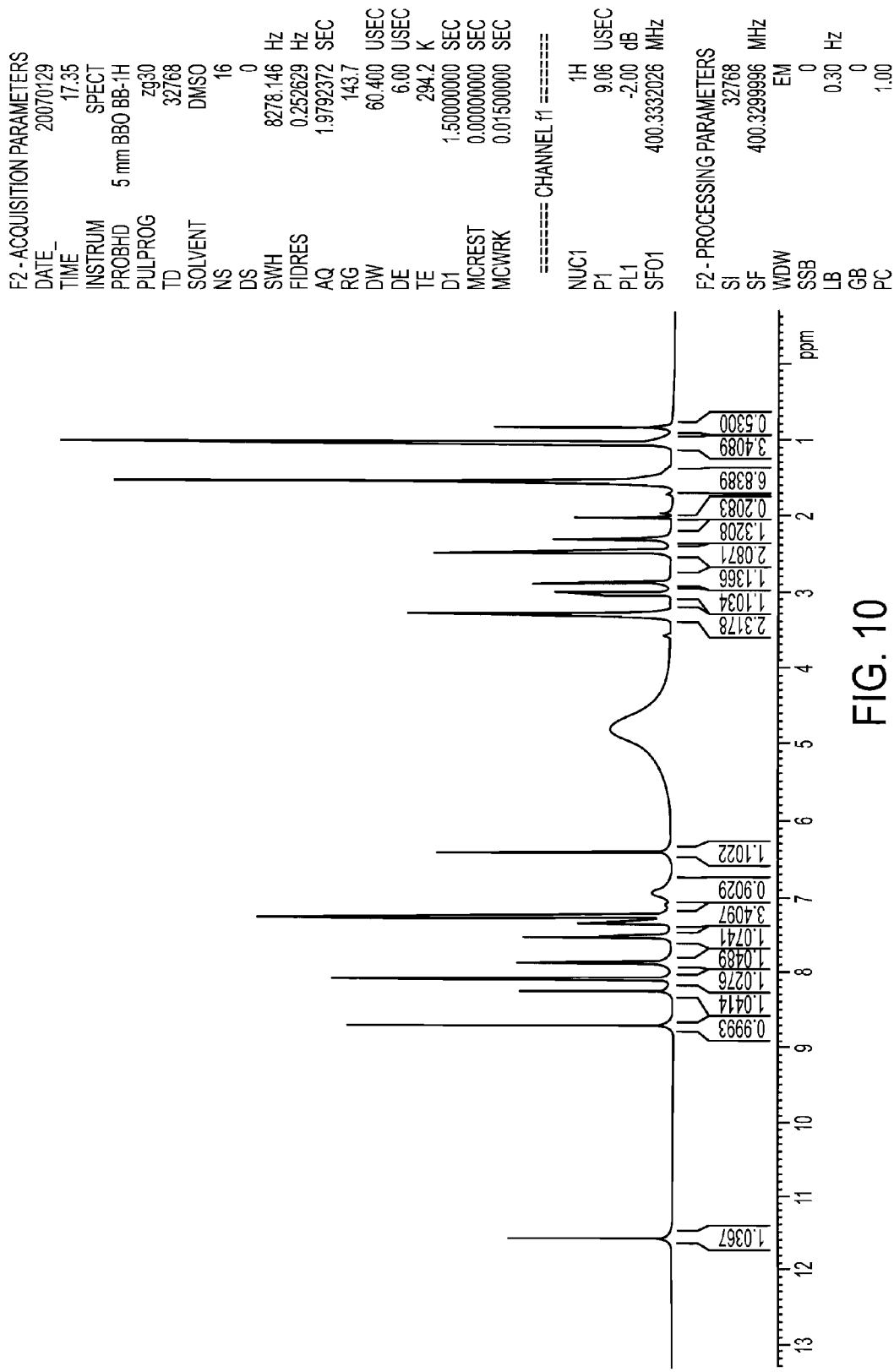
FIG. 10: $^1$H NMR of (R)-2-[3-(5-Ethanesulfonyl-1H-pyrrolo[2,3-c]pyridin-2-ylmethyl)-4,4,4-trifluoro-3-hydroxy-1,1-dimethylbutyl]benzamide Phosphoric Acid Co-Crystal.
Figure 11:
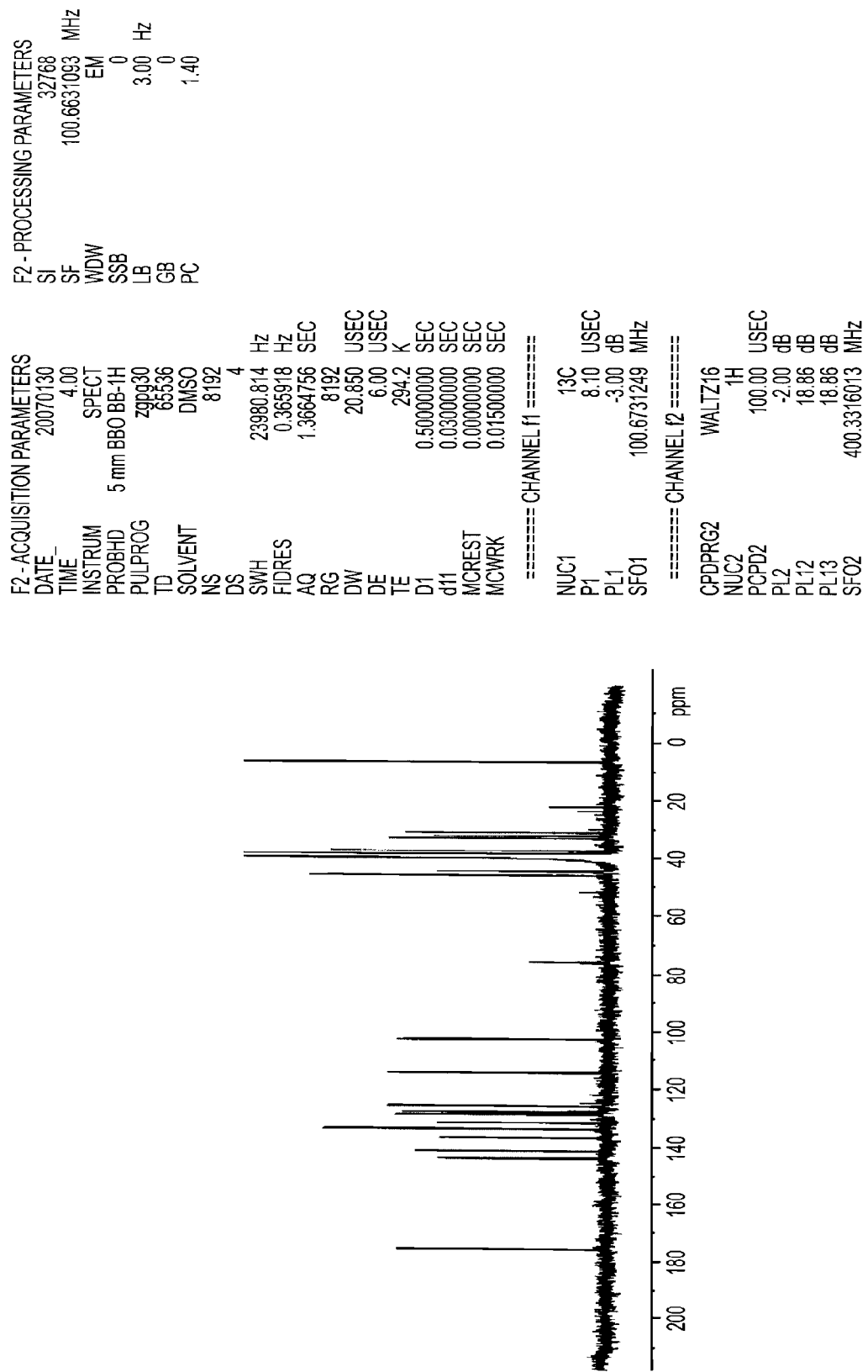
FIG. 11: $^{13}$C NMR of (R)-2-[3-(5-Ethanesulfonyl-1H-pyrrolo[2,3-c]pyridin-2-ylmethyl)-4,4,4-trifluoro-3-hydroxy-1,1-dimethylbutyl]benzamide Phosphoric Acid Co-Crystal.

Synthesis of (R)-2-[3-(5-Ethanesulfonyl-1H-pyrrolo[2,3-c]pyridin-2-ylmethyl)-4,4,4-trifluoro-3-hydroxy-1,1-dimethylbutyl]benzamide Phosphoric Acid Co-Crystal 1 g (2.01 mmol) of (R)-2-[3-(5-ethanesulfonyl-1H-pyrrolo[2,3-c]pyridin-2-ylmethyl)-4,4,4-trifluoro-3-hydroxy-1,1-dimethylbutyl]benzamide was dissolved in 20 mL of MIBK at 70° C. followed by addition of 2.01 mmol of phosphoric acid (85 wt. % H$_3$PO$_4$ in water) at 70° C. The reaction mixture was then seeded with (R)-2-[3-(5-ethanesulfonyl-1H-pyrrolo[2,3-c]pyridin-2-ylmethyl)-4,4,4-trifluoro-3-hydroxy-1,1-dimethylbutyl]benzamide phosphoric acid co-crystal crystal seeds, for example, made by the process in Example 25, stirred at 70° C. for 2 hours and then cooled to room temperature over 6 hours. The mixture was stirred at room temperature overnight. (R)-2-[3-(5-Ethanesulfonyl-1H-pyrrolo[2,3-c]pyridin-2-ylmethyl)-4,4,4-trifluoro-3-hydroxy-1,1-dimethylbutyl]benzamide phosphoric acid co-crystals were collected by filtration. FIGS. 7 to 11 show physical measurements and spectral data that characterize the product obtained.

Example 26

Synthesis of (R)-2-[3-(5-Ethanesulfonyl-1H-pyrrolo[2,3-c]pyridin-2-ylmethyl)-4,4,4-trifluoro-3-hydroxy-1,1-dimethylbutyl]benzamide Isonicotinamide Co-Crystal Seed Crystals (R)-2-[3-(5-Ethanesulfonyl-1H-pyrrolo[2,3-c]pyridin-2-ylmethyl)-4,4,4-trifluoro-3-hydroxy-1,1-dimethylbutyl]benzamide isonicotinamide co-crystal seed crystals were initially generated from ethanol. A mixture of 190.1 mg of (R)-2-[3-(5-ethanesulfonyl-1H-pyrrolo[2,3-c]pyridin-2-ylmethyl)-4,4,4-trifluoro-3-hydroxy-1,1-dimethylbutyl]benzamide (0.382 mmol) and 43.5 mg (0.356 mmol) of isonicotinamide in 4 mL of ethanol were kept at 70° C. for 2 hours to give a clear solution. The mixture was allowed to cool down to 20° C. over 20 hours thus affording (R)-2-[3-(5-ethanesulfonyl-1H-pyrrolo[2,3-c]pyridin-2-ylmethyl)-4,4,4-trifluoro-3-hydroxy-1,1-dimethylbutyl]benzamide isonicotinamide co-crystal seed crystals.

Example 27

Figure 12:
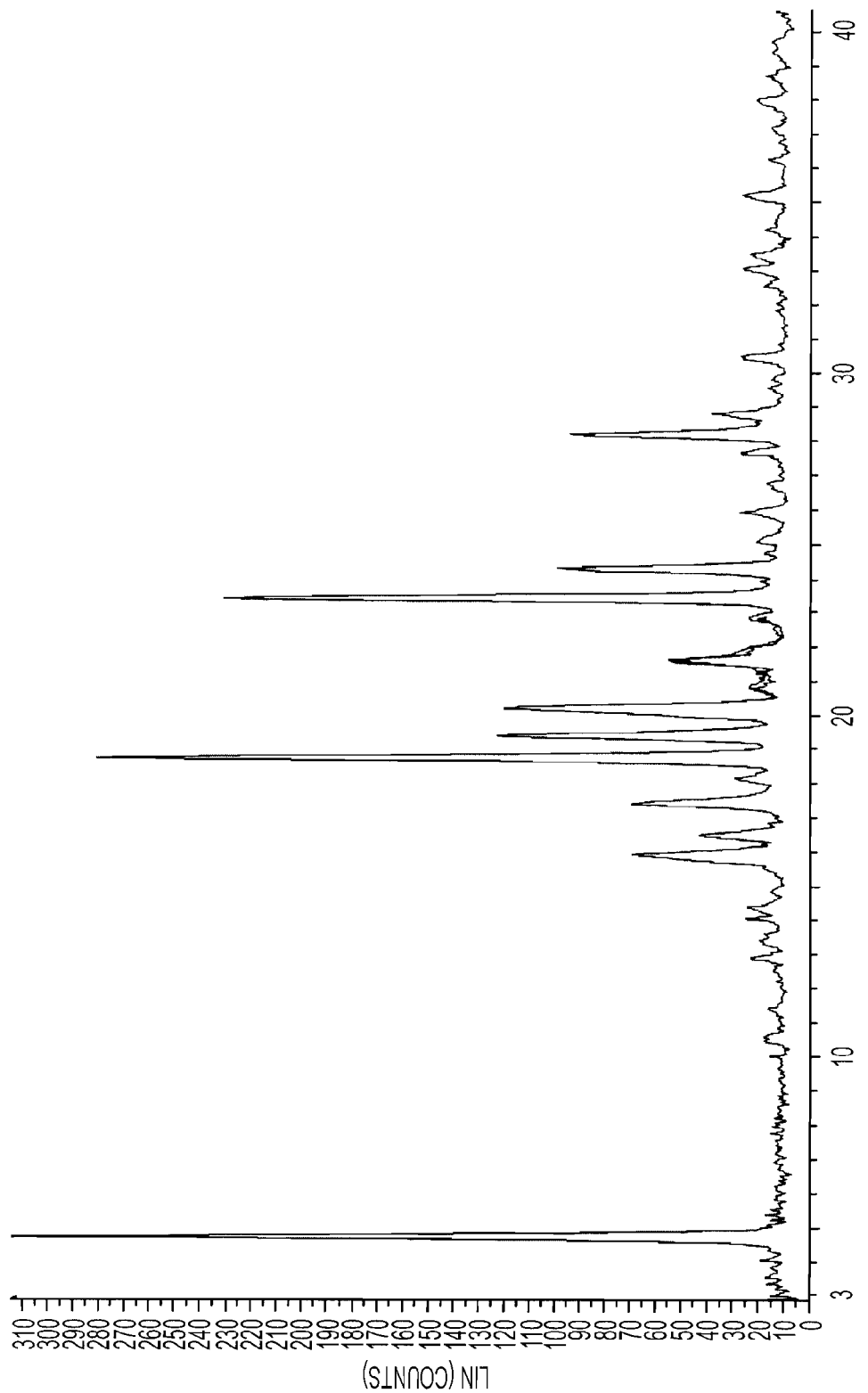
FIG. 12: XRPD of (R)-2-[3-(5-Ethanesulfonyl-1H-pyrrolo[2,3-c]pyridin-2-ylmethyl)-4,4,4-trifluoro-3-hydroxy-1,1-dimethylbutyl]benzamide Isonicotinamide Co-Crystal.
Figure 13:
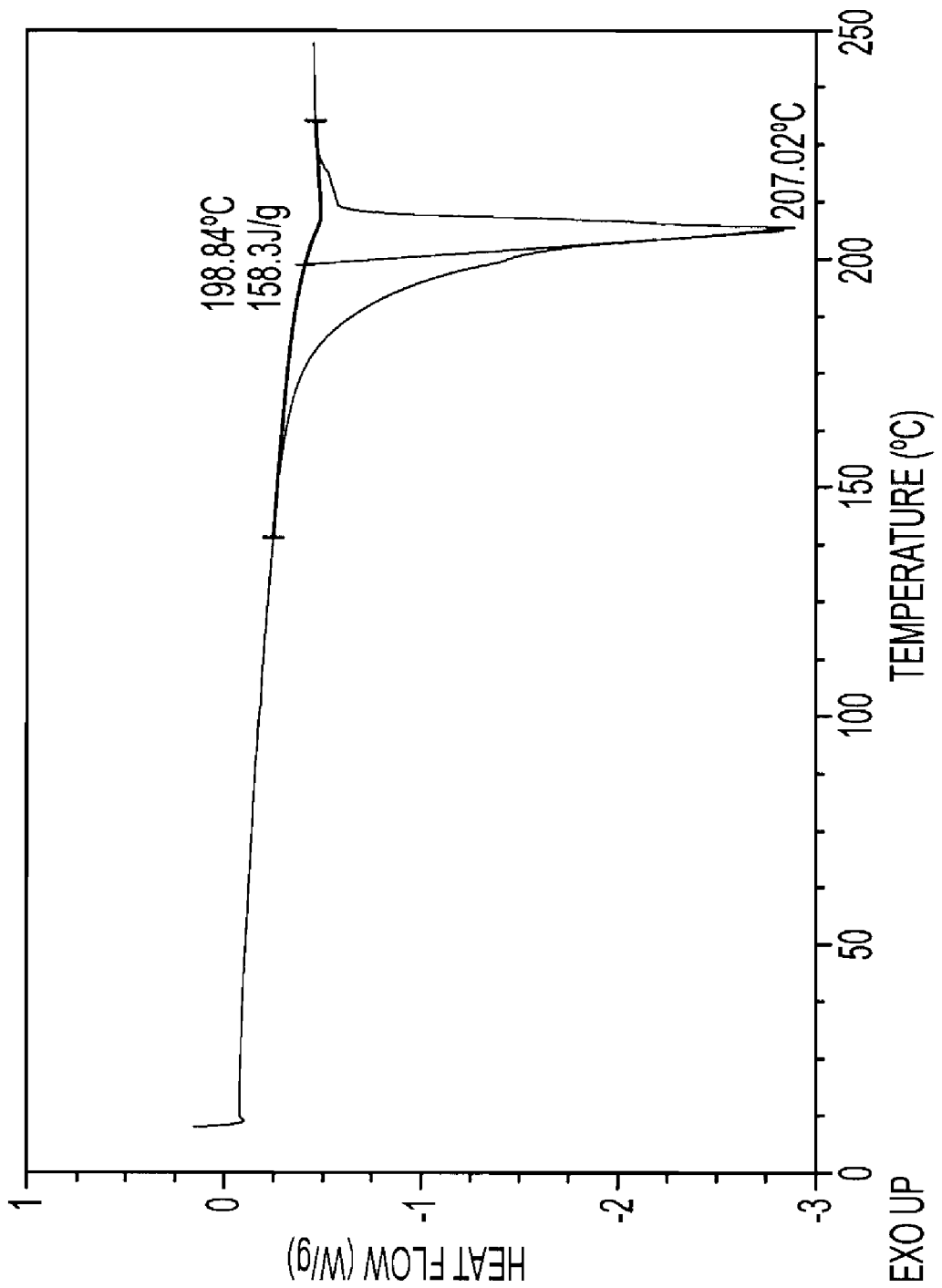
FIG. 13: DSC of (R)-2-[3-(5-Ethanesulfonyl-1H-pyrrolo[2,3-c]pyridin-2-ylmethyl)-4,4,4-trifluoro-3-hydroxy-1,1-dimethylbutyl]benzamide Isonicotinamide Co-Crystal.
Figure 14:
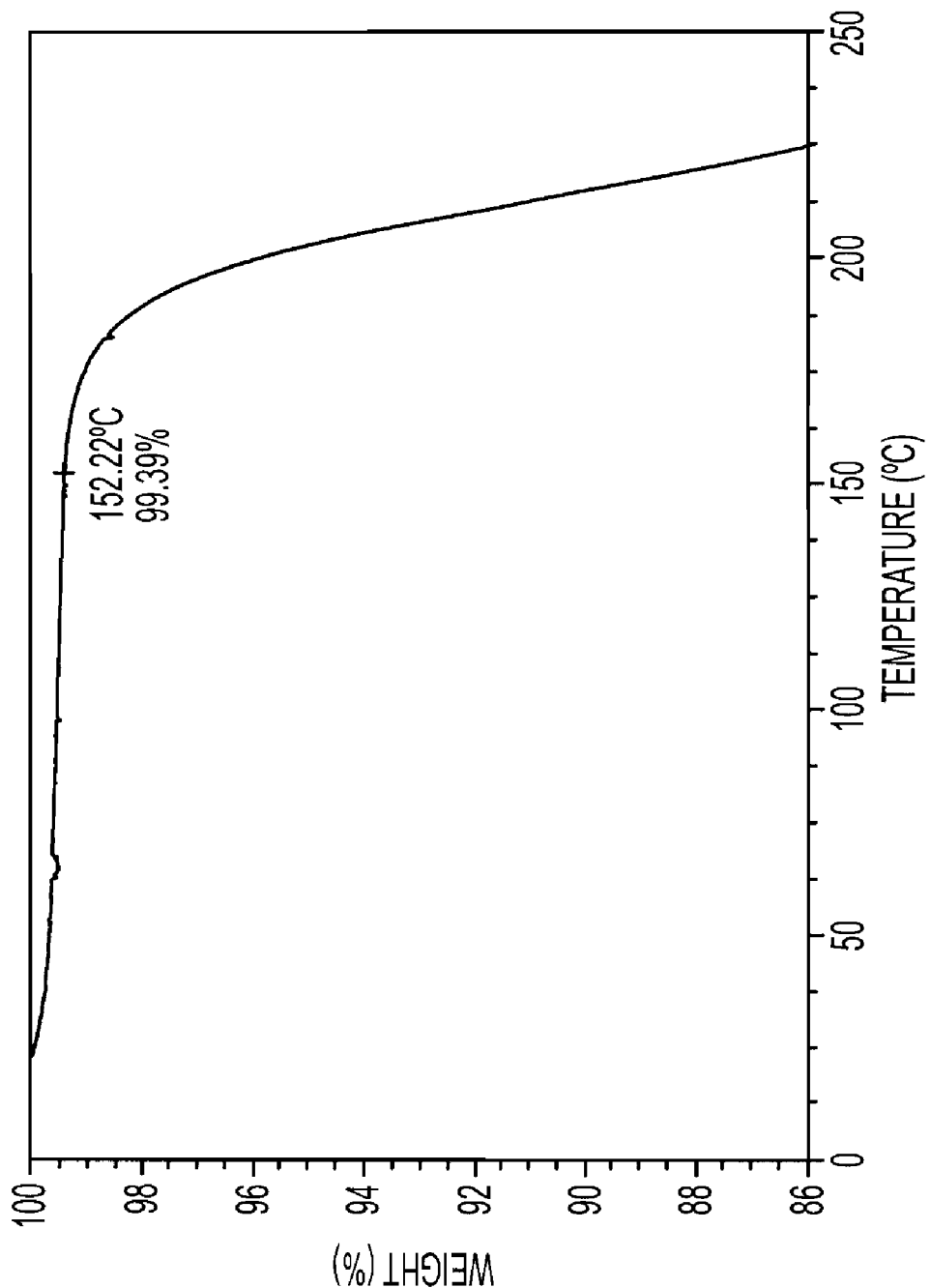
FIG. 14: TGA of (R)-2-[3-(5-Ethanesulfonyl-1H-pyrrolo[2,3-c]pyridin-2-ylmethyl)-4,4,4-trifluoro-3-hydroxy-1,1-dimethylbutyl]benzamide Isonicotinamide Co-Crystal.
Figure 15:
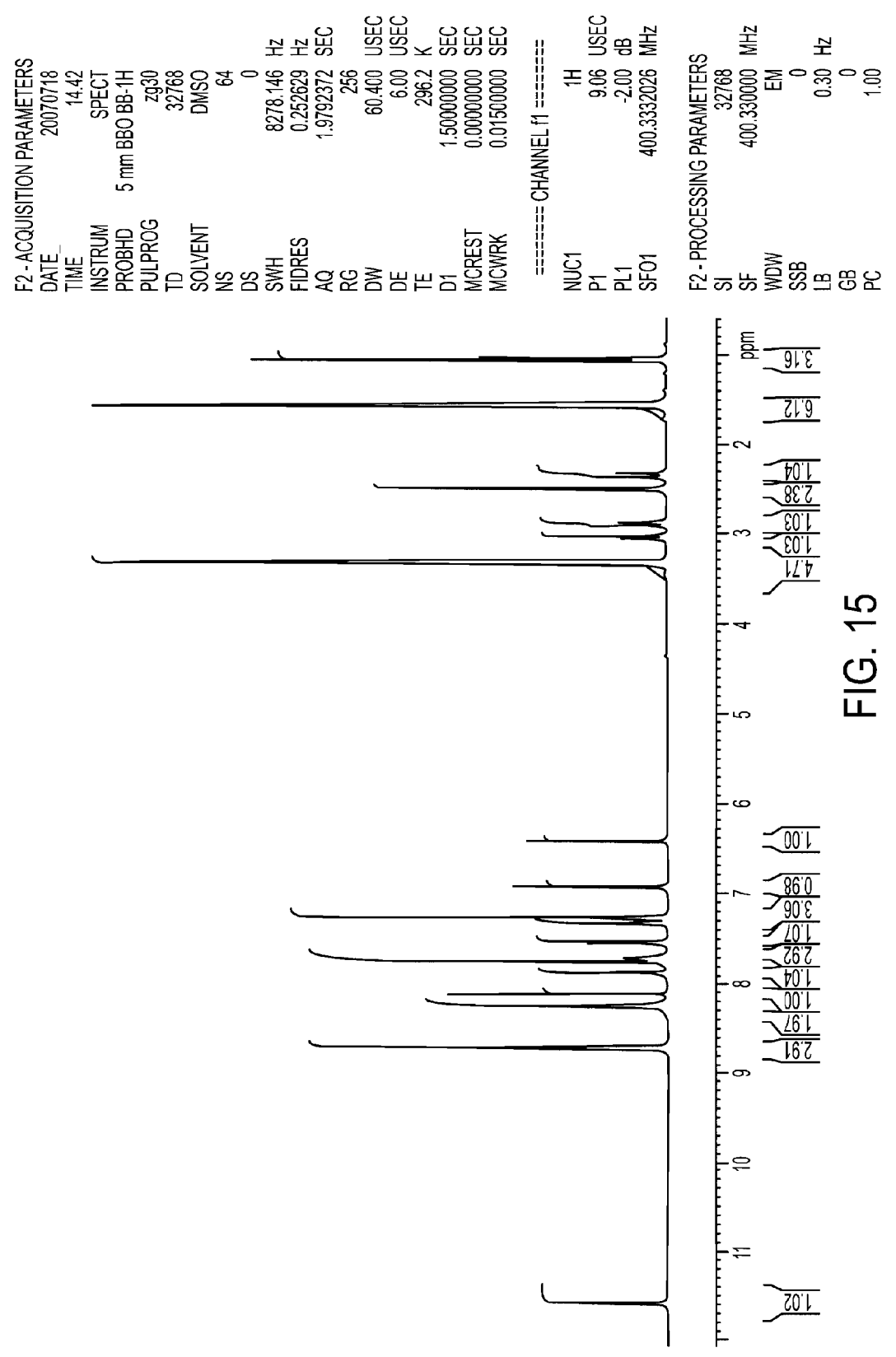
Figure 16:
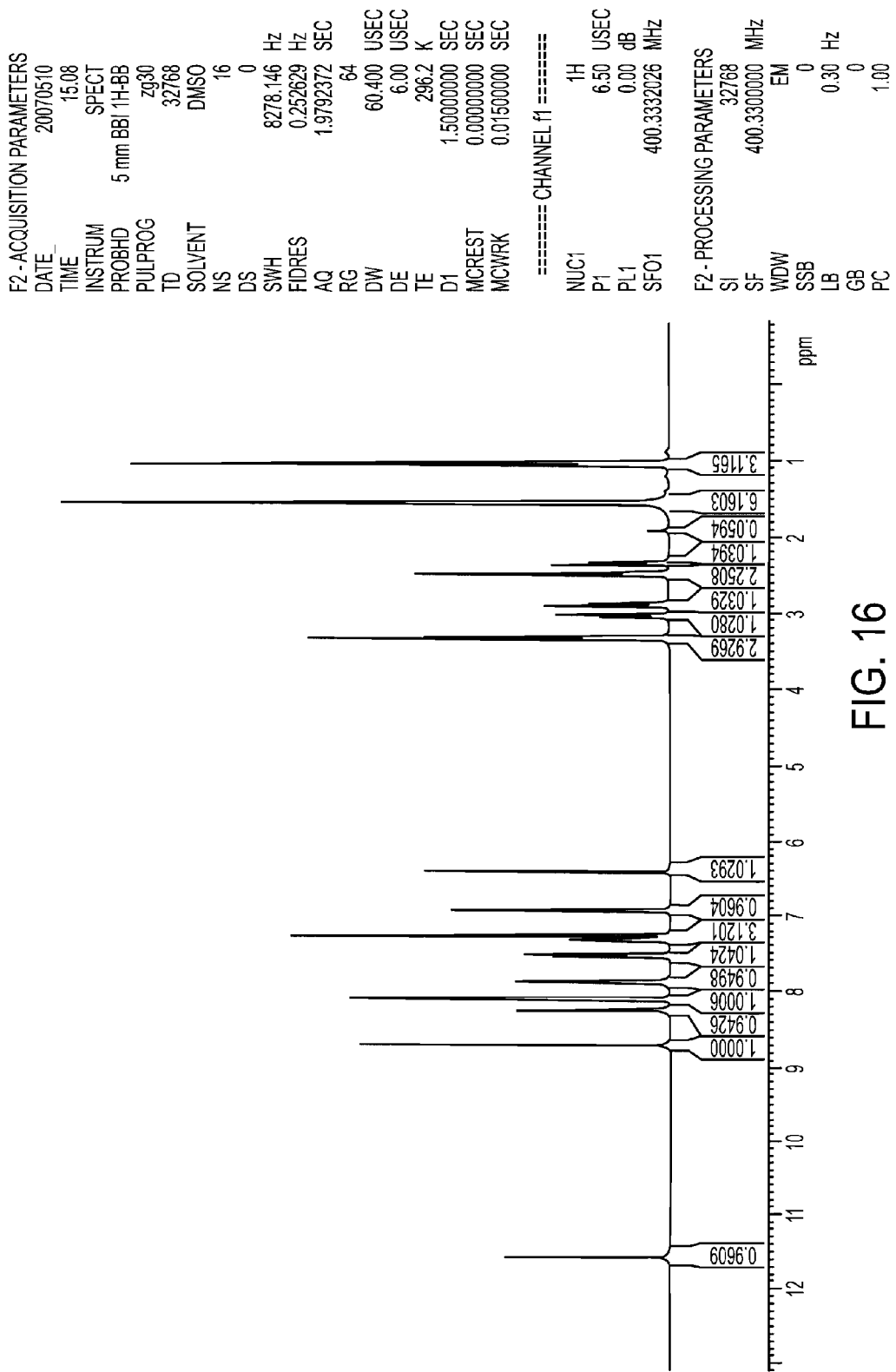
FIG. 16: $^1$H NMR of (R)-2-[3-(5-Ethanesulfonyl-1H-pyrrolo[2,3-c]pyridin-2-ylmethyl)-4,4,4-trifluoro-3-hydroxy-1,1-dimethylbutyl]benzamide.
Figure 17:
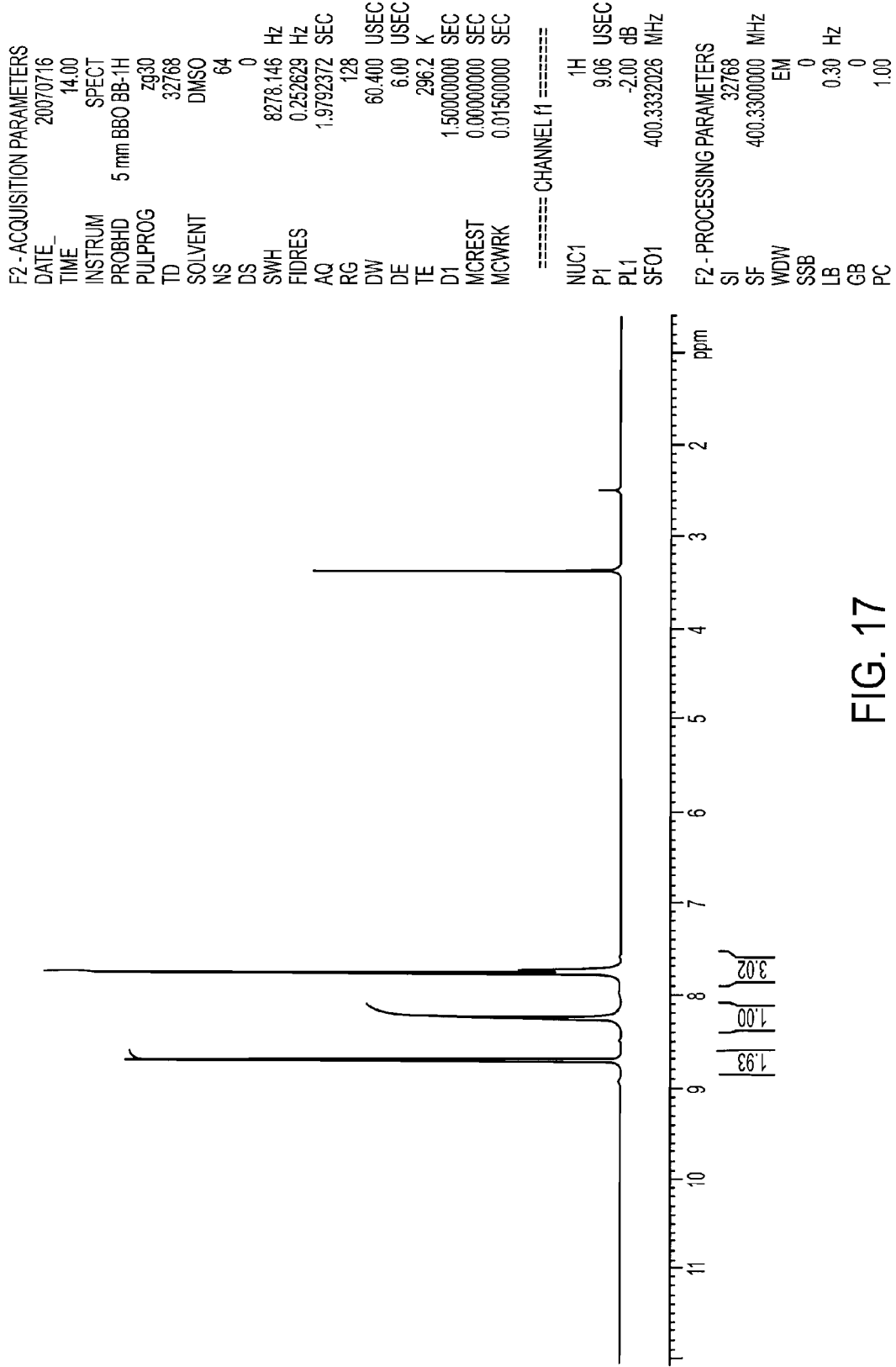
FIG. 17: $^1$H NMR of Isonicotinamide.

Synthesis of (R)-2-[3-(5-Ethanesulfonyl-1H-pyrrolo[2,3-c]pyridin-2-ylmethyl)-4,4,4-trifluoro-3-hydroxy-1,1-dimethylbutyl]benzamide Isonicotinamide Co-Crystal A mixture of 1.01 g of (R)-2-[3-(5-ethanesulfonyl-1H-pyrrolo[2,3-c]pyridin-2-ylmethyl)-4,4,4-trifluoro-3-hydroxy-1,1-dimethylbutyl]benzamide (2.03 mmol) and 249.1 mg (2.04 mmol) of isonicotinamide in 20 mL of ethanol was heated to 70° C. to give a clear solution. The reaction mixture was cooled down to 65° C. and seeded with (R)-2-[3-(5-ethanesulfonyl-1H-pyrrolo[2,3-c]pyridin-2-ylmethyl)-4,4,4-trifluoro-3-hydroxy-1,1-dimethylbutyl]benzamide isonicotinamide co-crystal seed crystals, for example, made by the process in Example 27. The reaction mixture was allowed to stand at 60° C. for 30 minutes and then it was cooled down to 20° C. over 10 hours. (R)-2-[3-(5-Ethanesulfonyl-1H-pyrrolo[2,3-c]pyridin-2-ylmethyl)-4,4,4-trifluoro-3-hydroxy-1,1-dimethylbutyl]benzamide isonicotinamide co-crystals formed and were collected by filtration. FIGS. 12 to 17 show physical measurements and spectral data that characterize the product obtained.

Example 28

Synthesis of 5-Fluoro-2-[(R)-4,4,4-trifluoro-3-hydroxy-3-(5-methanesulfonyl-1H-pyrrolo[2,3-c]pyridin-2-ylmethyl)-1,1-dimethylbutyl]benzamide Phosphoric Acid Co-Crystal Seed Crystals Approximately 200 mg of the free base of 5-fluoro-2-[(R)-4,4,4-trifluoro-3-hydroxy-3-(5-methanesulfonyl-1H-pyrrolo[2,3-c]pyridin-2-ylmethyl)-1,1-dimethylbutyl]benzamide was dissolved in 3 mL of 2-butanone at 70° C. To the solution at 70° C., approximately 47 mg of 85 wt. % of aqueous phosphoric acid ($H_3PO_4$, 1-1.05 equiv) was added. The reaction solution was then cooled down to 20° C. over 14 hours. During the cooling, crystallization was initiated and developed. The seed crystals were isolated and were confirmed to be approximately 1:1 molar ratio of 5-fluoro-2-[(R)-4,4,4-trifluoro-3-hydroxy-3-(5-methanesulfonyl-1H-pyrrolo[2,3-c]pyridin-2-ylmethyl)-1,1-dimethylbutyl]benzamide and phosphoric acid by titration.

Example 29

Figure 18:
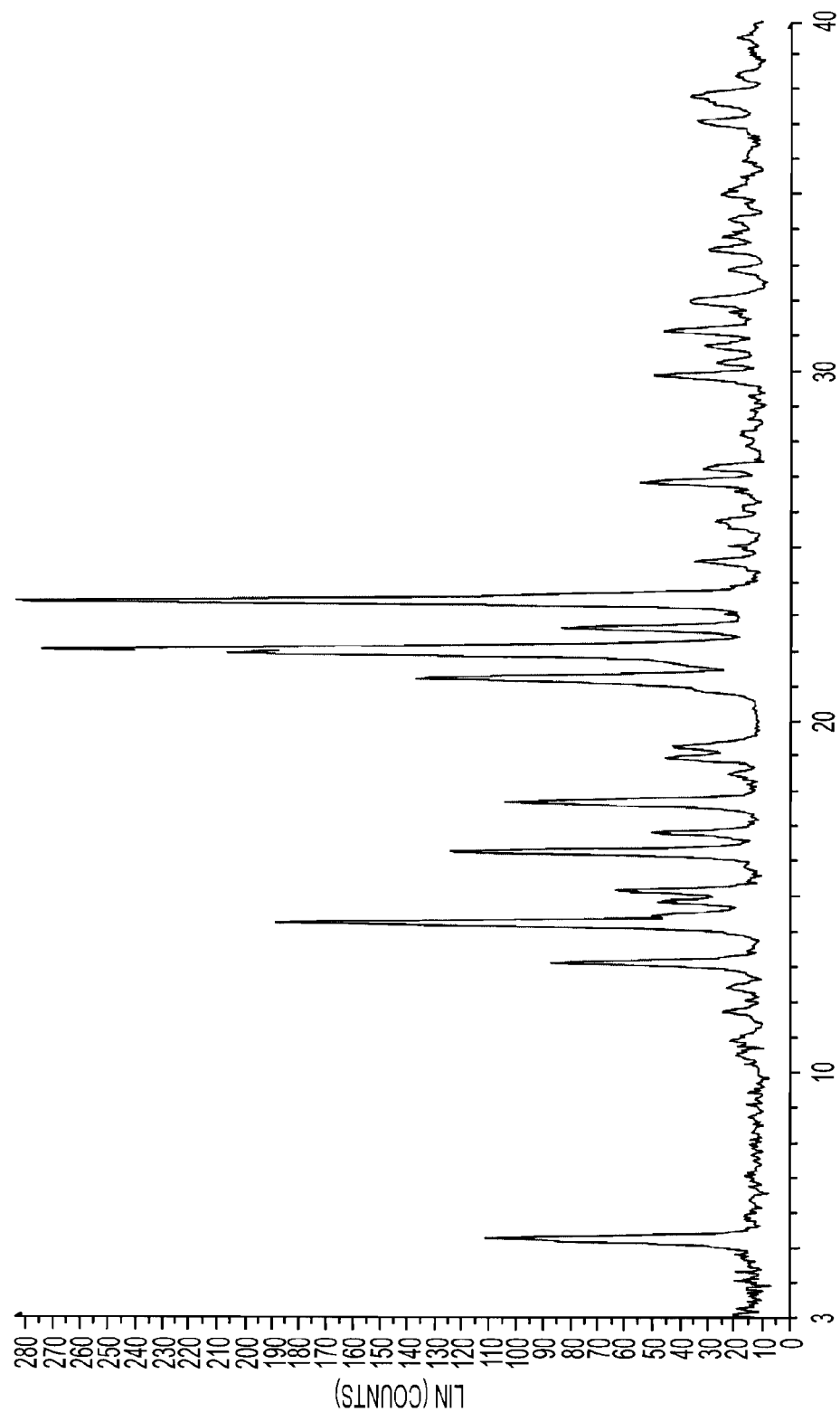
FIG. 18: XRPD of 5-Fluoro-2-[(R)-4,4,4-trifluoro-3-hydroxy-3-(5-methanesulfonyl-1H-pyrrolo[2,3-c]pyridin-2-ylmethyl)-1,1-dimethylbutyl]benzamide Phosphoric Acid Co-Crystal.
Figure 19:
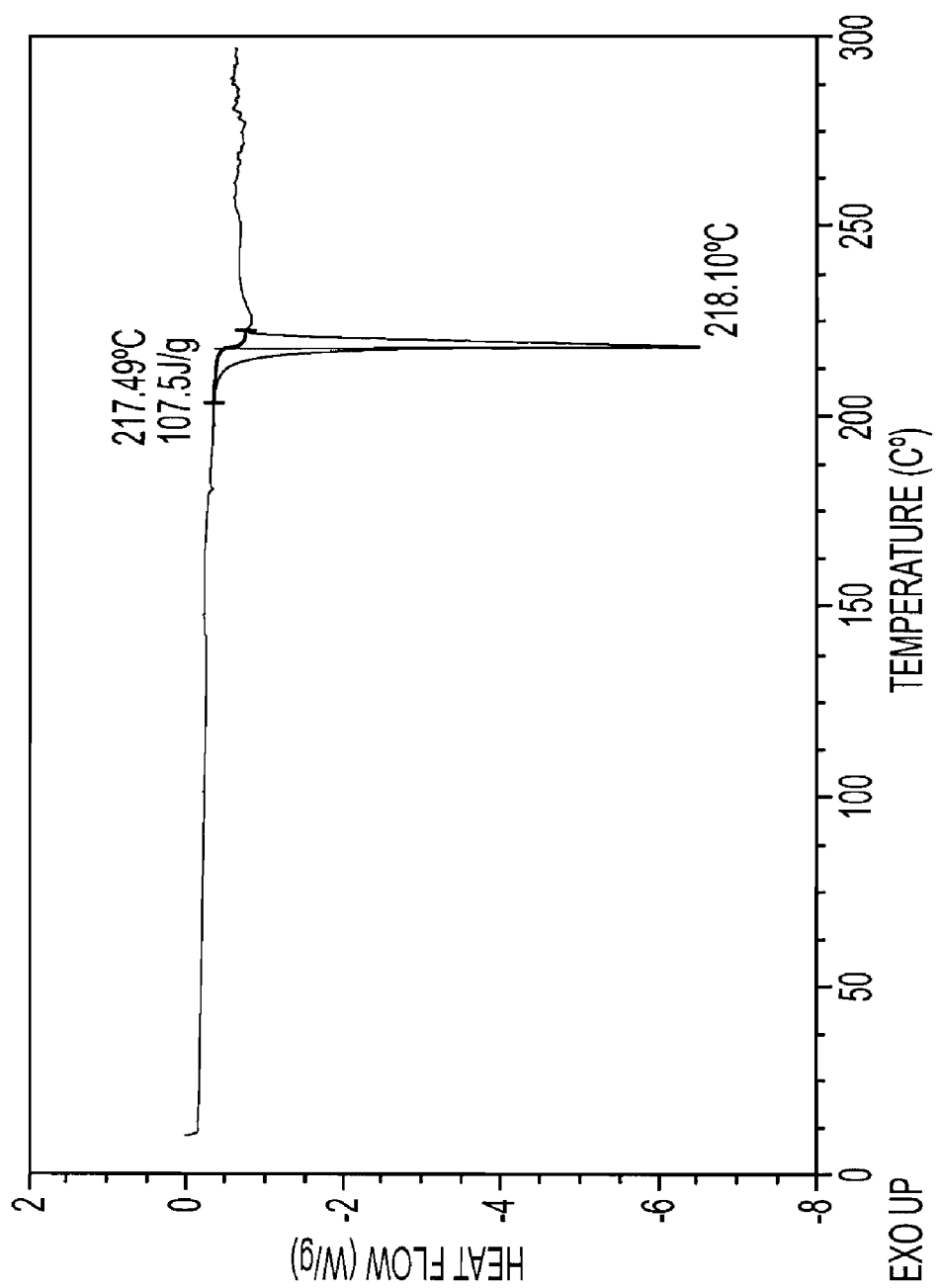
FIG. 19: DSC of 5-Fluoro-2-[(R)-4,4,4-trifluoro-3-hydroxy-3-(5-methanesulfonyl-1H-pyrrolo[2,3-c]pyridin-2-ylmethyl)-1,1-dimethylbutyl]benzamide Phosphoric Acid Co-Crystal.
Figure 20:
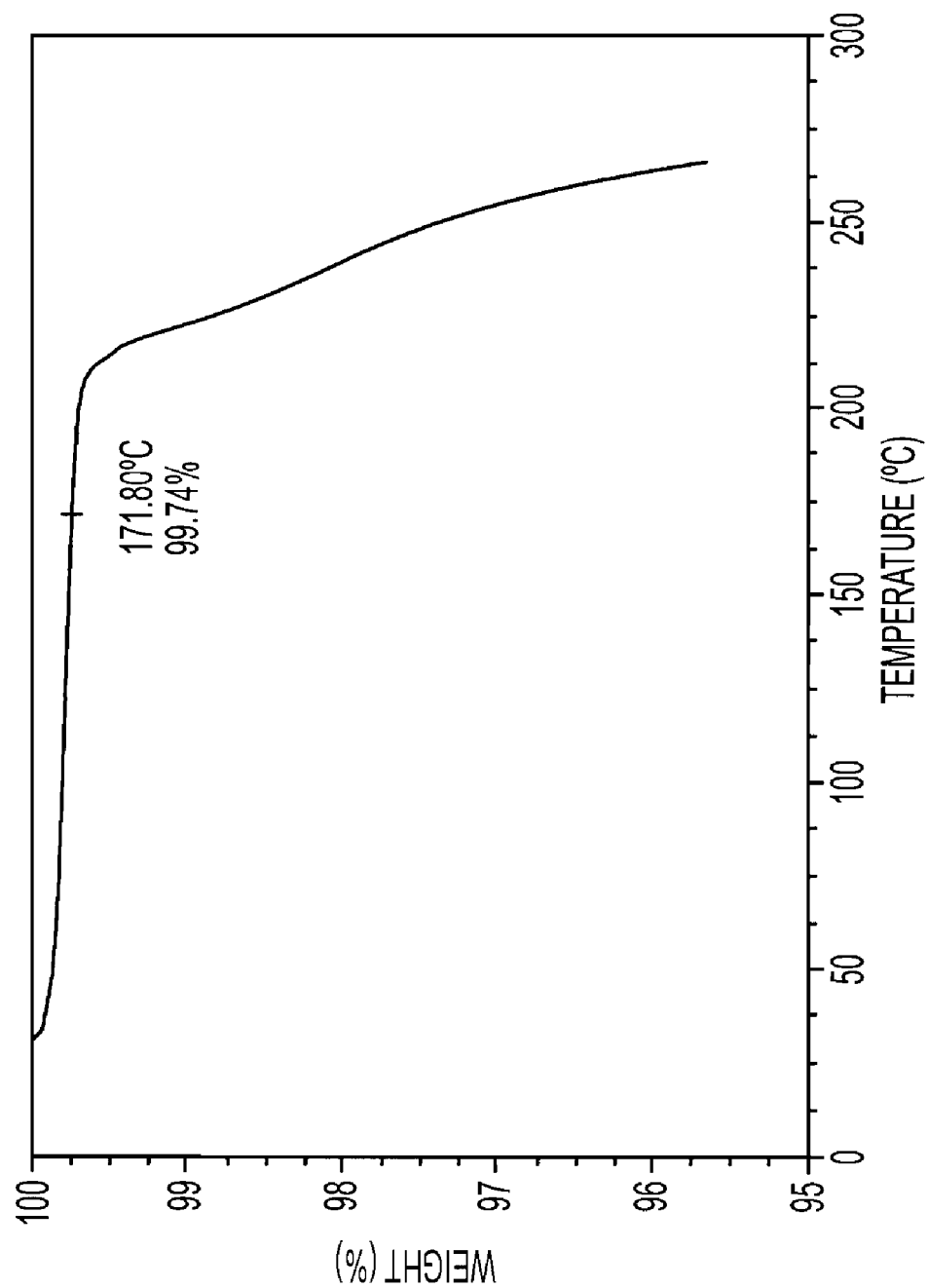
FIG. 20: TGA of 5-Fluoro-2-[(R)-4,4,4-trifluoro-3-hydroxy-3-(5-methanesulfonyl-1H-pyrrolo[2,3-c]pyridin-2-ylmethyl)-1,1-dimethylbutyl]benzamide Phosphoric Acid Co-Crystal.
Figure 21:
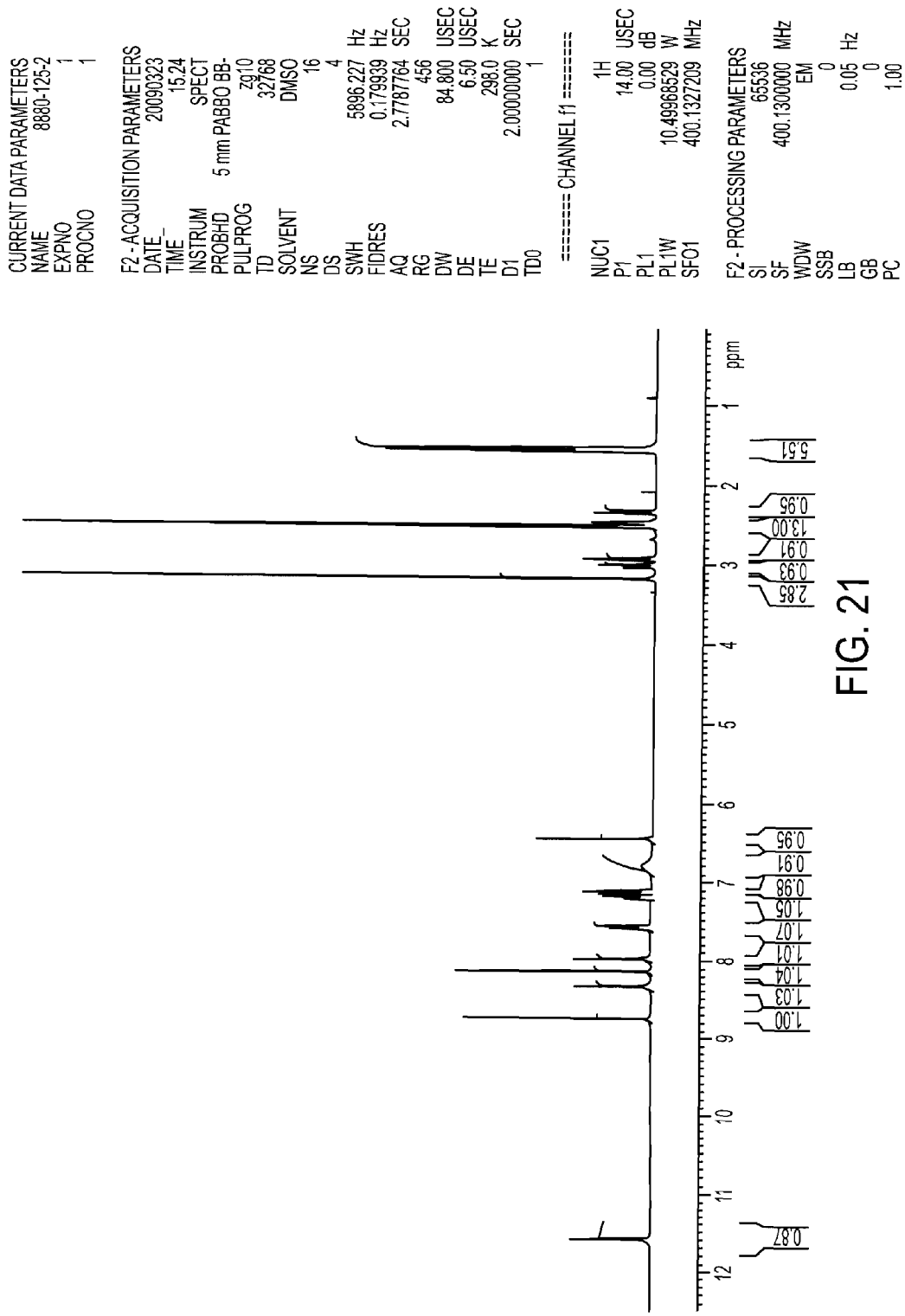
FIG. 21: $^1$H NMR of 5-Fluoro-2-[(R)-4,4,4-trifluoro-3-hydroxy-3-(5-methanesulfonyl-1H-pyrrolo[2,3-c]pyridin-2-ylmethyl)-1,1-dimethylbutyl]benzamide Phosphoric Acid Co-Crystal.
Figure 22:
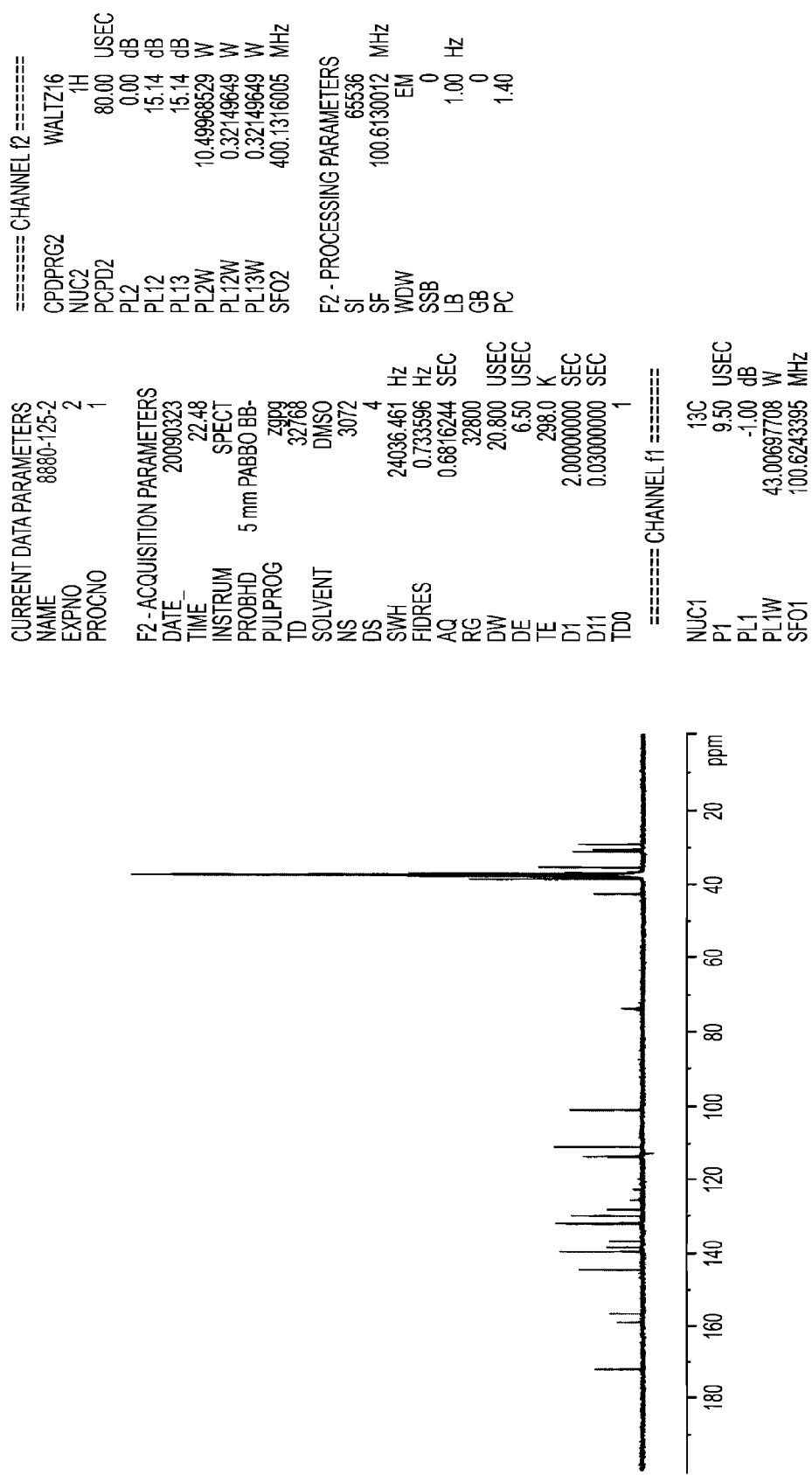
FIG. 22: $^{13}$C NMR of 5-Fluoro-2-[(R)-4,4,4-trifluoro-3-hydroxy-3-(5-methanesulfonyl-1H-pyrrolo[2,3-c]pyridin-2-ylmethyl)-1,1-dimethylbutyl]benzamide Phosphoric Acid Co-Crystal.
Figure 23:
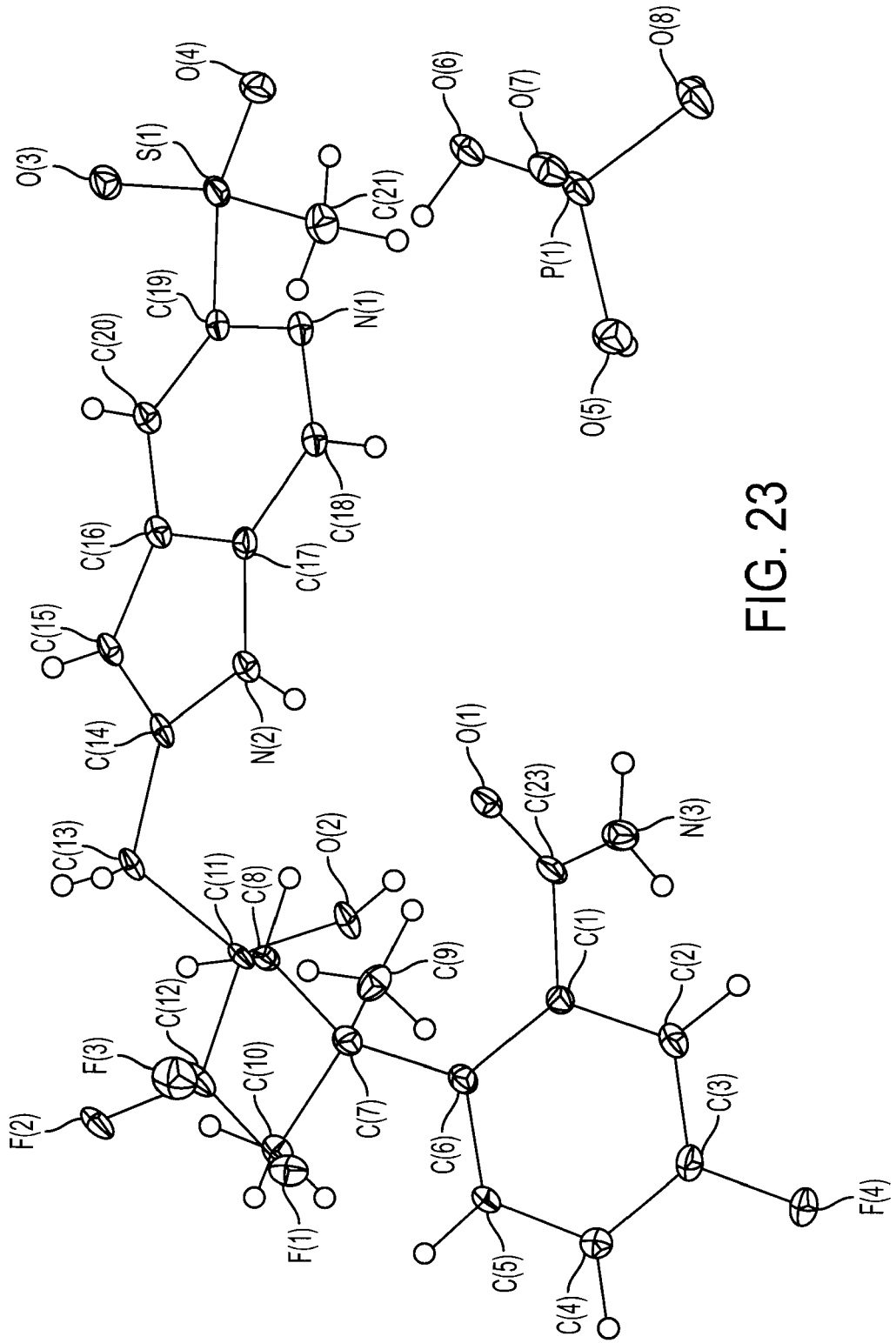
FIG. 23: ORTEP plot of 5-Fluoro-2-[(R)-4,4,4-trifluoro-3-hydroxy-3-(5-methanesulfonyl-1H-pyrrolo[2,3-c]pyridin-2-ylmethyl)-1,1-dimethylbutyl]benzamide Phosphoric Acid Co-Crystal.

Synthesis of 5-Fluoro-2-[(R)-4,4,4-trifluoro-3-hydroxy-3-(5-methanesulfonyl-1H-pyrrolo[2,3-c]pyridin-2-ylmethyl)-1,1-dimethylbutyl]benzamide Phosphoric Acid Co-Crystal Approximately 2.27 g of the free base of 5-fluoro-2-[(R)-4,4,4-trifluoro-3-hydroxy-3-(5-methanesulfonyl-1H-pyrrolo[2,3-c]pyridin-2-ylmethyl)-1,1-dimethylbutyl]benzamide was dissolved in 28.0 g of 2-butanone at 65° C. To the solution at 65° C., approximately 525 mg of 85 wt. % of aqueous phosphoric acid ($H_3PO_4$, 1-1.05 equiv) was added. After the 5-fluoro-2-[(R)-4,4,4-trifluoro-3-hydroxy-3-(5-methanesulfonyl-1H-pyrrolo[2,3-c]pyridin-2-ylmethyl)-1,1-dimethylbutyl]benzamide phosphoric acid co-crystal seed crystals, for example, made by the process in Example 29, were charged into the reaction, approximately 10 g of heptane was added over 4 hours. The reaction slurry was then cooled down to 15° C. over 12 hours. The slurry was aged at 20° C. for at least 2 hours and filtered. The solid was dried at 45° C.-55° C. for 24 to 48 hours. The dry solids, with the same XRPD patterns as the seed crystals, were obtained as a white powder in 85% yield. FIGS. 18 to 23 show physical measurements and spectral data that characterize the product obtained.

Example 30

Synthesis of 5-Fluoro-2-[(R)-4,4,4-trifluoro-3-hydroxy-3-(5-methanesulfonyl-1H-pyrrolo[2,3-c]pyridin-2-ylmethyl)-1,1-dimethylbutyl]benzamide Acetic Acid Co-Crystal Seed Crystals 5-Fluoro-2-[(R)-4,4,4-trifluoro-3-hydroxy-3-(5-methanesulfonyl-1H-pyrrolo[2,3-c]pyridin-2-ylmethyl)-1,1-dimethylbutyl]benzamide acetic acid co-crystal seed crystals were generated from acetic acid solution. Approximately 200 mg of the free base of 5-fluoro-2-[(R)-4,4,4-trifluoro-3-hydroxy-3-(5-methanesulfonyl-1H-pyrrolo[2,3-c]pyridin-2-ylmethyl)-1,1-dimethylbutyl]benzamide was dissolved in 3 mL of acetic acid at elevated temperature. The solution was then cooled down to room temperature with stirring. Crystalline solids were generated from the solution, and a 1:1 acetic acid to 5-fluoro-2-[(R)-4,4,4-trifluoro-3-hydroxy-3-(5-methanesulfonyl-1H-pyrrolo[2,3-c]pyridin-2-ylmethyl)-1,1-dimethylbutyl]benzamide molar ratio was confirmed by NMR.

Example 31

Figure 24:
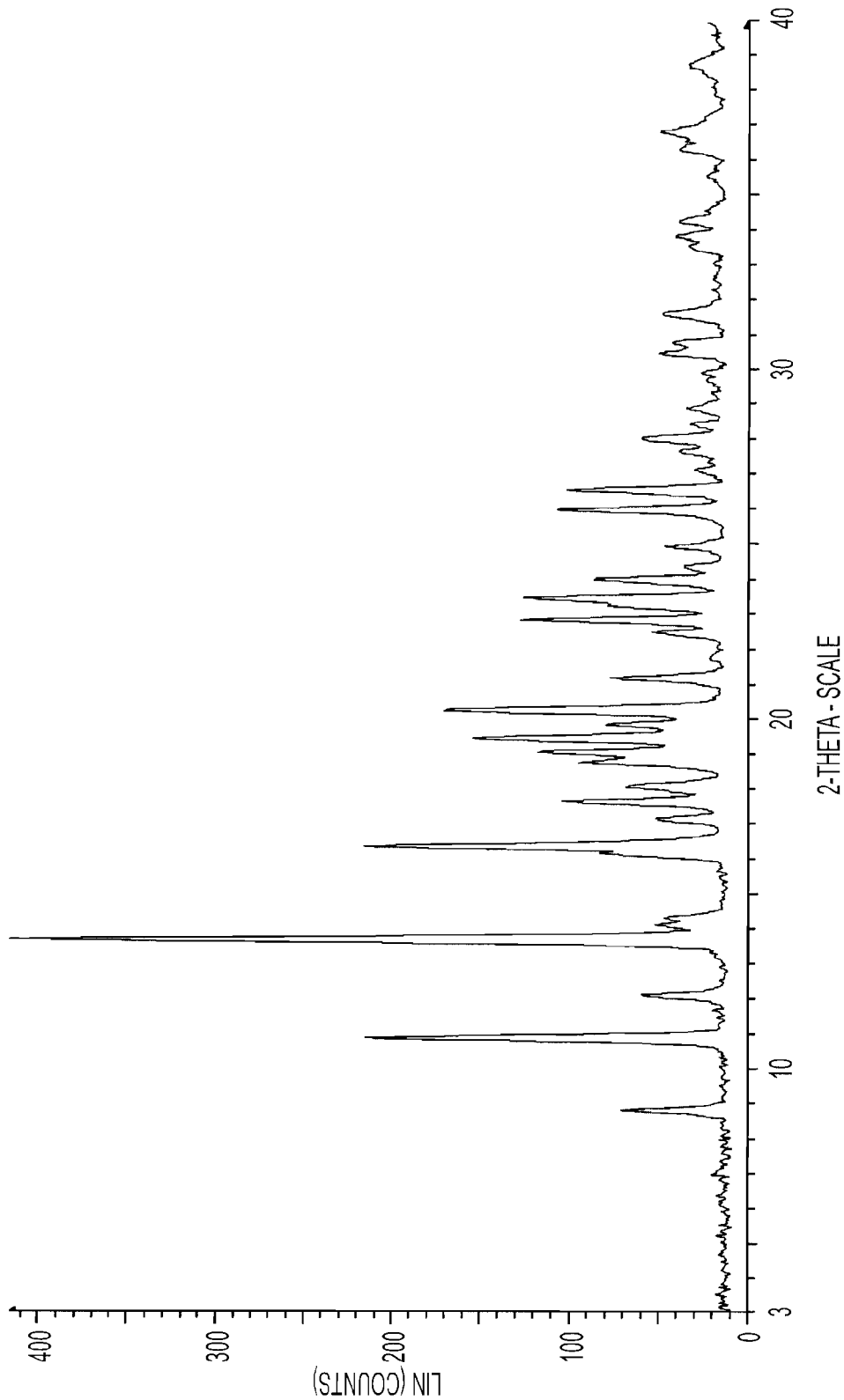
FIG. 24: XRPD of 5-Fluoro-2-[(R)-4,4,4-trifluoro-3-hydroxy-3-(5-methanesulfonyl-1H-pyrrolo[2,3-c]pyridin-2-ylmethyl)-1,1-dimethylbutyl]benzamide Acetic Acid Co-Crystal.
Figure 25:
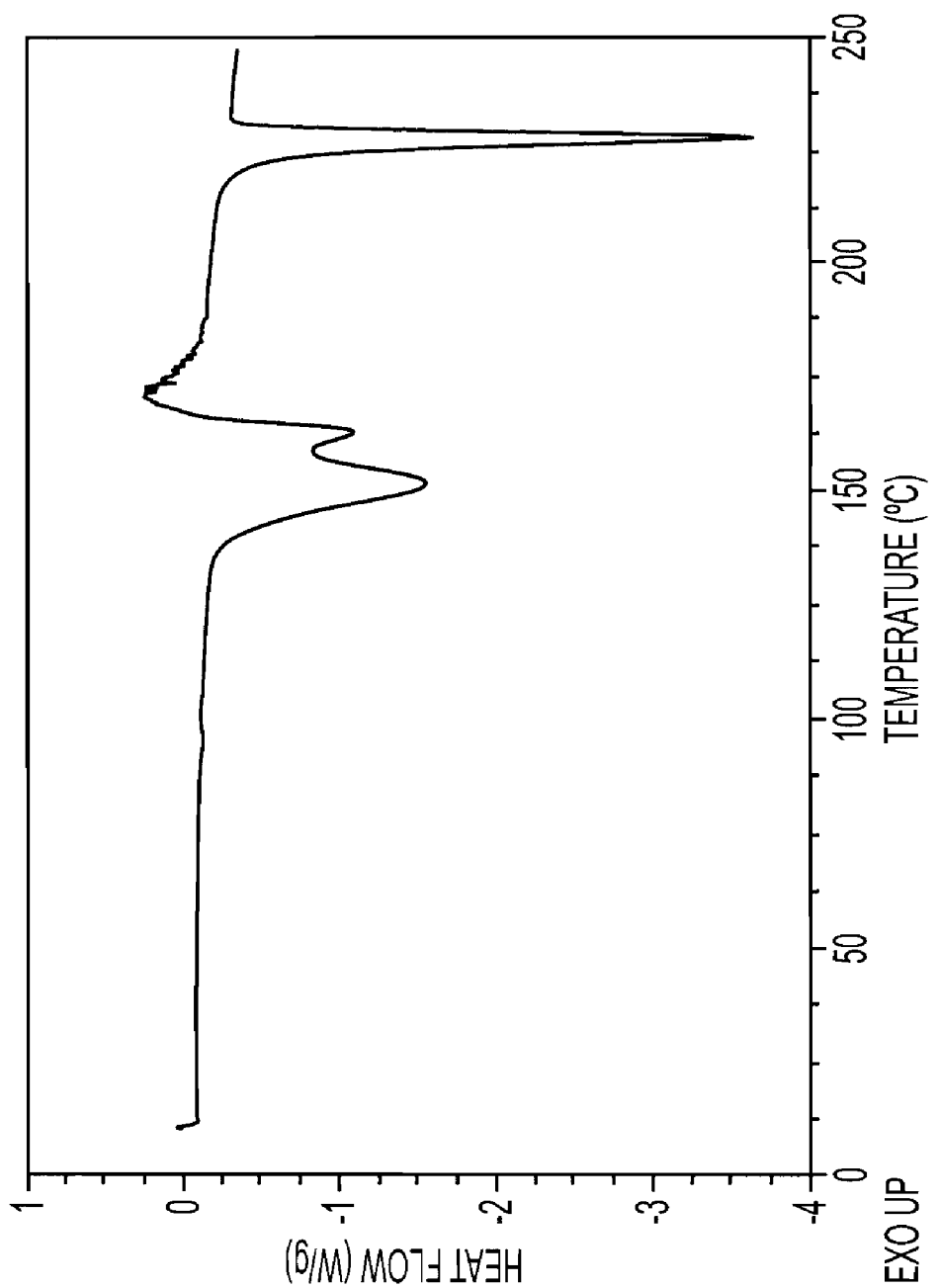
FIG. 25: DSC of 5-Fluoro-2-[(R)-4,4,4-trifluoro-3-hydroxy-3-(5-methanesulfonyl-1H-pyrrolo[2,3-c]pyridin-2-ylmethyl)-1,1-dimethylbutyl]benzamide Acetic Acid Co-Crystal.
Figure 26:
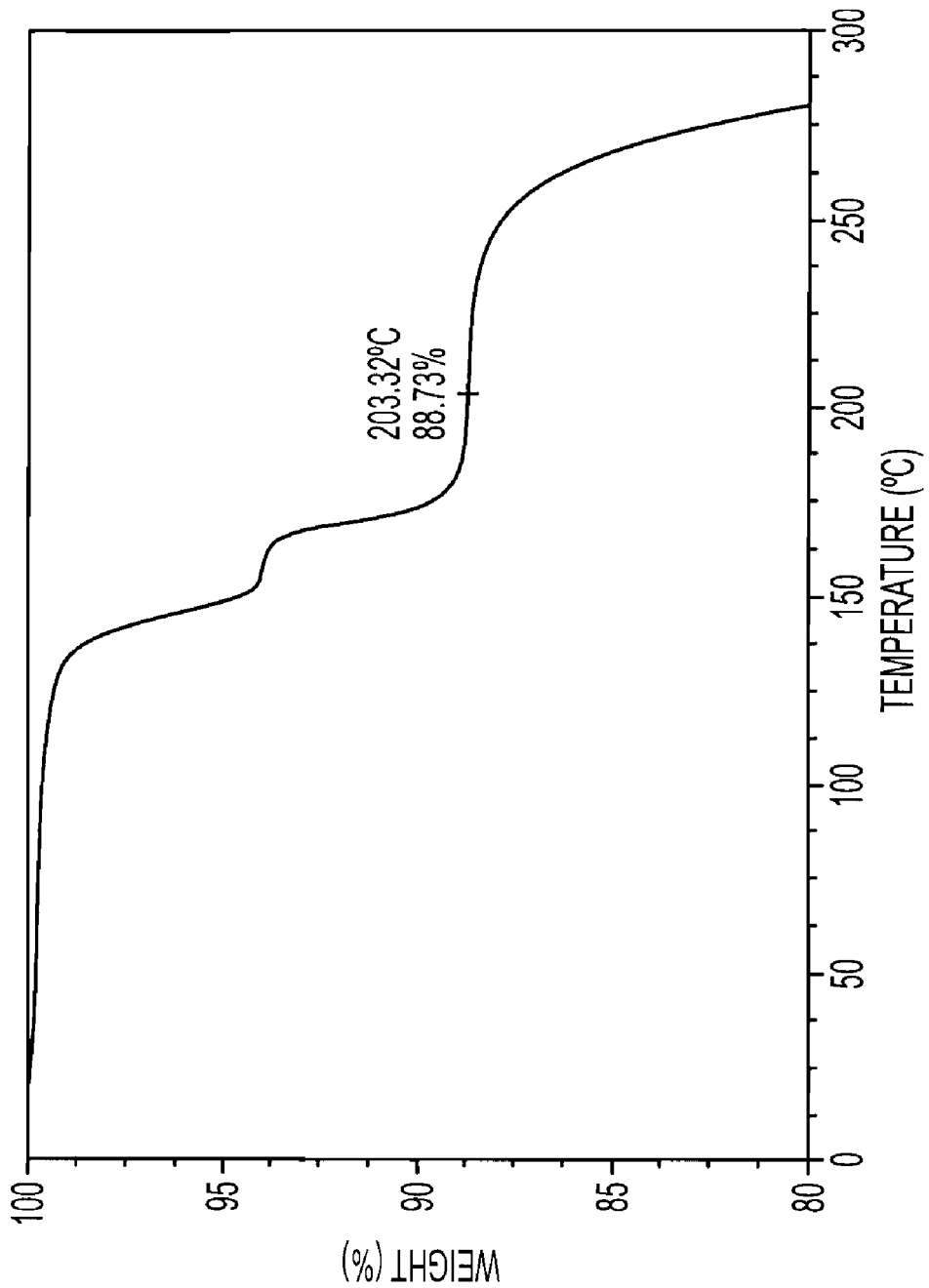
FIG. 26: TGA of 5-Fluoro-2-[(R)-4,4,4-trifluoro-3-hydroxy-3-(5-methanesulfonyl-1H-pyrrolo[2,3-c]pyridin-2-ylmethyl)-1,1-dimethylbutyl]benzamide Acetic Acid Co-Crystal.
Figure 27:
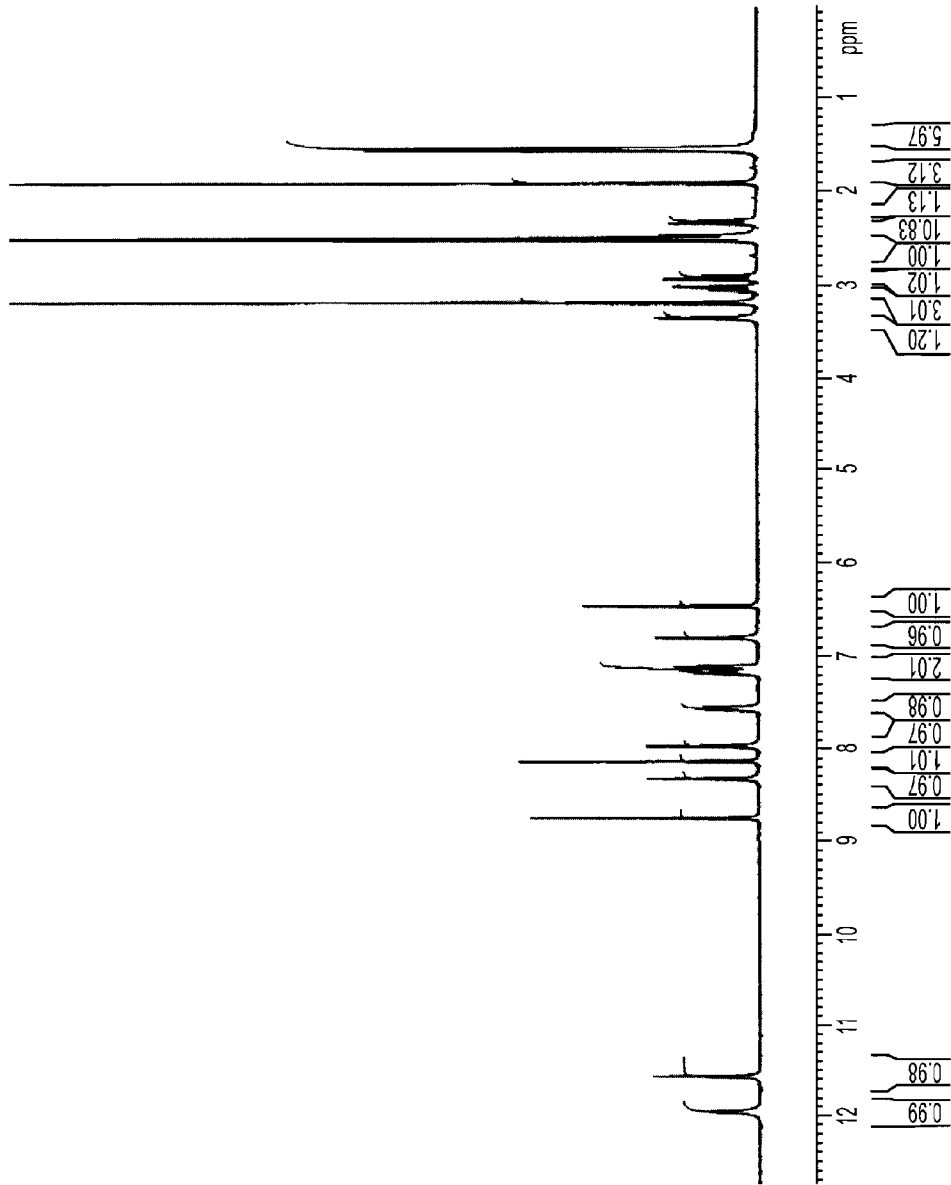
FIG. 27: $^1$H NMR of 5-Fluoro-2-[(R)-4,4,4-trifluoro-3-hydroxy-3-(5-methanesulfonyl-1H-pyrrolo[2,3-c]pyridin-2-ylmethyl)-1,1-dimethylbutyl]benzamide Acetic Acid Co-Crystal.
Figure 28:
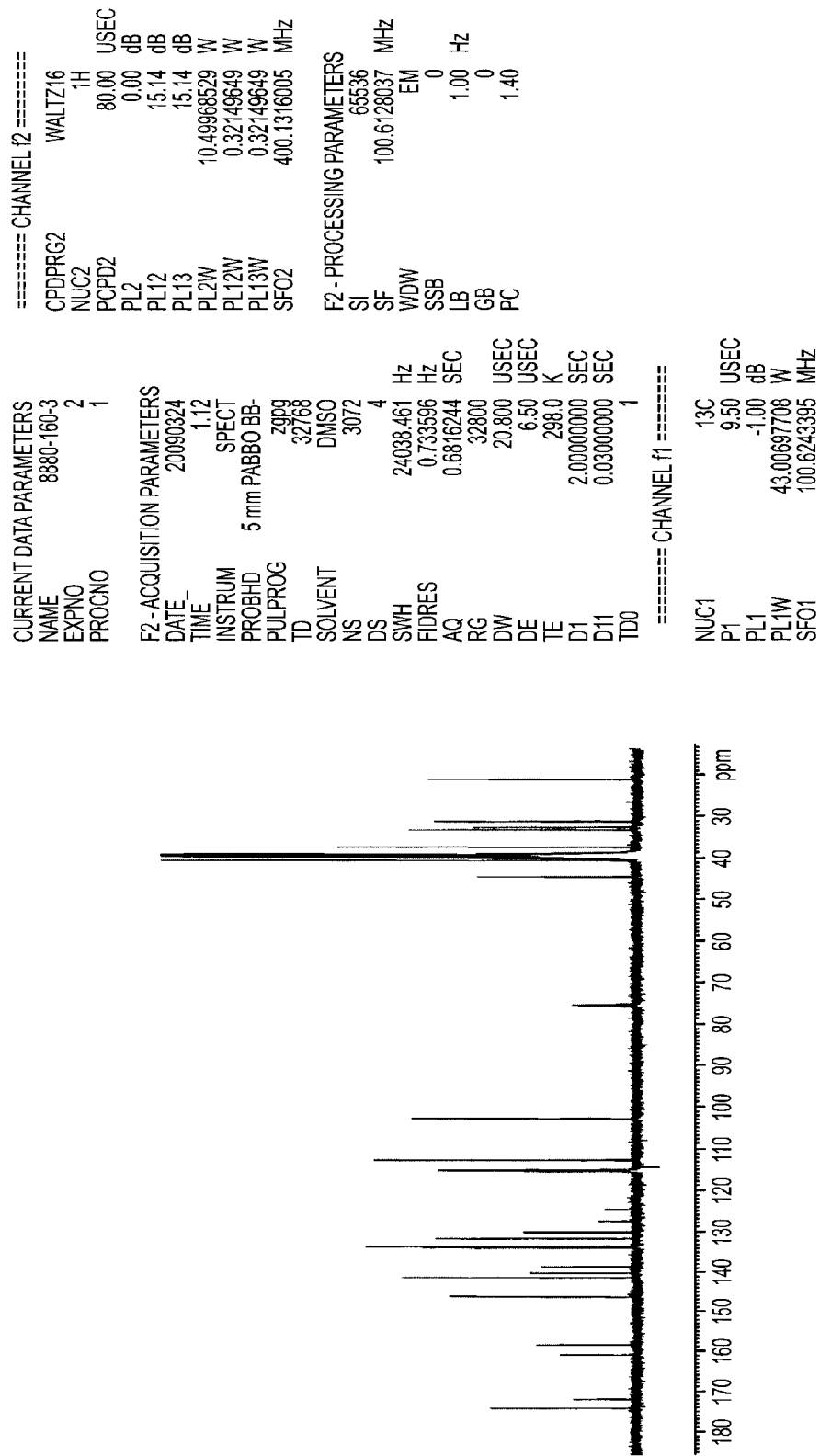
FIG. 28: $^{13}$C NMR of 5-Fluoro-2-[(R)-4,4,4-trifluoro-3-hydroxy-3-(5-methanesulfonyl-1H-pyrrolo[2,3-c]pyridin-2-ylmethyl)-1,1-dimethylbutyl]benzamide Acetic Acid Co-Crystal.
Figure 29:
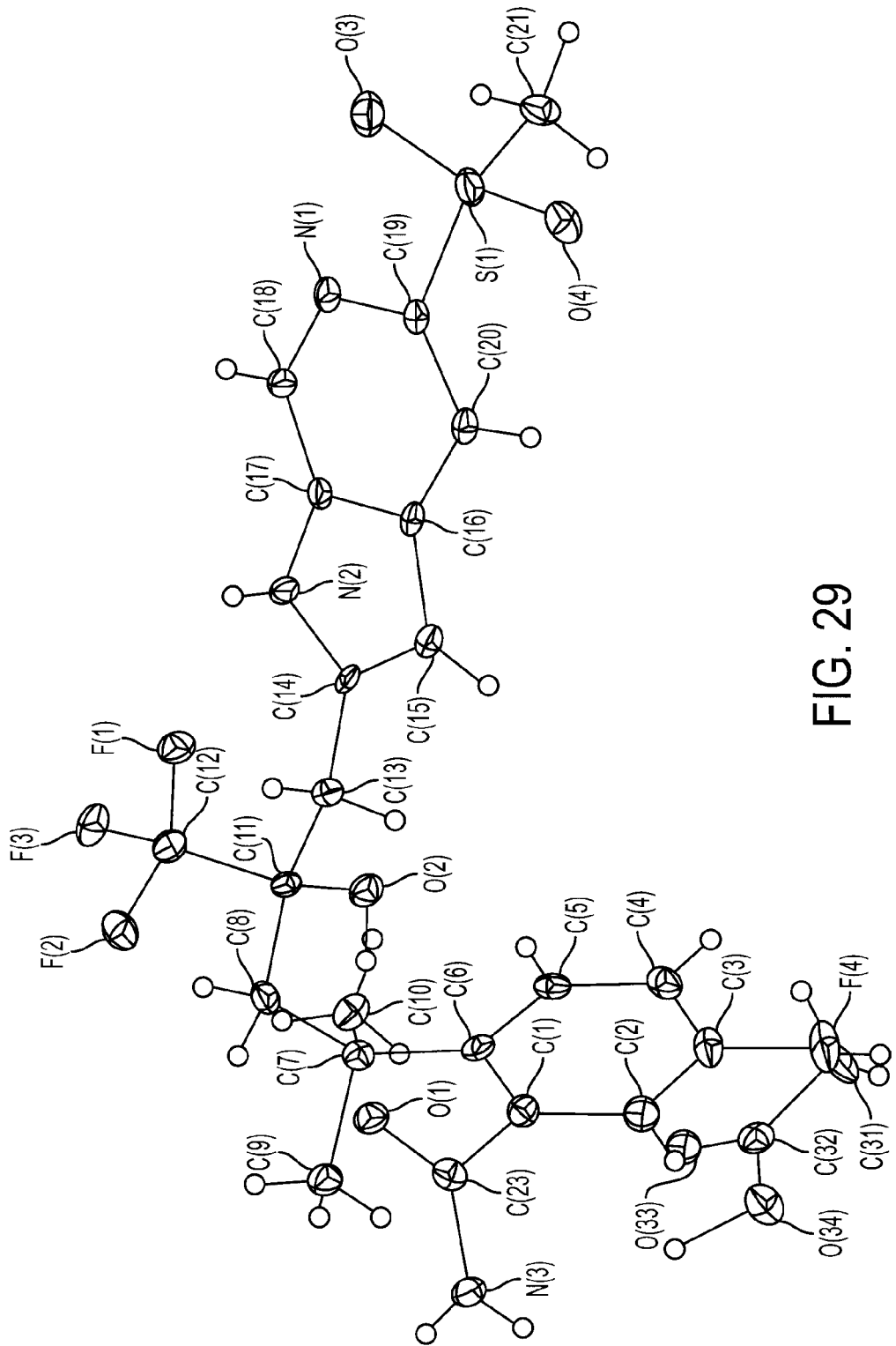
FIG. 29: ORTEP plot of 5-Fluoro-2-[(R)-4,4,4-trifluoro-3-hydroxy-3-(5-methanesulfonyl-1H-pyrrolo[2,3-c]pyridin-2-ylmethyl)-1,1-dimethylbutyl]benzamide Acetic Acid Co-Crystal.

Synthesis of 5-Fluoro-2-[(R)-4,4,4-trifluoro-3-hydroxy-3-(5-methanesulfonyl-1H-pyrrolo[2,3-c]pyridin-2-ylmethyl)-1,1-dimethylbutyl]benzamide Acetic Acid Co-Crystal Using Acetic Acid/Butyl Acetate Approximately 200 mg free base of 5-fluoro-2-[(R)-4,4,4-trifluoro-3-hydroxy-3-(5-methanesulfonyl-1H-pyrrolo[2,3-c]pyridin-2-ylmethyl)-1,1-dimethylbutyl]benzamide was dissolved in 3 mL of acetic acid at 70° C. To the solution at 70° C., approximately 3.0 mL of butyl acetate was added, followed by seeding with 5-fluoro-2-[(R)-4,4,4-trifluoro-3-hydroxy-3-(5-methanesulfonyl-1H-pyrrolo[2,3-c]pyridin-2-yl-methyl)-1,1-dimethylbutyl]benzamide acetic acid co-crystal seed crystals, for example, made by the process in Example 31. The reaction slurry was then cooled down to 20° C. over 8 hours. The slurry was aged at 20° C. for at least 2 hours and filtered. The solid was dried at 45° C.-55° C. for 24 to 48 hours. The dry solids were obtained as a white powder in approximately 90% yield. FIGS. 24 to 29 show physical measurements and spectral data that characterize the product obtained.

Example 32

Synthesis of (R)-2-(4-((5-(Ethylsulfonyl)-1H-pyrrolo[2,3-c]pyridin-2-yl)methyl)-5,5,5-trifluoro-4-hydroxy-2-methylpentan-2-yl)-5-fluorobenzamide Anisole Solvate

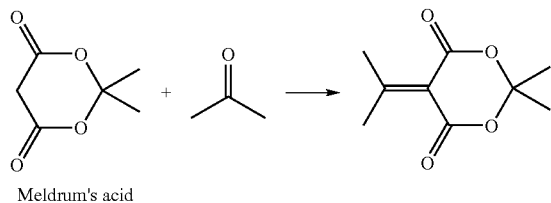

Meldrum's acid

Meldrum's acid (100.0 g) was charged to a dry, nitrogen flushed reactor. Acetone (632.1 mL) was then charged to the reactor and the mixture was agitated for about 5 minutes at 20° C.-25° C. until a solution was obtained. Acetic acid (0.791 mL) was then charged to the reactor, followed by 1.215 mL of morpholine, and the solution was agitated at 20° C.-25° C. for about 48 hours. An aliquot (~0.2 mL) was withdrawn for analysis of the conversion, which may be monitored by either GC or $^1$H-NMR. If the ratio of the area % of 2,2-dimethyl-5-(propan-2-ylidene)-1,3-dioxane-4,6-dione to Meldrum's acid is ≧80:20, proceed to the next step; if it is not, the batch should be aged for an additional 3 hours before repeating the check. The acetone was distilled at about 40° C. and 150-200 mmHg. After approximately two-thirds of the reaction volume was distilled out, 563 mL of methylcyclohexane was charged and the distillation continued until the acetone stopped distilling over. A total of 645 mL (508 g) of distillate was collected for this run. MTBE (500 mL) was charged to the batch at 40° C. and the batch was cooled to 20° C.-25° C. The solution was observed to make sure a cloudy solution was obtained (no solids). If there is solid present, additional MTBE may be charged to effect dissolution. The batch was quickly washed with two 50 g portions of 5 wt. % NaOH solution (prepared from 5 g of NaOH and 95 mL of water). The MTBE was distilled out at 40° C.-45° C. and 150-200 mmHg. A total of 400 mL (300 g) distillate was collected for this run. As distillation proceeds, a white slurry formed. The internal temperature was ramped to 0° C.-5° C. over 1 hour and then held at this temperature for at least 1 hour. The slurry was filtered, the cake was washed with two 100 mL portions of cold (~0° C.-5° C.) methylcyclohexane, and the solid was dried at 20° C.-35° C. and 25-50 mmHg for no less than 4 hours. 2,2-Dimethyl-5-(propan-2-ylidene)-1,3-dioxane-4,6-dione was obtained as a white solid (93.7 g, 70.4% yield, 96.0 wt. % purity by assay).

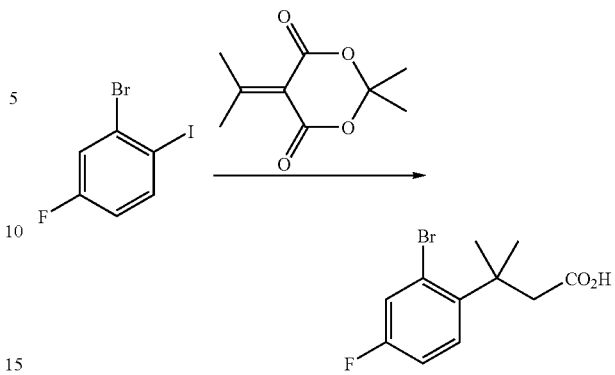

2-Bromo-4-fluoro-1-iodobenzene (42.2 mL) and 150 mL of THF were charged to the reactor. The batch was cooled to −30° C. Isopropyl magnesium chloride (i-PrMgCl, 162.9 mL, 2.0 M in THF) was added at a rate to maintain the temperature between −30° C. to −20° C. The reaction mixture was aged at about −25° C. to −20° C. for 30 minutes and GC or HPLC analysis showed >40:1 area % 3-fluorobromobenzene:2-bromo-4-fluoro-1-iodobenzene. A solution of 2,2-dimethyl-5-(propan-2-ylidene)-1,3-dioxane-4,6-dione (50.0 g) in THF (75.0 mL) was added at a rate to maintain the temperature between −20° C. to −10° C. The batch was aged at −15° C. to −10° C. for no longer than 2 hours. The reaction mixture was quenched with a solution of 35.0 mL of concentrated HCl in 120 mL of water and the temperature rose from −10° C. to 20° C. during the addition. DMF (150 mL) was added and a two phase mixture was obtained. The THF, residual 3-bromofluorobenzene, and other volatiles are distilled out under vacuum (100-150 mmHg) at 75° C. The batch was heated at 100° C. for 16 to 20 hours and then cooled to 20° C.-25° C. A solution of 25 mL of concentrated HCl in 175 mL of water was added. The batch was then seeded with 3-(2-bromo-4-fluorophenyl)-3-methylbutanoic acid (~300 mg), cooled to 0° C.-5° C., and held at this temperature for 2 hours. The solid was filtered, the cake washed with 100 mL of water, and the solid dried at 55±5° C. under vacuum (~100 mmHg) until water content determined by Karl Fischer Method (KF) <0.20% to give 3-(2-bromo-4-fluorophenyl)-3-methylbutanoic acid as a tan solid (60.5 g, 81.0% yield, 99.4 area % purity by HPLC (220 nm), KF=0.10%).

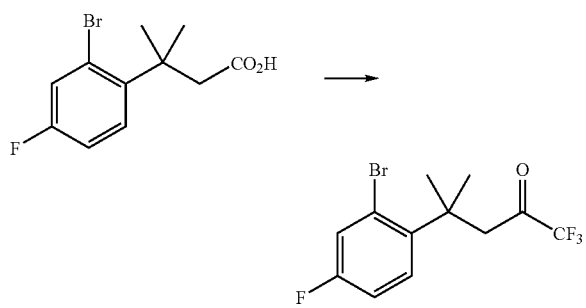

3-(2-bromo-4-fluorophenyl)-3-methylbutanoic acid (100.0 g) and 400 mL of toluene was added to the reactor. Trifluoroacetic anhydride (TFAA, 151.6 mL) was then added at 25° C. and the reaction mixture was cooled to 0° C.-5° C. Pyridine (132.3 mL) was then added at a rate that the temperature did not exceed 35° C. The reaction mixture was then heated to 60° C.-65° C. and held at this temperature for 12 to 16 hours. The reaction mixture was cooled to 0° C.-5° C. and quenched with 400 mL of water at a rate that the temperature did not exceed 50° C. The reaction mixture was heated at 55° C. for 1 to 2 hours and then cooled to 20° C.-25° C. The reaction mixture was then diluted with 400 mL of heptane, agitated for 5 minutes, and the layers were allowed to settle for 10 minutes and then separated. The reaction mixture was then treated with 400 mL of water, agitated for 5 minutes, and the layers allowed to settle for 10 minutes and then separated. The organic phase was distilled to the minimum stirrable volume under vacuum (~150 mmHg) at 60° C.-70° C. and 600 mL of heptane was added. The dark product solution was filtered through a silica gel pad (100 g of $SiO_2$) and the pad rinsed with 600 mL of heptane. The light yellow filtrate was distilled under vacuum (~150 mmHg) at 60° C.-70° C. to the minimum stirrable volume. A concentrated solution of 1,1,1-trifluoro-4-(2-bromo-4-fluorophenyl)-4-methyl-2-pentanone in heptane/toluene was obtained (125.0 g, 76.6 wt. % by assay, 80.5% yield).

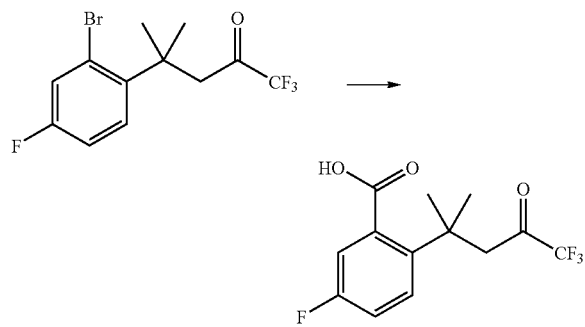

Sodium hydride (8.80 g, 60 wt. % dispersion in mineral oil) was added to the reactor under a nitrogen atmosphere, followed by 150.0 mL of THF (containing 300-500 ppm water as determined by KF) to the reactor. The slurry was cooled to an internal temperature of 0° C.-5° C. and a solution of 1,1,1-trifluoro-4-(2-bromo-4-fluorophenyl)-4-methyl-2-pentanone (109.0 g, 55.0 wt. %) in 70.0 mL of THF was added at a rate that internal temperature does not exceed 10° C. The reaction mixture was heated to 20° C.-25° C. over 30 minutes and set aside at 20° C.-25° C. for 18 hours. The reaction mixture was then cooled to 0° C.-5° C. and isopropylmagnesium chloride-lithium chloride complex (162.12 mL, 1.30 M in THF) was then added at a rate that the internal temperature did not exceed 20° C. 1,4-dioxane (40.0 mL) was added, the internal temperature was raised to 20° C.-25° C., and the reaction mixture was set aside at 20° C.-25° C. for 2 to 3 hours. The reaction mixture was then cooled to an internal temperature of −15° C. to −10° C. Carbon dioxide was then bubbled into the reaction mixture at a rate that the internal temperature did not exceed 20° C. and the carbon dioxide was bubbled in until at least 1.5 equivalents have been added as determined by weight. The reaction mixture was then set aside at 5° C.-15° C. for 30 minutes and then cooled to 0° C.±5° C. A solution of 62.5 mL of concentrated HCl in 187.5 mL of water was slowly added at a rate to control the evolution of hydrogen gas and such that internal temperature did not exceed 30° C. The THF and isopropyl bromide were distilled at batch temperature of not more than 35° C. and 50-100 mmHg. 150 mL of water was added to the reaction mixture and the temperature was lowered to 0° C.-5° C. and held at that temperature for 2 hours. The solid was filtered, the cake washed with 200 mL of water, and the solid dried under vacuum (25-100 mmHg) at 20° C.-25° C. for 8 to 12 hours.

This provided 54.7 g of 1,1,1-trifluoro-4-(2-carboxy-4-fluorophenyl)-4-methyl-2-pentanone in 86.1 wt. % purity by assay (88% yield) and 97.2 area % purity by HPLC (220 nm) and with water content of 0.37% as determined by KF.

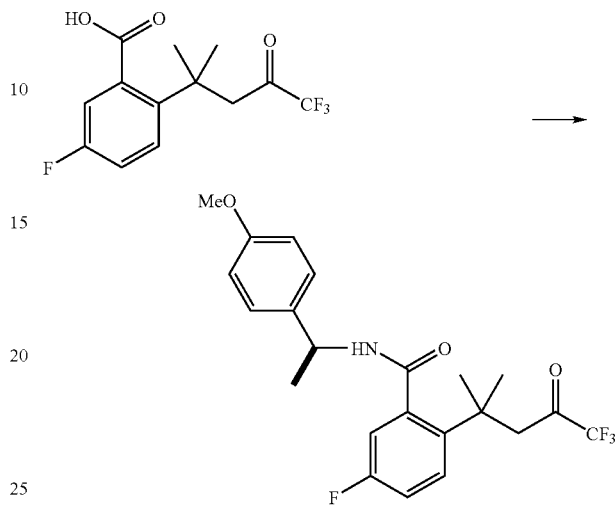

A reactor was charged with 1,1,1-trifluoro-4-(2-carboxy-4-fluorophenyl)-4-methyl-2-pentanone (54.7 g, 86.1 wt. %) and 250 mL of toluene and the slurry was agitated at ~150 rpm. Thionyl chloride (12.93 mL) was added to the reaction mixture, followed by dimethylacetamide (0.10 mL). The resulting slurry was heated to an internal temperature of about 55° C.±5° C. for at least 3 hours; on reaching 55° C., the slurry gradually became a solution. In a separate reactor S-1-(4-methoxyphenyl)ethylamine (26.18 mL), 37.1 mL of 2,6-lutidine, and 100.0 mL of THF were combined and cooled to 0° C.-5° C. The toluene/acid chloride solution was charged to the amine/2,6-lutidine/THF solution at a rate that internal temperature did not exceed 15° C. The resulting reaction mixture was set aside at 20° C.-25° C. for 30 minutes and then cooled to 0° C.-5° C. A solution of 50.0 mL of concentrated HCl in 200.0 mL of water was added to the reaction mixture at a rate that the internal temperature did not exceed 30° C. and then the reaction mixture was agitated for 10 minutes. The layers were allowed to settle for 10 minutes and the lower aqueous phase was drained. 200.0 mL of water was then added and the reaction mixture was agitated for 10 minutes, the layers were allowed to settle for 10 minutes, and the lower aqueous phase was drained. The organic phase was distilled to the minimum stirrable volume (~100 mL for this batch) at a jacket temperature of 50° C.-65° C. and ~100-150 mmHg. 300.0 mL of heptane was then added at a rate to maintain the reaction mixture at 65° C.-75° C. 50.0 mL of water was added and the temperature held at 70° C.-75° C. for 15 to 30 minutes and then the internal temperature was decreased linearly from 70° C.-75° C. to about 5° C. over 2 hours. The reaction mixture was set aside at about 5° C. for 2 hours, then the solid was filtered, washed with 100.0 mL of heptane, and dried under vacuum (25-50 mmHg) with a nitrogen bleed at 55° C.±5° C. for 12 hours. This provided 5-fluoro-N—[(S)-1-(4-methoxyphenyl)ethyl]-2-(4,4,4-trifluoro-1,1-dimethyl-3-oxobutyl)benzamide in 90% yield (61.7 g) and 99.1 area % purity by HPLC (220 nm) and with water content of 0.10% as determined by KF.

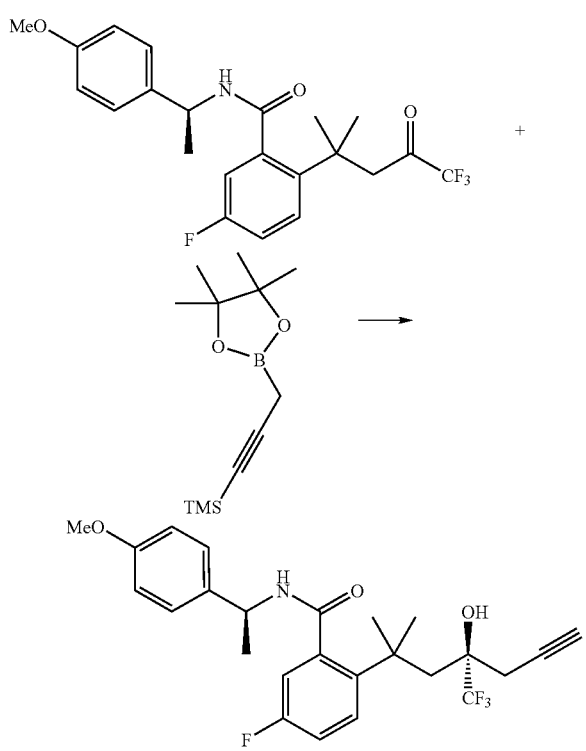

The ketone 5-fluoro-N—[(S)-1-(4-methoxyphenyl)ethyl]-2-(4,4,4-trifluoro-1,1-dimethyl-3-oxobutyl)benzamide (153 g, 97.8 wt. %, 353 mmol) was charged to a flask under nitrogen with 300 mL of THF (267 g, ACS grade, <500 ppm water). The reaction mixture was agitated at $T_{int}$=20° C. to 30° C. for 60 to 90 minutes to dissolve the solids. Trimethyl (3-(4,4,5,5-tetramethyl-1,3,2-dioxaborolan-2-yl)prop-1-ynyl)silane (93.5 wt. %, 108 g, 423 mmol) was then added to the reaction mixture and the solution was agitated for 10 to 60 minutes. N-Isopropyl-L-proline (98.7 wt. %, 69.08 g, 434 mmol) was then charged to a dried 2 L reactor and the system was flushed with nitrogen. 1000 mL of THF (889 g ACS grade, <500 ppm water) was then added to the reactor and the solution agitated and the batch temperature was adjusted to $T_{int}$=20° C.±2° C. Diethyl zinc (2.30 M solution in toluene, 184 mL, 173 g, 423 mmol) was added subsurface to the reactor at a rate to control the ethane gas evolution and to maintain $T_{int}$=20° C. to 35° C. The batch temperature was adjusted to $T_{int}$=40° C. and agitated at $T_{int}$=40° C. to 45° C. for 3 to 4 hours to afford a homogenous solution. The batch was then cooled to $T_{int}$=20±2° C. The 5-fluoro-N—[(S)-1-(4-methoxyphenyl)ethyl]-2-(4,4,4-trifluoro-1,1-dimethyl-3-oxobutyl)benzamide and trimethyl(3-(4,4,5,5-tetramethyl-1,3,2-dioxaborolan-2-yl)prop-1-ynyl)silane solution prepared earlier was then added at a constant rate such that the addition requires 10 to 20 hours while maintaining the batch temperature at $T_{int}$=20° C.±2° C. The reaction mixture was agitated for at least 2 hours at $T_{int}$=20° C.±2° C. Aqueous 3.0 M HCl (425 mL, 444 g) was added slowly to the reactor at a rate to control the ethane gas evolution and to maintain $T_{int}$=20° C. to 30° C. The biphasic solution was agitated for 60 to 90 minutes at $T_{int}$=20° C. to 30° C. and then agitation was stopped and the layers allowed to settle. The lower aqueous layer (731.1 g, pH=1.5) was separated. Sodium methoxide (25 wt. % in methanol, 205.6 mL, 194.3 g, 900 mmol) was charged to the reactor at a rate to maintain $T_{int}$=20° C. to 30° C., the $T_{int}$ was adjusted to 30° C.-34° C., and the slurry was agitated at this temperature for 60 to 90 minutes. The reaction was cooled to $T_{int}$=20° C.±2° C. and then 255 mL of aqueous 3M HCl was added to the reactor at a rate to maintain $T_{int}$=20° C.-30° C. 550 mL of water was then added to the reactor and the reaction mixture was agitated for 10 minutes at $T_{int}$=20° C.-25° C. The pH of the aqueous layer was adjusted to 5.0 to 7.0 by the addition of 3M HCl or 2M NaOH. The biphasic solution was concentrated in vacuo with $T_{int}$ no higher than 65° C. and $T_{jacket}$ no higher than 85° C. to approximately 880 mL by removing 1407 g (1565 mL) of distillate. The pressure in the reactor was then increased to 1 atmosphere and 1200 mL of isopropyl acetate (IpAc, 1046 g) was added to the reactor at $T_{int}$=60° C.±10° C. The reaction mixture was then cooled to $T_{int}$=25° C.±5° C. and the biphasic solution was agitated for 30 minutes this temperature. 60 mL of aqueous 3M HCl was then added to the reactor and the biphasic solution was agitated for 45 to 90 minutes at $T_{int}$=25° C.±5° C. Agitation was then stopped and the layers were allowed to separate. The lower aqueous layer (800.3 g, pH=1.0) was separated. 300 mL of water was added to the reactor and the biphasic solution was agitated for 20 minutes. Agitation was then stopped and the layers were allowed to separate. The lower aqueous layer (314.1 g, pH=2.0) was separated. The wet solution was concentrated in vacuo with $T_{int}$=60° C. to 75° C. and $T_{jacket}$=no higher than 85° C.) to 430 mL±28 mL by removing 815 g±24 g (935±28 mL) of distillate. The pressure was adjusted to 1 atmosphere and the reaction mixture temperature to $T_{int}$=83° C. to 89° C. and the solution was agitated for 30 minutes at this temperature. The reaction mixture temperature was then adjusted to 75° C. 5-Fluoro-2-((S)-4-hydroxy-2-methyl-4-(trifluoromethyl)hept-6-yn-2-yl)-N—((S)-1-(4-methoxyphenyl)ethyl)benzamide (>95:5 dr, 375 mg) was then added as a suspension in 25 vol. % IpAc in heptane (5 mL) to the reactor. The reaction mixture was cooled to $T_{int}$=60° C.±5° C. and agitated at this temperature for 15 minutes. The reaction mixture was then cooled to $T_{int}$=20° C. to 25° C. over no less than 1 hour. Heptane (123.5 g, 180.6 mL) was added to the reactor over no less than 1 hour and the reaction mixture agitated for 30 minutes. A 10 mL sample was removed from the reactor and analyzed by GC to obtain the GC-FID ratio between IpAc and heptane using the following equation to determine the actual quantity of IpAc present at this point in the reaction mixture:

$$\frac{M(IpAc)}{M(Heptane)} = \frac{A(IpAc) \times k}{A(Heptane)}$$

wherein:
M (IpAc)=mass of IpAc
M (Heptane)=mass of heptane
k=relative GC-FID response between IpAc to heptane
A (IpAc)=GC-FID peak area of IpAc
A (Heptane)=GC-FID peak area of heptane
Accordingly, $$k = \frac{M(IpAc) \times A(Heptane)}{M(Heptane) \times A(IpAc)}$$

and $$M(IpAc) = \frac{A(IpAc) \times k \times M(Heptane)}{A(Heptane)}$$

Calculate the amount of IpAc to charge to obtain 226.7 g of IpAc based on the following equation:

IpAc charge=$Y$=226.72−$M$(IpAc)

(a) if Y>0: charge the calculated quantity of IpAc to the reaction (Y).

(b) if Y<0: calculate the amount of heptane to charge based on the following equation, and charge this amount of heptane to the reactor over no less than 1 hour:

heptane charge=$Z$=−2.898×$Y$

Heptane (780 mL, 534 g) was added to the reactor over no less than 1 hour at $T_{int}$=20° C. to 24° C. and the reaction mixture was then agitated at $T_{int}$=20 to 24° C. for at least 10 hours. The solids were collected by filtration and the reactor was rinsed with the filtrate and the solids collected from the rinse by filtration. The solids were then washed with 15 vol. % i-PrOAc in heptane (two 125 mL portions) and dried in a vacuum oven at no higher than 55° C. until <1 wt. % is lost by TGA or LOD. The product was isolated as an off-white powder (119.61 g, 97.7 wt. %, 99.3:0.7 dr).

solid was filtered, washed with 100 mL of MTBE, and dried either on the filter or in a vacuum oven at 20° C.-30° C. and 50-200 mmHg until LOD≦40% was achieved. 97.4 g of white solid was obtained with 65.0 wt. % purity (90.8% yield). To reduce the Pd level, recrystallization was carried out as follows: the 2-((R)-4-((5-(ethylsulfonyl)-1H-pyrrolo[2,3-c]pyridin-2-yl)methyl)-5,5,5-trifluoro-4-hydroxy-2-methylpentan-2-yl)-5-fluoro-N—((S)-1-(4-methoxyphenyl)ethyl)benzamide (97.4 g, 65.0 wt. %) was charged to the reactor, 600 mL of methanol was added, followed 75.0 mL of 1-methylimidazole. The reaction mixture was heated to reflux ($T_{int}$=65° C.-67° C.; $T_{jacket}$ 80° C.) and hold at this temperature for no less than 10 minutes, or until a solution is obtained. 75.0 mL of water was added at a rate such that the internal temperature was maintained at no less than 62° C. 2-((R)-4-((5-(Ethylsulfonyl)-1H-pyrrolo[2,3-c]pyridin-2-yl)methyl)-5,5,5-trifluoro-4-hydroxy-2-methylpentan-2-yl)-5-fluoro-N—((S)-1-(4-methoxyphenyl)ethyl)benzamide seed crystals

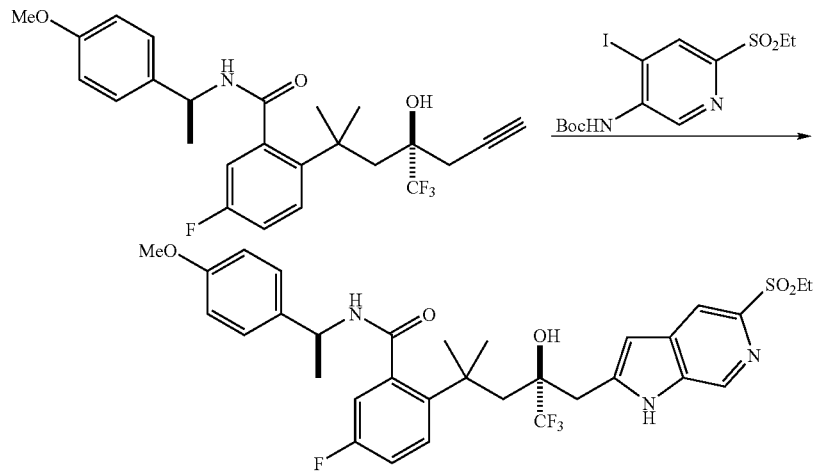

5-Fluoro-2-((S)-4-hydroxy-2-methyl-4-(trifluoromethyl) hept-6-yn-2-yl)-N—((S)-1-(4-methoxyphenyl)ethyl)benzamide (51.20 g, 97.6 wt. %, 107.35 mmol), tert-butyl 6-(ethylsulfonyl)-4-iodopyridin-3-ylcarbamate (45.00 g, 99.5 wt. %, 108.61 mmol), and DABCO (24.6 g, 214.7 mmol) were added to the reactor under a nitrogen atmosphere. 100 mL of degassed methanol was then added and agitation initiated to obtain a white slurry. Palladium acetate (120.0 mg, 0.524 mmol) as a slurry in degassed 10 mL of MeOH was then added and the reaction was slightly exothermic. The jacket temperature was then ramped to 50° C.±3° C. and held there for no less than 12 hours. DBU (24.76 g, 161.03 mmol) was then added at a rate such that the internal temperature did not exceed 53° C. and the reaction mixture was aged at 50° C.±3° C. for no less than 2 hours. 500 mL of MTBE followed by 250 mL of water was added at a rate to maintain the internal temperature between 45° C.-55° C. 2-((R)-4-((5-(Ethylsulfonyl)-1H-pyrrolo[2,3-c]pyridin-2-yl)methyl)-5,5,5-trifluoro-4-hydroxy-2-methylpentan-2-yl)-5-fluoro-N—((S)-1-(4-methoxyphenyl)ethyl)benzamide seed crystals (50 mg) as a slurry in 2 mL of MTBE was then added. The jacket temperature was then ramped linearly from 50° C. to 20° C.-25° C. over 1 hour and the reaction mixture was aged at 20° C.-25° C. for no less than 5 hours, but no more than 20 hours. The (15 mg) as a slurry in 0.5 mL of MeOH was then added. The agitator speed was adjusted to achieve good agitation of the slurry and then 115.0 mL of water was added at a rate such that the internal temperature was maintained at no less than 62° C. The reaction mixture was aged at 65° C.-70° C. for no less than 15 minutes, the temperature was then ramped linearly to 20° C.-25° C. over 1 hour, and the reaction mixture then aged at 20° C.-25° C. for no less than 2 hours, but not more than 18 hours. The solid was filtered, washed with two 100 mL portions of water/MeOH (60:40 v/v), and dried at 65° C.-75° C. and 50-200 mmHg with a nitrogen sweep until LOD≦4.0% was achieved. 57.5 g white solid was obtained with HPLC assay purity of 95.3 wt. % and LOD 0.56% (HPLC area %=99.3%; Pd=14 ppm; yield for reaction and recrystallization: 78.8%).

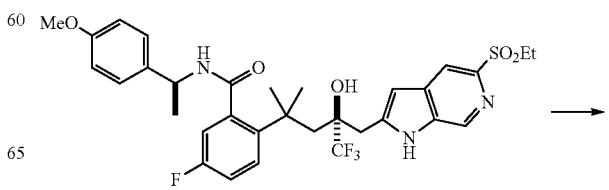

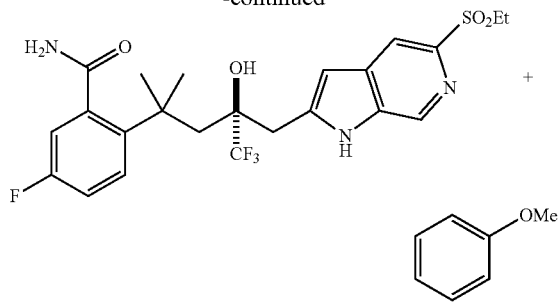

2-((R)-4-((5-(ethylsulfonyl)-1H-pyrrolo[2,3-c]pyridin-2-yl)methyl)-5,5,5-trifluoro-4-hydroxy-2-methylpentan-2-yl)-5-fluoro-N—((S)-1-(4-methoxyphenyl)ethyl)benzamide (50.0 g, 93.5 wt. %) and 200 mL of anisole are charged to a reactor and agitation at ~150 rpm initiated to obtain an off-white slurry. 100 mL of 85% aqueous $H_3PO_4$ was added and the reaction mixture heated to 100° C.±5° C. After 1.0 hour, the reaction was checked by HPLC after preparing a sample by adding a ~0.1 mL reaction mixture aliquot to 10 mL of MeOH. If the area % of 2-((R)-4-((5-(ethylsulfonyl)-1H-pyrrolo[2,3-c]pyridin-2-yl)methyl)-5,5,5-trifluoro-4-hydroxy-2-methylpentan-2-yl)-5-fluoro-N—((S)-1-(4-methoxyphenyl)ethyl)benzamide is <0.5%, proceed; if it is not, age another 30 minutes at 100° C.±5° C. and repeat the HPLC check. The reaction mixture was cooled to 65° C.-70° C. and 200.0 mL of water was added while maintaining the reaction mixture at 65° C.-70° C. A rough slurry was obtained and 150 mL of MEK was added while maintaining the reaction mixture at 65° C.-70° C. The reaction mixture became a smooth slurry, which was held at 65° C.-70° C. for 30 minutes, then ramped to 20° C.-25° C. over no less than 3 hours. The reaction mixture was then held at 20° C.-25° C. for 3 to 4 hours. The solid was filtered, washed with 150 mL of water and then 150 mL of a mixture of MEK/heptane (1:2 v/v), and transferred to a vacuum oven and dried at 65° C.-70° C. with a nitrogen sweep until KF<0.5%. (R)-2-(4-((5-(Ethylsulfonyl)-1H-pyrrolo[2,3-c]pyridin-2-yl)methyl)-5,5,5-trifluoro-4-hydroxy-2-methylpentan-2-yl)-5-fluorobenzamide anisole solvate was obtained as a white-yellow solid (44.1 g, 92.1% yield, HPLC: 98.0 area % (220 nm)).

Other analogs or related compounds (e.g., 5-fluoro-2-[(R)-4,4,4-trifluoro-3-hydroxy-3-(5-methanesulfonyl-1H-pyrrolo[2,3-c]pyridin-2-ylmethyl)-1,1-dimethylbutyl]benzamide, (R)-2-[3-(5-ethanesulfonyl-1H-pyrrolo[2,3-c]pyridin-2-ylmethyl)-4,4,4-trifluoro-3-hydroxy-1,1-dimethylbutyl]benzamide, and (R)-2-[4,4,4-trifluoro-3-hydroxy-3-(5-methanesulfonyl-1H-pyrrolo[2,3-c]pyridin-2-ylmethyl)-1,1-dimethylbutyl]benzamide) may be prepared using these procedures or their modified versions.

Assessment of Biological Properties

Compounds of the invention were evaluated for binding to the steroid receptor by a fluorescence polarization competitive binding assay. Detailed descriptions for preparation of recombinant glucocorticoid receptor (GR) complex used in the assay is described in U.S. Patent Application Publication No. US 2003/0017503, filed May 20, 2002, and incorporated herein by reference in its entirety. Preparation of the tetramethyl rhodamine (TAMRA)-labeled dexamethasone probe was accomplished using a standard literature procedure (M. Pons et al., J. Steroid Biochem., 1985, 22, pp. 267-273).

A. Glucocorticoid Receptor Competitive Binding Assay
Step 1. Characterization of the Fluorescent Probe The wavelengths for maximum excitation and emission of the fluorescent probe should first be measured. An example of such a probe is rhodamine (TAMRA)-labeled dexamethasone.

The affinity of the probe for the steroid receptor was then determined in a titration experiment. The fluorescence polarization value of the probe in assay buffer was measured on an SLM-8100 fluorometer using the excitation and emission maximum values described above. Aliquots of expression vector lysate were added and fluorescence polarization was measured after each addition until no further change in polarization value was observed. Non-linear least squares regression analysis was used to calculate the dissociation constant of the probe from the polarization values obtained for lysate binding to the probe.

Step 2. Screening for Inhibitors of Probe Binding

This assay uses fluorescence polarization (FP) to quantitate the ability of test compounds to compete with tetramethyl rhodamine (TAMRA)-labeled dexamethasone for binding to a human glucocorticoid receptor (GR) complex prepared from an insect expression system. The assay buffer was: 10 mM TES, 50 mM KCl, 20 mM $Na_2MoO_4.2H_2O$, 1.5 mM EDTA, 0.04% w/v CHAPS, 10% v/v glycerol, 1 mM dithiothreitol, pH 7.4. Test compounds were dissolved to 1 mM in neat DMSO and then further diluted to 10× assay concentration in assay buffer supplemented with 10% v/v DMSO. Test compounds were serially diluted at 10× assay concentrations in 10% DMSO-containing buffer in 96-well polypropylene plates. Binding reaction mixtures were prepared in 96-well black Dynex microtiter plates by sequential addition of the following assay components to each well: 15 μL of 10× test compound solution, 85 μL of GR-containing baculovirus lysate diluted 1:170 in assay buffer, and 50 μL of 15 nM TAMRA-labeled dexamethasone. Positive controls were reaction mixtures containing no test compound; negative controls (blanks) were reaction mixtures containing 0.7 μM to 2 μM dexamethasone. The binding reactions were incubated for 1 hour at room temperature and then read for fluorescence polarization in the LJL Analyst set to 550 nm excitation and 580 nm emission, with the Rhodamine 561 dichroic mirror installed. $IC_{50}$ values were determined by iterative non-linear curve fitting of the FP signal data to a 4-parameter logistic equation.

Compounds found to bind to the glucocorticoid receptor may be evaluated for binding to the progesterone receptor (PR), estrogen receptor (ER), and mineralocorticoid receptors (MR) to evaluate the compound's selectivity for GR. The protocols for PR and MR are identical to the above GR method, with the following exceptions: PR insect cell lysate is diluted 1:7.1 and MR lysate diluted 1:9.4. PR probe is TAMRA-labeled mifepristone, used at a final concentration of 5 nM in the assay, and the negative controls (blanks) were reactions containing mifepristone at 0.7 μM to 2 μM. The ER protocol is similar to the above protocols, but uses PanVera kit receptor, fluorescein-labeled probe. The assay components are made in the same volumes as above, to produce final assay concentrations for ER of 15 nM and ES2 probe of 1 nM. In addition, the component order of addition is modified from the above assays: probe is added to the plate first, followed by receptor and test compound. The plates are read in the LJL Analyst set to 485 nm excitation and 530 nm emission, with the Fluorescein 505 dichroic mirror installed.

Compounds found to bind to the glucocorticoid receptor may be evaluated for dissociation of transactivation and transrepression by assays cited in the Background of the Invention (C. M. Bamberger and H. M. Schulte, Eur. J. Clin. Invest., 2000, 30 (suppl. 3)6-9) or by the assays described below.

B. Glucocorticoid Receptor Cell Assays

1. Inhibition of IL-6 Production in Fibroblasts (Cell Assay for Transrepression)

Human foreskin fibroblast cells produce IL-6 in response to stimulation by proinflammatory cytokine IL-1. This inflammatory response, as measured by the production of IL-6, can be effectively inhibited by dexamethasone, a synthetic ligand to the glucocorticoid receptor (GR). Compounds that exhibit binding to GR are evaluated for their ability to inhibit IL-6 production in human foreskin fibroblasts.

Human foreskin fibroblast cells (ATCC Cat. No. CRL-2429) are plated on 96 well plates at 5,000 cells per well the day before use, in Iscove's Modified Dulbecco's Media (GibcoBRL Life Technologies Cat. No. 12440-053) supplemented with 10% charcoal filtered FBS (Clonetech Cat. No. SH30068) and Gentamycin (GibcoBRL Life Technologies Cat. No. 15710-064). On the next day, media in the wells is replaced with fresh media. Cells are treated with IL-1 (rhIL-1α, R&D Systems Cat. No. 200-LA) to a final concentration of 1 ng/mL, and with test compounds to final concentrations of $10^{-5}$ M to $10^{-8}$ M, in a total volume of 200 µL per well. Samples are done in duplicates. Background control wells do not receive test compounds or IL-1. Positive control wells receive IL-1 only and represent maximum (or 100%) amount of IL-6 production. Plates are incubated at 37° C. overnight (15 to 18 hours), and supernatants are harvested at the end of incubation. IL-6 levels in the supernatants are determined by the ELISA kits for IL-6 (MedSystems Diagnostics GmbH, Vienna, Austria, Cat. No. BMS213TEN) according to manufacture's instructions. The extent of inhibition of IL-6 by test compounds is expressed in percentage relative to positive controls. $IC_{50}$ values of test compounds are derived by non-linear curve fitting.

Evaluation of agonist or antagonist activity of compounds binding to the glucocorticoid receptor may be determined by any of the assays.

In general, the preferred potency range in the above assays is between 0.1 nM and 10 µM, the more preferred potency range is 0.1 nM to 1 µM, and the most preferred potency range is 0.1 nM to 100 nM.

2. Modulation of MMTV-Luc Induction in HeLa Cells

Testing of compounds for agonist or antagonist activity in stimulation of MMTV-(mouse mammary tumor virus) promoter in HeLa cells.

HeLa cells were stably co-transfected with the pHHLuc-plasmid containing a fragment of the MMTV-LTR (−200 to +100 relative to the transcription start site) cloned in front of the luciferase gene (Norden, 1988) and the pcDNA3.1 plasmid (Invitrogen) constitutively expressing the resistance for the selective antibiotic GENETICIN®. Clones with best induction of the MMTV-promoter were selected and used for further experiments.

Cells were cultured overnight in DMEM medium without phenol red, supplemented with 3% CCS (charcoal treated calf serum) and then transferred to 96 well plates (15,000 cells/100 µL/well). On the next day, activation of the MMTV-promoter was stimulated by addition of test compound or dexamethasone dissolved in DMSO (final concentration 0.2%). Control cells were treated with DMSO only. After 18 hours, the cells were lysed with cell lysis reagent (Promega, Cat. No. E1531), luciferase assay reagent (Promega, Cat. No. E1501) was added and the glow luminescence was measured using a luminometer (BMG, Offenburg).

For measuring antagonist activity, the MMTV-promoter was pre-stimulated by adding dexamethasone ($3 \times 10^{-9}$ M to $3 \times 10^{-8}$ M) shortly before the test compound was applied to the cells. The steroidal non-selective GR/PR antagonist mifepristone was used as control.

3. Inhibition of Osteocalcin Production from Osteoblast Cell Line MG-63

Human osteosarcoma MG-63 cells (ATCC, Cat. No. CRL-1427) are plated on 96 well plates at 20,000 cells per well the day before use in 200 µL media of 99% D-MEM/F-12 (Gibco-Invitrogen, Cat. No. 11039-021), supplemented with 1% penicillin and streptomycin (Gibco-Invitrogen, Cat. No. 15140-122), 10 µg/mL Vitamin C (Sigma, Cat. No. A-4544), and 1% charcoal filtered Fetal Bovine Serum (HyClone, Cat. No. SH30068.02). The next day, wells are replaced with fresh media. Cells are treated with Vitamin D (Sigma, Cat. No. D1530) to a final concentration of 10 nM, and with the test compounds in concentrations of $10^{-6}$ M to $10^{-9}$ M, in a total volume of 200 µL per well. Samples are done in duplicates. Background control wells do not receive Vitamin D or compounds. Positive control wells receive Vitamin D only, without compounds, and represent maximum (100%) amount of osteocalcin production. Plates are incubated at 37° C. incubator for 48 hours and supernatants are harvested at the end of incubation. Amounts of osteocalcin in the supernatants are determined by the Glype osteocalcin ELISA kit (Zymed, Cat. No. 99-0054) according to manufacture's protocol. Inhibition of osteocalcin by test compounds is expressed in percentage relative to positive controls. $IC_{50}$ values of the test compounds are derived by non-lineal curve fitting.

C. Cytochrome P450 Inhibition Assay

This assay is intended to measure the $IC_{50}$ of test compounds to inhibit the hepatic xenobiotic metabolizing enzyme CYP3A4, specifically for the substrate 7-benzyloxy-4-(trifluoromethyl)coumarin. The assay uses automated systems (Tecan or Zymark) to dispense reagents, buffers, and samples. Eight to ten concentrations (in half-log intervals) of each test compound are assayed in 200 mM $K_3PO_4$, 1.3 mM $NADP^+$, 3.3 mM glucose-6-phosphate, 3.3 mM $MgCl_2$, and 0.4 Units/mL glucose-6-phosphate dehydrogenase. Test samples, which were previously dissolved in acetonitrile or DMSO, are separately diluted in assay buffer. Replicate 100 mL aliquots of diluted test compound are dispensed into 96-well assay plates (Packard Optiplate), and the plates are preincubated for at least 10 minutes at 37° C. A 100 mL volume of human recombinant CYP3A4 (3.0 pmol) and substrate 7-benzyloxy-4-(trifluoromethyl)coumarin (50 mM) are then added to each test well. The reaction is incubated for 30 minutes at 37° C. A standard inhibition curve using ketoconazole is run with each assay plate. The reaction is terminated with the addition of 75 mL 80% acetonitrile/20% 0.5 M Tris base. The plate is read with a fluorescent plate reader (Tecan Spectrafluor or LJL Biosystems Analyst) at an excitation wavelength of 409 nm and an emission wavelength of 530 nm. The $IC_{50}$ values are calculated using SAS analysis.

D. High Throughput Solubility

1. Sample preparation: To 3 mg of drug substance, add 150 µL of DMSO. Sonicate the sample for 10-20 minutes followed by vortexing. Pipette 150 µL of each sample into a 96 well plate. Pipette 150 μL of DMSO into stock plate well as a control blank, with each run at each pH. Sample concentration is between 25 (in 300 μL DMSO) and 50 mM (in 150 μL DMSO).

2. Preparation of pH 4.5 and 7.4 buffers: (a) pH 4.5 buffer: 25 mL of system solution (pION) qs to 1000 mL with DI water (pH 2.85-2.90), adjust the pH to pH 4.5 with 0.5N NaOH. (b) pH 7.4 buffer: 25 mL of system solution (pION) qs to 1000 mL with DI water (pH 2.85-2.90), adjust the pH to pH 7.4 with 0.5N NaOH.

3. Preparation of sample for incubation: (a) Solubility at pH 7.4: 3 μL of each stock sample (including DMSO control) is added to the deep well plate containing 600 μL of pH 7.4 buffer, mixed, and incubated for 16-19 hours. The plate is sealed well during the incubation process. Final DMSO content is 0.5%. (b) Solubility at pH 4.5: 3 μL of each stock sample (including DMSO control) is added to the deep well plate containing 600 μL of pH 4.5 buffer, mixed, and incubated for 16-19 hours. The plate is sealed well during the incubation process. Final DMSO content is 0.5%. (c) Preparation of sample UV plate: At the end of the incubation period, 100 μL of sample from the deep well plate is vacuum filtered using a filter plate. Another 200 μL of the sample from the deep well plate is vacuum filtered using the same filter plate but a clean collector plate. 75 μL of the filtrate from the collector plate is transferred to a UV sample plate. 75 μL of propanol is added to this UV plate. The solution is mixed and the spectrum is read using the UV spectrophotometer. (d) Data Analysis: The spectra collected for blank, reference, and sample from 250 nm to 498 nm is analyzed using pION software. If the sample precipitates out, the solubility is reported as XX μg/mL. If there is no precipitation and the sample is soluble, solubility is reported as >YY μg/mL (YY being the initial concentration of the compound in 5 μL or 10 μL of stock sample).

E. Human Microsomal Stability

The single time point high throughput screen for human liver microsomal metabolic stability is used to measure the in vitro metabolism of test compounds by human liver microsomal enzymes. The data collected are analyzed to calculate a half-life ($t_{1/2}$, minutes) for test compounds. The assay is performed in 50 mM potassium phosphate buffer, pH 7.4, and 2.5 mM NADPH. Test samples are dissolved in acetonitrile for a final assay concentration of 1 μM to 10 μM. Human liver microsomes are diluted in assay buffer to a final assay concentration of 1 mg protein/mL. A volume of 25 μL compound solution and 50 μL microsome suspension are added to 825 μL assay buffer. The preparation is incubated for 5 minutes in a 37° C. water bath. The reaction is started by the addition of 100 μL NADPH. Volumes of 80 μL are removed from the incubation mix at times 0, 15, and 30 minutes after the start of the reaction and added to 160 μL of acetonitrile. The samples are shaken for 20 seconds and then centrifuged for 3 minutes at 3000 rpm. A 200 μL volume of the supernatant is transferred to 0.25 mm glass fiber filter plates and centrifuged for 5 minutes at 3000 rpm. Injection volumes of 10 μL are typically added to Zorbax SB C8 HPLC columns with formic acid in water or acetonitrile at a flow rate of 1.5 mL/min. Percent loss of parent compound is calculated from the area under each time point to determine the half-life.

F. hERG Assays

Compounds were tested in either of the following assays:

1. hERG Binding Assay

Potassium Channel HERG activity in Human recombinant HEK-293 cells. Ligand: 1.5 nM [$^3$H] Astemizole; vehicle 1% DMSO. Incubation Time/Temp: 60 min@25° C. Incubation Buffer: 10 mM HEPES, pH 7.4, 0.1% BSA, 5 mM KCl, 0.8 mM MgCl$_2$, 130 mM NaCl, 1 mM NaEGTA, 10 mM Glucose. Non-Specific Ligand: 10 μM Astemizole; $K_D$ 6.8 nM; $B_{max}$: 6.3 pmole/mg Protein; Specific Binding: 90%; Quantitation Method: Radioligand Binding; Significance Criteria: ≧50% of maximum stimulation or inhibition.

2. hERG Patch Clamp Assay

The objective of this experiment is to investigate the effects of test compounds on the HERG-mediated potassium current (IKr) in Human Embryonic Kidney 293 (HE 293) cells stably expressing the HERG-encoded (human ether-a-go-go related gene) potassium channel. Currents are recorded from HE 293 cells at room temperature (20° C.-22° C.), using the whole-cell patch-clamp technique. For investigating effects on the HERG potassium channel (IKr), HEK293 cells are clamped at a holding potential of 0 mV and measured using a pulse pattern with fixed amplitudes (hyperpolarization: −80 mV for 25 ms; depolarization: +40 mV for 80 ms) repeated at 10 second intervals. The experiments are performed with three to four concentrations and three different cells for each concentration. A steady state level of current is measured for at least 60 second before applying test article for 5 minutes. For evaluation of IC$_{50}$ peak current, this is measured 1.5 ms after the step to +40 mV and the amplitude in the presence of test and control articles is recorded over 5 minutes. All compounds are dissolved in DMSO to give a 10 mM stock solution and dilutions are prepared freshly before starting the experiments. Data acquisition and analysis is performed with pClamp 8.2 for Windows (Clampex and Clampfit, Axon Instruments Inc., USA). Results are expressed as fraction of current remaining (I/I0). Concentration-response data are fit to an equation of the following form: $I/I0 = 1/(1+([compound]/IC_{50}))$. Nonlinear least squares fits are made and using the graph pad prism software. The IC$_{50}$ is calculated with a sigmoidal dose-response curve model.

As shown in the Table 2, an unsubstituted azaindole compound (Table 2, Compound 7), a representative of compounds disclosed in U.S. Pat. No. 6,903,215, was a potent CYP inhibitor. Incorporation of an amide or a methyl sulfone moiety at the C(2) of the phenyl group (Table 2, compare Compounds 2 and 5 vs. Compound 7) did not improve the CYP profile. Additionally, substitution at the C(5) of the azaindole ring with groups such as the morpholinyl group, which was among the patterns that had been previously disclosed in U.S. Patent Application Publication No. 2005/0176706, did not significantly alter the overall CYP profile (Table 2, compare Compound 3 vs. Compound 2 and Compound 6 vs. Compound 5). In fact, these examples suggest that such substitutions are not advantageous.

However, the present invention surprisingly and unexpectedly demonstrates that substitution in the 5-position of the azaindole ring with an alkylsulfonyl group provides compounds that have significantly reduced CYP inhibition, as represented by CYP3A4 inhibition IC$_{50}$ values (Table 2, compare Compound 1 vs. Compounds 2, 3, and 7, and Compound 4 vs. Compounds 5, 6, and 7). Therefore, the reduced CYP inhibition activity displayed by the compounds of the instant invention compared with related prior art compounds is both surprising and unexpected.

TABLE 2

Comparison Compounds

| Compound No. | Structure | CYP3A4 Inhibition IC$_{50}$ [μM] |
|---|---|---|
| 1 | 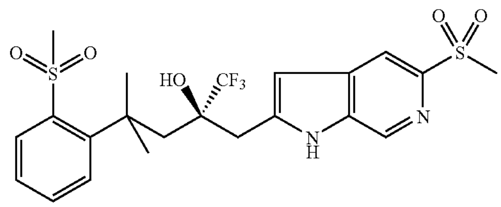 | >30 |
| 2 | 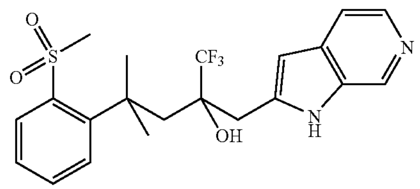 | 0.18 |
| 3 | 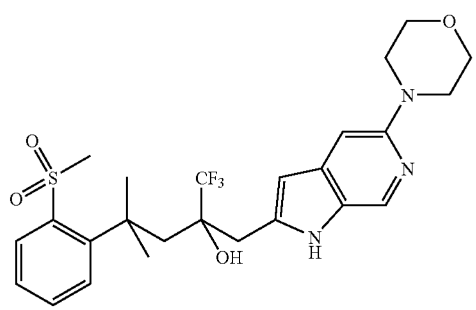 | 0.01 |
| 4 | 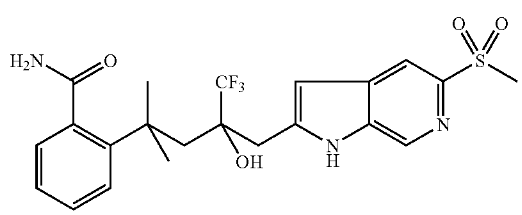 | >30 |
| 5 | 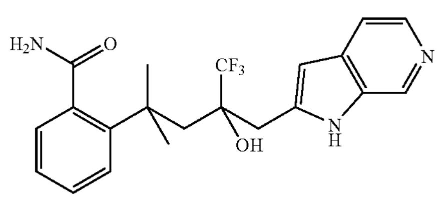 | 0.51 |
| 6 | 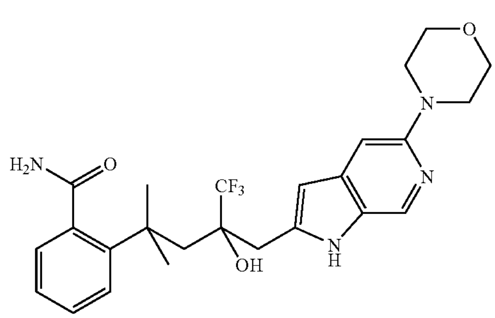 | 2.7 |

TABLE 2-continued

Comparison Compounds

| Compound No. | Structure | CYP3A4 Inhibition IC$_{50}$ [μM] |
|---|---|---|
| 7 | [structure: phenyl-C(CH$_3$)$_2$-CH$_2$-C(CF$_3$)(OH)-CH$_2$-pyrrolo[2,3-c]pyridine] | 0.9 |

Representative compounds of the present invention have been tested and have shown activity as modulators of the glucocorticoid receptor function in one or more of the above assays (Table 1). Additionally, compounds of the instant invention, as represented by examples in Table 3, have generally demonstrated desirable overall drug like properties, such as Cytochrome P450 inhibition that is indicative of drug-drug interaction potential (represented by CYP3A4 inhibition IC$_{50}$ values), hERG inhibition that is indicative of QT prolongation of the heart, and advantageous pharmacokinetic properties (represented by in vitro metabolic stability) and physical-chemical properties (represented by aqueous solubility).

TABLE 3

Additional Examples

| Structure | CYP3A4 Inhibition IC$_{50}$ [μM] | HERG IC$_{50}$ [μM] | aqueous solubility at pH 7 [μg/mL] | human liver microsome half life [min] |
|---|---|---|---|---|
| [structure: chloro-dihydrobenzofuran-C(CH$_3$)$_2$-CH$_2$-C(OH)(CF$_3$)-CH$_2$-pyrrolo[2,3-c]pyridine-SO$_2$CH$_3$] | 6.5 | 9.4 | not determined | <3 |
| [structure: (methylsulfonyl)phenyl-C(CH$_3$)$_2$-CH$_2$-C(CF$_3$)(OH)-CH$_2$-pyrrolo[2,3-c]pyridine-SO$_2$CH$_3$] | >30 | >10 | 59 | <3 |
| [structure: chloro-(methylsulfonyl)phenyl-C(CH$_3$)$_2$-CH$_2$-C(OH)(CF$_3$)-CH$_2$-pyrrolo[2,3-c]pyridine-SO$_2$CH$_3$] | 4.2 | >10 | 40 | 17 |

TABLE 3-continued

Additional Examples

| Structure | CYP3A4 Inhibition IC$_{50}$ [μM] | HERG IC$_{50}$ [μM] | aqueous solubility at pH 7 [μg/mL] | human liver microsome half life [min] |
|---|---|---|---|---|
| | >30 | >10 | 18 | 11 |
| | >30 | >30 | 52 | 7 |
| 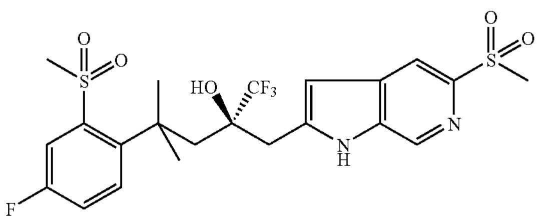 | 14 | >30 | >100 | 14 |
| | >30 | >30 | >100 | 17 |
| | >30 | >30 | 17 | 44 |
| 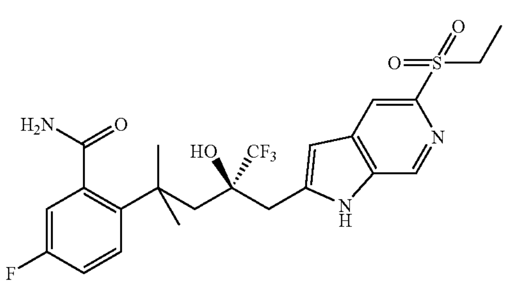 | 26 | >30 | >100 | >300 |

TABLE 3-continued

Additional Examples

| Structure | CYP3A4 Inhibition IC$_{50}$ [µM] | HERG IC$_{50}$ [µM] | aqueous solubility at pH 7 [µg/mL] | human liver microsome half life [min] |
|---|---|---|---|---|
| (structure with H$_2$N-C(=O)-, CF$_3$, OH, fluorophenyl, pyrrolopyridine, and SO$_2$Me groups) | 2.5 | >30 | >100 | 45 |

The invention also provides methods of modulating the glucocorticoid receptor function in a patient comprising administering to the patient a compound according to the invention. If the purpose of modulating the glucocorticoid receptor function in a patient is to treat a disease-state or condition, the administration preferably comprises a therapeutically or pharmaceutically effective amount of a pharmaceutically acceptable compound according to the invention. If the purpose of modulating the glucocorticoid receptor function in a patient is for a diagnostic or other purpose (e.g., to determine the patient's suitability for therapy or sensitivity to various sub-therapeutic doses of the compounds according to the invention), the administration preferably comprises an effective amount of a compound according to the invention, that is, the amount necessary to obtain the desired effect or degree of modulation.

Methods of Therapeutic Use

As pointed out above, the compounds of the invention are useful in modulating the glucocorticoid receptor function. In doing so, these compounds have therapeutic use in treating disease-states and conditions mediated by the glucocorticoid receptor function or that would benefit from modulation of the glucocorticoid receptor function.

As the compounds of the invention modulate the glucocorticoid receptor function, they have very useful anti-inflammatory and antiallergic, immune-suppressive, and anti-proliferative activity and they can be used in patients as drugs, particularly in the form of pharmaceutical compositions as set forth below, for the treatment of disease-states and conditions.

The agonist compounds according to the invention can be used in patients as drugs for the treatment of the following disease-states or indications that are accompanied by inflammatory, allergic, and/or proliferative processes:

(i) Lung diseases: chronic, obstructive lung diseases of any genesis, particularly bronchial asthma and chronic obstructive pulmonary disease (COPD); adult respiratory distress syndrome (ARDS); bronchiectasis; bronchitis of various genesis; all forms of restrictive lung diseases, particularly allergic alveolitis; all forms of lung edema, particularly toxic lung edema; all forms of interstitial lung diseases of any genesis, e.g., radiation pneumonitis; and sarcoidosis and granulomatosis, particularly Boeck disease.

(ii) Rheumatic diseases or autoimmune diseases or joint diseases: all forms of rheumatic diseases, especially rheumatoid arthritis, acute rheumatic fever, and polymyalgia rheumatica; reactive arthritis; rheumatic soft tissue diseases; inflammatory soft tissue diseases of other genesis; arthritic symptoms in degenerative joint diseases (arthrosis); traumatic arthritis; collagenosis of any genesis, e.g., systemic lupus erythematosus, scleroderma, polymyositis, dermatomyositis, Sjögren syndrome, Still disease, and Felty syndrome;

(iii) Allergic diseases: all forms of allergic reactions, e.g., angioneurotic edema, hay fever, insect bites, allergic reactions to drugs, blood derivatives, contrast agents, etc., anaphylactic shock (anaphylaxis), urticaria, angioneurotic edema, and contact dermatitis;

(iv) Vasculitis diseases: panarteritis nodosa, polyarteritis nodosa, arteritis temporalis, Wegner granulomatosis, giant cell arthritis, and erythema nodosum;

(v) Dermatological diseases: atopic dermatitis, particularly in children; psoriasis; pityriasis rubra pilaris; erythematosus diseases triggered by various noxa, e.g., rays, chemicals, burns, etc.; bullous dermatoses; diseases of the lichenoid complex; pruritus (e.g., of allergic genesis); seborrheic dermatitis; rosacea; pemphigus vulgaris; erythema multiforme exudativum; balanitis; vulvitis; hair loss, such as occurs in alopecia areata; and cutaneous T cell lymphomas;

(vi) Renal diseases: nephrotic syndrome; and all types of nephritis, e.g., glomerulonephritis;

(vii) Hepatic diseases: acute liver cell disintegration; acute hepatitis of various genesis, e.g., viral, toxic, drug-induced; and chronically aggressive and/or chronically intermittent hepatitis;

(viii) Gastrointestinal diseases: inflammatory bowel diseases, e.g., regional enteritis (Crohn disease), colitis ulcerosa; gastritis; peptic esophagitis (refluxoesophagitis); and gastroenteritis of other genesis, e.g., nontropical sprue;

(ix) Proctological diseases: anal eczema; fissures; hemorrhoids; and idiopathic proctitis;

(x) Eye diseases: allergic keratitis, uveitis, or iritis; conjunctivitis; blepharitis; neuritis nervi optici; choroiditis; and sympathetic ophthalmia;

(xi) Diseases of the ear, nose, and throat (ENT) area: allergic rhinitis or hay fever; otitis extema, e.g., caused by contact eczema, infection, etc.; and otitis media;

(xii) Neurological diseases: brain edema, particularly tumor-related brain edema; multiple sclerosis; acute encephalomyelitis; meningitis; acute spinal cord injury; stroke; and various forms of seizures, e.g., nodding spasms;

(xiii) Blood diseases: acquired hemolytic anemia; and idiopathic thrombocytopenia;

(xiv) Tumor diseases: acute lymphatic leukemia; malignant lymphoma; lymphogranulomatoses; lymphosarcoma; extensive metastases, particularly in mammary, bronchial, and prostatic carcinoma;

(xv) Endocrine diseases: endocrine ophthalmopathy; endocrine orbitopathia; thyrotoxic crisis; Thyroiditis de Quervain; Hashimoto thyroiditis; Morbus Basedow; granulomatous thyroiditis; struma lymphomatosa; and Grave disease;

(xvi) Organ and tissue transplantations and graft-versus-host diseases;

(xvii) Severe states of shock, e.g., septic shock, anaphylactic shock, and systemic inflammatory response syndrome (SIRS);

(xviii) Substitution therapy in: congenital primary adrenal insufficiency, e.g., adrenogenital syndrome; acquired primary adrenal insufficiency, e.g., Addison disease, autoimmune adrenalitis, post-infection, tumors, metastases, etc.; congenital secondary adrenal insufficiency, e.g., congenital hypopituitarism; and acquired secondary adrenal insufficiency, e.g., post-infection, tumors, metastases, etc.;

(xix) Pain of inflammatory genesis, e.g., lumbago; and (xx) various other disease-states or conditions including type I diabetes (insulin-dependent diabetes), osteoarthritis, Guillain-Barre syndrome, restenosis following percutaneous transluminal coronary angioplasty, Alzheimer disease, acute and chronic pain, atherosclerosis, reperfusion injury, bone resorption diseases, congestive heart failure, myocardial infarction, thermal injury, multiple organ injury secondary to trauma, acute purulent meningitis, necrotizing enterocolitis and syndromes associated with hemodialysis, leukopheresis, and granulocyte transfusion.

In addition, the compounds according to the invention can be used for the treatment of any other disease-states or conditions not mentioned above which have been treated, are treated, or will be treated with synthetic glucocorticoids (see, e.g., H. J. Hatz, *Glucocorticoide: Immunologische Grundlagen, Pharmakologie und Therapierichtlinien* [Glucocorticoids: Immunological Fundamentals, Pharmacology, and Therapeutic Guidelines], Stuttgart: Verlagsgesellschaft mbH, 1998, which is hereby incorporated by reference in its entirety). Most or all of the indications (i) through (xx) mentioned above are described in detail in H. J. Hatz, *Glucocorticoide: Immunologische Grundlagen, Pharmakologie und Therapierichtlinien*. Furthermore, the compounds of the invention can also be used to treat disorders other than those listed above or mentioned or discussed herein, including in the Background of the Invention.

Methods of Diagnostic Use

The compounds of the invention may also be used in diagnostic applications and for commercial and other purposes as standards in competitive binding assays. In such uses, the compounds of the invention may be used in the form of the compounds themselves or they may be modified by attaching a radioisotope, luminescence, fluorescent label or the like in order to obtain a radioisotope, luminescence, or fluorescent probe, as would be known by one of skill in the art and as outlined in *Handbook of Fluorescent Probes and Research Chemicals*, 6th Edition, R. P. Haugland (ed.), Eugene: Molecular Probes, 1996; *Fluorescence and Luminescence Probes for Biological Activity*, W. T. Mason (ed.), San Diego: Academic Press, 1993; *Receptor-Ligand Interaction, A Practical Approach*, E. C. Hulme (ed.), Oxford: IRL Press, 1992, each of which is hereby incorporated by reference in their entireties.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased inhibitory activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

In particular, the compounds of the invention are useful in combination with glucocorticoids or corticosteroids. As pointed out above, standard therapy for a variety of immune and inflammatory disorders includes administration of corticosteroids, which have the ability to suppress immunologic and inflammatory responses (A. P. Truhan et al., Annals of Allergy, 1989, 62, pp. 375-391; J. D. Baxter, Hospital Practice, 1992, 27, pp. 111-134; R. P. Kimberly, Curr. Opin. Rheumatol., 1992, 4, pp. 325-331; M. H. Weisman, Curr. Opin. Rheumatol., 1995, 7, pp. 183-190; W. Sterry, Arch. Dermatol. Res., 1992, 284 (Suppl.), pp. S27-S29). While therapeutically beneficial, however, the use of corticosteroids is associated with a number of side effects, ranging from mild to possibly life threatening, especially with prolonged and/or high dose steroid usage. Accordingly, methods and compositions that enable the use of a lower effective dosage of corticosteroids (referred to as the "steroid sparing effect") would be highly desirable to avoid unwanted side effects. The compounds of the invention provide such a steroid sparing effect by achieving the desired therapeutic effect while allowing the use of lower doses and less frequent administration of glucocorticoids or corticosteroids.

In particular, the compounds of the invention are useful in combination with other drugs commonly used to treat signs and symptoms as well as causes of inflammatory or immunological indications, as well as to treat, prevent, or avoid typical drug-induced side effects. Such drugs could be used with the compounds of the invention in a fixed dose combination product or administered in separate formulations. Examples of such drugs would include small molecules used for the treatment of rheumatoid arthritis such as methotrexate, ARAVA® (leflunomide), PLAQUENIL® (hydroxychloroquine), and AZULFIDINE® (sulfasalazine); gold compounds (e.g., MYOCHRYSINE® (sodium aurothiomalate)); antibiotics (e.g., minocycline); immunosuppressive agents (e.g., cyclosporine, azathiaprine cyclosporine, tacrolimus (FK-506), sirolimus (rapamycin), and mycophenolate mofetil); and non-steroidal anti-inflammatory agents (NSAIDs), such as ibuprofen, MOBIC® (meloxicam), CELEBREX® (celecoxib). Examples of such drugs would also include biologic agents used for the treatment of rheumatoid arthritis such as anti-TNF agents, e.g., ENBREL® (etanercept), REMICADE® (infliximab), HUMIRA® (adalimumab); other cytokine or cytokine receptor antagonists, e.g., IL-1 antagonists; agents that modulate cell interaction, cell trafficking, cell adhesion, or cell signaling, e.g., abatacept (ORENCIA®); and agents that cause cell depletion, e.g., RITUXAN® (rituximab).

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy*, 20th Edition, A. Gennaro (ed.), Lippincott Williams & Wilkins, 2000; *Handbook of Pharmaceutical Additives*, Michael & Irene Ash (eds.), Gower, 1995; *Handbook of Pharmaceutical Excipients*, A. H. Kibbe (ed.), American Pharmaceutical Ass'n, 2000; H. C. Ansel and N. G. Popovish, *Pharmaceutical Dosage Forms and Drug Delivery Systems*, 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that is required for the formulation to be efficacious.

Pharmaceutical compositions suitable for buccal (sub-lingual) administration include lozenges comprising a compound of the present invention in a flavored base, usually sucrose, and acacia or tragacanth, and pastilles comprising the compound in an inert base such as gelatin and glycerin or sucrose and acacia.

Pharmaceutical compositions suitable for parenteral administration comprise sterile aqueous preparations of a compound of the present invention. These preparations are preferably administered intravenously, although administration can also be effected by means of subcutaneous, intramuscular, or intradermal injection. Injectable pharmaceutical formulations are commonly based upon injectable sterile saline, phosphate-buffered saline, oleaginous suspensions, or other injectable carriers known in the art and are generally rendered sterile and isotonic with the blood. The injectable pharmaceutical formulations may therefore be provided as a sterile injectable solution or suspension in a nontoxic parenterally acceptable diluent or solvent, including 1,3-butanediol, water, Ringer's solution, isotonic sodium chloride solution, fixed oils such as synthetic mono- or diglycerides, fatty acids such as oleic acid, and the like. Such injectable pharmaceutical formulations are formulated according to the known art using suitable dispersing or setting agents and suspending agents. Injectable compositions will generally contain from 0.1 to 5% w/w of a compound of the invention.

Solid dosage forms for oral administration of the compounds include capsules, tablets, pills, powders, and granules. For such oral administration, a pharmaceutically acceptable composition containing a compound(s) of the invention is formed by the incorporation of any of the normally employed excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such solid pharmaceutical formulations may include formulations, as are well-known in the art, to provide prolonged or sustained delivery of the drug to the gastrointestinal tract by any number of mechanisms, which include, but are not limited to, pH sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form.

Liquid dosage forms for oral administration of the compounds include emulsions, microemulsions, solutions, suspensions, syrups, and elixirs, optionally containing pharmaceutical adjuvants in a carrier, such as, for example, water, saline, aqueous dextrose, glycerol, ethanol and the like. These compositions can also contain additional adjuvants such as wetting, emulsifying, suspending, sweetening, flavoring, and perfuming agents.

Topical dosage forms of the compounds include ointments, pastes, creams, lotions, gels, powders, solutions, sprays, inhalants, eye ointments, eye or ear drops, impregnated dressings and aerosols, and may contain appropriate conventional additives such as preservatives, solvents to assist drug penetration and emollients in ointments and creams. Topical application may be once or more than once per day depending upon the usual medical considerations. Furthermore, preferred compounds for the present invention can be administered in intranasal form via topical use of suitable intranasal vehicles. The formulations may also contain compatible conventional carriers, such as cream or ointment bases and ethanol or oleyl alcohol for lotions. Such carriers may be present as from about 1% up to about 98% of the formulation, more usually they will form up to about 80% of the formulation.

Transdermal administration is also possible. Pharmaceutical compositions suitable for transdermal administration can be presented as discrete patches adapted to remain in intimate contact with the epidermis of the recipient for a prolonged period of time. To be administered in the form of a transdermal delivery system, the dosage administration will, of course, be continuous rather than intermittent throughout the dosage regimen. Such patches suitably contain a compound of the invention in an optionally buffered, aqueous solution, dissolved and/or dispersed in an adhesive, or dispersed in a polymer. A suitable concentration of the active compound is about 1% to 35%, preferably about 3% to 15%.

For administration by inhalation, the compounds of the invention are conveniently delivered in the form of an aerosol spray from a pump spray device not requiring a propellant gas or from a pressurized pack or a nebulizer with the use of a suitable propellant, e.g., dichlorodifluoromethane, trichlorofluoromethane, dichlorotetrafluoroethane, tetrafluoroethane, heptafluoropropane, carbon dioxide, or other suitable gas. In any case, the aerosol spray dosage unit may be determined by providing a valve to deliver a metered amount so that the resulting metered dose inhaler (MDI) is used to administer the compounds of the invention in a reproducible and controlled way. Such inhaler, nebulizer, or atomizer devices are known in the prior art, for example, in PCT International Publication Nos. WO 97/12687 (particularly FIG. 6 thereof, which is the basis for the commercial RESPIMAT® nebulizer); WO 94/07607; WO 97/12683; and WO 97/20590, to which reference is hereby made and each of which is incorporated herein by reference in their entireties.

Rectal administration can be effected utilizing unit dose suppositories in which the compound is admixed with low-melting water-soluble or insoluble solids such as fats, cocoa butter, glycerinated gelatin, hydrogenated vegetable oils, mixtures of polyethylene glycols of various molecular weights, or fatty acid esters of polyethylene glycols, or the like. The active compound is usually a minor component, often from about 0.05 to 10% by weight, with the remainder being the base component.

In all of the above pharmaceutical compositions, the compounds of the invention are formulated with an acceptable carrier or excipient. The carriers or excipients used must, of course, be acceptable in the sense of being compatible with the other ingredients of the composition and must not be deleterious to the patient. The carrier or excipient can be a solid or a liquid, or both, and is preferably formulated with the compound of the invention as a unit-dose composition, for example, a tablet, which can contain from 0.05% to 95% by weight of the active compound. Such carriers or excipients include inert fillers or diluents, binders, lubricants, disintegrating agents, solution retardants, resorption accelerators, absorption agents, and coloring agents. Suitable binders include starch, gelatin, natural sugars such as glucose or β-lactose, corn sweeteners, natural and synthetic gums such as acacia, tragacanth or sodium alginate, carboxymethylcellulose, polyethylene glycol, waxes, and the like. Lubricants include sodium oleate, sodium stearate, magnesium stearate, sodium benzoate, sodium acetate, sodium chloride, and the like. Disintegrators include starch, methyl cellulose, agar, bentonite, xanthan gum, and the like.

Generally, a therapeutically effective daily dose is from about 0.001 mg to about 15 mg/kg of body weight per day of a compound of the invention; preferably, from about 0.1 mg to about 10 mg/kg of body weight per day; and most preferably, from about 0.1 mg to about 1.5 mg/kg of body weight per day. For example, for administration to a 70 kg person, the dosage range would be from about 0.07 mg to about 1050 mg per day of a compound of the invention, preferably from about 7.0 mg to about 700 mg per day, and most preferably from about 7.0 mg to about 105 mg per day. Some degree of routine dose optimization may be required to determine an optimal dosing level and pattern.

Pharmaceutically acceptable carriers and excipients encompass all the foregoing additives and the like.

Examples of Pharmaceutical Formulations

A. TABLETS

| Component | Amount per tablet (mg) |
|---|---|
| active substance | 100 |
| lactose | 140 |
| corn starch | 240 |
| polyvinylpyrrolidone | 15 |
| magnesium stearate | 5 |
| TOTAL | 500 |

The finely ground active substance, lactose, and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

B. TABLETS

| Component | Amount per tablet (mg) |
|---|---|
| active substance | 80 |
| lactose | 55 |
| corn starch | 190 |
| polyvinylpyrrolidone | 15 |
| magnesium stearate | 2 |
| microcrystalline cellulose | 35 |
| sodium-carboxymethyl starch | 23 |
| TOTAL | 400 |

The finely ground active substance, some of the corn starch, lactose, microcrystalline cellulose, and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

C. COATED TABLETS

| Component | Amount per tablet (mg) |
|---|---|
| active substance | 5 |
| lactose | 30 |
| corn starch | 41.5 |
| polyvinylpyrrolidone | 3 |
| magnesium stearate | 0.5 |
| TOTAL | 90 |

The active substance, corn starch, lactose, and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

D. CAPSULES

| Component | Amount per capsule (mg) |
|---|---|
| active substance | 50 |
| corn starch | 268.5 |
| magnesium stearate | 1.5 |
| TOTAL | 320 |

The substance and corn starch are mixed and moistened with water. The moist mass is screened and dried. The dry granules are screened and mixed with magnesium stearate. The finished mixture is packed into size 1 hard gelatine capsules.

E. AMPOULE SOLUTION

| Component | Amount per ampoule |
| --- | --- |
| active substance | 50 mg |
| sodium chloride | 50 mg |
| water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilized and sealed by fusion. The ampoules contain 5 mg, 25 mg, and 50 mg of active substance.

F. SUPPOSITORIES

| Component | Amount per suppository (mg) |
| --- | --- |
| active substance | 50 |
| solid fat | 1650 |
| TOTAL | 1700 |

The hard fat is melted. At 40° C., the ground active substance is homogeneously dispersed therein. The mixture is cooled to 38° C. and poured into slightly chilled suppository molds.

G. METERING AEROSOL

| Component | Amount |
| --- | --- |
| active substance | 0.005 |
| sorbitan trioleate | 0.1 |
| monofluorotrichloromethane and difluorodichloromethane (2:3) | to 100 |

The suspension is transferred into a conventional aerosol container with a metering valve. Preferably, 50 µL of suspension are delivered per spray. The active substance may also be metered in higher doses if desired (e.g., 0.02% by weight).

H. POWDER FOR INHALATION

| Component | Amount |
| --- | --- |
| active substance | 1.0 mg |
| lactose monohydrate | to 25 mg |

I. POWDER FOR INHALATION

| Component | Amount |
| --- | --- |
| active substance | 2.0 mg |
| lactose monohydrate | to 25 mg |

J. POWDER FOR INHALATION

| Component | Amount |
| --- | --- |
| active substance | 1.0 mg |
| lactose monohydrate | to 5 mg |

K. POWDER FOR INHALATION

| Component | Amount |
| --- | --- |
| active substance | 2.0 mg |
| lactose monohydrate | to 5 mg |

In Examples H, I, J, and K, the powder for inhalation is produced in the usual way by mixing the individual ingredients together.

We claim:

1. A compound of Formula (I)

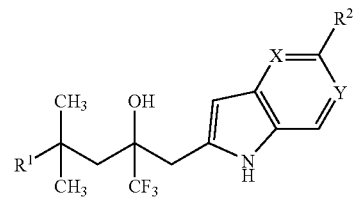

(I)

wherein:
$R^1$ is an aryl or heteroaryl group, each optionally independently substituted with one, two, or three substituent groups selected from $C_1$-$C_5$ alkyl, aminocarbonyl, $C_1$-$C_5$ alkylaminocarbonyl, $C_1$-$C_5$ dialkylaminocarbonyl, aminosulfonyl, $C_1$-$C_5$ alkylaminosulfonyl, $C_1$-$C_5$ dialkylaminosulfonyl, halogen, hydroxyl, cyano, and $C_1$-$C_5$ alkylthio wherein the sulfur atom is optionally oxidized to a sulfoxide or sulfone;
$R^2$ is $C_1$-$C_5$ alkylthio wherein the sulfur atom is optionally oxidized to a sulfoxide or sulfone, optionally independently substituted with one, two, or three substituent groups selected from halogen, hydroxy, oxo, cyano, alkoxyalkyl, and aminocarbonyl;
X is CH; and
Y is N,
or a tautomer, optical isomer, co-crystal, or salt thereof.

2. The compound of Formula (I) according to claim 1, wherein:
$R^1$ is an aryl or heteroaryl group, each optionally independently substituted with one, two, or three substituent groups selected from $C_1$-$C_5$ alkyl, aminocarbonyl, $C_1$-$C_5$ alkylaminocarbonyl, $C_1$-$C_5$ dialkylaminocarbonyl, aminosulfonyl, $C_1$-$C_5$ alkylaminosulfonyl, $C_1$-$C_5$ dialkylaminosulfonyl, halogen, hydroxyl, cyano, and $C_1$-$C_5$ alkylthio wherein the sulfur atom is optionally oxidized to a sulfoxide or sulfone;
$R^2$ is $C_1$-$C_5$ alkylthio wherein the sulfur atom is optionally oxidized to a sulfoxide or sulfone, each optionally independently substituted with one to three substituent groups selected from halogen, hydroxy, oxo, cyano, alkoxyalkyl, and aminocarbonyl;

X is CH; and

Y is N, or a tautomer, co-crystal, or salt thereof.

3. The compound of Formula (I) according to claim 1, wherein:

$R^1$ is an aryl group, optionally substituted with one, two, or three substituent groups independently selected from $C_1$, $C_2$, or $C_3$ alkyl, aminocarbonyl, halogen, and $C_1$, $C_2$, or $C_3$ alkylthio wherein the sulfur atom is optionally oxidized to a sulfoxide or sulfone;

$R^2$ is $C_1$, $C_2$, or $C_3$ alkylthio wherein the sulfur atom is optionally oxidized to a sulfoxide or sulfone, each optionally independently substituted with one to three substituent groups selected from halogen, hydroxy, oxo, cyano, alkoxyalkyl, and aminocarbonyl;

X is CH; and

Y is N, or a tautomer, co-crystal, or salt thereof.

4. The compound of Formula (I) according to claim 1, wherein:

$R^1$ is a phenyl group, optionally substituted with one or two substituent groups independently selected from aminocarbonyl, methyl, fluoro, chloro, bromo, and $C_1$ or $C_2$ alkylthio wherein the sulfur atom is optionally oxidized to a sulfoxide or sulfone;

$R^2$ is $C_1$, $C_2$, or $C_3$ alkylthio wherein the sulfur atom is optionally oxidized to a sulfoxide or sulfone;

X is CH; and

Y is N, or a tautomer, co-crystal, or salt thereof.

5. The compound of Formula (I) according to claim 1, wherein:

$R^1$ is a phenyl group, optionally substituted with one or two substituent groups independently selected from aminocarbonyl, methyl, fluoro, chloro, bromo, and $C_1$ or $C_2$ alkylthio wherein the sulfur atom is optionally oxidized to a sulfoxide or sulfone;

$R^2$ is $C_1$ or $C_2$ alkylthio wherein the sulfur atom is optionally oxidized to a sulfoxide or sulfone;

X is CH; and

Y is N, or a tautomer, co-crystal, or salt thereof.

6. The compound of Formula (I) according to claim 1, selected from:

(R)-4-(5-Chloro-2,3-dihydrobenzofuran-7-yl)-1,1,1-trifluoro-2-(5-methanesulfonyl-1H-pyrrolo[2,3-c]pyridin-2-ylmethyl)-4-methylpentan-2-ol;

(R)-1,1,1-Trifluoro-4-(2-methanesulfonylphenyl)-2-(5-methanesulfonyl-1H-pyrrolo[2,3-c]pyridin-2-ylmethyl)-4-methylpentan-2-ol;

(R)-4-(5-Chloro-2,3-dihydrobenzofuran-7-yl)-2-(5-ethanesulfonyl-1H-pyrrolo[2,3-c]pyridin-2-ylmethyl)-1,1,1-trifluoro-4-methylpentan-2-ol;

(R)-4-(3-Bromophenyl)-1,1,1-trifluoro-2-(5-methanesulfonyl-1H-pyrrolo[2,3-c]pyridin-2-ylmethyl)-4-methylpentan-2-ol;

2-(5-Ethanesulfonyl-1H-pyrrolo[2,3-c]pyridin-2-ylmethyl)-1,1,1-trifluoro-4-(2-methanesulfonylphenyl)-4-methylpentan-2-ol;

(R)-2-[4,4,4-Trifluoro-3-hydroxy-3-(5-methanesulfonyl-1H-pyrrolo[2,3-c]pyridin-2-ylmethyl)-1,1-dimethylbutyl]benzamide;

1,1,1-Trifluoro-4-(3-fluoro-2-methanesulfonylphenyl)-2-(5-methanesulfonyl-1H-pyrrolo[2,3-c]pyridin-2-ylmethyl)-4-methylpentan-2-ol;

(R)-1,1,1-Trifluoro-4-(4-fluoro-2-methanesulfonylphenyl)-2-(5-methanesulfonyl-1H-pyrrolo[2,3-c]pyridin-2-ylmethyl)-4-methylpentan-2-ol;

1,1,1-Trifluoro-4-(5-fluoro-2-methanesulfonylphenyl)-2-(5-methanesulfonyl-1H-pyrrolo[2,3-c]pyridin-2-ylmethyl)-4-methylpentan-2-ol;

4-(5-Chloro-2-methanesulfonylphenyl)-1,1,1-trifluoro-2-(5-methanesulfonyl-1H-pyrrolo[2,3-c]pyridin-2-ylmethyl)-4-methylpentan-2-ol;

(R)-4-(4-Chloro-2-methanesulfonylphenyl)-1,1,1-trifluoro-2-(5-methanesulfonyl-1H-pyrrolo[2,3-c]pyridin-2-ylmethyl)-4-methylpentan-2-ol;

4-(2-Bromophenyl)-1,1,1-trifluoro-2-(5-methanesulfonyl-1H-pyrrolo[2,3-c]pyridin-2-ylmethyl)-4-methylpentan-2-ol;

4-(4-Chloro-2-methanesulfonylphenyl)-2-(5-ethanesulfonyl-1H-pyrrolo[2,3-c]pyridin-2-ylmethyl)-1,1,1-trifluoro-4-methylpentan-2-ol;

2-(5-Ethanesulfonyl-1H-pyrrolo[2,3-c]pyridin-2-ylmethyl)-1,1,1-trifluoro-4-(4-fluoro-2-methanesulfonylphenyl)-4-methylpentan-2-ol;

(R)-2-[3-(5-Ethanesulfonyl-1H-pyrrolo[2,3-c]pyridin-2-ylmethyl)-4,4,4-trifluoro-3-hydroxy-1,1-dimethylbutyl]benzamide;

1,1,1-Trifluoro-4-(4-fluoro-2-methanesulfonylphenyl)-4-methyl-2-[5-(propane-2-sulfonyl)-1H-pyrrolo[2,3-c]pyridin-2-ylmethyl]pentan-2-ol;

4-Benzo[b]thiophen-7-yl-1,1,1-trifluoro-2-(5-methanesulfonyl-1H-pyrrolo[2,3-c]pyridin-2-ylmethyl)-4-methylpentan-2-ol;

1,1,1-Trifluoro-4-(2-methanesulfonylphenyl)-4-methyl-2-[5-(propane-2-sulfonyl)-1H-pyrrolo[2,3-c]pyridin-2-ylmethyl]pentan-2-ol;

1,1,1-Trifluoro-4-(5-fluoro-2-methanesulfonylphenyl)-4-methyl-2-[5-(propane-2-sulfonyl)-1H-pyrrolo[2,3-c]pyridin-2-ylmethyl]pentan-2-ol;

1,1,1-Trifluoro-4-(3-fluoro-2-methanesulfonylphenyl)-4-methyl-2-[5-(propane-2-sulfonyl)-1H-pyrrolo[2,3-c]pyridin-2-ylmethyl]pentan-2-ol;

2-(5-Ethanesulfonyl-1H-pyrrolo[2,3-c]pyridin-2-ylmethyl)-1,1,1-trifluoro-4-(3-fluoro-2-methanesulfonylphenyl)-4-methylpentan-2-ol;

2-[4,4,4-Trifluoro-3-hydroxy-3-(5-methanesulfonyl-1H-pyrrolo[2,3-c]pyridin-2-ylmethyl)-1,1-dimethylbutyl]benzenesulfonamide;

4-(1,1-Dioxo-1H-1$\lambda^6$-benzo[b]thiophen-7-yl)-1,1,1-trifluoro-2-(5-methanesulfonyl-1H-pyrrolo[2,3-c]pyridin-2-ylmethyl)-4-methylpentan-2-ol;

5-Methyl-2-[4,4,4-trifluoro-3-hydroxy-3-(5-methanesulfonyl-1H-pyrrolo[2,3-c]pyridin-2-ylmethyl)-1,1-dimethylbutyl]benzamide;

2-[3-(5-Ethanesulfonyl-1H-pyrrolo[2,3-c]pyridin-2-ylmethyl)-4,4,4-trifluoro-3-hydroxy-1,1-dimethylbutyl]-5-methylbenzamide;

4-(1,1-Dioxo-1H-1$\lambda^6$-benzo[b]thiophen-7-yl)-2-(5-ethanesulfonyl-1H-pyrrolo[2,3-c]pyridin-2-ylmethyl)-1,1,1-trifluoro-4-methylpentan-2-ol;

5-Fluoro-2-[4,4,4-trifluoro-3-hydroxy-3-(5-methanesulfonyl-1H-pyrrolo[2,3-c]pyridin-2-ylmethyl)-1,1-dimethylbutyl]benzamide;

(R)-2-[3-(5-Ethanesulfonyl-1H-pyrrolo[2,3-c]pyridin-2-ylmethyl)-4,4,4-trifluoro-3-hydroxy-1,1-dimethylbutyl]-5-fluorobenzamide;

4-(5-Chloro-2-methanesulfonylphenyl)-1,1,1-trifluoro-4-methyl-2-[5-(propane-2-sulfonyl)-1H-pyrrolo[2,3-c]pyridin-2-ylmethyl]pentan-2-ol;

4-Methyl-2-[4,4,4-trifluoro-3-hydroxy-3-(5-ethanesulfo-nyl-1H-pyrrolo[2,3-c]pyridin-2-ylmethyl)-1,1-dimethylbutyl]benzamide;

2-[3-(5-Ethanesulfonyl-1H-pyrrolo[2,3-c]pyridin-2-ylmethyl)-4,4,4-trifluoro-3-hydroxy-1,1-dimethylbutyl]benzenesulfonamide;

4-Methyl-2-[4,4,4-trifluoro-3-hydroxy-3-(5-methanesulfonyl-1H-pyrrolo[2,3-c]pyridin-2-ylmethyl)-1,1-dimethylbutyl]benzamide;

5-Methyl-2-{4,4,4-trifluoro-3-hydroxy-1,1-dimethyl-3-[5-(propane-2-sulfonyl)-1H-pyrrolo[2,3-c]pyridin-2-ylmethyl]butyl}benzamide;

5-Fluoro-2-{4,4,4-trifluoro-3-hydroxy-1,1-dimethyl-3-[5-(propane-2-sulfonyl)-1H-pyrrolo[2,3-c]pyridin-2-ylmethyl]butyl}benzamide;

1,1,1-Trifluoro-4-(5-fluoro-2-methanesulfonylphenyl)-4-methyl-2-[5-(propane-1-sulfonyl)-1H-pyrrolo[2,3-c]pyridin-2-ylmethyl]pentan-2-ol;

1,1,1-Trifluoro-4-(2-methanesulfonylphenyl)-4-methyl-2-[5-(propane-1-sulfonyl)-1H-pyrrolo[2,3-c]pyridin-2-ylmethyl]pentan-2-ol;

1,1,1-Trifluoro-4-(3-fluoro-2-methanesulfonylphenyl)-4-methyl-2-[5-(propane-1-sulfonyl)-1H-pyrrolo[2,3-c]pyridin-2-ylmethyl]pentan-2-ol;

445-Chloro-2-methanesulfonylphenyl)-1,1,1-trifluoro-4-methyl-2-[5-(propane-1-sulfonyl)-1H-pyrrolo[2,3-c]pyridin-2-ylmethyl]pentan-2-ol;

4-Fluoro-2-[4,4,4-trifluoro-3-hydroxy-3-(5-methanesulfonyl-1H-pyrrolo[2,3-c]pyridin-2-ylmethyl)-1,1-dimethylbutyl]phenol;

5-Chloro-2-[3-(5-ethanesulfonyl-1H-pyrrolo[2,3-c]pyridin-2-ylmethyl)-4,4,4-trifluoro-3-hydroxy-1,1-dimethylbutyl]benzamide;

5-Chloro-2-[4,4,4-trifluoro-3-hydroxy-3-(5-methanesulfonyl-1H-pyrrolo[2,3-c]pyridin-2-ylmethyl)-1,1-dimethylbutyl]benzamide;

2-[3-(5-Ethanesulfinyl-1H-pyrrolo[2,3-c]pyridin-2-ylmethyl)-4,4,4-trifluoro-3-hydroxy-1,1-dimethylbutyl]benzamide;

4-Bromo-2-[4,4,4-trifluoro-3-hydroxy-3-(5-methanesulfonyl-1H-pyrrolo[2,3-c]pyridin-2-ylmethyl)-1,1-dimethylbutyl]phenol;

4-(2-Bromo-5-fluorophenyl)-1,1,1-trifluoro-2-(5-methanesulfonyl-1H-pyrrolo[2,3-c]pyridin-2-ylmethyl)-4-methylpentan-2-ol;

or a tautomer, co-crystal, or salt thereof.

7. The compound of Formula (I) according to claim 6, selected from:

(R)-4-(5-Chloro-2,3-dihydrobenzofuran-7-yl)-1,1,1-trifluoro-2-(5-methanesulfonyl-1H-pyrrolo[2,3-c]pyridin-2-ylmethyl)-4-methylpentan-2-ol;

(R)-1,1,1-Trifluoro-4-(2-methanesulfonylphenyl)-2-(5-methanesulfonyl-1H-pyrrolo[2,3-c]pyridin-2-ylmethyl)-4-methylpentan-2-ol;

(R)-4-(5-Chloro-2,3-dihydrobenzofuran-7-yl)-2-(5-ethanesulfonyl-1H-pyrrolo[2,3-c]pyridin-2-ylmethyl)-1,1,1-trifluoro-4-methylpentan-2-ol;

(R)-4-(3-Bromophenyl)-1,1,1-trifluoro-2-(5-methanesulfonyl-1H-pyrrolo[2,3-c]pyridin-2-ylmethyl)-4-methylpentan-2-ol;

2-(5-Ethanesulfonyl-1H-pyrrolo[2,3-c]pyridin-2-ylmethyl)-1,1,1-trifluoro-4-(2-methanesulfonylphenyl)-4-methylpentan-2-ol;

(R)-2-[4,4,4-Trifluoro-3-hydroxy-3-(5-methanesulfonyl-1H-pyrrolo[2,3-c]pyridin-2-ylmethyl)-1,1-dimethylbutyl]benzamide;

1,1,1-Trifluoro-4-(3-fluoro-2-methanesulfonylphenyl)-2-(5-methanesulfonyl-1H-pyrrolo[2,3-c]pyridin-2-ylmethyl)-4-methylpentan-2-ol;

(R)-1,1,1-Trifluoro-4-(4-fluoro-2-methanesulfonylphenyl)-2-(5-methanesulfonyl-1H-pyrrolo[2,3-c]pyridin-2-ylmethyl)-4-methylpentan-2-ol;

1,1,1-Trifluoro-4-(5-fluoro-2-methanesulfonylphenyl)-2-(5-methanesulfonyl-1H-pyrrolo[2,3-c]pyridin-2-ylmethyl)-4-methylpentan-2-ol;

4-(5-Chloro-2-methanesulfonylphenyl)-1,1,1-trifluoro-2-(5-methanesulfonyl-1H-pyrrolo[2,3-c]pyridin-2-ylmethyl)-4-methylpentan-2-ol;

(R)-4-(4-Chloro-2-methanesulfonylphenyl)-1,1,1-trifluoro-2-(5-methanesulfonyl-1H-pyrrolo[2,3-c]pyridin-2-ylmethyl)-4-methylpentan-2-ol;

4-(2-Bromophenyl)-1,1,1-trifluoro-2-(5-methanesulfonyl-1H-pyrrolo[2,3-c]pyridin-2-ylmethyl)-4-methylpentan-2-ol;

4-(4-Chloro-2-methanesulfonylphenyl)-2-(5-ethanesulfonyl-1H-pyrrolo[2,3-c]pyridin-2-ylmethyl)-1,1,1-trifluoro-4-methylpentan-2-ol;

2-(5-Ethanesulfonyl-1H-pyrrolo[2,3-c]pyridin-2-ylmethyl)-1,1,1-trifluoro-4-(4-fluoro-2-methanesulfonylphenyl)-4-methylpentan-2-ol;

(R)-2-[3-(5-Ethanesulfonyl-1H-pyrrolo[2,3-c]pyridin-2-ylmethyl)-4,4,4-trifluoro-3-hydroxy-1,1-dimethylbutyl]benzamide;

1,1,1-Trifluoro-4-(4-fluoro-2-methanesulfonylphenyl)-4-methyl-2-[5-(propane-2-sulfonyl)-1H-pyrrolo[2,3-c]pyridin-2-ylmethyl]pentan-2-ol;

4-Benzo[b]thiophen-7-yl-1,1,1-trifluoro-2-(5-methanesulfonyl-1H-pyrrolo[2,3-c]pyridin-2-ylmethyl)-4-methylpentan-2-ol;

1,1,1-Trifluoro-4-(2-methanesulfonylphenyl)-4-methyl-2-[5-(propane-2-sulfonyl)-1H-pyrrolo[2,3-c]pyridin-2-ylmethyl]pentan-2-ol;

1,1,1-Trifluoro-4-(5-fluoro-2-methanesulfonylphenyl)-4-methyl-2-[5-(propane-2-sulfonyl)-1H-pyrrolo[2,3-c]pyridin-2-ylmethyl]pentan-2-ol;

1,1,1-Trifluoro-4-(3-fluoro-2-methanesulfonylphenyl)-4-methyl-2-[5-(propane-2-sulfonyl)-1H-pyrrolo[2,3-c]pyridin-2-ylmethyl]pentan-2-ol;

2-(5-Ethanesulfonyl-1H-pyrrolo[2,3-c]pyridin-2-ylmethyl)-1,1,1-trifluoro-4-(3-fluoro-2-methanesulfonylphenyl)-4-methylpentan-2-ol;

2-[4,4,4-Trifluoro-3-hydroxy-3-(5-methanesulfonyl-1H-pyrrolo[2,3-c]pyridin-2-ylmethyl)-1,1-dimethylbutyl]benzenesulfonamide;

4-(1,1-Dioxo-1H-1$\lambda^6$-benzo[b]thiophen-7-yl)-1,1,1-trifluoro-2-(5-methanesulfonyl-1H-pyrrolo[2,3-c]pyridin-2-ylmethyl)-4-methylpentan-2-ol;

5-Methyl-2-[4,4,4-trifluoro-3-hydroxy-3-(5-methanesulfonyl-1H-pyrrolo[2,3-c]pyridin-2-ylmethyl)-1,1-dimethylbutyl]benzamide;

2-[3-(5-Ethanesulfonyl-1H-pyrrolo[2,3-c]pyridin-2-ylmethyl)-4,4,4-trifluoro-3-hydroxy-1,1-dimethylbutyl]-5-methylbenzamide;

4-(1,1-Dioxo-1H-1$\lambda^6$-benzo[b]thiophen-7-yl)-2-(5-ethanesulfonyl-1H-pyrrolo[2,3-c]pyridin-2-ylmethyl)-1,1,1-trifluoro-4-methylpentan-2-ol;

5-Fluoro-2-[4,4,4-trifluoro-3-hydroxy-3-(5-methanesulfonyl-1H-pyrrolo[2,3-c]pyridin-2-ylmethyl)-1,1-dimethylbutyl]benzamide;

(R)-2-[3-(5-Ethanesulfonyl-1H-pyrrolo[2,3-c]pyridin-2-ylmethyl)-4,4,4-trifluoro-3-hydroxy-1,1-dimethylbutyl]-5-fluorobenzamide;

4-(5-Chloro-2-methanesulfonylphenyl)-1,1,1-trifluoro-4-methyl-2-[5-(propane-2-sulfonyl)-1H-pyrrolo[2,3-c]pyridin-2-ylmethyl]pentan-2-ol;

4-Methyl-2-[4,4,4-trifluoro-3-hydroxy-3-(5-ethanesulfonyl-1H-pyrrolo[2,3-c]pyridin-2-ylmethyl)-1,1-dimethylbutyl]benzamide;

2-[3-(5-Ethanesulfonyl-1H-pyrrolo[2,3-c]pyridin-2-ylmethyl)-4,4,4-trifluoro-3-hydroxy-1,1-dimethylbutyl]benzenesulfonamide;

4-Methyl-2-[4,4,4-trifluoro-3-hydroxy-3-(5-methanesulfonyl-1H-pyrrolo[2,3-c]pyridin-2-ylmethyl)-1,1-dimethylbutyl]benzamide;

5-Methyl-2-{4,4,4-trifluoro-3-hydroxy-1,1-dimethyl-3-[5-(propane-2-sulfonyl)-1H-pyrrolo[2,3-c]pyridin-2-ylmethyl]butyl}benzamide;

5-Fluoro-2-{4,4,4-trifluoro-3-hydroxy-1,1-dimethyl-3-[5-(propane-2-sulfonyl)-1H-pyrrolo[2,3-c]pyridin-2-ylmethyl]butyl}benzamide;

1,1,1-Trifluoro-4-(5-fluoro-2-methanesulfonylphenyl)-4-methyl-2-[5-(propane-1-sulfonyl)-1H-pyrrolo[2,3-c]pyridin-2-ylmethyl]pentan-2-ol;

1,1,1-Trifluoro-4-(2-methanesulfonylphenyl)-4-methyl-2-[5-(propane-1-sulfonyl)-1H-pyrrolo[2,3-c]pyridin-2-ylmethyl]pentan-2-ol;

1,1,1-Trifluoro-4-(3-fluoro-2-methanesulfonylphenyl)-4-methyl-2-[5-(propane-1-sulfonyl)-1H-pyrrolo[2,3-c]pyridin-2-ylmethyl]pentan-2-ol;

4-(5-Chloro-2-methanesulfonylphenyl)-1,1,1-trifluoro-4-methyl-2-[5-(propane-1-sulfonyl)-1H-pyrrolo[2,3-c]pyridin-2-ylmethyl]pentan-2-ol;

4-Fluoro-2-[4,4,4-trifluoro-3-hydroxy-3-(5-methanesulfonyl-1H-pyrrolo[2,3-c]pyridin-2-ylmethyl)-1,1-dimethylbutyl]phenol;

5-Chloro-2-[3-(5-ethanesulfonyl-1H-pyrrolo[2,3-c]pyridin-2-ylmethyl)-4,4,4-trifluoro-3-hydroxy-1,1-dimethylbutyl]benzamide;

5-Chloro-2-[4,4,4-trifluoro-3-hydroxy-3-(5-methanesulfonyl-1H-pyrrolo[2,3-c]pyridin-2-ylmethyl)-1,1-dimethylbutyl]benzamide;

2-[3-(5-Ethanesulfinyl-1H-pyrrolo[2,3-c]pyridin-2-ylmethyl)-4,4,4-trifluoro-3-hydroxy-1,1-dimethylbutyl]benzamide;

4-Bromo-2-[4,4,4-trifluoro-3-hydroxy-3-(5-methanesulfonyl-1H-pyrrolo[2,3-c]pyridin-2-ylmethyl)-1,1-dimethylbutyl]phenol; and 4-(2-Bromo-5-fluorophenyl)-1,1,1-trifluoro-2-(5-methanesulfonyl-1H-pyrrolo[2,3-c]pyridin-2-ylmethyl)-4-methylpentan-2-ol, or a tautomer, co-crystal, or salt thereof.

8. The compound of Formula (I) according to claim 7, selected from:

(R)-1,1,1-Trifluoro-4-(2-methanesulfonylphenyl)-2-(5-methanesulfonyl-1H-pyrrolo[2,3-c]pyridin-2-ylmethyl)-4-methylpentan-2-ol;

2-(5-Ethanesulfonyl-1H-pyrrolo[2,3-c]pyridin-2-ylmethyl)-1,1,1-trifluoro-4-(2-methanesulfonylphenyl)-4-methylpentan-2-ol;

(R)-2-[4,4,4-Trifluoro-3-hydroxy-3-(5-methanesulfonyl-1H-pyrrolo[2,3-c]pyridin-2-ylmethyl)-1,1-dimethylbutyl]benzamide;

1,1,1-Trifluoro-4-(3-fluoro-2-methanesulfonylphenyl)-2-(5-methanesulfonyl-1H-pyrrolo[2,3-c]pyridin-2-ylmethyl)-4-methylpentan-2-ol;

(R)-1,1,1-Trifluoro-4-(4-fluoro-2-methanesulfonylphenyl)-2-(5-methanesulfonyl-1H-pyrrolo[2,3-c]pyridin-2-ylmethyl)-4-methylpentan-2-ol;

1,1,1-Trifluoro-4-(5-fluoro-2-methanesulfonylphenyl)-2-(5-methanesulfonyl-1H-pyrrolo[2,3-c]pyridin-2-ylmethyl)-4-methylpentan-2-ol;

4-(5-Chloro-2-methanesulfonylphenyl)-1,1,1-trifluoro-2-(5-methanesulfonyl-1H-pyrrolo[2,3-c]pyridin-2-ylmethyl)-4-methylpentan-2-ol;

(R)-4-(4-Chloro-2-methanesulfonylphenyl)-1,1,1-trifluoro-2-(5-methanesulfonyl-1H-pyrrolo[2,3-c]pyridin-2-ylmethyl)-4-methylpentan-2-ol;

4-(4-Chloro-2-methanesulfonylphenyl)-2-(5-ethanesulfonyl-1H-pyrrolo[2,3-c]pyridin-2-ylmethyl)-1,1,1-trifluoro-4-methylpentan-2-ol;

2-(5-Ethanesulfonyl-1H-pyrrolo[2,3-c]pyridin-2-ylmethyl)-1,1,1-trifluoro-4-(4-fluoro-2-methanesulfonylphenyl)-4-methylpentan-2-ol;

(R)-2-[3-(5-Ethanesulfonyl-1H-pyrrolo[2,3-c]pyridin-2-ylmethyl)-4,4,4-trifluoro-3-hydroxy-1,1-dimethylbutyl]benzamide;

2-(5-Ethanesulfonyl-1H-pyrrolo[2,3-c]pyridin-2-ylmethyl)-1,1,1-trifluoro-4-(3-fluoro-2-methanesulfonylphenyl)-4-methylpentan-2-ol;

2-[4,4,4-Trifluoro-3-hydroxy-3-(5-methanesulfonyl-1H-pyrrolo[2,3-c]pyridin-2-ylmethyl)-1,1-dimethylbutyl]benzenesulfonamide;

5-Methyl-2-[4,4,4-trifluoro-3-hydroxy-3-(5-methanesulfonyl-1H-pyrrolo[2,3-c]pyridin-2-ylmethyl)-1,1-dimethylbutyl]benzamide;

2-[3-(5-Ethanesulfonyl-1H-pyrrolo[2,3-c]pyridin-2-ylmethyl)-4,4,4-trifluoro-3-hydroxy-1,1-dimethylbutyl]-5-methylbenzamide;

5-Fluoro-2-[4,4,4-trifluoro-3-hydroxy-3-(5-methanesulfonyl-1H-pyrrolo[2,3-c]pyridin-2-ylmethyl)-1,1-dimethylbutyl]benzamide;

(R)-2-[3-(5-Ethanesulfonyl-1H-pyrrolo[2,3-c]pyridin-2-ylmethyl)-4,4,4-trifluoro-3-hydroxy-1,1-dimethylbutyl]-5-fluorobenzamide;

4-Methyl-2-[4,4,4-trifluoro-3-hydroxy-3-(5-ethanesulfonyl-1H-pyrrolo[2,3-c]pyridin-2-ylmethyl)-1,1-dimethylbutyl]benzamide;

2-[3-(5-Ethanesulfonyl-1H-pyrrolo[2,3-c]pyridin-2-ylmethyl)-4,4,4-trifluoro-3-hydroxy-1,1-dimethylbutyl]benzenesulfonamide;

4-Methyl-2-[4,4,4-trifluoro-3-hydroxy-3-(5-methanesulfonyl-1H-pyrrolo[2,3-c]pyridin-2-ylmethyl)-1,1-dimethylbutyl]benzamide;

5-Chloro-2-[3-(5-ethanesulfonyl-1H-pyrrolo[2,3-c]pyridin-2-ylmethyl)-4,4,4-trifluoro-3-hydroxy-1,1-dimethylbutyl]benzamide; and 5-Chloro-2-[4,4,4-trifluoro-3-hydroxy-3-(5-methanesulfonyl-1H-pyrrolo[2,3-c]pyridin-2-ylmethyl)-1,1-dimethylbutyl]benzamide, or a tautomer, co-crystal, or salt thereof.

9. The compound of Formula (I) according to claim 8, selected from:

(R)-2-[3-(5-Ethanesulfonyl-1H-pyrrolo[2,3-c]pyridin-2-ylmethyl)-4,4,4-trifluoro-3-hydroxy-1,1-dimethylbutyl]-5-fluorobenzamide;

(R)-2-[3-(5-Ethanesulfonyl-1H-pyrrolo[2,3-c]pyridin-2-ylmethyl)-4,4,4-trifluoro-3-hydroxy-1,1-dimethylbutyl]benzamide;

5-Fluoro-2-[(R)-4,4,4-trifluoro-3-hydroxy-3-(5-methanesulfonyl-1H-pyrrolo[2,3-c]pyridin-2-ylmethyl)-1,1-dimethylbutyl]benzamide; and (R)-2-[4,4,4-Trifluoro-3-hydroxy-3-(5-methanesulfonyl-1H-pyrrolo[2,3-c]pyridin-2-ylmethyl)-1,1-dimethylbutyl]benzamide.

10. The compound of Formula (I) according to claim 8, selected from:

(R)-2-[3-(5-Ethanesulfonyl-1H-pyrrolo[2,3-c]pyridin-2-ylmethyl)-4,4,4-trifluoro-3-hydroxy-1,1-dimethylbutyl]-5-fluorobenzamide phosphoric acid co-crystal;

(R)-2-[3-(5-Ethanesulfonyl-1H-pyrrolo[2,3-c]pyridin-2-ylmethyl)-4,4,4-trifluoro-3-hydroxy-1,1-dimethylbutyl]benzamide phosphoric acid co-crystal;

(R)-2-[3-(5-Ethanesulfonyl-1H-pyrrolo[2,3-c]pyridin-2-ylmethyl)-4,4,4-trifluoro-3-hydroxy-1,1-dimethylbutyl]benzamide isonicotinamide co-crystal;

5-Fluoro-2[(R)-4,4,4-trifluoro-3-hydroxy-3-(5-methanesulfonyl-1H-pyrrolo[2,3-c]pyridin-2-ylmethyl)-1,1-dimethylbutyl]benzamide phosphoric acid co-crystal; and 5-Fluoro-2[(R)-4,4,4-trifluoro-3-hydroxy-3-(5-methanesulfonyl-1H-pyrrolo[2,3-c]pyridin-2-ylmethyl)-1,1-dimethylbutyl]benzamide acetic acid co-crystal.

11. A salt or co-crystal resulting from the reaction of a compound of Formula (I)

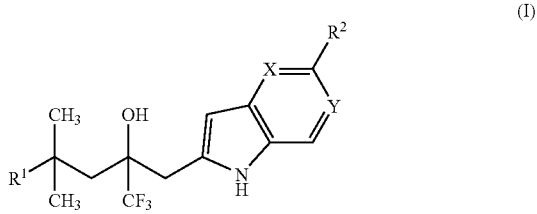

(I)

wherein:

$R^1$ is an aryl or heteroaryl group, each optionally independently substituted with one, two, or three substituent groups selected from $C_1$-$C_5$ alkyl, aminocarbonyl, $C_1$-$C_5$ alkylaminocarbonyl, $C_1$-$C_5$ dialkylaminocarbonyl, aminosulfonyl, $C_1$-$C_5$ alkylaminosulfonyl, $C_1$-$C_5$ dialkylaminosulfonyl, halogen, hydroxyl, cyano, and $C_1$-$C_5$ alkylthio wherein the sulfur atom is optionally oxidized to a sulfoxide or sulfone;

$R^2$ is $C_1$-$C_5$ alkylthio wherein the sulfur atom is optionally oxidized to a sulfoxide or sulfone, optionally independently substituted with one, two, or three substituent groups selected from halogen, hydroxy, oxo, cyano, alkoxyalkyl, and aminocarbonyl;

X is CH or N; and

Y is CH or N, wherein X and Y are not both CH, or a tautomer or optical isomer thereof, with a suitable acid wherein the suitable acid is hydrochloric acid, hydrobromic acid, hydroiodic acid, sulfuric acid, sulfamic acid, nitric acid, phosphoric acid, and the like, and organic acids such as acetic acid, trichloroacetic acid, trifluoroacetic acid, adipic acid, alginic acid, ascorbic acid, aspartic acid, benzenesulfonic acid, benzoic acid, 2-acetoxybenzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, heptanoic acid, hexanoic acid, formic acid, fumaric acid, 2-hydroxyethanesulfonic acid (isethionic acid), lactic acid, maleic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, picric acid, pivalic acid, propionic acid, pyruvic acid, pyruvic acid, salicylic acid, stearic acid, succinic acid, sulfanilic acid, tartaric acid, p-toluenesulfonic acid, or undecanoic acid.

12. A pharmaceutical composition comprising an effective amount of a compound according to one of claims 1 to 11, or a tautomer, co-crystal, or salt thereof, and a pharmaceutically acceptable excipient or carrier.

\* \* \* \* \*